US010793857B2

(12) United States Patent
Collard et al.

(10) Patent No.: US 10,793,857 B2
(45) Date of Patent: *Oct. 6, 2020

(54) TREATMENT OF SODIUM CHANNEL, VOLTAGE-GATED, ALPHA SUBUNIT (SCNA) RELATED DISEASES BY INHIBITION OF NATURAL ANTISENSE TRANSCRIPT TO SCNA

(71) Applicant: CuRNA, Inc., Miami, FL (US)

(72) Inventors: Joseph Collard, Delray Beach, FL (US); Olga Khorkova Sherman, Tequesta, FL (US); Belinda De Leon, San Francisco, CA (US); Carlos Coito, West Palm Beach, FL (US); Jane H. Hsiao, Miami, FL (US)

(73) Assignee: CuRNA, Inc., Miami, FL (US)

( * ) Notice: Subject to any disclaimer, the term of this patent is extended or adjusted under 35 U.S.C. 154(b) by 113 days.

This patent is subject to a terminal disclaimer.

(21) Appl. No.: 15/689,713

(22) Filed: Aug. 29, 2017

(65) Prior Publication Data

US 2018/0002696 A1 Jan. 4, 2018

Related U.S. Application Data

(62) Division of application No. 13/805,745, filed as application No. PCT/US2011/041664 on Jun. 23, 2011, now Pat. No. 9,771,579.

(60) Provisional application No. 61/357,774, filed on Jun. 23, 2010.

(51) Int. Cl.

*C12N 15/11* (2006.01)
*C12N 15/113* (2010.01)
*A61K 31/7088* (2006.01)
*C12Q 1/6813* (2018.01)

(52) U.S. Cl.

CPC ........ *C12N 15/113* (2013.01); *A61K 31/7088* (2013.01); *C12N 15/1138* (2013.01); *C12Q 1/6813* (2013.01); *C12N 2310/111* (2013.01); *C12N 2310/113* (2013.01); *C12N 2310/315* (2013.01)

(58) Field of Classification Search

None

See application file for complete search history.

(56) References Cited

U.S. PATENT DOCUMENTS 4,683,195 A 7/1987 Mullis et al.
4,683,202 A 7/1987 Mullis
4,754,065 A 6/1988 Levenson et al.
4,800,159 A 1/1989 Mullis et al.
5,034,506 A 7/1991 Summerton et al.
5,138,045 A 8/1992 Cook et al.
5,218,105 A 6/1993 Cook et al.
5,288,512 A 2/1994 Seiden
5,288,514 A 2/1994 Ellman
5,319,080 A 6/1994 Leumann
5,393,878 A 2/1995 Leumann
5,432,272 A 7/1995 Benner et al.
5,457,189 A 10/1995 Crooke et al.
5,459,255 A 10/1995 Cook et al.
5,474,796 A 12/1995 Brennan
5,491,084 A 2/1996 Chalfie et al.
5,506,337 A 4/1996 Summerton et al.
5,519,134 A 5/1996 Acevedo et al.
5,525,735 A 6/1996 Gallop et al.
5,539,083 A 7/1996 Cook et al.
5,549,974 A 8/1996 Holmes
5,569,588 A 10/1996 Ashby et al.
5,576,302 A 11/1996 Cook et al.
5,593,853 A 1/1997 Chen et al.
5,605,662 A 2/1997 Heller et al.
5,661,134 A 8/1997 Cook et al.
5,708,161 A 1/1998 Reese
5,739,119 A 4/1998 Galli et al.
5,739,311 A 4/1998 Lackey et al.
5,756,710 A 5/1998 Stein et al.
5,849,902 A 12/1998 Arrow et al.
5,891,725 A 4/1999 Soreq et al.
5,902,880 A 5/1999 Thompson
5,908,779 A 6/1999 Carmichael et al.
5,965,721 A 10/1999 Cook et al.
5,985,663 A 11/1999 Bennett et al.
6,005,095 A 12/1999 Capaccioli et al.

(Continued)

FOREIGN PATENT DOCUMENTS

CA 2686933 4/2008
EP 335451 A3 3/1988

(Continued)

OTHER PUBLICATIONS

Ausubel, Curent Protocols in Molecular Biology vol. 1, 1994, 6.0.1-6.4.10.

(Continued)

*Primary Examiner* — Ekaterina Poliakova-Gerogantas

(74) *Attorney, Agent, or Firm* — CuRNA, Inc.; Monte R. Browder

(57) ABSTRACT

The present invention relates to antisense oligonucleotides that modulate the expression of and/or function of Sodium channel, voltage-gated, alpha subunit (SCNA), in particular, by targeting natural antisense polynucleotides of Sodium channel, voltage-gated, alpha subunit (SCNA). The invention also relates to the identification of these antisense oligonucleotides and their use in treating diseases and disorders associated with the expression of SCNA.

10 Claims, 12 Drawing Sheets

Specification includes a Sequence Listing.

(56) References Cited

U.S. PATENT DOCUMENTS

| | | | |
|---|---|---|---|
| 6,013,639 | A | 1/2000 | Peyman et al. |
| 6,013,786 | A | 1/2000 | Chen et al. |
| 6,034,233 | A | 3/2000 | Ecker et al. |
| 6,100,090 | A | 8/2000 | Monia et al. |
| 6,140,492 | A | 10/2000 | Morelli et al. |
| 6,147,200 | A | 11/2000 | Manoharan et al. |
| 6,165,712 | A | 12/2000 | Foulkes et al. |
| 6,165,990 | A | 12/2000 | Singh et al. |
| 6,175,409 | B1 | 1/2001 | Nielsen et al. |
| 6,221,587 | B1 | 4/2001 | Ecker et al. |
| 6,239,265 | B1 | 5/2001 | Cook |
| 6,242,589 | B1 | 6/2001 | Cook et al. |
| 6,268,490 | B1 | 7/2001 | Imanishi et al. |
| 6,303,374 | B1 | 10/2001 | Zhang et al. |
| 6,307,040 | B1 | 10/2001 | Cook et al. |
| 6,316,198 | B1 | 11/2001 | Skouv et al. |
| 6,335,434 | B1 | 1/2002 | Guzaev et al. |
| 6,376,541 | B1 | 4/2002 | Nixon et al. |
| 6,403,566 | B1 | 6/2002 | Wang |
| 6,444,464 | B1 | 9/2002 | Wyatt |
| 6,451,991 | B1 | 9/2002 | Martin et al. |
| 6,525,191 | B1 | 2/2003 | Ramassamy |
| 6,528,262 | B1 | 3/2003 | Gilad et al. |
| 6,528,631 | B1 | 3/2003 | Cook et al. |
| 6,617,122 | B1 | 9/2003 | Hayden et al. |
| 6,617,442 | B1 | 9/2003 | Crooke et al. |
| 6,630,315 | B1 | 10/2003 | Miwa et al. |
| 6,639,059 | B1 | 10/2003 | Kochkine et al. |
| 6,656,730 | B1 | 12/2003 | Manoharan |
| 6,667,337 | B2 | 12/2003 | Wilson |
| 6,670,461 | B1 | 12/2003 | Wengel et al. |
| 6,710,174 | B2 | 3/2004 | Bennett et al. |
| 6,734,291 | B2 | 5/2004 | Kochkine et al. |
| 6,762,169 | B1 | 7/2004 | Manoharan |
| 6,794,499 | B2 | 9/2004 | Wengel et al. |
| 6,833,361 | B2 | 12/2004 | Hong et al. |
| 6,861,514 | B2 | 3/2005 | Cook et al. |
| 6,867,294 | B1 | 3/2005 | Sanghvi et al. |
| 6,936,467 | B2 | 8/2005 | Kmiec et al. |
| 6,936,593 | B1 | 8/2005 | Agrawal et al. |
| 6,977,295 | B2 | 12/2005 | Belotserkovskii et al. |
| 6,986,988 | B2 | 1/2006 | Gilad et al. |
| 7,034,133 | B2 | 4/2006 | Wengel et al. |
| 7,034,145 | B2 | 4/2006 | Shen et al. |
| 7,053,195 | B1 | 5/2006 | Goff |
| 7,053,199 | B2 | 5/2006 | Imanishi et al. |
| 7,053,207 | B2 | 5/2006 | Wengel |
| 7,060,809 | B2 | 6/2006 | Wengel et al. |
| 7,084,125 | B2 | 8/2006 | Wengel |
| 7,087,589 | B2 | 8/2006 | Jacobson et al. |
| 7,125,982 | B1 | 10/2006 | Frayne |
| 7,144,995 | B2 | 12/2006 | Wise et al. |
| 7,144,999 | B2 | 12/2006 | Ward et al. |
| 7,148,204 | B2 | 12/2006 | Bennett et al. |
| 7,153,954 | B2 | 12/2006 | Koch et al. |
| 7,169,916 | B2 | 1/2007 | Krotz et al. |
| 7,199,107 | B2 | 4/2007 | Dobie et al. |
| 7,202,357 | B2 | 4/2007 | Crooke et al. |
| 7,217,572 | B2 | 5/2007 | Ward et al. |
| 7,220,549 | B2 | 5/2007 | Buzby |
| 7,226,785 | B2 | 6/2007 | Kmiec et al. |
| 7,229,974 | B2 | 6/2007 | Peyman et al. |
| 7,229,976 | B2 | 6/2007 | Dobie et al. |
| 7,235,534 | B2 | 6/2007 | Tanguay et al. |
| 7,235,653 | B2 | 6/2007 | Bennett et al. |
| 7,238,858 | B2 | 7/2007 | Marraccini et al. |
| 7,276,599 | B2 | 10/2007 | Moore et al. |
| 7,285,288 | B1 | 10/2007 | Tormo et al. |
| 7,297,786 | B2 | 11/2007 | McCray et al. |
| 7,314,923 | B2 | 1/2008 | Kaneko et al. |
| 7,320,965 | B2 | 1/2008 | Sah et al. |
| 7,321,828 | B2 | 1/2008 | Cowsert et al. |
| 7,335,764 | B2 | 2/2008 | Crooke et al. |
| 7,335,765 | B2 | 2/2008 | Kaneko et al. |
| 7,339,051 | B2 | 3/2008 | Crooke et al. |
| 7,371,833 | B1 | 5/2008 | Weiss |
| 7,399,845 | B2 | 7/2008 | Seth et al. |
| 7,402,434 | B2 | 7/2008 | Newman et al. |
| 7,402,574 | B2 | 7/2008 | Iversen et al. |
| 7,420,050 | B2 | 9/2008 | Park et al. |
| 7,423,142 | B2 | 9/2008 | Vornlocher |
| 7,425,545 | B2 | 9/2008 | Crooke et al. |
| 7,427,675 | B2 | 9/2008 | Capaldi et al. |
| 7,456,154 | B2 | 11/2008 | Soreq et al. |
| 7,462,642 | B2 | 12/2008 | Wang et al. |
| 7,468,431 | B2 | 12/2008 | Bhanot et al. |
| 7,510,830 | B2 | 3/2009 | Baguley et al. |
| 7,541,544 | B2 | 6/2009 | Bhat et al. |
| 7,547,684 | B2 | 6/2009 | Seth et al. |
| 7,569,575 | B2 | 8/2009 | Sorensen et al. |
| 7,569,686 | B1 | 8/2009 | Bhat et al. |
| 7,572,582 | B2 | 8/2009 | Wengel et al. |
| 7,582,745 | B2 | 9/2009 | Sah et al. |
| 7,585,893 | B2 | 9/2009 | Baguley et al. |
| 7,589,190 | B2 | 9/2009 | Westergaard et al. |
| 7,598,227 | B2 | 10/2009 | Crooke et al. |
| 7,605,251 | B2 | 10/2009 | Tan et al. |
| 7,622,453 | B2 | 11/2009 | Frieden et al. |
| 7,662,948 | B2 | 2/2010 | Kurreck et al. |
| 7,666,854 | B2 | 2/2010 | Seth et al. |
| 7,674,895 | B2 | 3/2010 | Reich et al. |
| 7,687,617 | B2 | 3/2010 | Thrue et al. |
| 7,691,995 | B2 | 4/2010 | Zamore et al. |
| 7,695,902 | B2 | 4/2010 | Crooke |
| 7,696,345 | B2 | 4/2010 | Allerson et al. |
| 7,709,456 | B2 | 5/2010 | Corey et al. |
| 7,709,630 | B2 | 5/2010 | Gaarde et al. |
| 7,713,738 | B2 | 5/2010 | Hansen et al. |
| 7,718,629 | B2 | 5/2010 | Bumcrot et al. |
| 7,723,508 | B2 | 5/2010 | Crooke et al. |
| 7,732,422 | B2 | 6/2010 | Gleave et al. |
| 7,732,590 | B2 | 6/2010 | Bhanot et al. |
| 7,737,264 | B2 | 6/2010 | Thrue et al. |
| 7,737,265 | B2 | 6/2010 | Akinc et al. |
| 7,741,305 | B2 | 6/2010 | Crooke et al. |
| 7,741,309 | B2 | 6/2010 | Hansen et al. |
| 7,741,457 | B2 | 6/2010 | Seth et al. |
| 7,745,609 | B2 | 6/2010 | Bennett et al. |
| 7,749,978 | B2 | 7/2010 | Sah et al. |
| 8,916,743 | B2 | 12/2014 | Ohmori et al. |
| 9,133,496 | B2 | 9/2015 | Imaizumi et al. |
| 9,771,579 | B2 | 9/2017 | Collard et al. |
| 2003/0139359 | A1 | 7/2003 | Dobie |
| 2003/0186920 | A1 | 10/2003 | Sirois |
| 2003/0191075 | A1 | 10/2003 | Cook et al. |
| 2003/0228618 | A1 | 12/2003 | Levanon et al. |
| 2003/0233670 | A1 | 12/2003 | Edgerton et al. |
| 2004/0006031 | A1 | 1/2004 | Dean et al. |
| 2004/0033480 | A1 | 2/2004 | Wong |
| 2004/0101858 | A1 | 5/2004 | Ward et al. |
| 2004/0137423 | A1 | 7/2004 | Hayden et al. |
| 2004/0138155 | A1 | 7/2004 | Baird et al. |
| 2004/0175803 | A1 | 9/2004 | Meritet et al. |
| 2004/0180336 | A1 | 9/2004 | Gilad et al. |
| 2004/0241651 | A1* | 12/2004 | Olek .................. C07K 14/4703 435/6.16 |
| 2004/0254137 | A1 | 12/2004 | Ackermann et al. |
| 2005/0009771 | A1 | 1/2005 | Levanon et al. |
| 2005/0026160 | A1 | 2/2005 | Allerson et al. |
| 2005/0048531 | A1* | 3/2005 | Mittman ................ C07H 21/02 435/6.11 |
| 2005/0113326 | A1 | 5/2005 | Siwkowski et al. |
| 2005/0143357 | A1 | 6/2005 | Pousette et al. |
| 2005/0153286 | A1 | 7/2005 | Clements |
| 2005/0215504 | A1 | 9/2005 | Bennett et al. |
| 2005/0222029 | A1 | 10/2005 | Bartel et al. |
| 2005/0246794 | A1* | 11/2005 | Khvorova ............ A61K 31/713 800/286 |
| 2006/0009410 | A1 | 1/2006 | Crooke et al. |
| 2006/0142196 | A1 | 6/2006 | Klein et al. |
| 2006/0178333 | A1 | 8/2006 | Soreq et al. |
| 2007/0082848 | A1 | 4/2007 | Alitalo et al. |
| 2007/0197459 | A1 | 8/2007 | Milner |
| 2007/0213274 | A1 | 9/2007 | Salonen |

(56) References Cited

U.S. PATENT DOCUMENTS

| | | | |
|---|---|---|---|
| 2007/0213292 A1 | 9/2007 | Stoffel et al. | |
| 2007/0231816 A1 | 10/2007 | Chaussabel et al. | |
| 2007/0248590 A1 | 10/2007 | Milne et al. | |
| 2008/0113351 A1 * | 5/2008 | Naito | A61K 31/713 435/6.11 |
| 2008/0146788 A1 | 6/2008 | Bhat et al. | |
| 2008/0221051 A1 | 9/2008 | Becker et al. | |
| 2008/0293142 A1 | 11/2008 | Liu et al. | |
| 2009/0191763 A1 | 7/2009 | Reich et al. | |
| 2009/0192106 A1 | 7/2009 | Dobie et al. | |
| 2009/0208479 A1 | 8/2009 | Jaye et al. | |
| 2009/0258925 A1 | 10/2009 | Wahlestedt | |
| 2009/0318536 A1 | 12/2009 | Freíer et al. | |
| 2009/0326041 A1 | 12/2009 | Bhanot et al. | |
| 2010/0105760 A1 | 4/2010 | Collard et al. | |

FOREIGN PATENT DOCUMENTS

| | | | | |
|---|---|---|---|---|
| EP | 335451 A2 | 10/1989 | | |
| EP | 16242966 A1 | 5/2006 | | |
| WO | WO-1984/03564 | 9/1984 | | |
| WO | WO-1991/19735 | 12/1991 | | |
| WO | WO-1992/00091 | 1/1992 | | |
| WO | WO-1992/08796 | 5/1992 | | |
| WO | WO-1993/20242 | 10/1993 | | |
| WO | WO-1994-026887 A1 | 11/1994 | | |
| WO | WO-1994/28143 | 12/1994 | | |
| WO | WO-1995-015373 A2 | 6/1995 | | |
| WO | WO-1995/22618 | 8/1995 | | |
| WO | WO 1995/25116 | 10/1995 | | |
| WO | WO-1995/35505 | 12/1995 | | |
| WO | WO-1996-027663 A2 | 9/1996 | | |
| WO | WO-1997-039120 A1 | 10/1997 | | |
| WO | WO-1999-014226 A1 | 3/1999 | | |
| WO | WO-1999-039352 A1 | 8/1999 | | |
| WO | WO-2000-057837 A1 | 10/2000 | | |
| WO | WO-2000-061770 A2 | 10/2000 | | |
| WO | WO-2001-000669 A2 | 1/2001 | | |
| WO | WO-2001-21631 A2 | 1/2001 | | |
| WO | WO-2001-025488 A2 | 4/2001 | | |
| WO | WO-2001022972 A3 * | 4/2001 | A61K 39/39 | |
| WO | 2001038564 A2 | 5/2001 | | |
| WO | WO-2001-051630 A1 | 7/2001 | | |
| WO | WO-2002-062840 A1 | 8/2002 | | |
| WO | WO-2002-068688 A1 | 9/2002 | | |
| WO | 2003066893 A1 | 8/2003 | | |
| WO | 2004016754 A2 | 2/2004 | | |
| WO | WO-2004-016255 A1 | 2/2004 | | |
| WO | WO-2004-024079 A2 | 3/2004 | | |
| WO | WO-2004-030750 A1 | 4/2004 | | |
| WO | WO-2004028458 A2 * | 4/2004 | C12N 15/1137 | |
| WO | WO-2004-041838 A1 | 5/2004 | | |
| WO | WO 2004-104161 A2 | 12/2004 | | |
| WO | 2005035784 A1 | 4/2005 | | |
| WO | WO-2005-045034 A2 | 5/2005 | | |
| WO | WO-2005-070136 A2 | 8/2005 | | |
| WO | WO-2005-079862 A1 | 9/2005 | | |
| WO | 2006040357 A2 | 4/2006 | | |
| WO | 2006067056 A1 | 6/2006 | | |
| WO | WO-2007-028065 A2 | 3/2007 | | |
| WO | WO-2007-071182 A1 | 6/2007 | | |
| WO | WO-2007-087113 A2 | 8/2007 | | |
| WO | WO-2007-138023 A1 | 12/2007 | | |
| WO | 2008043561 A2 | 4/2008 | | |
| WO | WO 2008-057556 A2 | 5/2008 | | |
| WO | WO 2008-066672 A2 | 6/2008 | | |
| WO | WO-2008-087561 A2 | 7/2008 | | |
| WO | 2009143277 A2 | 11/2009 | | |
| WO | WO-2009143277 A2 * | 11/2009 | C12N 15/1138 | |
| WO | WO-2010-002984 A1 | 1/2010 | | |
| WO | WO-2010-040571 A2 | 4/2010 | | |
| WO | WO-2010-054364 A1 | 5/2010 | | |
| WO | WO-2010-058227 A2 | 5/2010 | | |
| WO | 2011163499 A2 | 12/2011 | | |

OTHER PUBLICATIONS

Barak, et al., "A β-Arrestin/Green Fluorescent Protein Biosensor for Detecting G Protein-Coupled Receptor Activation," J. Biol. Chem. 272:27497-27500 (1997).

Barber, et al., "Delivery of membrane-impermeant fluorescent probes into living neural cell populations by lipotransfer," Neuroscience Letters 207:17-20 (1996).

Baum, "Solid-phase synthesis of benzodiazepines," C&EN News, Jan. 18, p. 33-34 (1993).

Bernstein, E., et al., "Role for a Bidentate Ribonuclease in the Initiation Step of RNA Interference," Nature 409:363-366 (2001).

Boutla, A., et al., "Short 5'-phosphorylated double-stranded RNAs induce RNA interference in *Drosophila,*" Curr. Biol. 11:1776-1780 (2001).

Boyd-Kimball, et al., "Proteomic Identification of Proteins Specifically Oxidized by Intracerebral Injection of Antyloid β-Peptide (1-42) into Rat Brain: Implications for Aizheimer's Disease," Neuroscience 132, 313-324 (2005).

Brazma & Vilo, "Gene expression data analysis," FEBS Lett., 480:17-24 (2000).

Bright, et al., "Chapter 6, Fluorescence Ratio Imaging Microscopy," Methods in Cell Biology vol. 30, Taylor and Wang (eds) p. 157-192 (1989).

Bright, et al., "Delivery of Macromolecules Into Adherent Cells via Electroporation for Use in Fluorescence Spectroscopic Imaging and Metabolic Studies," Cytometry 24:226-233 (1996).

Bright, et al., "Fluorescence Ratio Imaging Microscopy: Temporal and Spatial Measurements of Cytoplasmic pH," J. Cell Biology 104:1019-1033 (1987).

Budni, J., et al., "The Involvement of BDNF, NGF and GDNF in Aging and Alzheimer's Disease," Aging and Disease, vol. 6, No. 5, pp. 331-341, (2016).

Campbell, et al., "Rhosphonmate Ester Synthesis Using a Modified Mitsunobu Condensation," J. Org. Chem. 59:658-660 (1994).

Caplen, N. J., et al., "Specific inhibition of gene expression by small double-stranded RNAs in invertebrate and vertebrate systems," PNAS Sci. USA 98:9742-9747 (2001).

Carninci, et al., "The transcriptional landscape of the mammalian genome," Science 309:1559-1563 (2005).

Carulli, et al., "High Throughput Analysis of Differential Gene Expression," J. Cell Biochem. Suppl., 3:286-296 (1998).

Celis, et al., "Gene expression profiling: monitoring transcription and translation products using DNA microarrays and proteomics." FEBS Lett., 480:2-16 (2000).

Chabala, J.C., "Solid-phase combinatorial chemistry and novel tagging methods for identifying leads," Curr Opin Biotechnol. 6:632-639 (1995).

Cech, J., "Ribozymes and Their Medical Implications," American. Med Assoc. 260:3030-3035 (1988).

Chen, et al., "Expression of ssDNA in Mammalian Cells," BioTechniques 34:167-171 (2003).

Chen, et al., "Analogous Organic Synthesis of Small-Compound Libraries: Validation of Combinatorial Chemistry in Small Molecule Synthesis." J. Amer. Chem. Soc. 116:2661-2662 (1994).

Cheng, J. et al., "Transcriptional maps of 10 human chromosomes at 5-nucleotide resolution," Science 308:5725:1149-1154 (2005).

Cho, et al., "An Unnatural Biopolymer," Science 261:1303-1305 (1993).

Christiensen, N.K. et al., "A Novel Class of Oligonucleotide Analogues Containing 2'-O,3'-C-Linked [3.2.0]Bicycloarabinonucleoside Monomers: Synthesis, Thermal Affinity Studies, and Molecular Modeling," J. Am. Chem. Soc., 120:5458-5463 (1998).

Cubitt, et al. , "Understanding, improving and using green fluorescent proteins," Trends in Biochemical Science 20:448-455 (1995).

Curiel, D. T. et al., "Adenovirus enhancement of transferrin-polylysine-mediated gene delivery," PNAS 88:8850-8854 (1991).

Dai et al., "SIRT1 Interacts With p73 and Suppresses p73-Dependent Transcriptional Activity," J Cell Physiol 210(1):161-165 (2007).

(56) References Cited

OTHER PUBLICATIONS

Davidson, et al., "A model system for in vivo gene transfer into the central nervous system using an adenoviral vector," Nat. Genet 3:219-223 (1993).
Davis, et al., "Direct Gene Transfer into Skeletal Muscle In Vivo: Factors Affecting Efficiency of Transfer and Stability of Expression," Hum Gene Ther 4:151-159 (1993).
De Mesmaeker, et al., "Antisense Oligonucleotides." Acc. Chem. Res. 28:366-374 (1995).
Deng et al., "Small Interfering RNA Targeting the PINK1 Induces Apoptosis in Dopaminergic Cells SH-SY5Y", Biochemical and Biophysical Research Communications, vol. 337, No. 4, pp. 1133-1138 (2005).
Dixon, et al., "Anthrax," New England J. Med. 341:815-826 (1999).
Dolle, "Discovery of Enzyme inhibitors through combinatorial chemistry," Mol Divers. 2:223-236 (1997).
Dykxhoorn, D., et al., "Determinants of Specific RNA Interference-Mediated Silencing of Human β-Globin Alleles Differing by a Single Nucleotide Polymorphism," PNAS, vol. 103, No. 15, pp. 5953-5958, (2006).
Eguchi, et al., "Antisense RNA," Annu. Rev. Biochem 60:631-652 (1991).
Eichler, et al., "Generation and utilization of synthetic combinatorial libraries," Mol Med Today 1:174-180 (1995).
Eichler, et al., "Peptide Peptidomimetic and organic synthetic combinatorial libraries," Med Res Rev 15:481-496 (1995).
Espeseth, et al., A genome wide analysis of ubiquitin ligases in APP processing identifies a novel regulator of BACE1 mRNA levels. Mol. Cell Neurosci. 33: 227-235 (2006).
Faghihi, M. & Wablestedt, C., "RNA interference is not involved in natural antisense mediated regulation of gene expression in mammals," Genome Biol (2005).
Fauchere, et al., "Peptide and nonpeptide lead discovery using robotically synthesized soluble libraries," Can J. Physiol Pharmacol 75:683-689 (1997).
Felgner and Holm, "Cationic Liposome-Mediated Transfection," Bethesda Res. Lab Focus, 11:2:21 (1989).
Fields, et al., "How many genes in the human genome?" Nature Genetics 7:345-346 (1994).
Freier & Altman, "The ups and downs of nucleic acid duplex stability: structure-stability studies on chemically-modified DNA:RNA duplexes," Nucl. Acid Res., 25:22:4429-4443 (1997).
Fuchs, et al., "Identification of Differentially Expressed Genes by Mutually Subtracted RNA Fingerprinting," Anal. Biochem., 286:91-98 (2000).
Gebeyehu, G., et al., "Novel biotinylated nucleotide-analogs for labeling and colorimetric detection of DNA," Nucl. Acids Res. 15:4513 (1987).
Geller, A.I. et al., "An HSV-1 Vector Expressing Tyrosine Hydroxylase Causes Production and Release of L-DOPA from Cultured Rat Striatal Cells," J. Neurochem 64:487-496 (1995).
Geller, A.I. et al., "Long-term increases in neurotransmitter release from neuronal cells expressing a constitutively active adenylate cyclase from a herpes simplex virus type 1 vector," PNAS U.S.A.:90:7603-7607 (1993).
Geller, A.I., et al.., "Infection of cultured central nervous system neurons with a defective herpes simplex virus 1 vector results in stable expression of *Escherichia coli* β-galactosidase," PNAS USA 87:1149-1153 (1990).
GenBank Accession No. NM_000559, *Homo sapiens* Hemoglobin, Gamma A (HBG1), mRNA, (2008).
Giuliano, et al., "FLuorescent Protein Biosensors: Measurement of Molecular Dynamics in Living Cells," Ann. Rev. of Biophysics and Biomolecular Structure 24:405-434 (1995).
Giuliano, et al., "Light-Optical-Based Reagents for the Measurement and Manipulation of Ions, Metabolites, and Macromolecules in Living Cells," Methods in Neuroscience 27:1-16 (1995).
Giuliano, et al., "Determination of Intracellular pH of BALB/c-3T3 Cells Using the Fluorescence of Pyranine," Anal. Biochem 167:362-371 (1987).
Going & Gusterson, "Molecular Pathology and Future Developments," Eur. J. Cancer, 35:1895-1904 (1999).
Hagihara, et al., "Vinylogons Polypeptides: An Alternate Peptide Backbone," J. Amer. Chem. Soc. 114:6568-6571 (1992).
Haussecker, D., et al., "Dicer-Dependent Turnover of Intergenic from the Human β-Globin Gene Cluster," Molecular and Cellular Biology, vol. 25, No. 21. pp. 9724-9731, (2005).
Heller, et al., "Discovery and Analysis of Inflammatory Disease-Related Genes Using cDNA Microarrays," PNAS U.S.A. 94:2150-2155 (1997).
Herdewijn P., "Heterocyclic Modifications of Oligonueleolides and Antisense Technology," Antisense & Nucleic Acid Drug Dev., 10:297-310 (2000).
Hirschmann, et al., J. Amer. Chem. Soc., 114:9217-9218 (1992).
Hobbs-DeWitt, et al., "Diversomers: An approach to nonpeptide, nonoligomeric chemical diversity," Proc. Nat. Acad. Sci. USA 90;6909-6913 (1993).
Houghton AN, Gold JS, Blachere NE, Immunity against cancer: lessons learned from melanoma,. Curr Opin Immunol 13:134-140 (2001).
International Human Genome Sequencing Consortium "Finishing the euchromatic sequence of the human genome." Nature 431:7011:931-945 (2004).
Janda, K.D. "Tagged versus untagged libraries: Methods for the generation and screening of combinatorial chemical libraries," PNAS 91:10779-10785 (1994).
Janowski, et al., "Inhibiting gene expression at transcription start sites in chromosomal DNA with antigene RNAs," Nature Chemical Biology, 1(4):216-222 (2005).
Jungblut, et al., "Proteomics in human disease: Cancer, heart and infections diseases," Electrophoresis 20:2100-2110 (1999).
Jurecic & Belmont, "Long-distance DD-PCR and cDNA microarrays," Curr. Opin. Microbiol., 3:316-321 (2000).
Kabanov, et al., "A new class of antivirals: antisense oligonucleotides combined with a hydrophobic substituent effectively inhibit influenza virus reproduction and synthesis of virus-specific proteins in MDCK cells," FEBS Lett. 259:327-330 (1990).
Kaplitt, M.G., et al., "Long-term gene expression and phenotypic correction using adeno-associated virus vectors in the mammalian brain," Nat. Genet. 8:148-154 (1994).
Kapranov, P. et al., "Examples of the complex architecture of the human transcriptome revealed by RACE and high-density tiling arrays," Genome Res 15:7:987-997 (2005).
Katayama, S. et al., "Antisense Transcription in the Mammalian Transcriptome," Science 309:1564-1566 (2005).
Kawahara & Nishikura, "Extensive adenosine-to-inosine editing detected in Alu repeats of antisense RNAs reveals scarcity of sense-antisense duplex formation," FEBS Lett 580:2301-2305 (2006).
Kay, et al., "Identification of enzyme inhibitors from phage-displayed combinatorial peptide libraries," Comb Chem High Throughput Screen 4:535-543 (2001).
Kenan, et al., "Exploring molecular diversity with combinatorial shape libraries," Trends Biochem Sci 19:57-64 (1994).
Kornberg, A., DNA Replication, W.H. Freeman & Co., San Francisco, pp. 75-77, (1980).
Larson, et al., "Rapid DNA Fingerprinting of Pathogens by Flow Cytometry," Cytometry, 2000, 41:203-208 (2000).
Larsson, et al., "High-Throughput Protein Expression of cDNA Products as a Tool in Functional Genomics," J. Biotechnology., 80:143-157 (2000).
Lebl, et al., "One-bead-one-structure combinatorial libraries," Biopolymers 37:177-198 (1995).
LeGal Lasalle et al., "An Adenovirus Vector for Gene Transfer into Neurons and Glia in teh Brain," Science 259:988-990 (1993).
Letsinger, et al, "Cholesteryl-conjugated oligonucleotides: Synthesis, Properties, and Activity as Inhibitors of Replication of Human Immunodeficiency Virus in Cell Culture," PNAS 86:6553-6556 (1989).
Li et al., "Control of APP processing and Aβ generation level by BACE1 enzymatic activity and transcription," Faseb J 20; 285-292 (2006).
Li, et al., J. Neurochem 89 1308-1312 (2004).

(56) References Cited

OTHER PUBLICATIONS

Liang, et al., "Parallel Synthesis and Screening of a Solid Phase Carbohydrate Library," Science 274:1520-1522 (1996).
Luther, "Role of endogenous antisense RNA in cardiac gene regulation," J. Mol. Med. 83:26-32 (2005).
Madden, et al., "Serial analysis of gene expression: from gene discovery to target identification," Drug Discov. Today 5:415-425 (2000).
Makalowska I, Lin CF, Makalowski W., "Overlapping genes in vertebrate genomes," Comput Biol. Chem 29:1:1-12 (2005).
Mannino and Could-Fogerite, "Liposome Mediated Gene Transfer," BisTechniques 6:682-690 (1988).
Manoharan et al., "Lipidic Nucleic Acids," Tetrahedron Lett 36:3651-3654 (1995).
Manoharan, et al., "Chemical Modifications to Improve Uptake and Bioavailability of Amisense Oligonucleotides," Ann N.Y. Acad. Scie 660:306-309 (1992).
Manoharan, et al., "Introduction of a Lipophilic Thioether in teh Minor Groove of Nucleic Acids for Antisense Applications," Bioorg. Med. Chem. Let 3:2765-2770 (1993).
Manoharan, et al., "Cholic Acid-Oligonucleotide Conjugates for Antisense Applications," Bioorg. Med. Chem. Let 4:1053 (1994).
Manoharan et al., "Oligonucleotide Conjugates: Alteration of the Pharmacokinetic Properties of Antisense Agents," Nucleosides & Nucleotides 14:969-973 (1995).
Manoharan, M., "2'-Carbohydrate modifications in antisense oligonucleolide therapy: importance of conformation, configurationj and conjugation," Biochemica et Biophysica Acta 1489:117-139 (1999).
Mattick, J. S. "RNA regulation: a new genetics?" Nat. Rev. Genet 5:4:316-323 (2004).
Maurer, R.A., "Cationic Liposome-Mediated Transfection of Primary Cultures of Rat Pituitary Cells," Bethesda Res. Lab. Focus 11:2:25 (1989).
McNeil in Methods in Cell Biology vol. 29, Taylor and Wang (eds.) p. 153-173 (1989).
Morelli et al., "The antisense bcl-2-IgH transcript is an optimal target for synthetic oligonucleotides," PNAS USA 94:8150-8155 (1997).
Nielsen, et al., "Sequence-Selective Recognition of DNA by Strand Displacement with a Thymine-Substituted Polyamide," Science 254;1497-1500 (1991).
Oberhauser, et al., "Effective incorporation of 2'-O-methyl-oligoribonucleotides into liposomes and enhanced cell association through modification with thiocholesterol," Nucl. Acids Res. 20:533-538 (1992).
Petit et al., "Wild-type PINK1 Prevents Basal and Induced Neuronal Apoptosis, a Protective Effect Abrogated by Parkinson Disease-Related Mutations", Journ. Biol. Chem., vol. 280, No. 40, pp. 14025-334032 (2005).
Prasanth, et al., "Regulating Gene Expression through RNA Nuclear Retention," Cell 123, 249-263 (2005).
Prashar & Weissman, "READS: A Method for Display of 3'-End Fragments of Restriction Enzyme-Digested cDNAs for Analysis of Differential Gene Expression," Methods Enzymol., 303:258-272 (1999).
Quantin, et al., "Adenovirus as an expression vector in muscle cells in vivo," PNAS 89:2581-2584 (1992).
Rosenfeld, et al., "In Vivo Transfer of the Homan Cystic Fibrosis Transmembrane Conductance Regulator Gene to the Airway Epithelium," Cell, 68:143-155 (1992).
Rosok and Sioud, "Systematic identification of sense-antisense transcripts in mammalian cells," Nature Biotech. 22(1):104-108 (2004).
Saison-Behmoaras, et al., "Short modified antisease oligonucleotides directed against Ha-ras point mutation induce selective cleavage of the mRNA and inhibit T24 cells proliferation," EMBO J. 10:1111-1118 (1991).
Sanghvi, Y.S, in Crooke, S.T. and Lebleu, B., eds., Antisense Research and Applications, CRC Press, Boca Raton, 1993, p. 276-278.
Scheele et al., "The Human PINK1 Locus is Regulated and Vivo by a Non-Coding Natural Antisense RNA During Modulation of Mitochondrial Function", BMC Genomics, vol. 8, No. 1, p. 74 (2007).
Schena, et al., "Parallel human genuine analysis: Microarray-based expression monitoring of 1000 genes," PNAS 93:10614-10619(1996).
Shea, et al., "Synthesis, hybridization properties and antiviral activity of lipid-oligonucleotide conjugates," Nucl. Acids Res 18:3777-3783 (1990).
Shen, T., et al., "Modification of Globin Gene Expression by RNA Targeting Strategies," Experimental Hematology, vol. 35, No. 8, pp. 1209-1218, (2007).
Shimomura et al., "Semi-synthetic aequorin," J. of Biochemistry (Tokyo) 251:405-410 (1988).
Singer, et al., "Targeting BACE1 with siRNAs ameliorates Alzheimer disease neuropathology in a transgenic model," Nat Neurosci 8:1343-1349 (2005).
Southwick, et al., "Cyanine Dye Labeling Reagents-Carboxymethylindocyanine Succinimidyl Esters." Cytometry 11:418-430 (1990).
Stratford-Perricadet, et al., "Widespread Long-term Gene Transfer to Mouse Skeletal Muscles and Heart," J. Clin. Invest., 90:626-630 (1992).
Sullenger, et al., "Overexpression of TAR sequences Renders Cells Resistant to Human Immunodeficiency Virus Replication," Cell63:601-608 (1990).
Sun, et al., "Downregulation of Sirt1 by antisense oligonucleotides induces apoptosis and enhances radiations sensitization in A549 lung cancer cells," Lung Cancer 58(1):21-29 (2007).
Sutcliffe, et al., "TOGA: An automated parsing technology for analyzing expression of nearly all genes," PNAS, 97:1976-1981 (2000).
Sutton, et al., "TIGR Assembler: A New Tool for Assembling Large Shotgun Sequencing Projects," Genome Science & Tech., 1:9-19 (1995).
Svinarchuk, et al., "Inhibition of HIV proliferation in MT-4 cells by antisense oligonucleotide conjugated to lipophilic groups," Biochimie 75:49-54 (1993).
Tamagno, et al., "The various aggregation states of β-amyloid 1-42 mediate different effects on oxidative stress, neurodegeneration, and BACE-1 expression," Free Radic Biol Med 41:202-212 (2006).
Thakker, D.R., et al., "siRNA-mediated knockdown of the serotonin transporter in the adult mouse brain," Mol Psychiatry 10:782-789 (2005).
Thakker, et al., "Neurochemical and behavioral consequences of widespread gene knockdown in the adult mouse brain by using nonviral RNA interference," PNAS 101:17270-17275 (2004).
Thomas et al., "Intracellular pH Measurements in Ehrlich Ascites Tumor Cells Utilizing Spectroscopic Probes Generated in Situ," Biochemistry 18:2210-2218 (1979).
Thompson, et al., "Synthesis and Applications of Small Molecule Libraries" Chem Rev 96:555-600 (1996).
To, KY, "Identification of Differential Gene Expressionm by High Throughput Analysis," Comb. Chem. High Throughput Screen 3:235-241 (2000).
Tong, et al., "Oxidative stress potentiates BACE1 gene expression," Neural Transm 112, 455-469 (2005).
Toulme, J.J., "New candidates for true antisense," Nature Biotechnology 19:17-18 (2001).
Tsien in Methods in Cell Biology vol. 30 Taylor and Wang (eds) p. 127-156 (1989).
Ulhman, E., "Recent advances in the medical chemistry of antisense oligonucleotide," Current Opinions in Drug Discovery & Development 3:203-213 (2000).
Van Den Eynde BJ, "T cell defined tumor antigens," Curr Opin Immunol 9:684-693 (1997).
Van Der Bruggen, et al., "Tumor-specific shared antigenic peptides recognized by human T cells," Immunol Rev188:51-64 (2002).

(56) References Cited

OTHER PUBLICATIONS

Vanhee-Brossolet and Vaquero, "Do natural antisense transcripts make sense in eukaryotes?" Gene 211:1-9 (1998).
Vaughn, et al., "Human Antibodies with Sub-nanomolar Affinities Isolated from a Large Non-immunized Phage Display Library," Nature Biotechnology, 14:309-314 (1996).
Velculescu, et al., "Serial Analysis of Gene Expression," Science 270:484-487 (1995).
Wahlestedt, "Natural antisense and noncoding RNA transcripts as potential drug targets," Drug Discovery Today 11 (11/12):503-508 (2006).
Wahlestedt, C., "Antisense oligonucleotide strategies in neuropharmacology," Trends Pharmacol Sci 15:2:42-46 (1994).
Walsh, et al., The role of cell-derived oligomers of Aβ in Alzheimer's disease and avenues for therapeutic intervention, Biochem Soc Trans 33: 1087-1090 (2005).
Wang, B.B. et al., "Identification of a nuclear-specific cyclophilin which interacts with the proteinase inhibitor eglin c," Biochem J. 314 (Pt 1)313-319 (1996).
Wiesenhofer, et al., "Glial cell line-derived neurotrophic factor (GDNP) is a proliferation factor for rat C6 glioma cells: evidence from antisense experiments," Antisense & Nucleic Acid Drug Development 10(5):311-321 (2000).
Xue, et al., "Hypoxia and reoxygenation increased BACE1 mRNA and protein levels in human neuroblastoma SH-SY5Y cells," Neurosci Lett 405,231-235 (2006).
Yamada, et al., "Endothelial Nitric-Oxide Synthase Amisense (NOS3AS) Gene Encodes an Autophagy-Related Protein (APG9-like2) Highly Expressed in Trophoblast" (2005).
Yang, et al., "Cellular and Humoral Immune Responses to Viral Antigens Create Barriers to Lung-Directed Gene Therapy with Recombinant Adenoviruses," J. Virol 69:2004-2015 (1995).
Yoshigai, et al., "Characterization of Natural Antisense Transcripts Expressed from Interleukin 1β-inducible Genes in Rat Hepatocytes," HOAJ Biology; 1-10 (2012).
EP Application No. 06850393.7 Examination Report dated Oct. 18, 2011.
International Search Report and Written Opinion for PCT Application No. PCT/US2010/033078 dated Jun. 29, 2011.
PCT/US2010/026119 Search Report and Written Opinion dated Feb. 7, 2011.
PCT/US2010/024079 Search Report and Written Opinion dated Jan. 31, 2011.
PCT/US2010/027394 Search Report and Written Opinion dated Nov. 5, 2010.
PCT/US96/10287 (WO97/000271) The Regents of the University of California 1.3.97.
Genbank Accession No. AAH56061, "Human SCN2A PCR-SSCP PCR primer SEQ ID No. 305", (2001).
Genbank Accession No. ADU59612, "Connectron Nucleic Acid #234", (2005).
Genbank Accession No. ASQ74198, "Influenza A Virus Viral Replication siRNA Target SEQ ID No. 16385", (2008).
Genbank Accession No. BC051759.1, "*Homo sapiens* cDNA Clone Image:5582690, Partial CDS", (2003).
Genbank Accession No. HC048936, "Sequence 145 from Patent EP2112234", (2009).
Goto, J., et al., "Sodium Channel SCN1A", JP2001352987 (A), (2001).
Higurashi, N., et al., "A Human Dravet Syndrome Model From Patient Induced Pluripotent Stena Cells" Molecular Brain, vol. 6, No. 19, pp. 1-12, (2013).
Lebedeva, I., et al., "Phosphorothioate Oligodeoxynucleotides as Inhibitors of Gene Expression: Antisense and Non-Antisense Effects", Application of Antisense Therapies to Restenosis, vol. 3, pp. 99-118, (1999). Abstract.
Omori, I., et al., "Method for Acquiring Data for Determining Morbid Risk for Encephalitis or Encephalopathy and its Utilization and Method for Acquiring Data for Determining Transition Risk of Febrile Convulsion to Epilepsy and its Utilization", JP2009131247 (A), (2009).
Scheffer, I., et al., "Methods for Diagnosing and Treating Epilepsy by Detecting Mutations in the SCN1A Gene", JP2008546376 (A), (2008).
Yamakawa, K., et al., "Mutation of SCN2A Gene in Intractable Childhood Epilepsy Accompanied by Involution of Critical Mental Faculty", JP2004275115 (A), (2004).

* cited by examiner

A.

B.

TREATMENT OF SODIUM CHANNEL, VOLTAGE-GATED, ALPHA SUBUNIT (SCNA) RELATED DISEASES BY INHIBITION OF NATURAL ANTISENSE TRANSCRIPT TO SCNA

This application is a Divisional of U.S. Ser. No. 13/805,745 filed Dec. 20, 2012, which is a National Phase application of PCT/US2011/041664 filed on Jun. 23, 2011, which claims priority of U.S. Provisional Application No. 61/357,774 filed on Jun. 23, 2010, which are all incorporated herein by reference in their entirety.

FIELD OF THE INVENTION

Embodiments of the invention comprise oligonucleotides modulating expression and/or function of SCN1A and associated molecules.

BACKGROUND

DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides (ODNs), or they can be expressed from endogenous genes as RNA molecules. The FDA recently approved an antisense drug, VITRAVENE™ (for treatment of cytomegalovirus retinitis), reflecting that antisense has therapeutic utility.

SUMMARY

This Summary is provided to present a summary of the invention to briefly indicate the nature and substance of the invention. It is submitted with the understanding that it will not be used to interpret or limit the scope or meaning of the claims.

In one embodiment, the invention provides methods for inhibiting the action of a natural antisense transcript by using antisense oligonucleotide(s) targeted to any region of the natural antisense transcript resulting in up-regulation of the corresponding sense gene. It is also contemplated herein that inhibition of the natural antisense transcript can be achieved by siRNA, ribozymes and small molecules, which are considered to be within the scope of the present invention.

One embodiment provides a method of modulating function and/or expression of an SCNA polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of a polynucleotide comprising 5 to 30 consecutive nucleotides within nucleotides 1 to 1123 of SEQ ID NO: 12 and 1 to 2352 of SEQ ID NO: 13, 1 to 267 of SEQ ID NO: 14, 1 to 1080 of SEQ ID NO:15, 1 to 173 of SEQ ID NO: 16, 1 to 618 of SEQ ID NO: 17, 1 to 871 of SEQ ID NO: 18, 1 to 304 of SEQ ID NO: 19, 1 to 293 of SEQ ID NO: 20, 1 to 892 of SEQ ID NO: 21, 1 to 260 of SEQ ID NO: 22, 1 to 982 of SEQ ID NO: 23, 1 to 906 of SEQ ID NO: 24, 1 to 476 of SEQ ID NO: 25, 1 to 185 of SEQ ID NO: 26, 1 to 162 of SEQ ID NO: 27 and 1 to 94 of SEQ ID NO: 28 thereby modulating function and/or expression of the SCNA polynucleotide in patient cells or tissues in vivo or in vitro.

In an embodiment, an oligonucleotide targets a natural antisense sequence of SCNA polynucleotides, for example, nucleotides set forth in SEQ ID NOS: 12 to 28, and any variants, alleles, homologs, mutants, derivatives, fragments and complementary sequences thereto. Examples of antisense oligonucleotides are set forth as SEQ ID NOS: 29 to 94.

Another embodiment provides a method of modulating function and/or expression of an SCNA polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of the an antisense of the SCNA polynucleotide; thereby modulating function and/or expression of the SCNA polynucleotide in patient cells or tissues in vivo or in vitro.

Another embodiment provides a method of modulating function and/or expression of an SCNA polynucleotide in patient cells or tissues in vivo or in vitro comprising contacting said cells or tissues with an antisense oligonucleotide 5 to 30 nucleotides in length wherein said oligonucleotide has at least 50% sequence identity to an antisense oligonucleotide to an SCNA antisense polynucleotide; thereby modulating function and/or expression of the SCNA polynucleotide in patient cells or tissues in vivo or in vitro.

In an embodiment, a composition comprises one or more antisense oligonucleotides which bind to sense and/or antisense SCNA polynucleotides wherein said polynucleotides are selected from the group consisting of SCNA to SCN 12A and variants thereof. In a preferred embodiment, the target polynucleotide is selected from SCNA.

In an embodiment, the oligonucleotides comprise one or more modified or substituted nucleotides.

In another preferred embodiment, the oligonucleotides comprise one or more modified bonds.

In yet another embodiment, the modified nucleotides comprise modified bases comprising phosphorothioate, methylphosphonate, peptide nucleic acids, 2'-O-methyl, fluoro- or carbon, methylene or other locked nucleic acid (LNA) molecules. Preferably, the modified nucleotides are locked nucleic acid molecules, including α-L-LNA.

In another preferred embodiment, the oligonucleotides are administered to a patient subcutaneously, intramuscularly, intravenously or intraperitoneally.

In another preferred embodiment, the oligonucleotides are administered in a pharmaceutical composition. A treatment regimen comprises administering the antisense compounds at least once to patient; however, this treatment can be modified to include multiple doses over a period of time. The treatment can be combined with one or more other types of therapies.

In another preferred embodiment, the oligonucleotides are encapsulated in a liposome or attached to a carrier molecule (e.g. cholesterol, TAT peptide).

Other aspects are described infra.

Figure 1:
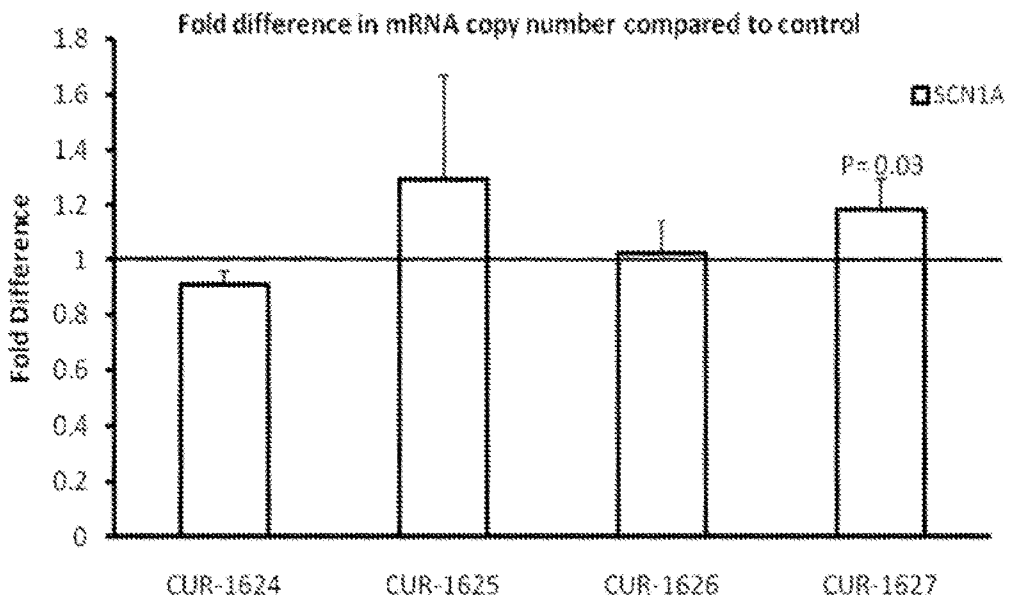
FIG. 1 shows the fold change and standard deviation in ATOH1 mRNA in HEP G2 cells 48 hours after treatment with phosphorothioate oligonucleotides introduced using Lipofectamien 2000, as compared to control. Real time PCR results show that the levels of ATOH1 mRNA in HEP G2 cells are significantly increased 48 h after treatment with one of the oligos designed to ATOH1 antisense Hs.611058. Bars denoted as CUR-1488 and CUR-1489 correspond to samples treated with SEQ ID NOS: 3 and 4 respectively.

Sequence Listing Description-SEQ ID NO: 1: *Homo sapiens* sodium channel, voltage-gated, type I, alpha subunit (SCNIA), transcript variant 1, mRNA (NCBI Accession No.: NM_001165963); SEQ ID NO: 2: *Homo sapiens* sodium channel, voltage-gated, type II, alpha subunit (SCN2A), transcript variant 1, mRNA (NCBI Accession No.: NM 021007); SEQ ID NO: 3: *Homo sapiens* sodium channel, voltage-gated, type III, alpha subunit (SCN3A), transcript variant 1, mRNA (NCBI Accession No.: NM_006922); SEQ ID NO: 4: *Homo sapiens* sodium channel, voltage-gated, type IV, alpha subunit (SCN4A), mRNA (NCBI Accession No.: NM_000334); SEQ ID NO: 5: *Homo sapiens* sodium channel, voltage-gated, type V, alpha subunit (SCNSA), transcript variant 1, mRNA (NCBI Accession No.: NMJ98056); SEQ ID NO: 6: *Homo sapiens* sodium channel, voltage-gated, type VII, alpha (SCNIA), mRNA (NCBI Accession No.: NM_002976); SEQ ID NO: 7: *Homo sapiens* sodium channel, voltage gated, type VIII, alpha subunit (SCNIA), transcript variant 1, mRNA (NCBI Accession No.: NM_014191); SEQ ID NO: 8: *Homo sapiens* sodium channel, voltage-gated, type IX, alpha subunit (SCN9A), mRNA (NCBI Accession No.: NM 002977); SEQ ID NO: 9: *Homo sapiens* sodium channel, voltage-gated, type X, alpha subunit (SCN10A), mRNA (NCBI Accession No.: NM 006514); SEQ ID NO: 10: *Homo sapiens* sodium channel, voltage-gated, type XI, alpha subunit (SCN11A), mRNA (NCBI Accession No.: NM 014139); SEQ ID NO: 11: *Homo sapiens* voltage-gated sodium channel alpha subunit SCN12A (SCN12A) mRNA, complete cds (NCBI Accession No.: AF109737); SEQ ID NO: 12: Natural SCNIA antisense sequence (BG724147 extended); SEQ ID NO: 13: Natural SCN1A antisense sequence (Hs.662210); SEQ ID NO: 14: Natural SCNIA antisense sequence (AA383040); SEQ ID NO: 15: Natural SCNIA antisense sequence (BC029452); SEQ ID NO: 16: Natural SCNIA antisense sequence (AA630035); SEQ ID NO: 17: Natural SCNIA antisense sequence (BE566126); SEQ ID NO: 18: Natural SCNIA antisense sequence (BF673100); SEQ ID NO: 19: Natural SCNIA antisense sequence (BG181807); SEQ ID NO: 20: Natural SCNIA antisense sequence (BG183871);

SEQ ID NO: 21: Natural SCNIA antisense sequence (BG215777); SEQ ID NO: 22: Natural SCNIA antisense sequence (BG227970); SEQ ID NO: 23: Natural SCNIA antisense sequence (BM905527); SEQ ID NO: 24: Natural SCNIA antisense sequence (BUI 80772); SEQ ID NO: 25: Mouse Natural SCNIA antisense sequence (BG724147 Ext-Mouse); SEQ ID NO: 26: Mouse Natural SCNIA antisense sequence (Hs.662210mouseAS1); SEQ ID NO: 27: Mouse Natural SCNIA antisense sequence (Hs.662210mouseAS2); SEQ ED NO: 28: Mouse Natural SCNIA antisense sequence (Hs.662210mouseAS3); SEQ ID NOs: 29 to 94: Antisense oligonucleotides. SEQ ID NO: 95 and 96 are the reverse complements of the antisense oligonucleotides SEQ ID NO: 58 and 59 respectively. * indicates a phosphothioate bond, + indicates LNA, 'r' indicates RNA and 'm' indicates a methyl group on the 2' oxygen atom on the designated sugar moiety of the oligonucleotide.

DETAILED DESCRIPTION

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "mRNA" means the presently known mRNA transcript(s) of a targeted gene, and any further transcripts which may be elucidated.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA. An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

In the context of this invention, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoögsteen or reverse Hoögsteen types of base pairing, or the like.

The oligonucleotide may be "chimeric", that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in "register", that is, when the monomers are linked consecutively, as in native DNA, or linked via spacers. The spacers are intended to constitute a covalent "bridge" between the regions and have in preferred cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alpha-helices.

As used herein "SCN1A" and "Sodium channel, voltage-gated, type I, alpha subunit" are inclusive of all family members, mutants, alleles, fragments, species, coding and noncoding sequences, sense and antisense polynucleotide strands, etc.

As used herein, the words 'Sodium channel, voltage-gated, type I, alpha subunit', SCN1A, FEB3, FEB3A, GEFSP2, HBSCI, NAC1, Nav1.1, SCN1, SMEI, Sodium channel protein brain I subunit alpha, Sodium channel protein type 1 subunit alpha, Sodium channel protein type I subunit alpha and Voltage-gated sodium channel subunit alpha Nav1.1, are considered same in the literature and are used interchangeably in the present application.

As used herein, the term "oligonucleotide specific for" or "oligonucleotide which targets" refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays. Exemplary assays for determining stability of hybridization complexes and duplexes are described in the Examples below.

As used herein, the term "target nucleic acid" encompasses DNA, RNA (comprising premRNA and mRNA) transcribed from such DNA, and also cDNA derived from such RNA, coding, noncoding sequences, sense or antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences. In certain embodiments of the present invention, the mediators are 5-25 nucleotide "small interfering" RNA duplexes (siRNAs). The siRNAs are derived from the processing of dsRNA by an RNase enzyme known as Dicer. siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 nt, about 15 to about 25 nt, or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products.

Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

By "enzymatic RNA" is meant an RNA molecule with enzymatic activity (Cech, (1988) *J. American. Med. Assoc.* 260, 3030-3035). Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through base pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA. This is meant to be a specific example. Those in the art will recognize that this is but one example, and other embodiments can be readily generated using techniques generally known in the art.

As used herein, the term "monomers" typically indicates monomers linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphomates, phosphoroselenoate, phosphoramidate, and the like, as more fully described below.

The term "nucleotide" covers naturally occurring nucleotides as well as nonnaturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in Benner et al., U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, e.g., as described in Kornberg and Baker, DNA Replication, 2nd Ed. (Freeman, San Francisco, 1992) as well as their analogs.

"Analogs" in reference to nucleotides includes synthetic nucleotides having modified base moieties and/or modified sugar moieties (see e.g., described generally by Scheit, Nucleotide Analogs, John Wiley, New York, 1980; Freier & Altmann, (1997) *Nucl. Acid. Res.,* 25(22), 4429-4443, Toulmé, J. J., (2001) *Nature Biotechnology* 19:17-18; Manoharan M., (1999) *Biochemica et Biophysica Acta* 1489:117-139; Freier S. M., (1997) *Nucleic Acid Research,* 25:4429-4443, Uhlman, E., (2000) *Drug Discovery & Development,* 3: 203-213, Herdewin P., (2000) *Antisense & Nucleic Acid Drug Dev.,* 10:297-310); 2'-O, 3'-C-linked [3.2.0] bicycloarabinonucleosides. Such analogs include synthetic nucleotides designed to enhance binding properties, e.g., duplex or triplex stability, specificity, or the like.

As used herein, "hybridization" means the pairing of substantially complementary strands of oligomeric compounds. One mechanism of pairing involves hydrogen bonding, which may be Watson-Crick, Hoögsteen or reversed Hoögsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. In general, stringent hybridization conditions comprise low concentrations (<0.15M) of salts with inorganic cations such as $Na++$ or $K++$(i.e., low ionic strength), temperature higher than 20° C.-25° C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1× sodium chloride-sodium citrate buffer (SSC)/0.1% (w/v) SDS at 60° C. for 30 minutes.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art. Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math*., (1981) 2, 482-489).

As used herein, the term "Thermal Melting Point (Tm)" refers to the temperature, under defined ionic strength, pH, and nucleic acid concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent conditions may also be achieved with the addition of destabilizing agents such as formamide.

As used herein, "modulation" means either an increase (stimulation) or a decrease (inhibition) in the expression of a gene.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Neurological disease or disorder" refers to any disease or disorder of the nervous system and/or visual system. "Neurological disease or disorder" include disease or disorders that involve the central nervous system (brain, brainstem and cerebellum), the peripheral nervous system (including cranial nerves), and the autonomic nervous system (parts of which are located in both central and peripheral nervous system). Examples of neurological disorders include but are not limited to, headache, stupor and coma, dementia, seizure, sleep disorders, trauma, infections, neoplasms, neuroopthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological disorder. The following is a list of several neurological disorders, symptoms, signs and syndromes that can be treated using compositions and methods according to the present invention: acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Vascular dementia; amyotrophic lateral sclerosis; anencephaly; Angelman syndrome; angiomatosis; anoxia; aphasia; apraxia; arachnoid cysts; arachnoiditis; Anronl-Chian malformation; arteriovenous malformation; Asperger syndrome; ataxia telegiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; DandyWalker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactic a polyneuritiformis; herpes zoster oticus; herpes zoster; Hirayama syndrome; HIVassociated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Keams-Sayre syndrome; Kennedy disease Kinsboume syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; teaming disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease—neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; p muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae oflupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Neurodegenerative disease or disorder (Parkinson's disease, Huntington's disease, Alzheimer's disease, amyotrophic lateral sclerosis (ALS), dementia, multiple sclerosis and other diseases and disorders associated with neuronal cell death); paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocalleukoencephalopathy; progressive sclerosing poliodystrophy; progressive supranuclear palsy; pseudotumor cerebri; Ramsay-Hunt syndrome (types I and 11); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; and Zellweger syndrome.

A cardiovascular disease or disorder includes those disorders that can either cause ischemia or are caused by reperfusion of the heart. Examples include, but are not limited to, atherosclerosis, coronary artery disease, granulomatous myocarditis, chronic myocarditis (non-granulomatous), primary hypertrophic cardiomyopathy, peripheral artery disease (PAD), peripheral vascular disease, venous thromboembolism, pulmonary embolism. stroke, angina pectoris, myocardial infarction, cardiovascular tissue damage caused by cardiac arrest, cardiovascular tissue damage caused by cardiac bypass, cardiogenic shock, and related conditions that would be known by those of ordinary skill in the art or which involve dysfunction of or tissue damage to the heart or vasculature, especially, but not limited to, tissue damage related to SCN1A activation. CVS diseases include, but are not limited to, atherosclerosis, granulomatous myocarditis, myocardial infarction, myocardial fibrosis secondary to valvular heart disease, myocardial fibrosis without infarction, primary hypertrophic cardiomyopathy, and chronic myocarditis (non-granulomatous).

Examples of diseases or disorders associated with sodium channel dysfunction include, but are not restricted to, malignant hyperthermia, myasthenia, episodic ataxia, neuropathic and inflammatory pain, Alzheimer's disease, Parkinson's disease, schizophrenia, hyperekplexia, myotonias such as hypo- and hyperkalaemic periodic paralysis, paramyotonia congenita and potassium aggravated myotonia as well as cardiac arrhythmias such as long QT syndrome.

Polynucleotide and Oligonucleotide Compositions and Molecules

Targets: In one embodiment, the targets comprise nucleic acid sequences of Sodium channel, voltage-gated, type I, alpha subunit (SCN1A), including without limitation sense and/or antisense noncoding and/or coding sequences associated with SCN1A.

Voltage-sensitive ion channels are a class of transmembrane proteins that provide a basis for cellular excitability and the ability to transmit information via ion-generated membrane potentials. In response to changes in membrane potentials, these molecules mediate rapid ion flux through selective channels in a cell membrane. If channel density is high enough, a regenerative depolarization results, which is called an action potential.

The voltage-gated sodium channel is responsible for the generation and propagation of action potentials in most electrically excitable cells, including neurons, heart cells, and muscle. Electrical activity is triggered by depolarization of the membrane, which opens channels through the membrane that are highly selective for sodium ions. Ions are then driven intracellularly through open channels by an electrochemical gradient. Although sodium-based action potentials in different tissues are similar, electrophysiological studies have demonstrated that multiple structurally and functionally distinct sodium channels exist, and numerous genes encoding sodium channels have been cloned. The SCNA gene belongs to a gene family of voltage-gated sodium channels.

Voltage-gated sodium channels can be named according to a standardized form of nomenclature outlined in Goldin, et al. (2000) Neuron 28:365-368. According to that system, voltage-gated sodium channels are grouped into one family from which nine mammalian isoforms and have been identified and expressed. These nine isoforms are given the names Nav1.1 through Nav1.9. Also, splice variants of the various isoforms are distinguished by the use of lower case letters following the numbers (e.g., "Nav1.1a").

Voltage-gated sodium channels play an important role in the generation of action potential in nerve cells and muscle. The alpha subunit (SCNA) is the main component of the channel, and would be sufficient to generate an efficient channel when expressed in cells in vitro. In turn, the beta-1 and 2 subunits need an alpha subunit to give an effective channel. The role of these subunits would be to modify the kinetic properties of the channel, mainly by fast inactivation of the sodium currents. The mutation found in the GEFS syndrome on the SCN1B gene is shown to reduce the fast inactivation of the sodium channels as compared to a normal SCNB1, when co-expressed with an alpha subunit.

In preferred embodiments, antisense oligonucleotides are used to prevent or treat diseases or disorders associated with SCNA family members. Exemplary Sodium channel, voltage-gated, type I, alpha subunit (SCNA) mediated diseases and disorders which can be treated with cell/tissues regenerated from stem cells obtained using the antisense compounds comprise: a neurological disease or disorder, convulsion, pain (including chronic pain), impaired electrical excitability involving sodium channel dysfunction, a disease or disorder associated with sodium channel dysfunction, a disease or disorder associated with misregulation of voltage-gated sodium channel alpha subunit activity (e.g., paralysis, hyperkalemic periodic paralysis, paramyotonia congenita, potassium-aggravated myotonia, long Q-T syndrome 3, motor endplate disease, ataxia etc.), a gastrointestinal tract disease due to dysfunction of the enteric nervous system (e.g., colitis, ileitis, inflammatory bowel syndrome etc.), a cardiovascular disease or disorder (e.g., hypertension, congestive heart failure etc.); a disease or disorder of the genitourinary tract involving sympathetic and parasympathetic innervation (e.g., benign prostrate hyperplasia, impotence); a disease or disorder associated with neuromuscular system (e.g., muscular dystrophy, multiple sclerosis, epilepsy, autism, migraine (e.g., Sporadic and familial hemiplegic migraines etc.), Severe myoclonic epilepsy of infancy (SMEI or Dravet's syndrome), Generalised epilepsy with febrile seizure plus (GEFS+) etc.) and SCNA-related seizure disorders.

The present invention further relates to a pharmaceutical composition comprising at least one of an oligonucleotide that targets a natural antisense transcript to at least one or more of a target selected from the group consisting of SCN1A to SCN12A genes or mRNAs or isoforms or variants thereof. The present invention further relates to a method of treating a neurological disease or disorder comprising administering an oligonucleotide that targets a natural antisense transcript of at least one or more of a target selected from the group consisting of mRNA SCNIA, SCN2A, SCN3A, SCN4A, SCN5A, SCN6A, SCN7A, SCN8A, SCN9A, SCN10A, SCN11A and SCN12A or variant thereof. In a preferred embodiment, oligos are selected to upregulate the expression of a fully functional expression product of said SCNA family. In a preferred embodiment, the oligos of the invention upregulate transcription and or translation of any one of the mRNAs of an SCNXA family of genes to provide fully functional sodium channels in a patient in need of treatment thereof. In patients having a disease or disorder associated with a mutated version of a voltage gated sodium channel, in a preferred embodiment administration or treatment with a pharmaceutical composition comprising an oligonucleotide that targets a natural antisense transcript of a voltage gated sodium channel alpha gene or mRNA of such a gene upregulates a fully functional expression product in a ratio that is greater than the upregulation of an expression product derived from a mutated form of the gene. In another embodiment, the present invention relates to a combination of oligonucleotides that target at least one natural antisense transcript of at least two SCNXA family members wherein X is selected from 1-12. For example, in the treatment of Dravett's Syndrome, a combination of oligonucleotides may be used to upregulate the expression products of, for example, SCN1A and SCN9A. In another embodiment, at least one oligonucleotide may be selected to target a natural antisense transcript of at least two genes selected from any one of SCN1A to SCN12A. Preferred oligonucleotides of the invention are between about 5 to about 30 nucleotides in length and are at least 50% complementary to a 5 to about 30 nucleotide segment of an NAT. Preferred NATs of any one of the SCNA genes or transcription products thereof are those which, when targeted by an oligonucleotide of the invention, interfere with and modulate the expression of mRNA and/or the translation product of said mRNA. In a preferred embodiment, the oligonucleotides upregulate the expression of the functional protein of the target to treat or mitigate an SCNA associated disease. In a preferred embodiment, this "upregulation" is not associated with a cause or promotion of a disease such as cancer.

Alterations in an SCNA gene may include or encompass many or all forms of gene mutations including insertions, deletions, rearrangements and/or point mutations in the coding and/or non-coding regions of a gene. Deletions may be of the entire gene or a portion of the gene. Point mutations may result in amino acid substitutions, frame shifts or stop codons. Point mutations may also occur in a regulatory region of an SCNA gene, such as a promoter, resulting in a loss or a decrease of expression of an mRNA or may result in improper processing of such mRNA leading to a decrease in stability or translation efficiency. Such alterations in humans may lead to various forms of disease and there are many publications which describe the association of an alteration in an SCNA gene with, for example, epilepsy or SMEI. Such alterations may be "de novo" or may be inherited. The present invention is not limited to treating diseases associated with alterations in an SCNA gene and also includes treatment of an SCNA associated disease or condition wherein a patient does not have or necessarily have an alteration or mutation in the SCNA gene. It is believed that any modulation or upregulation of functional voltage gated sodium channel expression products will result in mitigation or treatment of an associated SCNA disease or condition in a patient in need of treatment thereof. Such mitigation also may include at least one measurable indicia of clinical improvement including fewer seizures, less frequent seizures, less severe seizures, development of fewer seizure types, improvement in neurological development or any other treatment benefit.

In an embodiment, modulation of SCNA by one or more antisense oligonucleotides is administered to a patient in need thereof, to prevent or treat any disease or disorder related to SCNA abnormal expression, function, activity as compared to a normal control.

In a preferred embodiment, the oligonucleotides are specific for polynucleotides of SCN1A, which includes, without limitation noncoding regions. The SCNA targets comprise variants of SCNA; mutants of SCNA, including SNPs; noncoding sequences of SCNA; alleles, fragments and the like. Preferably the oligonucleotide is an antisense RNA molecule.

In accordance with embodiments of the invention, the target nucleic acid molecule is not limited to SCN1A polynucleotides alone but extends to any of the isoforms, receptors, homologs, non-coding regions and the like of SCN1A.

In another preferred embodiment, an oligonucleotide targets a natural antisense sequence (natural antisense to the coding and non-coding regions) of SCN1A targets, including, without limitation, variants, alleles, homologs, mutants, derivatives, fragments and complementary sequences thereto. Preferably the oligonucleotide is an antisense RNA or DNA molecule.

In another preferred embodiment, the oligomeric compounds of the present invention also include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound. These compounds are then tested using the methods described herein to determine their ability to inhibit expression of a target nucleic acid.

In some embodiments, homology, sequence identity or complementarity, between the antisense compound and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired. Such conditions include, i.e., physiological conditions in the case of in vivo assays or therapeutic treatment, and conditions in which assays are performed in the case of in vitro assays.

An antisense compound, whether DNA, RNA, chimeric, substituted etc, is specifically hybridizable when binding of the compound to the target DNA or RNA molecule interferes with the normal function of the target DNA or RNA to cause a loss of utility, and there is a sufficient degree of complementarily to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

In another preferred embodiment, targeting of SCN1A including without limitation, antisense sequences which are identified and expanded, using for example, PCR, hybridization etc., one or more of the sequences set forth as SEQ ID NOS: 2 and 3, and the like, modulate the expression or function of SCN1A. In one embodiment, expression or function is up-regulated as compared to a control. In another preferred embodiment, expression or function is down-regulated as compared to a control.

In another preferred embodiment, oligonucleotides comprise nucleic acid sequences set forth as SEQ ID NOS: 4 to 16 including antisense sequences which are identified and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like. In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric antisense compounds, particularly oligonucleotides, bind to target nucleic acid molecules and modulate the expression and/or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The antisense compounds, include, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes Sodium channel, voltage-gated, type I, alpha subunit (SCNA).

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In an embodiment, the antisense oligonucleotides bind to the natural antisense sequences of Sodium channel, voltage-gated, alpha subunit (SCNA) and modulate the expression and/or function of SCNA (SEQ ID NO: 1 to 11). Examples of natural antisense sequences include SEQ ED NOS: 12 to 28. Examples of antisense oligonucleotides include SEQ ID NOS.29 to 94.

In another preferred embodiment, the antisense oligonucleotides bind to one or more segments of Sodium channel, voltage-gated, type I, alpha subunit (SCN1A) polynucleotides and modulate the expression and/or function of Sodium channel, voltage-gated, type I, alpha subunit (SCNA). The segments comprise at least five consecutive nucleotides of the Sodium channel, voltage-gated, type I, alpha subunit (SCNA) sense or antisense polynucleotides.

In an embodiment, the antisense oligonucleotides are specific for natural antisense sequences of SCNA wherein binding of the oligonucleotides to the natural antisense sequences of SCNA modulate expression and/or function of SCNA.

In another preferred embodiment, oligonucleotide compounds comprise sequences set forth as SEQ ID NOS: 29 to 94, antisense sequences which are identified and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like. In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding Sodium channel, voltage-gated, type I, alpha subunit (SCNA), regardless of the sequence(s) of such codons. A translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a targeted region is the intragenic region encompassing the translation initiation or termination codon of the open reading frame (ORF) of a gene.

Another target region includes the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene). Still another target region includes the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. Another target region for this invention is the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In one embodiment, targeting splice sites, i.e., intron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources are known as "fusion transcripts". Introns can be effectively targeted using antisense compounds targeted to, for example, DNA or pre-mRNA.

In another preferred embodiment, the antisense oligonucleotides bind to coding and/or non-coding regions of a target polynucleotide and modulate the expression and/or function of the target molecule.

In another preferred embodiment, the antisense oligonucleotides bind to natural antisense polynucleotides and modulate the expression and/or function of the target molecule.

In another preferred embodiment, the antisense oligonucleotides bind to sense polynucleotides and modulate the expression and/or function of the target molecule.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also embodiments of target nucleic acids.

The locations on the target nucleic acid to which the antisense compounds hybridize are defined as at least a 5-nucleotide long portion of a target region to which an active antisense compound is targeted.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure.

Target segments 5-100 nucleotides in length comprising a stretch of at least five (5) consecutive nucleotides selected from within the illustrative preferred target segments are considered to be suitable for targeting as well.

Target segments can include DNA or RNA sequences that comprise at least the 5 consecutive nucleotides from the 5'-terminus of one of the illustrative preferred target segments (the remaining nucleotides being a consecutive stretch of the same DNA or RNA beginning immediately upstream of the 5'-terminus of the target segment and continuing until the DNA or RNA contains about 5 to about 100 nucleotides). Similarly preferred target segments are represented by DNA or RNA sequences that comprise at least the 5 consecutive nucleotides from the 3'-terminus of one of the illustrative preferred target segments (the remaining nucleotides being a consecutive stretch of the same DNA or RNA beginning immediately downstream of the 3'-terminus of the target segment and continuing until the DNA or RNA contains about 5 to about 100 nucleotides). One having skill in the art armed with the target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non coding regions.

In one embodiment, it is preferred to target specific nucleic acids by antisense oligonucleotides. Targeting an antisense compound to a particular nucleic acid, is a multistep process. The process usually begins with the identification of a nucleic acid sequence whose function is to be modulated. This may be, for example, a cellular gene (or mRNA transcribed from the gene) whose expression is associated with a particular disorder or disease state, or a non coding polynucleotide such as for example, non coding RNA (ncRNA).

RNAs can be classified into (1) messenger RNAs (mRNAs), which are translated into proteins, and (2) non-protein-coding RNAs (ncRNAs). ncRNAs comprise microRNAs, antisense transcripts and other Transcriptional Units (TU) containing a high density of stop codons and lacking any extensive "Open Reading Frame". Many ncRNAs appear to start from initiation sites in 3' untranslated regions (3'UTRs) of protein-coding loci. ncRNAs are often rare and at least half of the ncRNAs that have been sequenced by the FANTOM consortium seem not to be polyadenylated. Most researchers have for obvious reasons focused on polyadenylated mRNAs that are processed and exported to the cytoplasm. Recently, it was shown that the set of non-polyadenylated nuclear RNAs may be very large, and that many such transcripts arise from so-called intergenic regions. The mechanism by which ncRNAs may regulate gene expression is by base pairing with target transcripts. The RNAs that function by base pairing can be grouped into (1) cis encoded RNAs that are encoded at the same genetic location, but on the opposite strand to the RNAs they act upon and therefore display perfect complementarity to their target, and (2) trans-encoded RNAs that are encoded at a chromosomal location distinct from the RNAs they act upon and generally do not exhibit perfect base-pairing potential with their targets.

Without wishing to be bound by theory, perturbation of an antisense polynucleotide by the antisense oligonucleotides described herein can alter the expression of the corresponding sense messenger RNAs. However, this regulation can either be discordant (antisense knockdown results in messenger RNA elevation) or concordant (antisense knockdown results in concomitant messenger RNA reduction). In these cases, antisense oligonucleotides can be targeted to overlapping or non-overlapping parts of the antisense transcript resulting in its knockdown or sequestration. Coding as well as non-coding antisense can be targeted in an identical manner and that either category is capable of regulating the corresponding sense transcripts—either in a concordant or disconcordant manner. The strategies that are employed in identifying new oligonucleotides for use against a target can be based on the knockdown of antisense RNA transcripts by antisense oligonucleotides or any other means of modulating the desired target.

Strategy 1: In the case of discordant regulation, knocking down the antisense transcript elevates the expression of the conventional (sense) gene. Should that latter gene encode for a known or putative drug target, then knockdown of its antisense counterpart could conceivably mimic the action of a receptor agonist or an enzyme stimulant.

Strategy 2: In the case of concordant regulation, one could concomitantly knock down both antisense and sense transcripts and thereby achieve synergistic reduction of the conventional (sense) gene expression. If, for example, an antisense oligonucleotide is used to achieve knockdown, then this strategy can be used to apply one antisense oligonucleotide targeted to the sense transcript and another antisense oligonucleotide to the corresponding antisense transcript, or a single energetically symmetric antisense oligonucleotide that simultaneously targets overlapping sense and antisense transcripts.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, doublestranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

In another preferred embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

dsRNA can also activate gene expression, a mechanism that has been termed "small RNA-induced gene activation" or RNAa. dsRNAs targeting gene promoters induce potent transcriptional activation of associated genes. RNAa was demonstrated in human cells using synthetic dsRNAs, termed "small activating RNAs" (saRNAs). It is currently not known whether RNAa is conserved in other organisms.

Small double-stranded RNA (dsRNA), such as small interfering RNA (siRNA) and microRNA (miRNA), have been found to be the trigger of an evolutionary conserved mechanism known as RNA interference (RNAi). RNAi invariably leads to gene silencing via remodeling chromatin to thereby suppress transcription, degrading complementary mRNA, or blocking protein translation. However, in instances described in detail in the examples section which follows, oligonucleotides are shown to increase the expression and/or function of the Sodium channel, voltage-gated, type I, alpha subunit (SCNA) polynucleotides and encoded products thereof dsRNAs may also act as small activating RNAs (saRNA). Without wishing to be bound by theory, by targeting sequences in gene promoters, saRNAs would induce target gene expression in a phenomenon referred to as dsRNA-induced transcriptional activation (RNAa).

In a further embodiment, the "preferred target segments" identified herein may be employed in a screen for additional compounds that modulate the expression of Sodium channel, voltage-gated, alpha subunit (SCNA) polynucleotides. "Modulators" are those compounds that decrease or increase the expression of a nucleic acid molecule encoding SCNA and which comprise at least a 5-micleotide portion that is complementary to a preferred target segment. The screening method comprises the steps of contacting a preferred target segment of a nucleic acid molecule encoding sense or natural antisense polynucleotides of SCNA with one or more candidate modulators, and selecting for one or more candidate modulators which decrease or increase the expression of a nucleic acid molecule encoding SCNA polynucleotides, e.g. SEQ ID NOS: 29 to 94. Once it is shown that the candidate modulator or modulators are capable of modulating (e.g. either decreasing or increasing) the expression of a nucleic acid molecule encoding SCNA polynucleotides, the modulator may then be employed in further investigative studies of the function of SCNA polynucleotides, or for use as a research, diagnostic, or therapeutic agent in accordance with the present invention.

Targeting the natural antisense sequence preferably modulates the function of the target gene. For example, the SCNA gene (e.g. accession number NM 001165963, NM_021007, NM_006922, NM 000334, NMJ98056, NM 002976, NM 014191, NM 002977, NM 006514, NM 014139, AF109737). In an embodiment, the target is an antisense polynucleotide of the SCNA gene. In an embodiment, an antisense oligonucleotide targets sense and/or natural antisense sequences of SCNA polynucleotides (e.g. accession number NM_001165963, NM_021007, NM 006922, NM 000334, NM_198056, NM_002976, NM 014191, NM 002977, NM 006514, NM 014139, AF 109737), variants, alleles, isoforms, homologs, mutants, derivatives, fragments and complementary sequences thereto. Preferably the oligonucleotide is an antisense molecule and the targets include coding and noncoding regions of antisense and/or sense SCNA polynucleotides.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications. For example, such double-stranded moieties have been shown to inhibit the target by the classical hybridization of antisense strand of the duplex to the target, thereby triggering enzymatic degradation of the target.

In an embodiment, an antisense oligonucleotide targets Sodium channel, voltage-gated, alpha subunit (SCNA) polynucleotides (e.g. accession number NM 001165963, NM 021007, NM 006922, NM 000334, NMJ98056, NM_002976, NM 014191, NM_002977, NM_006514, NM_014139, AF109737), variants, alleles, isoforms, homologs, mutants, derivatives, fragments and complementary sequences thereto. Preferably the oligonucleotide is an antisense molecule.

In accordance with embodiments of the invention, the target nucleic acid molecule is not limited to SCNA alone but extends to any of the isoforms, receptors, homologs and the like of SCNA molecules.

In an embodiment, an oligonucleotide targets a natural antisense sequence of SCNA polynucleotides, for example, polynucleotides set forth as SEQ ID NOS: 12 to 28, and any variants, alleles, homologs, mutants, derivatives, fragments and complementary sequences thereto. Examples of antisense oligonucleotides are set forth as SEQ ID NOS: 29 to 94.

In one embodiment, the oligonucleotides are complementary to or bind to nucleic acid sequences of SCNA antisense, including without limitation noncoding sense and/or antisense sequences associated with SCNA polynucleotides and modulate expression and/or function of SCNA molecules.

In an embodiment, the oligonucleotides are complementary to or bind to nucleic acid sequences of SCNA natural antisense, set forth as SEQ ID NOS: 12 to 28, and modulate expression and/or function of SCNA molecules.

In an embodiment, oligonucleotides comprise sequences of at least 5 consecutive nucleotides of SEQ ID NOS: 29 to 94 and modulate expression and/or function of SCNA molecules.

The polynucleotide targets comprise SCNA, including family members thereof, variants of SCNA; mutants of SCNA, including SNPs; noncoding sequences of SCNA; alleles of SCNA; species variants, fragments and the like. Preferably the oligonucleotide is an antisense molecule.

In an embodiment, the oligonucleotide targeting SCNA polynucleotides, comprise: antisense RNA, interference RNA (RNAi), short interfering RNA (siRNA); micro interfering RNA (miRNA); a small, temporal RNA (stRNA); or a short, hairpin RNA (shRNA); small RNA-induced gene activation (RNAa); or, small activating RNA (saRNA).

In an embodiment, targeting of Sodium channel, voltage-gated, alpha subunit (SCNA) polynucleotides, e.g. SEQ ID NOS: 1 to 1, modulate the expression or function of these targets. In one embodiment, expression or function is upregulated as compared to a control. In an embodiment, expression or function is down-regulated as compared to a control. In a further embodiment, targeting of the natural antisense transcripts (e.g. SEQ ID NOS. 12 to 28) as well as any other target NATs of such target polynucleotides results in the upregulation of said target mRNA and corresponding protein.

In an embodiment, antisense compounds comprise sequences set forth as SEQ ID NOS: 29 to 94. These oligonucleotides can comprise one or more modified nucleotides, shorter or longer fragments, modified bonds and the like.

In an embodiment, SEQ ID NOS: 29 to 94 comprise one or more LNA nucleotides. Table 1 shows exemplary antisense oligonucleotides useful in the methods of the invention.

TABLE 1

| Sequence ID | Antisense Sequence Name | Sequence |
|---|---|---|
| Seq_29 | CUR-1462 | mC*mC*mU*mA*mU*mC*T*T*T*C*C*C*C*C*C*C*C*T*mA*mC*mC*mU*mU*mU |
| Seq_30 | CUR-1624 | T*C*G*G*T*G*T*C*C*A*C*T*C*T*G*G*C*A*G*T |
| Seq_31 | CUR-1625 | T*G*C*A*C*T*G*T*G*G*A*G*C*C*T*G*T*C*T |
| Seq_32 | CUR-1626 | G*T*A*G*C*A*C*T*G*T*G*G*A*C*A*T*C*G*G*C |
| Seq_33 | CUR-1627 | G*T*A*G*A*A*G*A*A*C*A*G*C*C*C*G*T*A*G*T*G |
| Seq_34 | CUR-1628 | G*T*G*G*T*C*T*C*T*G*C*A*T*T*C*T*G*T*C*A |
| Seq_35 | CUR-1629 | G*T*G*G*T*A*T*A*G*G*A*A*C*T*G*G*C*A*G*C*A |

TABLE 1-continued

| Sequence ID | Antisense Sequence Name | Sequence |
|---|---|---|
| Seq_36 | CUR-1630 | G*T*C*C*A*A*T*C*A*T*A*C*A*G*C*A*G*A*A |
| Seq_37 | CUR-1631 | G*T*G*A*C*T*G*T*A*C*C*A*A*T*T*G*C*T*G*T |
| Seq_38 | CUR-1632 | A*C*T*T*C*T*T*C*C*A*C*T*C*C*T*T*C*C*T |
| Seq_39 | CUR-1633 | G*A*T*G*T*C*C*C*T*T*C*C*T*G*C*G*T*T*G*T |
| Seq_40 | CUR-1634 | T*G*T*G*G*A*T*G*C*T*G*G*G*T*G*T*C*T*C*T*C |
| Seq_41 | CUR-1635 | T*C*C*C*A*G*T*G*A*C*T*C*C*C*G*A*T*G*C*T |
| Seq_42 | CUR-1636 | A*G*T*C*T*C*A*G*T*T*G*T*C*A*G*T*A*C*C*T*C |
| Seq_43 | CUR-1738 | G*T*T*A*T*T*G*A*A*T*G*C*C*C*T*G*G*T*G*T |
| Seq_44 | CUR-1739 | T*C*G*G*A*T*C*A*T*C*A*G*G*G*T*T*G*T*A*G*T |
| Seq_45 | CUR-1740 | G*T*G*G*T*A*T*A*G*G*A*A*C*T*G*G*C*A*G*C*A |
| Seq_46 | CUR-1741 | T*C*T*G*C*T*C*T*T*C*C*C*T*A*C*A*T*T*G*G |
| Seq_47 | CUR-1742 | G*T*A*A*T*C*T*G*C*T*C*T*T*C*C*C*T*A*C |
| Seq_48 | CUR-1743 | G*G*G*A*G*A*A*C*T*T*G*A*G*A*G*C*A*A*C*A*G |
| Seq_49 | CUR-1744 | G*C*C*A*G*T*C*A*C*A*A*A*T*T*C*A*G*A*T*C*A |
| Seq_50 | CUR-1762 | +G* + T*A*T*A*G*G*A*A*C*T*G* + G* + C* + A |
| Seq_51 | CUR-1763 | +G* + T*G*G*T*A* + T*A*G*G*A*A* + C* + T* + G |
| Seq_52 | CUR-1764 | mG*mU*mG*G*mU*A*mU*A*G*G*A*A*mC*T*G*G*mC*A*mG*mC*mA |
| Seq_53 | CUR-1766 | +A* + G*A*A*C*T*T*G*A*G*A*G* + C* + A* + A |
| Seq_54 | CUR-1767 | mG*mG*mG*A*G*A*A*mC*T*mU*G*A*G*A*G*mC*A*A*mC*mA*mG |
| Seq_55 | CUR-1768 | +G* + C*C*A*G* + T*C*A* + C*A*A*A* + T* + T* + C |
| Seq_56 | CUR-1769 | +C* + A*C*A*A*A*T*T*C*A*G*A* + T* + C* + A |
| Seq_57 | CUR-1770 | mG*mC*mC*A*G*T*mC*A*C*A*A*A*mU*T*mC*A*G*A*mU*mC*mA |
| Seq_58 | CUR-1798 | rArUrUrUrArArArCrArCrGrGrArArGrArCrUrUrUrArGrUrArGrUrG |
| Seq_59 | CUR-1799 | rUrCrArCrArArArUrUrCrArGrArUrCrArCrCrCrArUrCrUrUrCrUrA |
| Seq_60 | CUR-1836 | +G* + T*GGTA + T*AGGAA + C* + T* + G |
| Seq_61 | CUR-1837 | mG*mU*mG*GmU*AmU*AGGAAmC*TGGmC*AmG*mC*mA |
| Seq_62 | CUR-1838 | +G* + C*CAGT*C*A + C*AAA + T* + T* + C |
| Seq_63 | CUR-1839 | +C* + A*CAAATTCAGA + T* + C* + A |
| Seq_64 | CUR-1891 | mG*mG*mU*A*mU*A*G*G*mA*A*C*mU*G*G*mC*A*G*mC*A*G*mU*G*mU*mU*mG |
| Seq_65 | CUR-1892 | mU*mG*mG*T*A*mU*A*G*mG*A*A*mC*T*G*G*mC*A*G*C*mA*mG*mU |
| Seq_66 | CUR-1895 | mG*G*T*A*mU*A*G*G*A*A*mC*T*G*G*mC*A*G*mC*A*G*T*G*T*T*mG |
| Seq_67 | CUR-1896 | mA*mA*G*mC*G*G*mU*A*T*A*G*G*A*A*mC*T*G*G*mC*A*G*mC*A*mG |
| Seq_68 | CUR-1900 | G*T*G*G*C*A*T*A*G*G*G*A*C*G*G*G*C*A*G*C*A |
| Seq_69 | CUR-1901 | mG*mU*mG*G*mC*A*mU*A*G*mG*G*A*mC*G*G*G*mC*A*mG*mC*mA |
| Seq_70 | CUR-1916 | mG*mA*mG*C*C*A*G*mU*C*A*mC*A*A*A*mU*T*C*A*G*mA*T*C*A*mC*mC*mC |
| Seq_71 | CUR-1917 | mA*A*mU*G*G*G*A*G*A*A*mC*mU*mU*G*A*G*A*G*mC*mA*mA |
| Seq_72 | CUR-1918 | mA*mC*mA*mA*mG*mU*G*G*C*A*T*A*G*G*G*A*C*G*G*mG*mC*mA*mG*mC*mA |
| Seq_73 | CUR-1919 | mA*mC*A*A*G*mU*G*G*mC*A*T*A*mG*G*G*A*mC*G*G*G*mC*A*G*mC*mA |
| Seq_74 | CUR-1920 | mA*A*G*mU*G*G*mC*A*mU*A*G*mG*G*A*mC*G*G*G*mC*A*G*mC*A*G*mU |
| Seq_75 | CUR-1921 | mA*mA*mG*mU*mG*G*C*A*T*A*G*G*G*A*C*G*G*G*C*A*mG*mC*mA*mG*mU |
| Seq_76 | CUR-1922 | G*T*G*ACTGTGCCCATTG*C*T*G |
| Seq_77 | CUR-1923 | G*C*C*ACTT*GATGAT*CTA*A*A*C |
| Seq_78 | CUR-1924 | G*T*G*GAC*AGGAT*GCAC*AAAGG*A |
| Seq_79 | CUR-1925 | mG*TGACmU*GTGCCmC*ATTGCTmG |
| Seq_80 | CUR-1926 | mG*TGACTGTGCCCATTGCTmG |
| Seq_81 | CUR-1927 | mC*CTCmU*TTCmU*GGCmC*TTGmC*TTmC |
| Seq_82 | CUR-1928 | mG*ACAAmC*CTTGmC*AGCCAmC*TGAmU*GATGmA |
| Seq_83 | CUR-1929 | T*G*G*T*A*T*A*G*G*A*A*C*T*G*G*C*A*G*C*A |
| Seq_84 | CUR-1930 | mU*mG*G*mU*A*mU*A*G*G*A*A*mC*T*G*G*mC*A*mG*mC*mA |
| Seq_85 | CUR-1931 | mC*mC*A*G*T*mC*A*C*A*A*A*mU*T*mC*A*G*A*mU*mC*mA |
| Seq_86 | CUR-1932 | mU*mG*GmU*AmU*AGGAAmC*TGGmC*AmG*mC*mA |
| Seq_87 | CUR-1933 | mA*mG*C*C*A*G*mU*C*A*mC*A*A*A*mU*T*C*A*G*mA*T*C*A*mC*mC*mC |

TABLE 1-continued

| Sequence ID | Antisense Sequence Name | Sequence |
|---|---|---|
| Seq_88 | CUR-1940 | mG*mC*C*A*G*mU*C*A*mC*A*A*A* mU*T*C*mA*mG |
| Seq_89 | CUR-1941 | mG*mC*C*A*G*mU*C*A*mC*A*A*A* mU*mU*mC |
| Seq_90 | CUR-1942 | +G* + C*C*A*G*mU*C*A*mC*A*A* mA*mU* + T* + C |
| Seq_91 | CUR-1943 | +G*C*C*A*G* + T*C*A* + C*A*A*A*T* + T* + C |
| Seq_92 | CUR-1944 | +G* + C*mC*A*G*mU*C*A*mC*A*mA* + A* + T |
| Seq_93 | CUR-1945 | +G* + C*C*A*G*T*C*A*C*A* + A* + A* + T |
| Seq_94 | CUR-1946 | +G*C*C*A*G*T*C*A* + C* + A* + A |

* indicates a phosphothioate bond, + indicates LNA, ‘r’ indicates RNA and ‘m’ indicates a methyl group on the 2' oxygen atom on the designated sugar moiety of the oligonucleotide. To avoid ambiguity, this LNA has the formula:

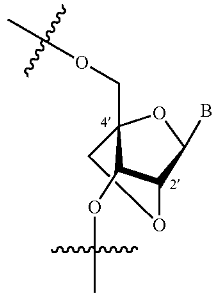

wherein B is the particular designated base.

Table 2: Relative expression of SCN1A mRNA in cells treated with antisense oligonucleotides targeting SCN1 A—specific natural antisense transcript Avg—average fold difference in SCNIA expression compared to mock transfected control; Std—standard deviation, P—probability that the treated samples are not different from mock control. N—total number of replicates

TABLE 2

| | SCN1A fibroblasts | | | SK-N-AS | | | Vero76 | | | 3T3 | | | HepG2 | | | CHP-212 | | |
|---|---|---|---|---|---|---|---|---|---|---|---|---|---|---|---|---|---|---|
| ID# | Avg | Std | N | Avg | Std | N | Avg | Std | N | Avg | Std | N | Avg | Std | N | Avg | Std | N |
| CUR-1462 | | | | 1.0 | 0.2 | 4 | 1.2 | 0.3 | 8 | 0.8 | 0.1 | 5 | | | | | | |
| CUR-1624 | | | | | | | 2.9 | 1.1 | 5 | | | | 0.9 | 0.0 | 5 | | | |
| CUR-1625 | 0.7 | 0.7 | 4 | | | | | | | | | | 1.3 | 0.4 | 4 | | | |
| CUR-1626 | | | | | | | | | | | | | 1.0 | 0.1 | 5 | | | |
| CUR-1627 | | | | | | | | | | | | | 1.2 | 0.1 | 4 | | | |
| CUR-1628 | | | | | | | | | | | | | 0.9 | 0.1 | 5 | | | |
| CUR-1629 | | | | 12.6 | 1.5 | 5 | | | | | | | 0.9 | 0.1 | 4 | | | |
| CUR-1630 | | | | | | | | | | | | | 1.0 | 0.1 | 5 | | | |
| CUR-1631 | 4.0 | 2.8 | 1 | | | | | | | 1.3 | 0.1 | 14 | 1.1 | 0.1 | 3 | | | |
| CUR-1632 | | | | | | | 1.2 | 0.7 | 4 | | | | 1.0 | 0.1 | 5 | | | |
| CUR-1633 | | | | | | | | | | | | | 1.0 | 0.2 | 4 | | | |
| CUR-1634 | | | | | | | 2.9 | 1.1 | 5 | | | | 1.2 | 0.1 | 4 | | | |
| CUR-1635 | | | | | | | | | | | | | 1.1 | 0.3 | 4 | | | |
| CUR-1636 | | | | | | | | | | | | | 1.1 | 0.1 | 4 | | | |
| CUR-1719 | | | | | | | 1.2 | 0.3 | 4 | | | | | | | | | |
| CUR-1738 | 0.8 | 0.6 | 7 | | | | | | | | | | | | | | | |
| CUR-1739 | 0.9 | 0.4 | 7 | | | | | | | | | | | | | | | |
| CUR-1740 | 8.2 | 2.0 | 27 | 18.2 | 2.0 | 16 | 4.3 | 1.1 | 12 | 1.7 | 0.5 | 10 | 1.1 | 0.3 | 9 | 8.8 | 1.7 | 5 |
| CUR-1741 | 1.8 | 1.3 | 5 | | | | | | | | | | | | | | | |
| CUR-1742 | 1.9 | 0.8 | 5 | | | | 5.5 | 1.0 | 12 | | | | | | | | | |
| CUR-1743 | 3.3 | 1.1 | 5 | | | | 5.6 | 1.7 | 5 | | | | | | | | | |
| CUR-1744 | 2.7 | 1.4 | 5 | | | | 6.8 | 1.3 | 6 | | | | | | | | | |
| CUR-1762 | 2.8 | 1.6 | 5 | 0.9 | 0.1 | 4 | 1.1 | 0.5 | 2 | | | | | | | | | |
| CUR-1763 | 2.9 | 1.5 | 6 | 1.2 | 0.1 | 11 | 1.5 | 0.5 | 10 | | | | | | | | | |
| CUR-1764 | 15.0 | 5.1 | 12 | 2.3 | 0.5 | 20 | 1.3 | 0.5 | 18 | 0.8 | 0.2 | 5 | 0.7 | 0.2 | 4 | | | |
| CUR-1766 | 0.6 | 0.3 | 5 | 0.7 | 0.1 | 3 | 1.5 | 0.6 | 6 | | | | | | | | | |
| CUR-1767 | | | | | | | 1.3 | 0.8 | 5 | | | | | | | | | |
| CUR-1768 | 1.1 | 0.5 | 3 | 1.5 | 0.3 | 5 | 1.5 | 0.8 | 5 | | | | | | | 1.9 | 0.7 | 5 |
| CUR-1769 | 0.8 | 0.7 | 10 | 1.0 | 0.1 | 3 | 2.6 | 0.8 | 7 | | | | | | | | | |
| CUR-1770 | 22.9 | 4.1 | 25 | 6.7 | 2.0 | 12 | 2.7 | 1.0 | 20 | | | | | | | | | |
| CUR-1798 | | | | | | | | | | | | | | | | 1.0 | 0.3 | 5 |
| CUR-1799 | | | | | | | 3.2 | | | | | | | | | 1.1 | 0.2 | 5 |
| CUR-1836 | | | | 1.1 | 0.3 | 8 | 1.3 | 0.6 | 5 | | | | 1.1 | 0.3 | 5 | | | |
| CUR-1837 | 3.2 | 0.6 | 9 | 2.4 | 0.3 | 11 | 4.2 | 1.0 | 24 | 1.0 | 0.1 | 9 | 1.2 | 0.5 | 10 | | | |
| CUR-1838 | 2.0 | 0.6 | 6 | 1.7 | 0.2 | 5 | 34.1 | 4.0 | 14 | | | | 1.3 | 0.3 | 5 | | | |

The modulation of a desired target nucleic acid can be carried out in several ways known in the art. For example, antisense oligonucleotides, siRNA etc. Enzymatic nucleic acid molecules (e.g., ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript.

Because of their sequence-specificity, trans-cleaving enzymatic nucleic acid molecules show promise as therapeutic agents for human disease (Usman & McSwiggen, (1995) *Ann. Rep. Med. Chem.* 30, 285-294; Christoffersen and Marr, (1995) *J. Med. Chem.* 38, 2023-2037). Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, (1979) *Proc. R. Soc. London*, B 205, 435) have been used to evolve new nucleic acid catalysts capable of catalyzing a variety of reactions, such as cleavage and ligation of phosphodiester linkages and amide linkages.

The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min-1 in the presence of saturating (10 mM) concentrations of Mg2+ cofactor. An artificial "RNA ligase" ribozyme has been shown to catalyze the corresponding self-modification reaction with a rate of about 100 min−1. In addition, it is known that certain modified hammerhead ribozymes that have substrate binding arms made of DNA catalyze RNA cleavage with multiple turn-over rates that approach 100 min−1. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain selfcleaving ribozymes may be optimized to give maximal catalytic activity, or that entirely new RNA motifs can be made that display significantly faster rates for RNA phosphodiester cleavage.

Intermolecular cleavage of an RNA substrate by an RNA catalyst that fits the "hammerhead" model was first shown in 1987 (Uhlenbeck, O. C. (1987) *Nature,* 328: 596-600). The RNA catalyst was recovered and reacted with multiple RNA molecules, demonstrating that it was truly catalytic.

Catalytic RNAs designed based on the "hammerhead" motif have been used to cleave specific target sequences by making appropriate base changes in the catalytic RNA to maintain necessary base pairing with the target sequences. This has allowed use of the catalytic RNA to cleave specific target sequences and indicates that catalytic RNAs designed according to the "hammerhead" model may possibly cleave specific substrate RNAs in vivo.

RNA interference (RNAi) has become a powerful tool for modulating gene expression in mammals and mammalian cells. This approach requires the delivery of small interfering RNA (siRNA) either as RNA itself or as DNA, using an expression plasmid or virus and the coding sequence for small hairpin RNAs that are processed to siRNAs. This system enables efficient transport of the pre-siRNAs to the cytoplasm where they are active and permit the use of regulated and tissue specific promoters for gene expression.

In a preferred embodiment, an oligonucleotide or antisense compound comprises an oligomer or polymer of ribonucleic acid (RNA) and/or deoxyribonucleic acid (DNA), or a mimetic, chimera, analog or homolog thereof. This tem includes oligonucleotides composed of naturally occurring nucleotides, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

According to the present invention, the oligonucleotides or "antisense compounds" include antisense oligonucleotides (e.g. RNA, DNA, mimetic, chimera, analog or homolog thereof), ribozymes, external guide sequence (EGS) oligonucleotides, siRNA compounds, single- or double-stranded RNA interference (RNAi) compounds such as siRNA compounds, saRNA, aRNA, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded.

Specific modulation of gene expression can be achieved by stable expression of dsRNA hairpins in transgenic cell lines. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

The antisense compounds in accordance with this invention can comprise an antisense portion from about 5 to about 80 nucleotides (i.e. from about 5 to about 80 linked nucleosides) in length. This refers to the length of the antisense strand or portion of the antisense compound. In other words, a single-stranded antisense compound of the invention comprises from 5 to about 80 nucleotides, and a double-stranded antisense compound of the invention (such as a dsRNA, for example) comprises a sense and an antisense strand or portion of 5 to about 80 nucleotides in length. One of ordinary skill in the art will appreciate that this comprehends antisense portions of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or any range therewithin.

In one embodiment, the antisense compounds of the invention have antisense portions of 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length.

In one embodiment, the antisense or oligonucleotide compounds of the invention have antisense portions of 12 or 13 to 30 nucleotides in length. One having ordinary skill in the art will appreciate that this embodies antisense compounds having antisense portions of 12, 13, 14, 15, 16, 17, 18, 19, 20, 21, 22, 23, 24, 25, 26, 27, 28, 29 or 30 nucleotides in length, or any range therewithin.

In another preferred embodiment, the oligomeric compounds of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the antisense or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In another preferred embodiment, the antisense oligonucleotides, such as for example, nucleic acid molecules set forth in SEQ ID NOS: 29 to 94 comprise one or more substitutions or modifications. In one embodiment, the nucleotides are substituted with locked nucleic acids (LNA).

In another preferred embodiment, the oligonucleotides target one or more regions of the nucleic acid molecules sense and/or antisense of coding and/or non-coding sequences associated with SCNA and the sequences set forth as SEQ ID NOS: 1 to 28. The oligonucleotides are also targeted to overlapping regions of SEQ ID NOS: 1 to 28.

Certain preferred oligonucleotides of this invention are chimeric oligonucleotides. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense modulation of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one preferred embodiment, a chimeric oligonucleotide comprises at least one region modified to increase target binding affinity, and, usually, a region that acts as a substrate for RNAse H Affinity of an oligonucleotide for its target (in this case, a nucleic acid encoding ras) is routinely determined by measuring the Tm of an oligonucleotide/target pair, which is the temperature at which the oligonucleotide and target dissociate; dissociation is detected spectrophotometrically. The higher the Tm, the greater is the affinity of the oligonucleotide for the target.

Chimeric antisense compounds of the invention may be formed as composite structures of two or more oligonucleotides, modified oligonucleotides, oligonucleosides and/or oligonucleotides mimetics as described above. Such; compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In preferred embodiment, the region of the oligonucleotide which is modified comprises at least one nucleotide modified at the 2' position of the sugar, most preferably a 2'-Oalkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target. The effect of such increased affinity is to greatly enhance RNAi oligonucleotide inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance.

Specific examples of some preferred oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2—NH—O—CH2, CH, —N(CH3)—O—CH2 [known as a methylene (methylimino) or MMI backbone], CH2—O—N(CH3)—CH2, CH2—N(CH3)—N(CH3)—CH2 and O—N(CH3)—CH2-CH2 backbones, wherein the native phosphodiester backbone is represented as O—P—O—CH). The amide backbones disclosed by De Mesmaeker et al. (1995) *Acc. Chem. Res.* 28:366-374 are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleotides being bound directly or indirectly to the aza nitrogen atoms of the polyamide backbone. Oligonucleotides may also comprise one or more substituted sugar moieties. Preferred oligonucleotides comprise one of the following at the 2' position: OH, SH, SCH3, F, OCN, OCH3 OCH3, OCH3 O(CH2)n CH3, O(CH2)n NH2 or O(CH2)n CH3 where n is from 1 to about 10; C1 to C10 lower alkyl, alkoxyalkoxy, substituted lower alkyl, alkaryl or aralkyl; Cl; Br; CN; CF3; OCF3; O—, S—, or N-alkyl; O—, S—, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH2 CH2 OCH3, also known as 2'-O-(2-methoxyethyl)]. Other preferred modifications include 2'-methoxy (2'-O—CH3), 2'-propoxy (2'-OCH2 CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleotides, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. A "universal" base known in the art, e.g., inosine, may be included. 5-Me-C substitutions have been shown to increase nucleic acid duplex stability by 0.6-1.2° C. and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety, an aliphatic chain, e.g., dodecandiol or undecyl residues, a polyamine or a polyethylene glycol chain, or Adamantane acetic acid. Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc. This can be achieved by substituting some of the monomers in the current oligonucleotides by LNA monomers. The LNA modified oligonucleotide may have a size similar to the parent compound or may be larger or preferably smaller. It is preferred that such LNA-modified oligonucleotides contain less than about 70%, more preferably less than about 60%, most preferably less than about 50% LNA monomers and that their sizes are between about 5 and 25 nucleotides, more preferably between about 12 and 20 nucleotides.

Preferred modified oligonucleotide backbones comprise, but not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus containing linkages comprise, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleosides comprise, but are not limited to, U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen, et al. (1991) Science 254, 1497-1500.

In another preferred embodiment of the invention the oligonucleotides with phosphorothioate backbones and oligonucleosides with heteroatom backbones, and in particular —CH2—NH—O—CH2-, —CH2—N(CH3)—O—CH2— known as a methylene (methylimino) or MMI backbone, —CH2—O—N(CH3)—CH2—, —CH2N(CH3)—N(CH3) CH2— and —O—N(CH3)—CH2—CH2— wherein the native phosphodiester backbone is represented as —O—P—O—CH2— of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O alkyl-O-alkyl, wherein the alkyl, alkenyl and alkynyl may be substituted or unsubstituted C to CO alkyl or C2 to CO alkenyl and alkynyl. Particularly preferred are 0 (CH2)n OmCH3, O(CH2)n, OCH3, O(CH2)nNH2, O(CH2)nCH3, O(CH2)nONH2, and O(CH2nON(CH2)nCH3)2 where n and m can be from 1 to about 10. Other preferred oligonucleotides comprise one of the following at the 2' position: C to CO, (lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification comprises 2'-methoxyethoxy (2'-O—CH2CH2OCH3, also known as 2'-O-(2-methoxyethyl) or 2'-MOE) i.e., an alkoxyalkoxy group. A further preferred modification comprises 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2—O—CH2—N(CH2)2.

Other preferred modifications comprise 2'-methoxy (2'-OCH3), 2'-aminopropoxy (2'-OCH2CH2CH2NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5,319,080; 5,359,044; 5,393,878; 5,446,137; 5,466,786; 5,514, 785; 5,519,134; 5,567,811; 5,576,427; 5,591,722; 5,597,909; 5,610,300; 5,627,053; 5,639,873; 5,646, 265; 5,658,873; 5,670,633; and 5,700,920, each of which is herein incorporated by reference.

Oligonucleotides may also comprise nucleobase (often referred to in the art simply as "base") modifications or substitutions. As used herein, "unmodified" or "natural" nucleotides comprise the purine bases adenine (A) and guanine (G), and the pyrimidine bases thymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleotides comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleotides are particularly useful for increasing the binding affinity of the oligomeric compounds of the invention. These comprise 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-Omethoxyethyl sugar modifications.

Representative United States patents that teach the preparation of the above noted modified nucleotides as well as other modified nucleotides comprise, but are not limited to, U.S. Pat. No. 3,687,808, as well as U.S. Pat. Nos. 4,845,205; 5,130,302; 5,134,066; 5,175, 273; 5, 367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or Adamantane acetic acid, a palmityl moiety, or an octadecylamine or hexylamino-carbonyl-t oxycholesterol moiety.

Representative United States patents that teach the preparation of such oligonucleotides conjugates comprise, but are not limited to, U.S. Pat. Nos. 4,828,979; 4,948,882; 5,218, 105; 5,525,465; 5,541,313; 5,545,730; 5,552, 538; 5,578, 717, 5,580,731; 5,580,731; 5,591,584; 5,109,124; 5,118, 802; 5,138,045; 5,414,077; 5,486, 603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082, 830; 5,112,963; 5,214,136; 5,082, 830; 5,112,963; 5,214,136; 5, 245,022; 5,254,469; 5,258, 506; 5,262,536; 5,272,250; 5,292,873; 5,317,098; 5,371, 241, 5,391, 723; 5,416,203, 5,451,463; 5,510,475; 5,512, 667; 5,514,785; 5, 565,552; 5,567,810; 5,574,142; 5,585, 481; 5,587,371; 5,595,726; 5,597,696; 5,599,923; 5,599, 928 and 5,688,941, each of which is herein incorporated by reference.

Drug Discovery:

The compounds of the present invention can also be applied in the areas of drug discovery and target validation. The present invention comprehends the use of the compounds and preferred target segments identified herein in drug discovery efforts to elucidate relationships that exist between Sodium channel, voltage-gated, type I, alpha subunit (SCN1A) polynucleotides and a disease state, phenotype, or condition. These methods include detecting or modulating Sodium channel, voltage-gated, type I, alpha subunit (SCN1A) polynucleotides comprising contacting a sample, tissue, cell, or organism with the compounds of the present invention, measuring the nucleic acid or protein level of Sodium channel, voltage-gated, type I, alpha subunit (SCN1A) polynucleotides and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Assessing Up-Regulation or Inhibition of Gene Expression:

Transfer of an exogenous nucleic acid into a host cell or organism can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods including gene expression analysis. For instance, mRNA produced from an exogenous nucleic acid can be detected and quantified using a Northern blot and reverse transcription PCR (RT-PCR).

Expression of RNA from the exogenous nucleic acid can also be detected by measuring an enzymatic activity or a reporter protein activity. For example, antisense modulatory activity can be measured indirectly as a decrease or increase in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non coding region can be used. Each control gene is assembled by inserting each coding region between a reporter coding region and its poly (A) signal. These plasmids would produce an mRNA with a reporter gene in the upstream portion of the gene and a potential RNAi target in the 3' non-coding region. The effectiveness of individual antisense oligonucleotides would be assayed by modulation of the reporter gene. Reporter genes useful in the methods of the present invention include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

Target nucleic acid segments can also be detected in the cell based assays. Experiments are conducted to detect the Scnla natural antisense BG724147 in HepG2, in Primary human fibroblasts carrying a Dravet syndrome-associated mutation and also in human Testis. For HepG2 as well as Primary human fibroblasts carrying a Dravet syndrome-associated mutation the cells are grown and RNA is extracted for the human Testis, polyA isolated RNA is purchased and utilized. This experiment is called a RACE (Rapid Amplification of cDNA Ends) and specific primers for the BG724147 RNA transcript are used.

A PCR product very similar in polyA isolated RNA from HepG2 and polyA isolated RNA from Primary human fibroblasts carrying a Dravet syndrome-associated mutation was detected but this product was not detected in poly A isolated RNA from human Testis. Furthermore, that PCR product was not detected (or in very very low amounts) in the total RNA from HepG2 cells and total RNA from Primary human fibroblasts carrying a Dravet syndrome-associated mutation. The results suggest that the natural antisense for Scnla called BG724147 is present in HepG2 cells and Primary human fibroblasts carrying a Dravet syndrome-associated mutation but not in human Testis.

SCNA protein and mRNA expression can be assayed using methods known to those of skill in the art and described elsewhere herein. For example, immunoassays such as the ELISA can be used to measure protein levels. SCNA ELISA assay kits are available commercially, e.g., from R&D Systems (Minneapolis, Minn.).

In embodiments, SCNA expression (e.g., mRNA or protein) in a sample (e.g., cells or tissues in vivo or in vitro) treated using an antisense oligonucleotide of the invention is evaluated by comparison with SCNA expression in a control sample. For example, expression of the protein or nucleic acid can be compared using methods known to those of skill in the art with that in a mock-treated or untreated sample. Alternatively, comparison with a sample treated with a control antisense oligonucleotide (e.g., one having an altered or different sequence) can be made depending on the information desired. In another embodiment, a difference in the expression of the SCNA protein or nucleic acid in a treated vs. an untreated sample can be compared with the difference in expression of a different nucleic acid (including any standard deemed appropriate by the researcher, e.g., a housekeeping gene) in a treated sample vs. an untreated sample.

Observed differences can be expressed as desired, e.g., in the form of a ratio or fraction, for use in a comparison with control. In embodiments, the level of SCN1A mRNA or protein, in a sample treated with an antisense oligonucleotide of the present invention, is increased or decreased by about 1.25-fold to about 10-fold or more relative to an untreated sample or a sample treated with a control nucleic acid. In embodiments, the level of SCN1A mRNA or protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more.

Kits, Research Reagents, Diagnostics, and Therapeutics

The compounds of the present invention can be utilized for diagnostics, therapeutics, and prophylaxis, and as research reagents and components of kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics and in various biological systems, the compounds of the present invention, either alone or in combination with other compounds or therapeutics, are useful as tools in differential and/or combinatorial analyses to elucidate expression patterns of a portion or the entire complement of genes expressed within cells and tissues.

As used herein the term “biological system” or “system” is defined as any organism, cell, cell culture or tissue that expresses, or is made competent to express products of the Sodium channel, voltage-gated, type I, alpha subunit (SCN1A) genes. These include, but are not limited to, humans, transgenic animals, cells, cell cultures, tissues, xenografts, transplants and combinations thereof.

As one non limiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays, SAGE (serial analysis of gene expression), READS (restriction enzyme amplification of digested cDNAs), TOGA (total gene expression analysis), protein arrays and proteomics, expressed sequence tag (EST) sequencing, subtractive RNA fingerprinting (SuRF), subtractive cloning, differential display (DD), comparative genomic hybridization, FISH (fluorescent in situ hybridization) techniques and mass spectrometry methods.

The compounds of the invention are useful for research and diagnostics, because these compounds hybridize to nucleic acids encoding Sodium channel, voltage-gated, alpha subunit (SCNA). For example, oligonucleotides that hybridize with such efficiency and under such conditions as disclosed herein as to be effective SCNA modulators are effective primers or probes under conditions favoring gene amplification or detection, respectively. These primers and probes are useful in methods requiring the specific detection of nucleic acid molecules encoding SCNA and in the amplification of said nucleic acid molecules for detection or for use in further studies of SCNA. Hybridization of the antisense oligonucleotides, particularly the primers and probes, of the invention with a nucleic acid encoding SCNA can be detected by means known in the art. Such means may include conjugation of an enzyme to the oligonucleotide, radio labeling of the oligonucleotide, or any other suitable detection means. Kits using such detection means for detecting the level of SCNA in a sample may also be prepared.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an ardmal, preferably a human, suspected of having a disease or disorder which can be treated by modulating the expression of SCNA polynucleotides is treated by administering antisense compounds in accordance with this invention. For example, in one non-limiting embodiment, the methods comprise the step of actaamistering to the animal in need of treatment, a therapeutically effective amount of SCNA modulator. The SCNA modulators of the present invention effectively modulate the activity of the SCNA or modulate the expression of the SCNA protein. In one embodiment, the activity or expression of SCNA in an animal is inhibited by about 10% as compared to a control. Preferably, the activity or expression of SCNA in an animal is inhibited by about 30%. More preferably, the activity or expression of SCNA in an animal is inhibited by 50% or more. Thus, the oligomeric compounds modulate expression of Sodium channel, voltage-gated, alpha subunit (SCNA) mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

In one embodiment, the activity or expression of Sodium channel, voltage-gated, alpha subunit (SCNA) and/or in an animal is increased by about 10% as compared to a control. Preferably, the activity or expression of SCNA in an animal is increased by about 30%. More preferably, the activity or expression of SCNA in an animal is increased by 50% or more. Thus, the oligomeric compounds modulate expression of SCNA mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

For example, the reduction of the expression of Sodium channel, voltage-gated, alpha subunit (SCNA) may be measured in serum, blood, adipose tissue, liver or any other body fluid, tissue or organ of the animal. Preferably, the cells contained within said fluids, tissues or organs being analyzed contain a nucleic acid molecule encoding SCNA peptides and/or the SCNA protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

Conjugates

Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H phosphonate, a polyamine or a polyethylene glycol chain, or Adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Representative United States patents that teach the preparation of such oligonucleotides conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,165; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Although, the antisense oligonucleotides do not need to be administered in the context of a vector in order to modulate a target expression and/or function, embodiments of the invention relates to expression vector constructs for the expression of antisense oligonucleotides, comprising promoters, hybrid promoter gene sequences and possess a strong constitutive promoter activity, or a promoter activity which can be induced in the desired case.

In an embodiment, invention practice involves administering at least one of the foregoing antisense oligonucleotides with a suitable nucleic acid delivery system. In one embodiment, that system includes a non-viral vector operably linked to the polynucleotide. Examples of such nonviral vectors include the oligonucleotide alone (e.g. any one or more of SEQ ID NOS: 29 to 94) or in combination with a suitable protein, polysaccharide or lipid formulation.

Additionally suitable nucleic acid delivery systems include viral vector, typically sequence from at least one of an adenovirus, adenovirus-associated virus (AAV), helper-dependent adenovirus, retrovirus, or hemagglutinatin virus of Japan-liposome (HVJ) complex. Preferably, the viral vector comprises a strong eukaryotic promoter operably linked to the polynucleotide e.g., a cytomegalovirus (CMV) promoter.

Additionally preferred vectors include viral vectors, fusion proteins and chemical conjugates. Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector, Adenovirus Vectors and Adeno-associated Virus Vectors.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein by reference.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

For treating tissues in the central nervous system, administration can be made by, e.g., injection or infusion into the cerebrospinal fluid. Administration of antisense RNA into cerebrospinal fluid is described, e.g., in U.S. Pat. App. Pub. No. 2007/0117772, "Methods for slowing familial ALS disease progression," incorporated herein by reference in its entirety.

When it is intended that the antisense oligonucleotide of the present invention be administered to cells in the central nervous system, administration can be with one or more agents capable of promoting penetration of the subject antisense oligonucleotide across the blood-brain barrier. Injection can be made, e.g., in the entorhinal cortex or hippocampus. Delivery of neurotrophic factors by administration of an adenovirus vector to motor neurons in muscle tissue is described in, e.g., U.S. Pat. No. 6,632,427, "Adeno-viral-vector-mediated gene transfer into medullary motor neurons," incorporated herein by reference. Delivery of vectors directly to the brain, e.g., the striatum, the thalamus, the hippocampus, or the substantia nigra, is known in the art and described, e.g., in U.S. Pat. No. 6,756,523, "Adenovirus vectors for the transfer of foreign genes into cells of the central nervous system particularly in brain," incorporated herein by reference. Administration can be rapid as by injection or made over a period of time as by slow infusion or administration of slow release formulations.

The subject antisense oligonucleotides can also be linked or conjugated with agents that provide desirable pharmaceutical or pharmacodynamic properties. For example, the antisense oligonucleotide can be coupled to any substance, known in the art to promote penetration or transport across the blood-brain barrier, such as an antibody to the transferrin receptor, and administered by intravenous injection. The antisense compound can be linked with a viral vector, for example, that makes the antisense compound more effective and/or increases the transport of the antisense compound across the blood-brain barrier. Osmotic blood brain barrier disruption can also be accomplished by, e.g., infusion of sugars including, but not limited to, meso erythritol, xylitol, D(+) galactose, D(+) lactose, D(+) xylose, dulcitol, myo-inositol, L(−) fructose, D(−) mannitol, D(+) glucose, D(+) arabinose, D(−) arabinose, cellobiose, D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose, or amino acids including, but not limited to, glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 4,866,042, "Method for the delivery of genetic material across the blood brain barrier," U.S. Pat. No. 6,294,520, "Material for passage through the blood-brain barrier," and U.S. Pat. No. 6,936,589, "Parenteral delivery systems," all incorporated herein by reference in their entirety.

The subject antisense compounds may be admixed, encapsulated, conjugated or otherwise associated with other molecules, molecule structures or mixtures of compounds, for example, liposomes, receptor-targeted molecules, oral, rectal, topical or other formulations, for assisting in uptake, distribution and/or absorption. For example, cationic lipids may be included in the formulation to facilitate oligonucleotide uptake. One such composition shown to facilitate uptake is LIPOFECTIN (available from GIBCO-BRL, Bethesda, Md.).

Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogeneous systems of one liquid dispersed in another in the form of droplets usually exceeding 0.1 μm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids. When incorporated into liposomes, these specialized lipids result in liposomes with enhanced circulation lifetimes relative to liposome slacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein by reference.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating nonsurfactants. Penetration enhancers and their uses are further described in U.S. Pat. No. 6,287,860, which is incorporated herein by reference.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoyl-phosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein by reference. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein by reference.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bischloroethyl-nitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclo-phosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. For example, the first target may be a particular antisense sequence of Sodium channel, voltage-gated, type I, alpha subunit (SCN1A), and the second target may be a region from another nucleotide sequence. Alternatively, compositions of the invention may contain two or more antisense compounds targeted to different regions of the same Sodium channel, voltage-gated, type I, alpha subunit (SCN1A) nucleic acid target. Numerous examples of antisense compounds are illustrated herein and others may be selected from among suitable compounds known in the art. Two or more combined compounds may be used together or sequentially.

Dosing:

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

In embodiments, a patient is treated with a dosage of drug that is at least about 1, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100 mg/kg body weight. Certain injected dosages of antisense oligonucleotides are described, e.g., in U.S. Pat. No. 7,563,884, "Antisense modulation of PTP1B expression," incorporated herein by reference in its entirety.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1: Design of Antisense Oligonucleotides Specific for a Nucleic Acid Molecule Antisense to a Sodium Channel, Voltage-Gated, Alpha Subunit (SCNA) and/or a Sense Strand of SCNA Polynucleotide As indicated above the term "oligonucleotide specific for" or "oligonucleotide targets" refers to an oligonucleotide having a sequence (i) capable of forming a stable complex with a portion of the targeted gene, or (ii) capable of forming a stable duplex with a portion of an mRNA transcript of the targeted gene.

Selection of appropriate oligonucleotides is facilitated by using computer programs (e.g. IDT AntiSense Design, IDT OligoAnalyzer) that automatically identify in each given sequence subsequences of 1-25 nucleotides that will form hybrids with a target polynucleotide sequence with a desired melting temperature (usually 50-60° C.) and will not form self-dimers or other complex secondary structures.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays The hybridization properties of the oligonucleotides described herein can be determined by one or more in vitro assays as known in the art. For example, the properties of the oligonucleotides described herein can be obtained by determination of binding strength between the target natural antisense and a potential drug molecules using melting curve assay.

The binding strength between the target natural antisense and a potential drug molecule (Molecule) can be estimated using any of the established methods of measuring the strength of intermolecular interactions, for example, a melting curve assay.

Melting curve assay determines the temperature at which a rapid transition from double-stranded to single-stranded conformation occurs for the natural antisense/Molecule complex. This temperature is widely accepted as a reliable measure of the interaction strength between the two molecules.

A melting curve assay can be performed using a cDNA copy of the actual natural antisense RNA molecule or a synthetic DNA or RNA nucleotide corresponding to the binding site of the Molecule. Multiple kits containing all necessary reagents to perform this assay are available (e.g. Applied Biosystems Inc. MeltDoctor kit). These kits include a suitable buffer solution containing one of the double strand DNA (dsDNA) binding dyes (such as ABI HRM dyes, SYBR Green, SYTO, etc.). The properties of the dsDNA dyes are such that they emit almost no fluorescence in free form, but are highly fluorescent when bound to dsDNA.

To perform the assay the cDNA or a corresponding oligonucleotide are mixed with Molecule in concentrations defined by the particular manufacturer's protocols. The mixture is heated to 95° C. to dissociate all pre-formed dsDNA complexes, then slowly cooled to room temperature or other lower temperature defined by the kit manufacturer to allow the DNA molecules to anneal. The newly formed complexes are then slowly heated to 95° C. with simultaneous continuous collection of data on the amount of fluorescence that is produced by the reaction. The fluorescence intensity is inversely proportional to the amounts of dsDNA present in the reaction. The data can be collected using a real time PCR instrument compatible with the kit (e.g.ABI's StepOne Plus Real Time PCR System or LightTyper instrument, Roche Diagnostics, Lewes, UK).

Melting peaks are constructed by plotting the negative derivative of fluorescence with respect to temperature (−d (Fluorescence)/dT) on the y-axis) against temperature (x-axis) using appropriate software (for example LightTyper (Roche) or SDS Dissociation Curve, ABI). The data is analyzed to identify the temperature of the rapid transition from dsDNA complex to single strand molecules. This temperature is called Tm and is directly proportional to the strength of interaction between the two molecules. Typically, Tm will exceed 40° C.

Example 2: Modulation of SCNA Polynucleotides

Treatment of HepG2 Cells with Antisense Oligonucleotides

HepG2 cells from ATCC (cat # HB-8065) were grown in growth media (MEM/EBSS (Hyclone cat #SH30024, or Mediatech cat # MT-10-010-CV)+10% FBS (Mediatech cat # MT35-011-CV)+penicillin/streptomycin (Mediatech cat # MT30-002-CI)) at 37° C. and 5% CO2. One day before the experiment the cells were replated at the density of 1.5×

$10^5$/ml into 6 well plates and incubated at 37° C. and 5% $CO_2$. On the day of the experiment the media in the 6 well plates was changed to fresh growth media. All antisense oligonucleotides were diluted to the concentration of 20 μM. Two μl of this solution was incubated with 400 μl of Opti-MEM media (Gibco cat #31985-070) and 4 μl of Lipofectamine 2000 (Invitrogen cat #11668019) at room temperature for 20 min and applied to each well of the 6 well plates with HepG2 cells. A Similar mixture including 2 μl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat # Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Tatman Gene Expression Assay: Hs00374696_ml by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Figure 2:
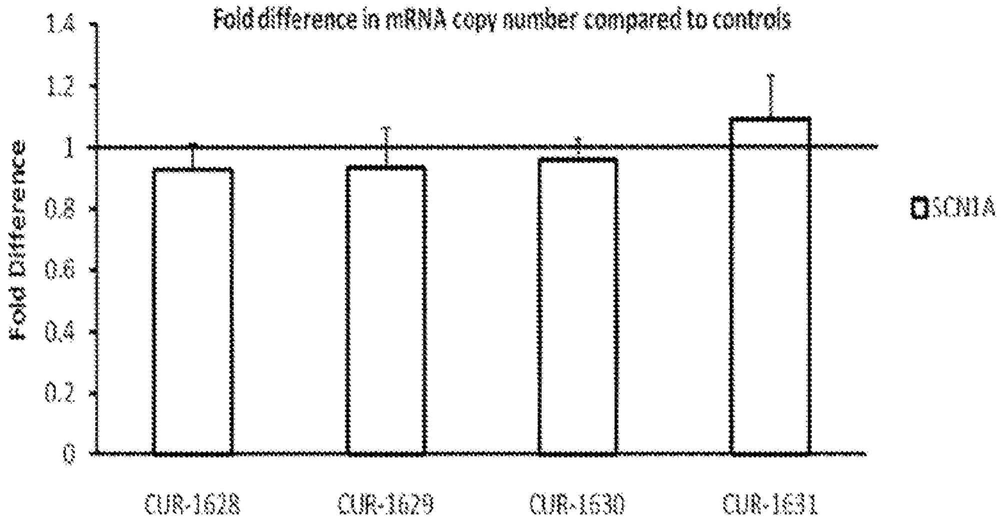
FIG. 2 is a graph of real time PCR results showing the fold change+standard deviation in SCNIA mRNA after treatment of HepG2 cells with phosphorothioate oligonucleotides introduced using Lipofectamine 2000, as compared to control. Bars denoted as CUR-1628 to CUR-1631 correspond to samples treated with SEQ ED NOS: 34 to 37 respectively.

Results:

Real Time PCR results show that levels of SCN1A mRNA in HepG2 cells are significantly increased 48 h after treatment with antisense oligonucleotides to SCN1 A antisense BG724147 (FIG. 1,4). Other oligonucleotides designed to SCN1A antisense BG724147 and Hs.662210 did not elevate SCN1A levels. (FIG. 2, 3).

Example 3: Upregulation of SCNA mRNA in Different Cell Lines by Treatment with Antisense Oligonucleotides Targeting SCNA-Specific Natural Antisense Transcript In Example 3 antisense oligonucleotides of different chemistries targeting SCNIA-specific natural antisense transcript were screened in a panel of various cell lines at a final concentration of 20 nM. The cell lines used originate from different organs and different animal species. The data below confirms that upregulation of SCN1A mRNA/protein through modulation of the function of the SCNIA-specific natural antisense transcript is not limited to a single oligonucleotide, tissue or species and thus represents a general phenomenon.

Materials and Methods

Primary human fibroblasts carrying a Dravet syndrome-associated mutation. Primary human skin fibroblasts carrying a Dravet syndrome-associated mutation E1099X introduced into culture by Dr. N. Kenyon (University of Miami) were grown in Growth Media consisting of a-MEM (Gibco, cat: 12561-056)+10% FBS (Mediatech, cat: 35-015 CV)+ 1% Antimycotic-Antibiotic (Gibco, cat: 15240-062) at 37° C. and 5% C(¼. The cells were treated with antisense oligonucleotides using one of the following methods. For the Next Day Method, one day before the experiment the cells were replated at the density of approximately 2×105/well into 6 well plates in Growth Media and incubated at 37° C. and 5% $CO_2$ overnight. Next day, the media in the 6 well plates was changed to fresh Growth Media (1.5 ml/well) and the cells were dosed with antisense oligonucleotides. All antisense oligonucleotides were manufactured by DDT Inc. (Coralville, Iowa) or Exiqon (Vedbaek, Denmark). The sequences for all oligonucleotides are listed in Table 1. Stock solutions of oligonucleotides were diluted to the concentration of 20 μM in DNAse RNAse-free sterile water. To dose one well, 2 μï of this solution was incubated with 400 μï of Opti-MEM media (Gibco cat #31985-070) and 4 μï of Lipofectamine 2000 (Invitrogen cat #1166801) at room temperature for 20 min and applied dropwise to one well of a 6 well plate with cells. Similar mixture including 2 μï of water instead of the oligonucleotide solution was used for the mock-transfected controls. Additionally an inactive oligonucleotide CUR-1462 at the same concentration was used as control. After about 18 h of incubation at 37° C. and 5% $C0_2$ the media was changed to fresh Growth Media. Forty eight hours after addition of antisense oligonucleotides the media was removed and RNA was extracted from the cells using SV Total RNA Isolation System from Promega (cat # Z3105) following the manufacturers' instructions. Six hundred nanograms of purified total RNA was added to the reverse transcription reaction performed using Superscript VILO cDNA Synthesis Kit from Invitrogen (cat #1 1754-250) as described in the manufacturer's protocol. The cDNA from this reverse transcription reaction was used to monitor gene expression by real time PCR using ABI Taqman Gene Expression Mix (cat #4369510) and primers/probes designed by ABI (assays Hs00374696_ml, Hs00897350_ml or Hs00897341_ml for human SCN1A). Results obtained using all three assays were very similar. The following PCR cycle was used: 50° C. for 2 min, 95° C. for 10 min, 40 cycles of (95° C. for 15 seconds, 60° C. for 1 min) using StepOne plus Real Time PCR system (Applied Biosystems). The assay for 18S was manufactured by ABI (cat #4319413E). Fold change in gene expression after treatment with antisense oligonucleotides was calculated based on the difference in 18S-normalized dCt values between treated and mock-transfected samples. For the alternative Same Day Method all procedures were performed similarly, but cells were dosed with antisense oligonucleotides on the first day, immediately after they were distributed into 6-well plates.

SK-N-AS cell line. SK-N-AS human neuroblastoma cells from ATCC (cat # CRL-2137) were grown in Growth Media (DMEM (Mediatech cat #10-013-CV) +10% FBS (Mediatech cat # MT35-011-CV>+penicillin/streptomycin (Mediatech cat # MT30-002-CI)+Non-Essential Amino Acids (NEAA)(HyClone SH30238.01)) at 37° C. and 5% $C0_2$. The cells were treated with antisense oligonucleotides using one of the following methods. For the Next Day Method, one day before the experiment the cells were replated at the density of approximately 3×105/well into 6 well plates in Growth Media and incubated at 37° C. and 5% C(¾ overnight. Next day, the media in the 6 well plates was changed to fresh Growth Media (1.5 ml/well) and the cells were dosed with antisense oligonucleotides. All antisense oligonucleotides were manufactured by IDT Inc. (Coralville, Iowa) or Exiqon (Vedbaek, Denmark). The sequences for all oligonucleotides are listed in Table 1. Stock solutions of oligonucleotides were diluted to the concentration of 20 uM in DNAse RNAse-free sterile water. To dose one well, 2 μï of this solution was incubated with 400 μï of Opti-MEM media (Gibco cat #31985-070) and 4 µï; of Lipofectamine 2000 (Invitrogen cat #11668019) at room temperature for 20 min and applied dropwise to one well of a 6 well plate with cells. Similar mixture including 2 µï of water instead of the oligonucleotide solution was used for the mock-transfected controls. Additionally an inactive oligonucleotide CUR-1462 at the same concentration was used as control. After about 18 h of incubation at 37° C. and 5% $C0_2$ the media was changed to fresh Growth Media. Forty eight hours after addition of antisense oligonucleotides the media was removed and RNA was extracted from the cells using SV Total RNA Isolation System from Promega (cat # Z3105) following the manufacturers' instructions. Six hundred nanograms of purified total RNA was added to the reverse transcription reaction performed using Superscript VILO cDNA Synthesis Kit from Invitrogen (cat #11754-250) as described in the manufacturer's protocol. The cDNA from this reverse transcription reaction was used to monitor gene expression by real time PCR using ABI Taqman Gene Expression Mix (cat #4369510) and primers probes designed by ABI (assays Hs00374696_ml, Hs00897350_ml or Hs00897341_ml for human SCN1A). Results obtained using all three assays were very similar. The following PCR cycle was used: 50° C. for 2 min, 95° C. for 10 min, 40 cycles of (95° C. for 15 seconds, 60° C. for 1 min) using StepOne Plus Real Time PCR system (Applied Biosystems). The assay for 18S was manufactured by ABI (cat #4319413E). Fold change in gene expression after treatment with antisense oligonucleotides was calculated based on the difference in 18S-normalized dCt values between treated and mock-transfected samples. For the alternative Same Day Method all procedures were performed similarly, but cells were dosed with antisense oligonucleotides on the first day, immediately after they were distributed into 6-well plates.

CHP-212 cell line. CHP-212 human neuroblastoma cells from ATCC (cat* CRL-2273) were grown in growth media (1: mixture of MEM and F12 (ATCC cat #30-2003 and Mediatech cat #10-080-CV respectively) +10% FBS (Mediatech cat # MT35-011-CV)+penicillin/streptomycin (Mediatech cat # MT30-002-CI)) at 37° C. and 5% $C0_2$. The cells were treated with antisense oligonucleotides using one of the following methods. For the Next Day Method, one day before the experiment the cells were replated at the density of approximately 2×105/well into 6 well plates in Growth Media and incubated at 37° C. and 5% C02 overnight. Next day, the media in the 6 well plates was changed to fresh Growth Media (1.5 ml/well) and the cells were dosed with antisense oligonucleotides. All antisense oligonucleotides were manufactured by IDT Inc. (Coralville, Iowa) or Exiqon (Vedbaek, Denmark). The sequences for all oligonucleotides are listed in Table 1. Stock solutions of oligonucleotides were diluted to the concentration of 20 µM in DNAse RNAse-free sterile water. To dose one well, 2µï; of this solution was incubated with 400 µï of Opti-MEM media (Gibco cat #31985-070) and 4 µï of Lipofectamine 2000 (Invitrogen cat #11668019) at room temperature for 20 min and applied dropwise to one well of a 6 well plate with cells. Similar mixture including 2 µï of water instead of the oligonucleotide solution was used for the mock-transfected controls. Additionally an inactive oligonucleotide CUR-1462 at the same concentration was used as control. After about 18 h of incubation at 37° C. and 5% $CO_2$ the media was changed to fresh Growth Media. Forty eight hours after addition of antisense oligonucleotides the media was removed and RNA was extracted from the cells using SV Total A Isolation System from Promega (cat # Z3105) following the manufacturers' instructions. Six hundred nanograms of purified total RNA was added to the reverse transcription reaction performed using Superscript VILO cDNA Synthesis Kit from Invitrogen (cat #1 1754-250) as described in the manufacturer's protocol. The cDNA from this reverse transcription reaction was used to monitor gene expression by real time PCR using ABI Taqman Gene Expression Mix (cat #4369510) and primers/probes designed by ABI (assays Hs00374696_ml, Hs00897350_ml or Hs00897341_ml for human SCNIA). Results obtained using all three assays were very similar. The following PCR cycle was used: 50° C. for 2 min, 95° C. for 10 min, 40 cycles of (95° C. for 15 seconds, 60° C. for 1 min) using StepOne Plus Real Time PCR system (Applied Biosystems). The assay for 18S was manufactured by ABI (cat #4319413E). Fold change in gene expression after treatment with antisense oligonucleotides was calculated based on the difference in 18S-normalized dCt values between treated and mock-transfected samples. For the alternative Same Day Method all procedures were performed similarly, but cells were dosed with antisense oligonucleotides on the first day, immediately after they were distributed into 6-well plates.

Vero76 cell line. Vero76 African green monkey embryonic kidney cells from ATCC (cat # CRL-1587) were grown in growth media (Dulbecco's Modified Eagle's Medium (Cellgrow 10-013-CV)+5% FBS (Mediatech cat # MT35-011-CV)+penicillin/streptomycin (Mediatech cat # MT30-002-CI)) at 37° C. and 5% $C0_2$. The cells were treated with antisense oligonucleotides using one of the following methods. For the Next Day Method, one day before the experiment the cells were replated at the density of approximately 105/well into 6 well plates in Growth Media and incubated at 37° C. and 5% $C0_2$ overnight. Next day, the media in the 6 well plates was changed to fresh Growth Media (1.5 ml/well) and the cells were dosed with antisense oligonucleotides. All antisense oligonucleotides were manufactured by IDT Inc. (Coralville, Iowa) or Exiqon (Vedbaek, Denmark). The sequences for all oligonucleotides are listed in Table 1. Stock solutions of oligonucleotides were diluted to the concentration of 20 µM in DNAse RNAse-free sterile water. To dose one well, 2µï; of this solution was incubated with 400 µï of Opti-MEM media (Gibco cat #31985-070) and 4 µï of Lipofectamine 2000 (Invitrogen cat #1166801) at room temperature for 20 min and applied dropwise to one well of a 6 well plate with cells. Similar mixture including 2 µï of water instead of the oligonucleotide solution was used for the mock-transfected controls. Additionally an inactive oligonucleotide CUR-1462 at the same concentration was used as control. After about 18 h of incubation at 37° C. and 5% CO2 the media was changed to fresh Growth Media. Forty eight hours after addition of antisense oligonucleotides the media was removed and RNA was extracted from the cells using SV Total RNA Isolation System from Promega (cat # Z3105) following the manufacturers' instructions. Six hundred nanograms of purified total RNA was added to the reverse transcription reaction performed using Superscript VILO cDNA Synthesis Kit from Invitrogen (cat #1 1754-250) as described in the manufacturer's protocol. The cDNA from this reverse transcription reaction was used to monitor gene expression by real time PCR using ABI Taqman Gene Expression Mix (cat #4369510) and primers/probes designed by ABI (assays Hs00374696_ml, Hs00897350_ml or Hs00897341_ml for human SCN1A). The following PCR cycle was used: 50° C. for 2 min, 95° C. for 10 min, 40 cycles of (95° C. for 15 seconds, 60° C. for 1 min) using StepOne Plus Real Time PCR system (Applied Biosystems). The assay for 18S was manufactured by ABI (cat #4319413E). Fold change in gene expression after treatment with antisense oligonucleotides was calculated based on the difference in 18S-normalized dCt values between treated and mock-transfected samples. For the alternative Same Day Method all procedures were performed similarly, but cells were dosed with antisense oligonucleotides on the first day, immediately after they were distributed into 6-well plates.

3T3 cell line. 3T3 mouse embryonic fibroblast cells from ATCC (cat # CRL-1658) were grown in Growth Media (Dulbecco's Modified Eagle's Medium (Cellgrow 10-013-CV)+10% Fetal Calf Serum (Cellgrow 35-22-CV)+-penicillin/streptomycin (Mediatech cat # MT30-002-CI)) at 37° C. and 5% CO2. The cells were treated with antisense oligonucleotides using one of the following methods. For the Next Day Method, one day before the experiment the cells were replated at the density of approximately 105/well into 6 well plates in Growth Media and incubated at 37° C. and 5% $CO_2$ overnight. Next day, the media in the 6 well plates was changed to fresh Growth Media (1.5 ml/well) and the cells were dosed with antisense oligonucleotides. All antisense oligonucleotides were manufactured by IDT Inc. (Coralville, Iowa) or Exiqon (Vedbaek, Denmark). The sequences for all oligonucleotides are listed in Table 1. Stock solutions of oligonucleotides were diluted to the concentration of 20 uM in DNAse RNAse-free sterile water. To dose one well, 2µï of this solution was incubated with 400 µï of Opti-MEM media (Gibco cat #31985-070) and 4 µï of Lipofectamine 2000 (Invitrogen cat #11668019) at room temperature for 20 min and applied dropwise to one well of a 6 well plate with cells. Similar mixture including 2 µï of water instead of the oligonucleotide solution was used for the mock-transfected controls. Additionally an inactive oligonucleotide CUR-1462 at the same concentration was used as control. After about 18 h of incubation at 37° C. and 5% $C0_2$ the media was changed to fresh Growth Media, Forty eight hours after addition of antisense oligonucleotides the media was removed and RNA was extracted from the cells using SV Total RNA Isolation System from Promega (cat # Z3105) following the manufacturers' instructions. Six hundred nanograms of purified total RNA was added to the reverse transcription reaction performed using Superscript VILO cDNA Synthesis Kit from Invitrogen (cat #1 1754-250) as described in the manufacturer's protocol. The cDNA from this reverse transcription reaction was used to monitor gene expression by real time PCR using ABI Taqman Gene Expression Mix (cat #4369510) and primers/probes designed by ABI (assays Hs00374696_ml, Hs00897350_ml or Hs00897341_ml for human SCN1A). Results obtained using all three assays were very similar. The following PCR cycle was used: 50° C. for 2 min, 95° C. for 10 min, 40 cycles of (95° C. for 15 seconds, 60° C. for 1 min) using StepOne Plus Real Time PCR system (Applied Biosystems). The assay for 18S was manufactured by ABI (cat #4319413E). Fold change in gene expression after treatment with antisense oligonucleotides was calculated based on the difference in 18S-normalized dCt values between treated and mock-transfected samples. For the alternative Same Day Method all procedures were performed similarly, but cells were dosed with antisense oligonucleotides on the first day, immediately after they were distributed into 6-well plates.

HepG2 cell line. HepG2 human hepatocellular carcinoma cells from ATCC (cat # HB-8065) were grown in growth media (MEM EBSS (Hyclone cat #SH30024, or Mediated, cat # MT-10-O1O-CV)+10% FBS (Mediated. cat # MT35-011-CV)+penicillin/streptomycin (Mediatech cat # MT30-002-CI)) at 37° C. and 5% C<¾. The cells were treated with antisense oligonucleotides using one of the following methods. For the Next Day Method, one day before the experiment the cells were replated at the density of approximately 3×105/well into 6 well plates in Growth Media and incubated at 37° C. and 5% $C0_2$ overnight. Next day, the media in the 6 well plates was changed to fresh Growth Media (1.5 ml/well) and the cells were dosed with antisense oligonucleotides. All antisense oligonucleotides were manufactured by IDT Inc. (Coralville, Iowa) or Exiqon (Vedbaek, Denmark). The sequences for all oligonucleotides are listed in Table 1. Stock solutions of oligonucleotides were diluted to the concentration of 20 µM in DNAse RNAse-free sterile water. To dose one well, 2 µï of this solution was incubated with 400 µï of Opti-MEM media (Gibco cat #31985-070) and 4 µï of Lipofectamine 2000 (Invitrogen cat #11668019) at room temperature for 20 min and applied dropwise to one well of a 6 well plate with cells. Similar mixture including 2µï of water instead of the oligonucleotide solution was used for the mock-transfected controls. Additionally an inactive oligonucleotide CUR-1462 at the same concentration was used as control. After about 18 h of incubation at 37° C. and 5% $C0_2$ the media was changed to fresh Growth Media. Forty eight hours after addition of antisense oligonucleotides the media was removed and RNA was extracted from the cells using SV Total RNA Isolation System from Promega (cat # Z3105) following the manufacturers' instructions. Six hundred nanograms of purified total RNA was added to the reverse transcription reaction performed using Superscript VILO cDNA Synthesis Kit from Invitrogen (cat #1 1754-250) as described in the manufacturer's protocol. The cDNA from this reverse transcription reaction was used to monitor gene expression by real time PCR using ABI Taqman Gene Expression Mix (cat #4369510) and primers/probes designed by ABI (assays Hs00374696_ml, Hs00897350_ml or Hs00897341_ml for human SCN1A). Results obtained using all three assays were very similar. The following PCR cycle was used: 50° C. for 2 min, 95° C. for 10 min, 40 cycles of (95° C. for 15 seconds, 60° C. for 1 min) using StepOne Plus Real Time PCR system (Applied Biosystems). The assay for 18S was manufactured by ABI (cat #4319413E). Fold change in gene expression after treatment with antisense oligonucleotides was calculated based on the difference in 18S-normalized dCt values between treated and mock-transfected samples. For the alternative Same Day Method all procedures were performed similarly, but cells were dosed with antisense oligonucleotides on the first day, immediately after they were distributed into 6-well plates.

Results.

SCNIA mR A levels in different cell lines after treatment with 20 nM of antisense oligonucleotides compared to mock-transfected control are shown in Table 2. As seen from the data some of the oligonucleotides when applied at 20 nM were highly active at upregulating the levels of SCNIA mRNA and showed upregulation consistently in several species (human, African green monkey and mouse), in cell lines derived from different organs/cell types (liver, kidney, brain, embryonic fibroblasts) and primary skin fibroblasts carrying the SCNIA mutation. Upregulation of SCNIA protein in cells carrying the Dravet mutation supports the suitability of the method for the treatment of diseases associated with mutations in SCNIA gene. Some of the oligonucleotides designed against the natural antisense sequence did not affect or only marginally affected the SCNIA mRNA levels in all, or some, of the cell lines tested. These differences are in agreement with literature data which indicates that binding of oligonucleotides may depend on the secondary and tertiary structures of the oligonucleotide's target sequence. Notably the SCNIA levels in cells treated with an oligonucleotide with no homology to the SCNIA natural antisense sequence but of similar chemistry (CUR-1462) are not significantly different from mock transfected control which confirms that the effects of the targeted oligonucleotides do not depend on the non-specific toxicity of these molecules.

Example 4: Dose-Dependency of SCNA mRNA Upregulation in Different Cell Lines by Treatment with Antisense Oligonucleotides Targeting SCNA-Specific Natural Antisense Transcript In Example 4 antisense oligonucleotides of different chemistries targeting SCNA-specific natural antisense transcript were screened in a panel of various cell lines at final concentrations ranging from 5 to 80 nM. The cell lines used originated from different organs and different animal species. The data below confirms that the degree of upregulation of SCNA mRNA through modulation of the function of the SCNA-specific natural antisense transcript can be varied by applying varying amounts of active oligonucleotides.

Materials and Methods

SK-N-AS, Vero 76 and primary human fibroblasts carrying a Dravet mutation were treated with antisense oligonucleotides as described in Example 2 with the exception of oligonucleotide and Lipofectamine 2000 concentrations used to treat each well. The oligonucleotide and Lipofectamine 2000 concentrations were adjusted so as to ensure the final oligonucleotide concentrations of 5, 10, 20, 40 and 80 nM and the ratio of Lipofectamine 2000 to 20 μM oligonucleotide stock solution of 2:1 (v:v).

Results.

Figure 3:
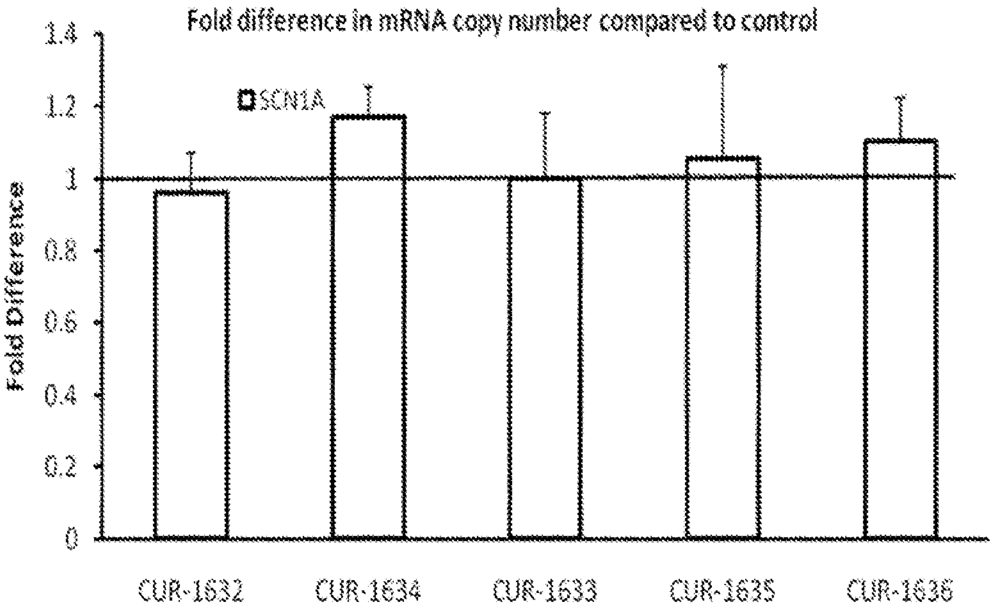
FIG. 3 is a graph of real time PCR results showing the fold change+standard deviation in SCNIA mRNA after treatment of HepG2 cells with phosphorothioate oligonucleotides introduced using Lipofectamine 2000, as compared to control. Bars denoted as CUR-1632 to CUR-1636 correspond to samples treated with SEQ ED NOS: 38 to 42 respectively.
Figure 4:
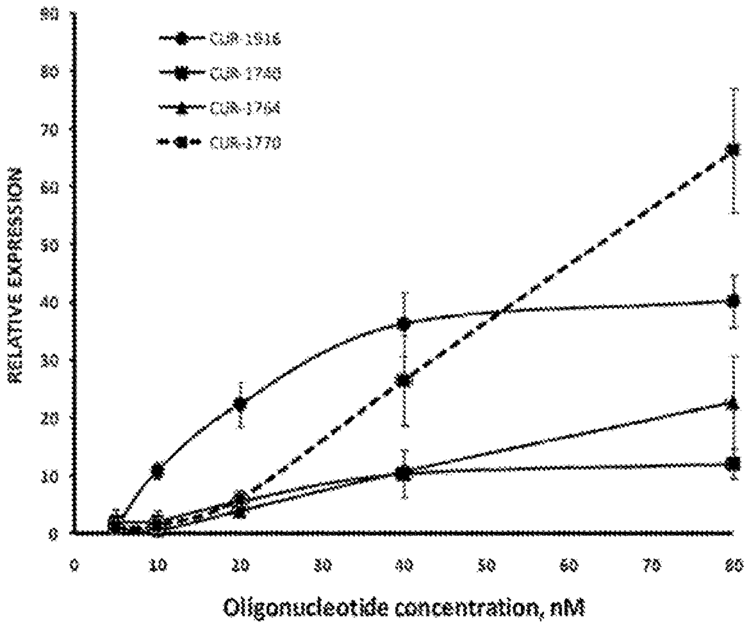
FIG. 4 shows dose-dependent up regulation of SCNIA mRNA in primary human skin fibroblasts carrying a Dravet syndrome-associated mutation. CUR-1916, CUR-1740, CUR-1764 and CUR-1770 correspond to samples treated with SEQ ID NOS: 70, 45, 52 and 57 respectively.
Figure 5:
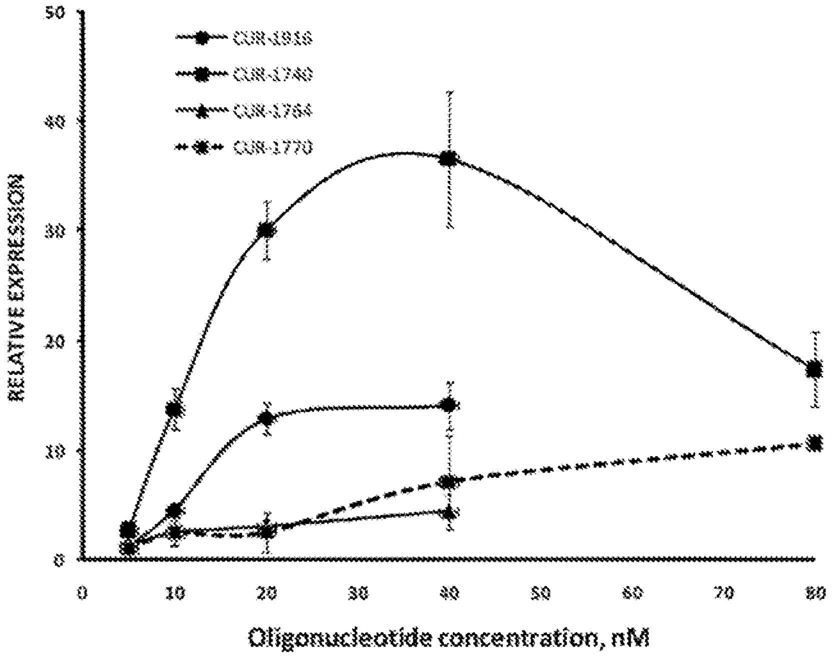
FIG. 5 shows dose-dependent upregulation of SCNIA mRNA in SK-N-AS cells. CUR-1916, CUR-1740, CUR-1764 and CUR-1770 correspond to samples treated with SEQ ID NOS: 70, 45, 52 and 57 respectively.
Figure 6:
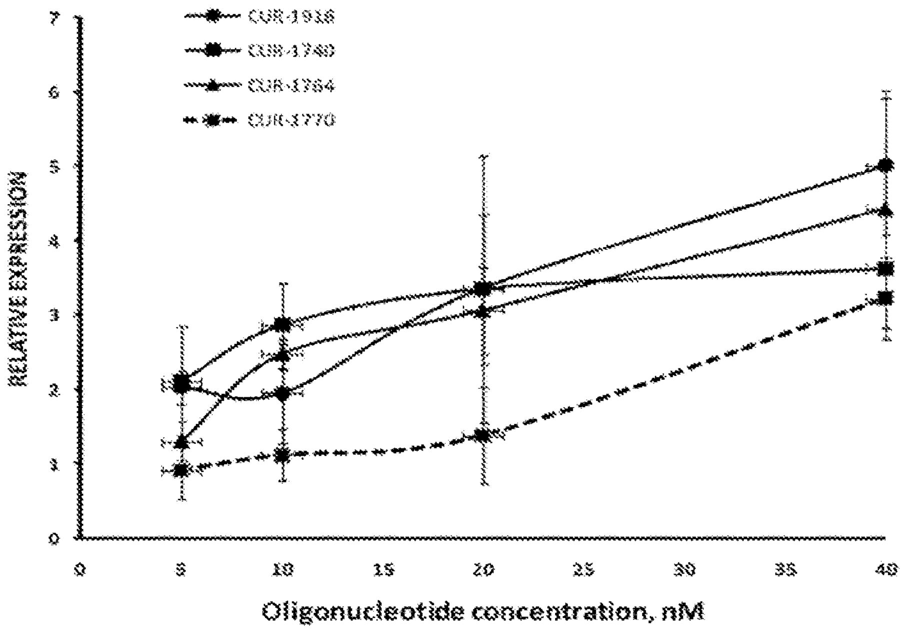
FIG. 6 shows dose-dependent upregulation of SCNIA mRNA in Vero76 cells. CUR-1916, CUR-1740, CUR-1764 and CUR-1770 correspond to samples treated with SEQ ID NOS: 70, 45, 52 and 57 respectively.

The results of dose response experiments have confirmed that the antisense oligonucleotides targeted against SCNIA-specific natural antisense RNA can induce dose-dependent upregulation of SCNIA mRNA (FIG. 1-3). In some cases this upregulation was very potent (up to 60-fold) at higher doses (FIG. 1-3). The degree of upregulation induced by the same nucleotide in different cell lines appeared to be different, for example upregulation achieved in primary fibroblasts at 40 nM was at the level of 10-40 fold, while upregulation in Vero 76 cells by the same oligonucleotides at the same concentration was 2-6 fold (FIG. 1 vs FIG. 3). These differences could be due to different transfection efficiency of different cell lines and or various feedback pathways expressed by them. The effect of most oligonucleotides reached plateau at about 40 nM, with the exception of CUR-1764 and CUR-1770 in SCNIA fibroblasts and all oligonucleotides tested in Vero 76 cells where the plateau was not reached at the highest concentration tested (FIG. 1-3).

Example 5: Sequence Specificity of the SCNA mRNA Upregulation by Antisense Oligonucleotides Targeting SCNA-Specific Natural Antisense Transcript In Example 5 antisense oligonucleotides targeting SCN1A-specific natural antisense transcript were tested in experiments designed to confirm the independence of the SCN1 A upregulation caused by the oligonucleotides from the non-specific toxicity associated with the oligonucleotide chemistry used. The data below confirms that the degree of upregulation of SCN1 A mRNA through modulation of the function of the SCN1 A-specific natural antisense transcript only depends on the amounts of active oligonucleotides, and not on the total amount of molecules of similar chemistry.

Materials and Methods

Vero 76 and primary human fibroblasts carrying a Dravet mutation were treated with antisense oligonucleotides as described in Example 2 with the exception of oligonucleotide concentrations used to treat each well. The active oligonucleotide was co-administered with an inactive oligonucleotide of similar chemistry but with no known target in the human genome (CUR-1462) and no effect on the expression of multiple genes tested (data not shown). The total amount of oligonucleotides as well as the amount of Lipofectamine 2000 were kept constant while the proportion of the active oligonucleotide in the mix was varied. The oligonucleotide concentrations were adjusted so as to ensure the final active oligonucleotide concentrations of 5, 10, 20 and 40 nM and the total oligonucleotide concentration (active+inactive) of 40 nM.

Figure 7:
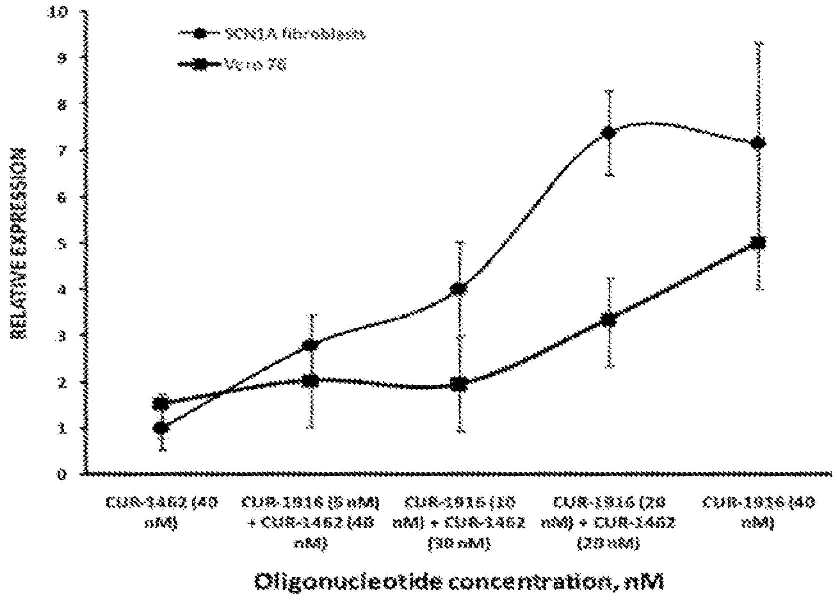
FIG. 7 shows that upregulation of SCNIA mRNA is not caused by non-specific toxicity of antisense oligonucleotides. A—upregulation by CUR-1916; B—upregulation by CUR-1770. CUR-1462 is an inactive control oligonucleotide of similar chemistry.
Figure 7:
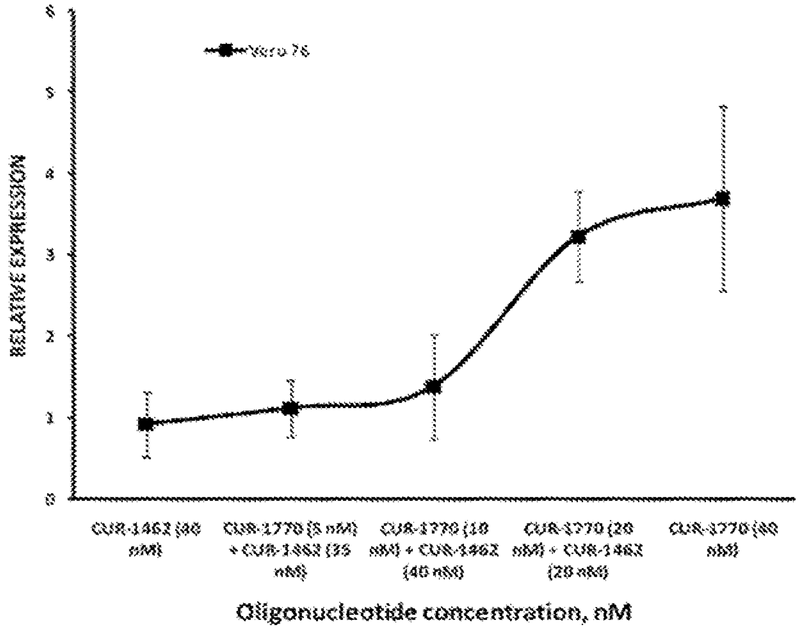

As seen from the data (FIG. 7), the dose-dependent effect of oligonucleotides targeted against SCN1 A natural antisense did not result from the non-specific toxicity potentially associated with such molecules. The SCN1A mRNA levels depended on the dose of the active oligonucleotide used to treat them (FIG. 7).

Example 6: Target Specificity of the SCNA mRNA Upregulation by Antisense Oligonucleotides Targeting SCNA-Specific Natural Antisense Transcript In Example 6 antisense oligonucleotides targeting SCN1A-specific natural antisense transcript were tested in experiments designed to confirm the specificity of their target, i.e. SCN1A. The data below confirms that the upregulation of SCN 1 A mRNA through modulation of the function of the SCN 1 A-specific natural antisense transcript was limited to the SCN1A mRNA and did not affect the related sodium channels SCN9A, SCN8A, SCN7A, SCN3A and SCN2A.

Materials and Methods

Vero 76 and primary human fibroblasts carrying a Dravet mutation were treated with antisense oligonucleotides as described in Example 3. Post-treatment the isolated RNA was analyzed as described in Example 2 with the exception that the Taqman gene expression assays used to run the real time PCR detected mRNA for SCN9A, SCN8A, SCN7A, SCN3A and SCN2A channels. The assays for alpha subunits of human SCN9A, SCN8A, SCN7A, SCN3A and SCN2A channels were obtained from ABI Inc. (cat # Hs00161567_ml, Hs00274075_ml, Hs00161546_ml, Hs00366902_ml, and Hs00221379_ml respectively).

Results.

Figure 8:
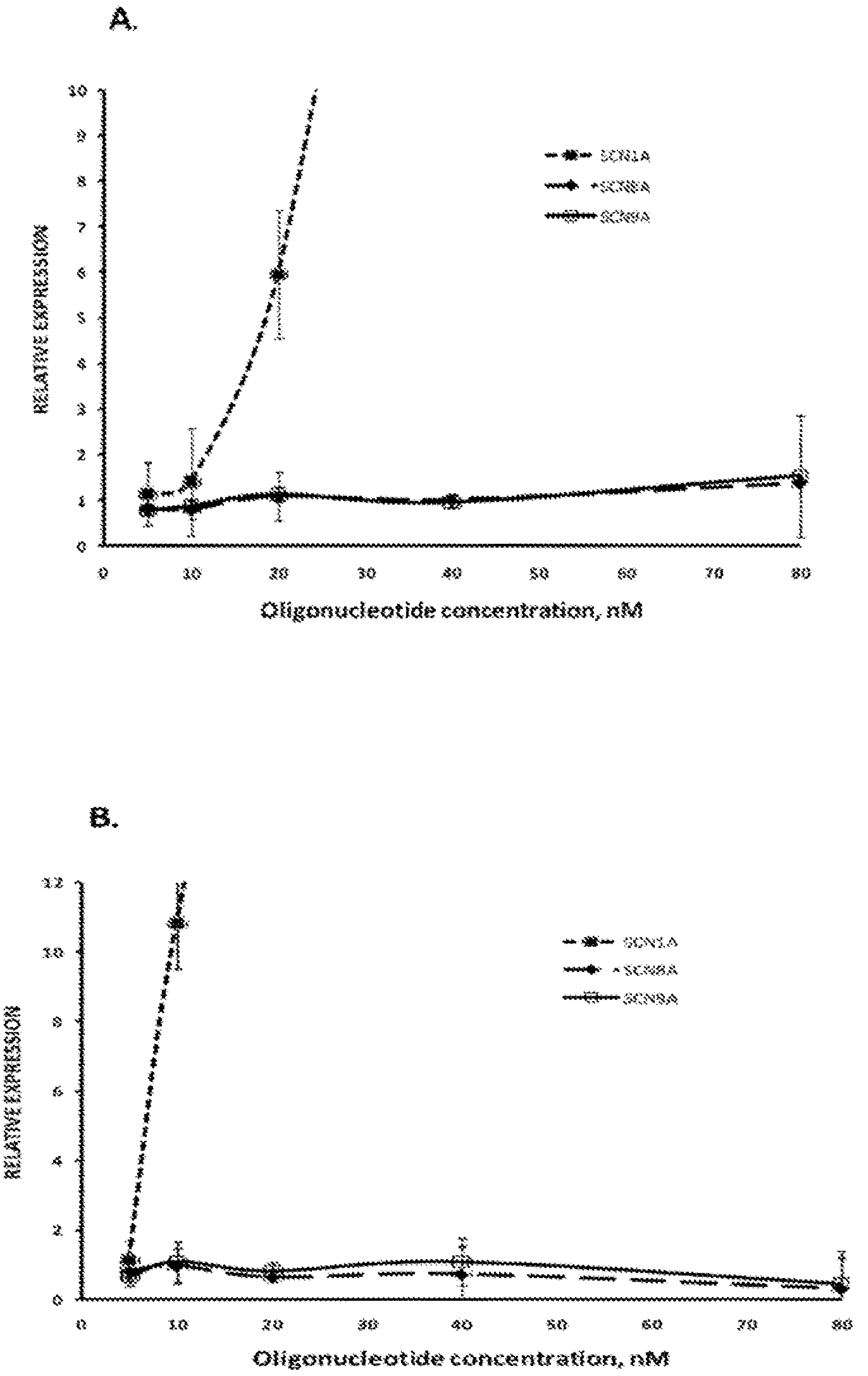
FIG. 8 shows that expression of the SCN8A and SCN9A channels in human fibroblasts carrying a Dravet-associated mutation is not significantly affected by the treatment with antisense oligonucleotides targeted against SCNIA natural antisense transcript. A—treatment with CUR-1770; B—treatment with CUR-1916.

As shown in FIG. 8, treatment with oligonucleotides CUR-1916 and CUR-1770 did not significantly affect the expression of SCN8A and SCN9A channels in human fibroblasts carrying Dravet mutation. Expression of SCN7A, SCN3A and SCN2A channels was undetectable in these cells before or after treatment (data not shown). The data confirms the specificity of the gene expression modulation using oligonucleotides directed against the natural antisense RNA for a given gene.

Example 7: Stability of Antisense Oligonucleotides Targeting SCNA-Specific Natural Antisense Transcript In Example 7 two batches of an antisense oligonucleotide targeting SCN1A-specific natural antisense transcript were tested in experiments designed to check its stability after storage in a dilute (1 mM) aqueous solution at 4° C. The data below shows that the oligonucleotides can be stable in these conditions for periods of at least 6 months without significant loss of activity.

Materials and Methods

Veto 76 cells were treated with two different batches of an antisense oligonucleotide as described in Example 2. The batches were synthesized in August 2010 and March 2011. The oligonucleotide synthesized in August 2010 was stored as a 1 mM aqueous solution at 4° C. The oligonucleotide synthesized in March 2011 was shipped in lyophilized form within 3 days after synthesis and tested immediately upon arrival.

Figure 9:
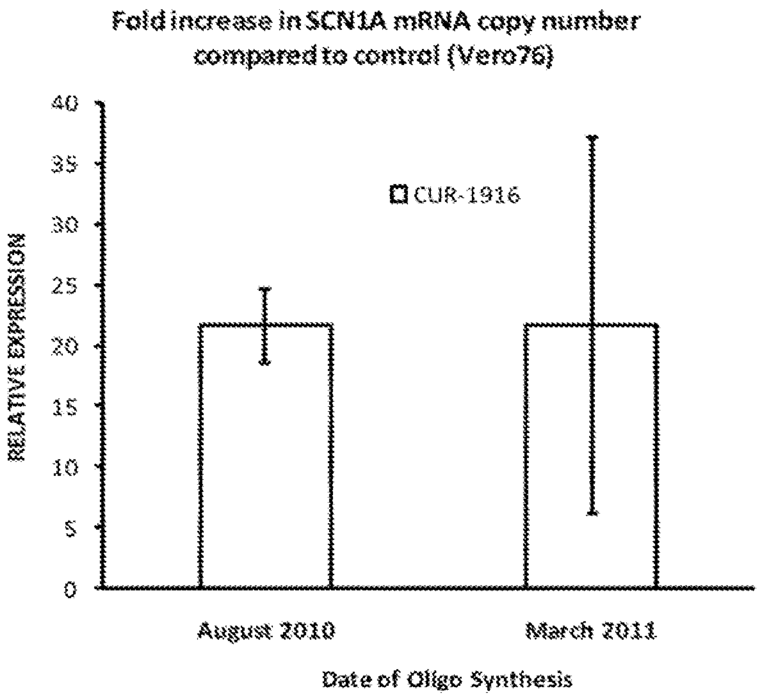
FIG. 9 shows stability of antisense oligonucleotides targeting SCN1A-specific natural antisense transcript. Vero 76 cells were treated as described in Example 2 with two different batches of CUR-1916 synthesized in August 2010 and March 2011. The oligonucleotide synthesized in August 2010 was stored as a 1 mM aqueous solution at 4° C. The oligonucleotide synthesized in March 2011 was shipped in lyophilized form and tested immediately upon arrival.

Results:

As shown in FIG. 9 there was no significant loss of biological activity after a 6 month long storage of the oligonucleotides in aqueous solution at 4° C.

Example 8: SCNA Protein Upregulation in Primary Human Fibroblasts Carrying a Dravet Syndrome-Associated Mutation Treated with Antisense Oligonucleotides Targeting SCNA-Specific Natural Antisense Transcript The purpose of this experiment was to rank the antisense oligonucleotides CUR-1740, CUR-1770 and CUR-1916 according to their ability to upregulate the SCNA protein expression in fibroblast cells carrying a Dravet syndrome-associated mutation.

Materials and Methods

Fibroblasts carrying a Dravet syndrome-associated mutation introduced into culture by Dr. N. Kenyon (University of Miami) were grown in Growth Media consisting of a-MEM (Gibco, cat: 12561-056)+10% FBS (Mediatech, cat: 35-015 CV)+1% Antimycotic-Antibiotic (Gibco, cat: 15240-062) at 37° C. and 5% CO2. The cells were treated with antisense oligonucleotides using one of the following methods. For the Next Day Method, one day before the experiment the cells were replated at the density of approximately $4\times10^4$/well into 24 well plates in Growth Media and incubated at 37° C. and 5% CO2 overnight. Next day, the media in the 24 well plates was changed to fresh Growth Media (1 ml/well) and the cells were dosed with antisense oligonucleotides CUR-1740, CUR-1770 and CUR-1916. All antisense oligonucleotides were manufactured by IDT Inc. (Coralville, La.) or Exiqon (Vedbaek, Denmark). The sequences for oligonucleotides CUR-1740, CUR-1770 and CUR-1916 are listed in Table 1. Stock solutions of oligonucleotides were diluted to the concentration of 20 uM in DNAse RNAse-free sterile water. To dose one well at a final concentration of 20 nM, 1µï of the 20 uM oligonucleotide stock solution was incubated with room temperature for 20 min and applied dropwise to one well of a 24 well plate with cells. To achieve final concentrations of 5, 10, 40 and 80 nM the volumes of the 20 µM oligonucleotide stock used were adjusted accordingly. The ratio of the 20 µM oligonucleotide stock solution to Lipofectamine 2000 was 1:2 (v:v). Similar mixture including 8 µï of water instead of the oligonucleotide solution and the corresponding volume of Lipofectamine 2000 was used for the mock-transfected controls. After about 18 h of incubation at 37° C. and 5% $C0_2$ the media was changed to fresh Growth Media. Forty eight hours after addition of antisense oligonucleotides the media was removed and cells were washed 3 times with Dulbecco's phosphate-buffered saline without calcium and magnesium (PBS) (Mediated. cat #21-031-CV). Then PBS was discarded and the cells were fixed in the 24 well plate using 300 µï of 100% methanol for 15 min at −20° C. After removing the methanol and washing with PBS, the cells were incubated with 3% hydrogen peroxide (Fisher Chemical cat #H325-100) for 5 min at 21° C. The cells were washed three times for 5 min with PBS, then incubated with 300 µï of bovine serum albumin (BSA) (Sigma cat # A-9647) at 0.1% in PBS for 30 min at 21° C. The cells were washed three times for 5 min with PBS then incubated with 300 µï of avidin solution (Vector Laboratories cat # SP-2001) for 30 min at 21° C. The cells were briefly rinsed three times with PBS then incubated with biotin solution (Vector Laboratories cat # SP-2001) for 30 min at 21° C. The cells were washed three times with PBS and then incubated overnight at 4° C. with 300 µï per well of rabbit antibody against human SCN1A (Abeam cat # ab24820) diluted at 1:250 in PBS BSA 0.1%. After equilibrating the plate for 5 min at 21° C., the cells were washed three times 5 min each with PBS then incubated with goat anti-rabbit antibody diluted 1:200 in PBS BSA 0.1% for 30 min at 21° C. The cells were washed three times 5 min with PBS and then incubated with 300 µï of Vectastain Elite ABC reagent A+B solution (Vector Laboratories cat # PK-6101) for 30 min; the Vectastain Elite ABC reagent A+B solution was prepared at 21° C. 30 min before incubation with the cells by adding and mixing successively 2 drops of reagent A to 5 ml of PBS and then 2 drops of reagent B. The cells were washed 3 times 5 min each with PBS at 21° C. and then incubated with Dianiinobenzidine (DAB) peroxidase substrate solution (Vector Laboratories cat # SK-4105) until cells are stained; the DAB peroxidase substrate solution is reconstituted before being added to the cells by mixing 1 ml of ImmPACT™ DAB Diluent with 30 µï of ImmPACT™ DAB Chromogen concentrate. At this time, the cells are briefly washed three times with PBS and 300 µï of PBS is left in each well. The staining of the cells was analyzed directly inside the wells of the 24-well plate using an inverted Nikon Eclipse TSIOO microscope equipped with a Nikon DS-Ril camera coupled with Nikon Digital-Sight equipment on the screen of a Dell Latitude D630 laptop. Photos of individual wells were made using the software provided with the Nikon camera, the NIS-Elements D 3.0.

Results.

Figure 10:
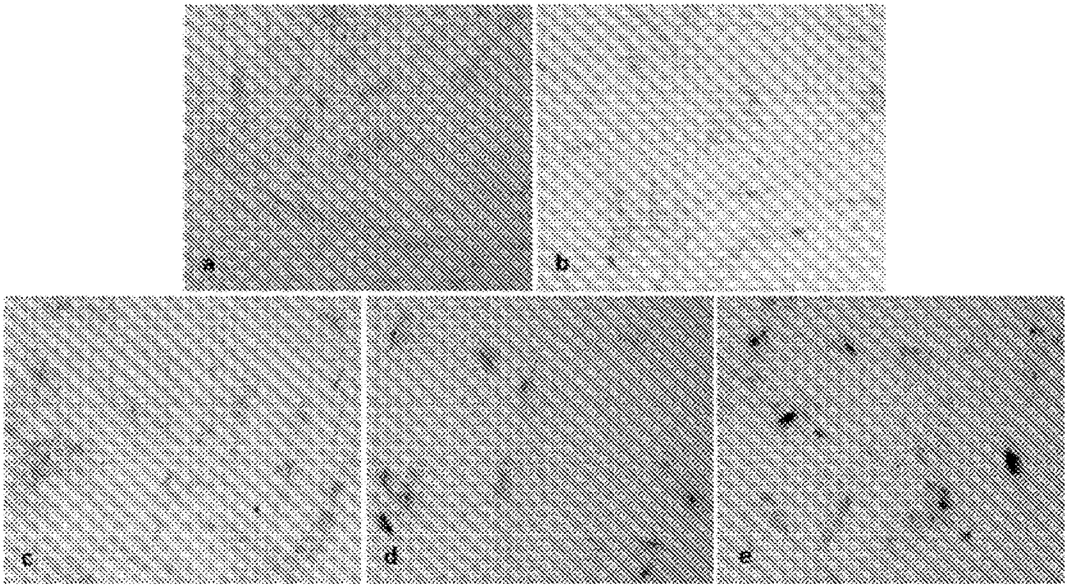
FIG. 10 shows upregulation of SCNIA protein in fibroblasts carrying a Dravet syndrome mutation treated with antisense oligonucleotides complementary to the SCNIA natural antisense. Fibroblasts were grown in 24 well plates and treated with antisense oligonucleotides complementary to the SCN1A natural antisense at 20 nM (panel c: CUR-1740; d: CUR-1770; e: CUR-1916) and at 0 nM (b). The cells were stained for SCN1A (b-c) by indirect immunohistochemistry using an anti-SCNIA antibody (Abeam cat # ab24820) and a secondary antibody staining/amplification with the avidin/biotin method (Vector Laboratories cat # SP-2001; Vector Laboratories cat # PK-6101; Vector Laboratories cat # S-4105); panel a—negative control, a rabbit anti-mouse antibody was used as a primary antibody followed by the same staining procedure as in panels b-e.

All antisense oligonucleotides tested efficiency upregulated SCN1A protein, CUR-1770 and CUR-1916 being the two best (FIG. 10).

Example 9: SCNA Protein Upregulation in SK-N-AS Cells Treated with Antisense Oligonucleotides Targeting SCNA-Specific Natural Antisense Transcript The purpose of this experiment was to rank the antisense oligonucleotides CU-1740, CUR-1764, CUR-1770 and CUR-1916 according to their ability to upregulate the SCN1A protein expression in SK-N-AS cells. SK-N-AS is a human neuroblastoma cell line.

Materials and Methods

SK-N-AS human neuroblastoma cells from ATCC (cat # CRL-2137) were grown in Growth Media (DMEM (Mediatech cat #10-013-CV)+10% FBS (Mediatech cat # MT35-011-CV)+penicillinstreptomycin (Mediatech cat # MT30-002-CI)+Non-Essential Amino Acids (NEAAXHyClone SH30238.01)) at 37° C. and 5% CO2. The cells were treated with antisense oligonucleotides using one of the following methods. For the Next Day Method, one day before the experiment the cells were replated at the density of approximately $5\times10^4$/well into 24 well plates in Growth Media and incubated at 37° C. and 5% $CO_2$ overnight. Next day, the media in the 24 well plates was changed to fresh Growth Media (1 ml/well) and the cells were dosed with antisense oligonucleotides CUR-1740, CUR-1764, CUR-1770 and CUR-1916. All antisense oligonucleotides were manufactured by IDT Inc. (Coralville, Iowa) or Exiqon (Vedbaek, Denmark). The sequences for oligonucleotides CUR-1740, CUR-1764, CUR-1770 and CUR-1916 are listed in Table 1. Stock solutions of oligonucleotides were diluted to the concentration of 20 μM in DNAse RNAse-free sterile water. To dose one well at a final concentration of 20 nM, 1 μï of the 20 μM oligonucleotide stock solution was incubated with 200 μï of Opti-MEM media (Gibco cat #31985-070) and 2 μï of Lipofectamine 2000 (Invitrogen cat #1166801) at room temperature for 20 min and applied dropwise to one well of a 24 well plate with cells. To achieve final concentrations of 5, 10, 40 and 80 nM the volumes of the 20 μM oligonucleotide stock used were adjusted accordingly. The ratio of the 20 μM oligonucleotide stock solution to Lipofectamine 2000 was 1:2 (v:v). Similar mixture including 8 μï of water instead of the oligonucleotide solution and the corresponding volume of Lipofectamine 2000 was used for the mock-transfected controls. After about 18 h of incubation at 37° C. and 5% $C0_2$ the media was changed to fresh Growth Media. Forty eight hours after addition of antisense oligonucleotides the media was removed and cells were washed 3 times with Dulbecco's phosphate-buffered saline without calcium and magnesium (PBS) (Mediatech cat #21-031-CV). Then PBS was discarded and the cells were fixed in the 24 well plate using 300 μï of 100% methanol for 15 min at −20° C. After removing the methanol and washing with PBS, the cells were incubated with 3% hydrogen peroxide (Fisher Chemical cat #H325-100) for 5 min at 21° C. The cells were washed three times for 5 min with PBS then incubated with 300 μï of bovine serum albumin (BSA) (Sigma cat # A-9647) at 0.1% in PBS for 30 min at 21° C. The cells were washed three times for 5 min with PBS then incubated with 300 μï of avidin solution (Vector Laboratories cat # SP-2001) for 30 min at 21° C. The cells were briefly rinsed three times with PBS then incubated with biotin solution (Vector Laboratories cat # SP-2001) for 30 min at 21° C. The cells were washed three times with PBS and then incubated overnight at 4° C. with 300 μï per well of rabbit antibody against human SCN1A (Abeam cat # ab24820) diluted at 1:250 in PBS/BSA 0.1%. After equilibrating the plate for 5 min at 21° C., the cells were washed three times for 5 min each with PBS then incubated with goat anti-rabbit antibody diluted 1:200 in PBS BSA 0.1% for 30 min at 21° C. The cells were washed three times for 5 min with PBS and then incubated with 300 μï of Vectastain Elite ABC reagent A+B solution (Vector Laboratories cat # PK-6101) for 30 min; the Vectastain Elite ABC reagent A+B solution was prepared at 21° C. 30 min before incubation with the cells by adding and mixing successively 2 drops of reagent A to 5 ml of PBS and then 2 drops of reagent B. The cells were washed 3 times for 5 min each with PBS at 21° C. and then incubated with Diaminobenzidine (DAB) peroxidase substrate solution (Vector Laboratories cat # SK-4105) until cells are stained; the DAB peroxidase substrate solution is reconstituted before being added to the cells by mixing 1 ml of ImmPACP$^W$DAB Diluent with 30 ul of TmmPACT™ DAB Chromogen concentrate. At this time, the cells are briefly washed three times with PBS and 300 μï of PBS is left in each well. The staining of the cells was analyzed directly inside the wells of the 24-well plate using an inverted Nikon Eclipse TS100 microscope equipped with a Nikon DS-Ril camera coupled with Nikon Digital-Sight equipment on the screen of a Dell Latitude D630 laptop. Photos of individual wells were made using the software provided with the Nikon camera, the NIS-Elements D 3.0.

Figure 11:
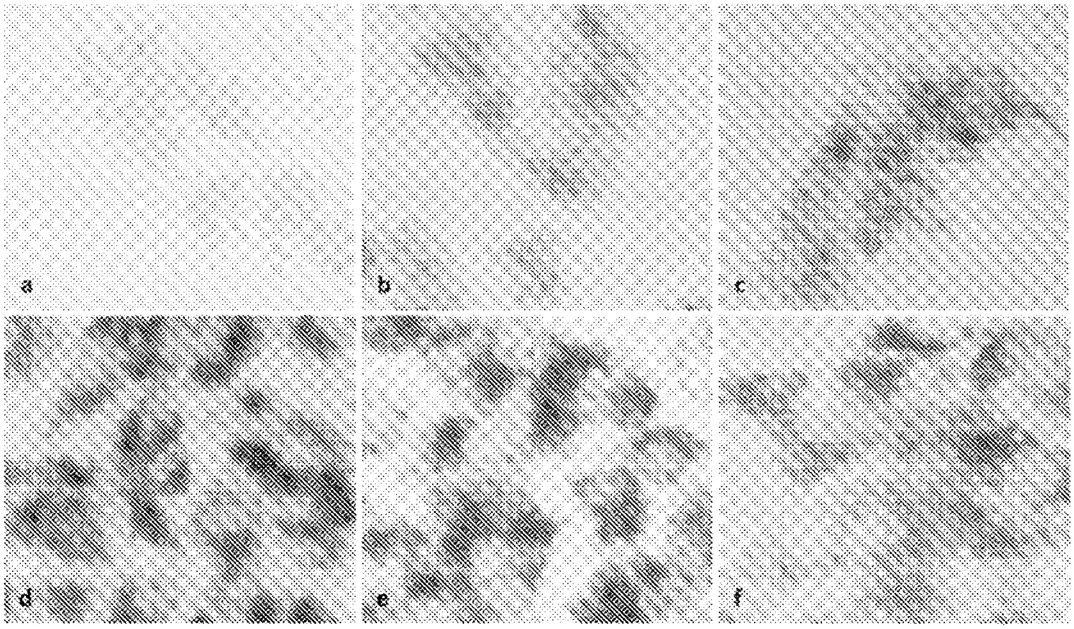
FIG. 11 shows upregulation of SC 1A protein in SK-N-AS cells treated with antisense oligonucleotides complementary to the SCN1A natural antisense. SK-N-AS cells were grown in 24 well plates and treated with oligonucleotides at 20 nM (c: CUR-1740; d: CUR-1764; e: CUR-1770; f: CUR-1916) and at (b: 0 nM). The SK-N-AS cells were stained for SCNIA (b-f) by indirect immunohistochemistry using an anti-SCN1A antibody (Abeam cat # ab24820) and secondary antibody staining/amplification using the avidin/biotin method (Vector Laboratories cat # SP-2001; Vector Laboratories cat # PK-6101; Vector Laboratories cat # SK-4105); as a negative control, a rabbit anti-mouse antibody was used as a primary antibody followed by the same staining procedure as in panels b-f (panel a).

Results:

All antisense oligonucleotide tested upregulated SCN1A protein, CUR-1764 and CUR-1770 being the two best (FIG. 11).

Example 10: SCNA Protein Upregulation in Vero 76 Cells Treated with Antisense Oligonucleotides Targeting SCNA-Specific Natural Antisense Transcript The purpose of this experiment was to rank the antisense oligonucleotides CUR-1740, CUR-1770, CUR-1916, CUR-1924 and CUR-1945 according to their ability to upregulate SCN1A protein expression in Vero 76 cells. The Vero76 is a *Cercopithecus aethiops* (vervet or African green monkey) kidney cell line.

Materials and Methods

Vero76 African green monkey embryonic kidney cells from ATCC (cat # CRL-1587) were grown in growth media (Dulbecco's Modified Eagle's Medium (Cellgrow 10-013-CV)+5% FBS (Mediated. cat # MT35-011-CV)+penicillin/streptomycin (Mediated. cat # MT30-002-CI)) at 37° C. and 5% $C0_2$. The cells were treated with antisense oligonucleotides using one of the following methods. For the Next Day Method, one day before the experiment the cells were replated at the density of approximately $4\times10^4$ well into 24 well plates in Growth Media and incubated at 37° C. and 5% $C0_2$ overnight. Next day, the media in the 24 well plates was changed to fresh Growth Media (1 ml/well) and the cells were dosed with antisense oligonucleotides CUR-1740, CUR-1770 and CUR-1916. All antisense oligonucleotides were manufactured by IDT Inc. (Coralville, La.) or Exiqon (Vedbaek, Denmark). The sequences for oligonucleotides CUR-1740, CUR-1770, CUR-1916, CUR-1924 and CUR-1945 are listed in Table 1. Stock solutions of oligonucleotides were diluted to the concentration of 20 μM in DNAse/RNAse-free sterile water. To dose one well at a final concentration of 20 nM, 1μï of the 20 uM oligonucleotide solution was incubated with 200 μï of Opti-MEM media (Gibco cat #31985-070) and 2 μï of Lipofectarnine 2000 (Invitrogen cat #11668019) at room temperature for 20 min and applied dropwise to one well of a 24 well plate with cells. To achieve final concentrations of 5, 10, 40 and 80 nM the volumes of the 20 μM oligonucleotide stock used were adjusted accordingly. The ratio of the 20 μM oligonucleotide stock solution to Lipofectarnine 2000 was 1:2 (v:v). Similar mixture including 8 μï of water instead of the oligonucleotide solution and the corresponding volume of Lipofectamine 2000 was used for the mock-transfected controls. After about 18 h of incubation at 37° C. and 5% $C0_2$ the media was changed to fresh Growth Media. Forty eight hours after addition of antisense oligonucleotides the media was removed and cells were washed 3 times with Dulbecco's phosphate-buffered saline without calcium and magnesium (PBS) (Mediatech cat #21-031-CV). The PBS was discarded and the Vero 76 cells were fixed in the 24 well plate using 300 μï methanol 100% for 15 min at −20° C. After removing the methanol and washing the cells with PBS, the cells were incubated with 3% hydrogen peroxide (Fisher Chemical cat #H325-100) for 5 min at 21° C. The cells were washed three times for 5 min with PBS then incubated with 300 μl of bovine serum albumin (BSA) (Sigma cat # A-9647) at 0.1% in PBS for 30 min at 21° C. The cells were washed three times for 5 min with PBS then incubated with 300 μï of avidin solution (Vector Laboratories cat # SP-2001) for 30 min at 21° C. The cells were briefly rinsed three times with PBS then incubated with biotin solution (Vector Laboratories cat # SP-2001) for 30 min at 21° C. The cells were washed three times with PBS and then incubated overnight at 4° C. with 300 µï per well of rabbit antibody against human SCN1A (Abeam cat # ab24820) diluted at 1:250 in PBS BSA 0.1%. After equilibrating the plate for 5 min at 21° C., the cells were washed three times 5 min each with PBS then incubated with goat anti-rabbit antibody diluted 1:200 in PBS BSA 0.1% for 30 min at 21° C. The cells were washed three times 5 min with PBS and then incubated with 300 µï of Vectastain Elite ABC reagent A+B solution (Vector Laboratories cat # PK-6101) for 30 min; the Vectastain Elite ABC reagent A+B solution was prepared at 21° C. 30 min before incubation with the cells by adding and mixing successively 2 drops of reagent A to 5 ml of PBS and then 2 drops of reagent B. The cells were washed 3 times 5 min each with PBS at 21° C. and men incubated with Diaminobenzidine (DAB) peroxidase substrate solution (Vector Laboratories cat # SK-4105) until cells are stained; the DAB peroxidase substrate solution is reconstituted before being added to the cells by mixing 1 ml of InimPACTF$^{M}$DAB Diluent with 30 ul of IrnrnPACT™ DAB Chromogen concentrate. At this time, the cells are briefly washed three times with PBS and 300 µï of PBS is left in each well. The staining of the cells was analyzed directly inside the wells of the 24-well plate using an inverted Nikon Eclipse TSIOO microscope equipped with a Nikon DS-Ril camera coupled with Nikon Digital-Sight equipment on the screen of a Dell Latitude D630 laptop. Photos of individual wells were made using the software provided with the Nikon camera, the N1S-ElementsD 3.0.

Results.

Figure 12:
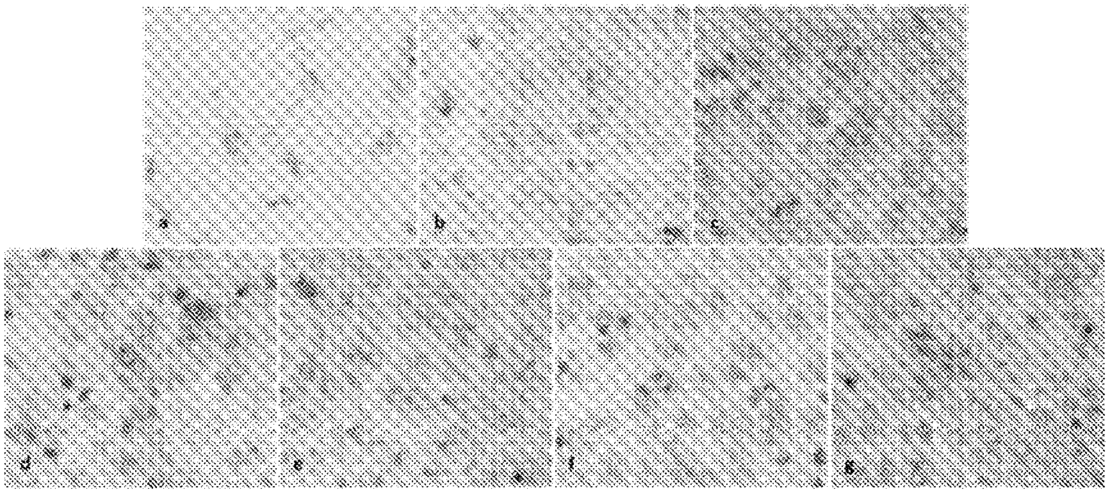
FIG. 12 shows upregulation of SCNIA protein in Vero 76 cells treated with antisense oligonucleotides complementary to the SCNIA natural antisense. Vero 76 cells were grown in 24 well plates and treated with antisense oligonucleotides complementary to the SCNIA natural antisense at 20 nM (c: CUR-1740; d: CUR-1945; e: CUR-1770; f: CUR-1916; g: CUR-1924) and at 0 nM (b). The Vero 76 cells were stained for SCNIA (b-f) by indirect immunohistochemistry using an anti-SCNIA antibody (Abeam cat # ab24820) and secondary antibody staining/amplification with the avidin/biotin method (Vector Laboratories cat # SP-2001; Vector Laboratories cat # PK-6101; Vector Laboratories cat # SK-4105); panel a—as a negative control, a rabbit anti-mouse antibody was used as primary antibody followed by the same staining procedure as in panels b-g.

All antisense oligonucleotides tested upregulated SCN1A protein, CUR-1764 and CUR-1770 producing the highest upregulation (FIG. 12).

Example 11: Oligonucleotides Targeting SCNA-Specific Natural Antisense Transcript Powerful at Upregulating SCNA tnRNA do not Upregulate Actin mRNA in Vero76 Cells The purpose of this experiment was to check whether antisense oligonucleotides (CUR-1924, CUR-1740, CUR-1838) targeting SCN1A-specific natural antisense transcript that were shown to upregulate SCN1A mRNA and protein are able to regulate the mRNA of other non-related genes such as actin in Vero76 African green monkey embryonic kidney cells.

Materials and Methods

Vero76 African green monkey embryonic kidney cell line from ATCC (cat # CRL-1587) was dosed in the same conditions as described in Example 2. The actin mRNA was quantified by real-time PCR as described in Example 2 except that this time primers/probes designed by ABI were specific for actin (cat # Hs99999903_ml). The data is presented in FIG. 13.

Results.

Figure 13:
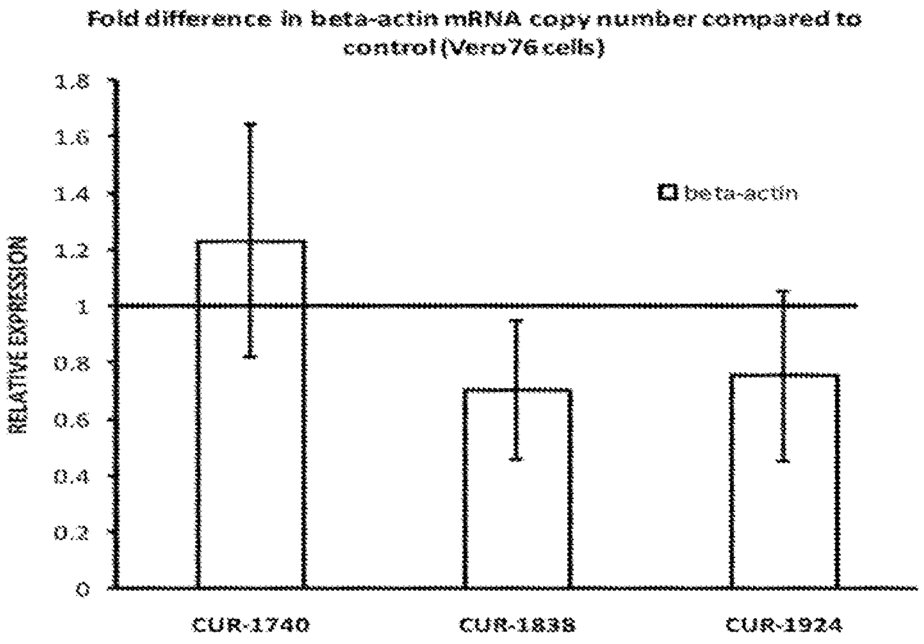
FIG. 13 show that oligonucleotides targeting SCN1A-specific natural antisense transcript that upregulate SCNIA mRNA do not upregulate actin in Vero76 cells. The same antisense oligonucleotides (CUR-1740, CUR-1838, CUR-1924) targeting SCN1A-specific natural antisense transcript that were shown in Examples 5 and 12 to upregulate SCNIA mRNA and protein were tested for their effect on beta-actin mRNA expression in Vero 76 cells. The data confirms that oligonucleotide targeting SCN1A-specific natural antisense transcript do not upregulate a non-related gene such as actin. Bars denoted as CUR-1740, CUR-1838 and CUR-1924 correspond to samples treated with SEQ ID NOS: 45, 62 and 78 respectively.

As shown in FIG. 13, oligonucleotide targeting SCNIA-specific natural antisense transcript (CUR-1924, CUR-1740, CUR-1838) that were shown in Examples 3 and 10 to upregulate SCN1A mRNA and protein in Vero76 cells were tested for their effect on actin mRNA expression in Vero 76 cells. The data in FIG. 13 confirms that the oligonucleotides targeting SCNIA-specific natural antisense transcript do not upregulate a non related gene such as actin. Thus these oligonucleotides are specific in upregulating SCN1 A.

Example 12: Oligonucleotides Targeting SCNA-Specific Natural Antisense Transcript Shown to Upregulate SCNA mRNA and Protein do not Upregulate Actin mRNA in Primary Fibroblasts Carrying a Dravet-Associated Mutation The purpose of this experiment was to check whether antisense oligonucleotides (CUR-1916, CUR-1945) targeting SCNIA-specific natural antisense transcript that were shown to upregulate SCN1 A mRNA and protein are able to regulate the mRNA of other non-related genes such as actin in primary human skin fibroblasts carrying a Dravet syndrome-associated mutation E1099X.

Materials and Methods

Primary human skin fibroblasts carrying a Dravet syndrome-associated mutation E1099X introduced into culture by Dr. NXenyon (University of Miami) were dosed in the same conditions as described in Example 3. The actin mRNA was quantified by real-time PCR as described in Example 3 except that this time primers probes designed by ABI were specific for actin (cat # Hs99999903_ml). The data is presented in FIG. 14.

Figure 14:
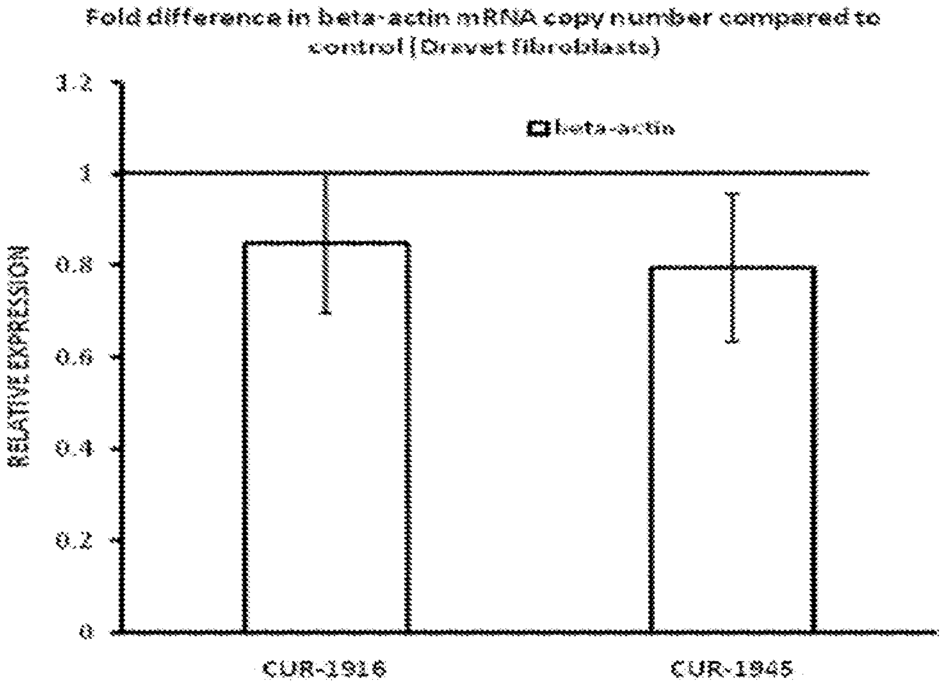
FIG. 14 shows that oligonucleotide targeting SCN1A-specific natural antisense transcript shown to upregulate SCNIA mRNA and protein do not upregulate actin in fibroblasts carrying a Dravet-associated mutation. The oligonucleotides (CUR-1916, CUR-1945) targeting SCN1A-specific natural antisense transcript that were shown in Examples 2 and 7 to upregulate SCNIA mRNA and protein were tested for their effect on actin mRNA expression in fibroblasts carrying a Dravet-associated mutation. The data below confirms that oligonucleotides targeting SCNIA-specific natural antisense transcript do not upregulate a non-related gene such as actin. Bars denoted as CUR-1916, and CUR-1945 correspond to samples treated with SEQ ID NOS: 70 and 93 respectively.

Results:

As shown in FIG. 14 oligonucleotides targeting SCNIA-specific natural antisense transcript do not upregulate a non-related gene such as actin. Thus these oligonucleotides are specific in upregulating SCN1 A.

Example 13: Oligonucleotides Targeting SCNA-Specific Natural Antisense Transcript Shown to Upregulate SCNA mRNA and Protein do not Upregulate Actin mRNA in SK-N-AS Cells The purpose of this experiment was to check whether antisense oligonucleotides (CUR-1740, CUR-1764, CUR-1770, CUR-1838, CUR-1916) targeting SCNIA-specific natural antisense transcript that were shown to upregulate SCN1 A mRNA and protein are able to regulate the mRNA of other non-related genes such as actin in SK-N-AS human neuroblastoma cells.

Materials and Methods

SK-N-AS human neuroblastoma cells from ATCC (cat # CRL-2137) were dosed in the same conditions as described in Example 2. The actin mRNA was quantified by real-time PCR as described in. Example 2 except that this time primers/probes designed by ABI were specific for actin (cat # Hs99999903_ml). The data is presented in FIG. 15.

Results.

Figure 15:
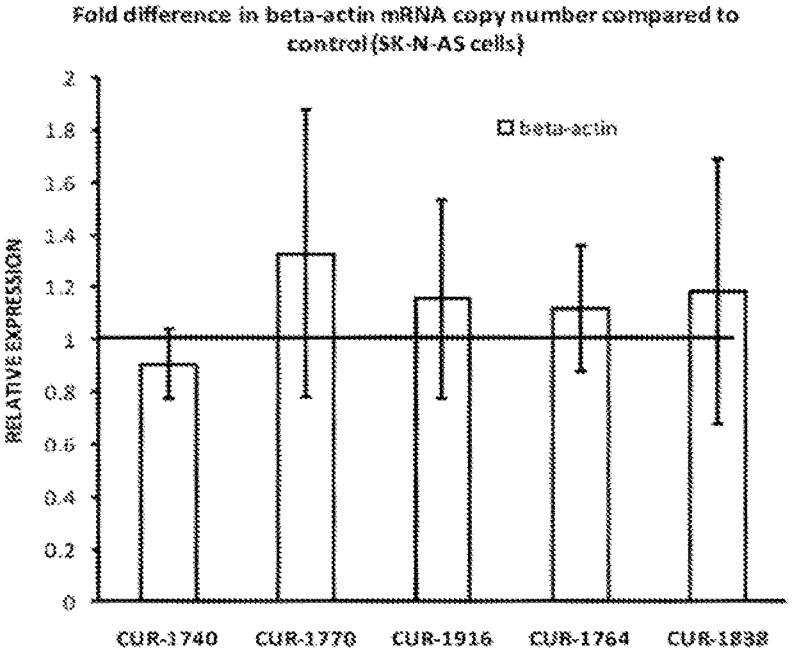
FIG. 15 show that oligonucleotides targeting SCN1A-specific natural antisense transcript shown to upregulate SCNIA mRNA and protein do not upregulate actin in S-N-AS cells. The same antisense oligonucleotides (CUR-1740, CUR-1770, CUR-1916, CUR-1764, CUR-1838) that were shown in Examples to upregulate SCNIA mRNA and protein were tested for their effect on actin mRNA expression in SK-N-AS cells. The data confirms that oligonucleotides targeting SCN1A-specific natural antisense transcript do not upregulate a non-related gene such as actin. Bars denoted as CUR-1740, CUR-1770, CUR-1916, CUR-1764, CUR-1838 correspond to samples treated with SEQ ED NOS: 45, 57, 70, 52 and 62 respectively.

As shown in FIG. 15 oligonucleotides targeting SC IA-specific natural antisense transcript do not upregulate a non-related gene such as actin. Thus these oligonucleotides are specific in upregulating SCN1A.

Example 14: Actin Protein is not Upregulated in SK-N-AS Cells Treated with Antisense Oligonucleotides Targeting SCNA-Specific Natural Antisense Transcript The purpose of this experiment was to determine whether oligonucleotides targeting SCNIA-specific natural antisense transcript (CUR-1740, CUR-1764, CUR-1770 and CUR-1916) and able to upregulate SCN1A protein are also able to regulate the expression of non-relevant proteins such as actin in SK-N-AS cells. SK-N-AS is a human neuroblastoma cell line.

Materials and Methods

SK-N-AS human neuroblastoma cells from ATCC (cat # CRL-2137) were grown in the same conditions as described in Example 9. The cells were fixed and stained exactly in the same conditions as described in Example 8, except that the first antibody was a rabbit anti-actin (Abeam cat #ab1801) used at a dilution of 1:500. The staining of the cells was analyzed directly inside the wells of the 24-well plate using the same process as described in Example 9.

Figure 16:
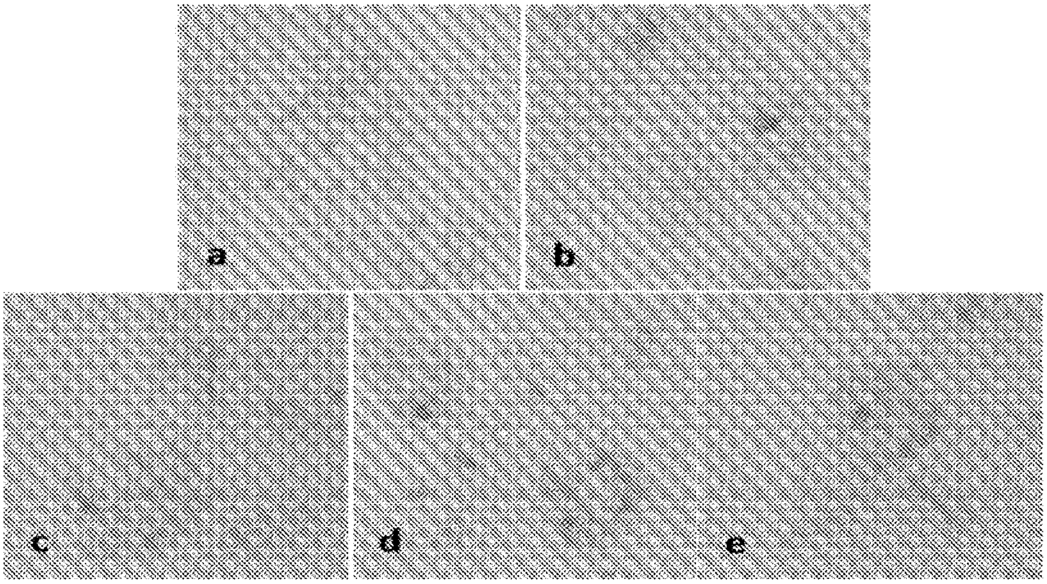
FIG. 16 shows staining of actin protein in SK-N-AS cells treated with antisense oligonucleotides complementary to the SCNIA natural antisense. SK-N-AS cells were grown in 24 well plates and treated with oligonucleotides at 20 nM (b: CUR-1740; c: CUR-1764; d: CUR-1770; e: CUR-1916) and at 0 nM (a). The SK-N-AS cells were stained for actin (a-e) by indirect immunohistochemistry using an anti-actin antibody (Abeam cat #ab1801) and secondary antibody staining/amplification using the avidin/biotin method (Vector Laboratories cat # SP-2001; Vector Laboratories cat # PK-6101; Vector Laboratories cat # SK-4105).

Results:

As shown in FIG. 16, none of the antisense oligonucleotides tested upregulated actin protein. Thus, these oligonucleotides are specific at upregulating SCN1 A protein.

Example 15: Actin Protein is not Upregulated in Vero 76 Cells Treated with Antisense Oligonucleotides Targeting SCNA-Specific Natural Antisense Transcript The purpose of this experiment was to determine whether specific antisense oligonucleotides targeting SCNIA-specific natural antisense transcript (CUR-1740, CUR-1770, CUR-1916, CUR-1924 and CUR-1945) and able to upregulate SCNIA protein are also able to regulate the protein expression of non-relevant genes such as actin in Vero76 cells. The Vero76 is a *Cercopithecus aethiops* (vervet or African green monkey) kidney cell line.

Materials and Methods

Vero76 African green monkey embryonic kidney cell line from ATCC (cat # CRL-1587) was grown in the same conditions that described in Example 10. The cells were fixed and stained exactly in the same conditions as described in Example 10, except that the first antibody was a rabbit anti-actin (Abeam cat #ab1801) used at a dilution of 1:500. The staining of the cells was analyzed directly inside the wells of the 24-well plate using the same process as described in Example 10.

Results.

Figure 17:
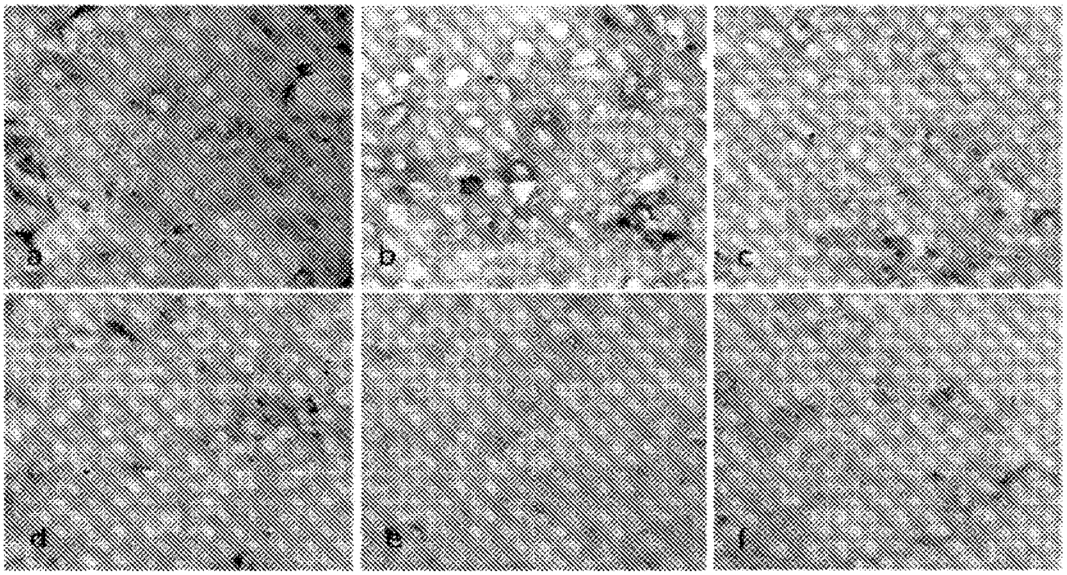
FIG. 17 shows staining of actin protein in Vera 76 cells treated with antisense oligonucleotides complementary to the SCNIA natural antisense. Vera 76 cells were grown in 24 well plates and treated with antisense oligonucleotides complementary to the SCNIA natural antisense at 20 nM (b: CUR-1740; c: CUR-1770; d: CUR-1916; e: CUR-1924; f: CUR-1945) and at 0 nM (a). The Vera 76 cells were stained for actin (b-f) by indirect immunohistochemistry using an anti-actin antibody (Abeam cat #ab1801) and secondary antibody staining amplification with the avidin/biotin method (Vector Laboratories cat # SP-2001; Vector Laboratories cat # PK-6101; Vector Laboratories cat # SK-4105); panel a—negative control, a rabbit anti-mouse antibody was used as primary antibody followed by the same staining procedure as in panels b-g.

As shown in FIG. 17, none of the antisense oligonucleotides tested upregulated actin protein. Thus, these oligonucleotides are specific at upregulating SCN 1 A protein.

Example 16: Actin Protein is not Upregulated in Primary Human Fibroblasts Carrying a Dravet Syndrome-Associated Mutation Treated with Antisense Oligonucleotides Targeting SCNA-Specific Natural Antisense Transcript The purpose of this experiment was to determine whether oligonucleotides targeting SCN1A-specific natural antisense transcript (CUR-1740, CUR-1764, CUR-1770, CUR-1838 and CUR-1916) and able to upregulate SCNA protein are also able to regulate the protein expression of non-relevant genes such as actin in primary human fibroblasts carrying a Dravet syndrome-associated mutation.

Materials and Methods

Fibroblasts carrying a Dravet syndrome-associated mutation introduced into culture by Dr. RKenyon (University of Miami) were grown in the same conditions as described in Example 8. The cells were fixed and stained exactly in the same conditions as described in Example 8, except that the first antibody was a rabbit anti-actin (Abeam cat #ab1801) used at a dilution of 1:500. The staining of the cells was analyzed directly inside the wells of the 24-well plate using the same process as described in Example 8.

Figure 18:
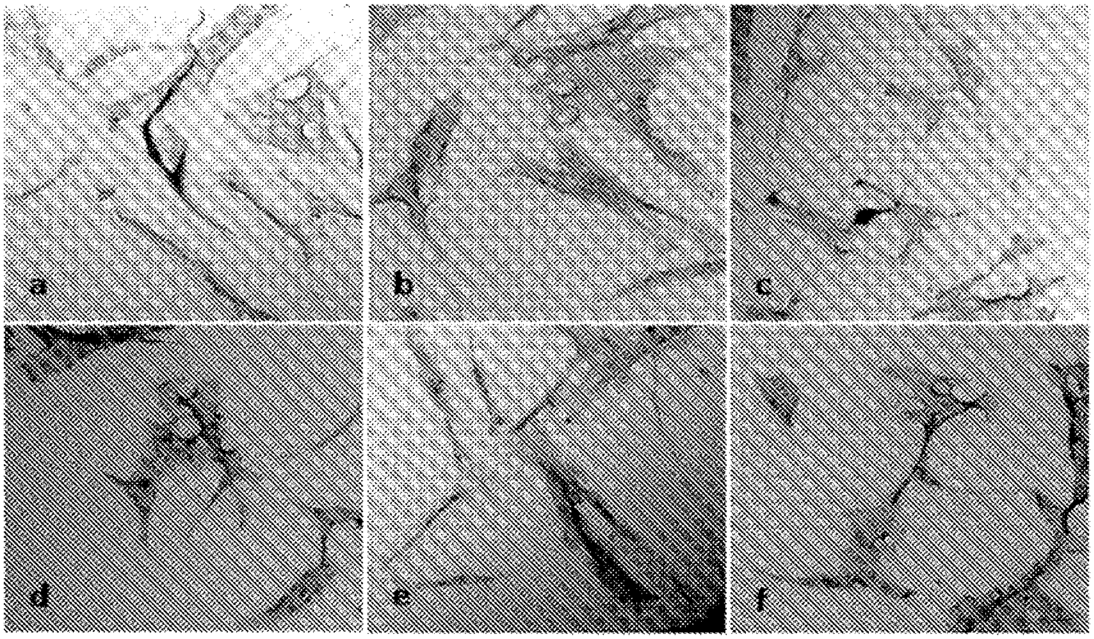
FIG. 18 shows upregulation of actin protein in fibroblasts carrying a Dravet syndrome mutation treated with antisense oligonucleotides complementary to the SCNIA natural antisense. Fibroblasts were grown in 24 well plates and treated with antisense oligonucleotides complementary to the SCNIA natural antisense at 20 nM (panel b: CUR-1740; c: CUR-1764; d: CUR-1770; e: CUR-1838 and f: CUR-1916) and at 0 nM (a). The cells were stained for actin (a-f) by indirect immunohistochemistry using an anti-actin antibody (Abeam cat #ab1801) and a secondary antibody staining/amplification with the avidin/biotin method (Vector Laboratories cat # SP-2001; Vector Laboratories cat # PK-6101; Vector Laboratories cat # SK-4105).

Results:

As shown in FIG. 18, none of the antisense oligonucleotides tested upregulated actin protein. Thus, these oligonucleotides are specific at upregulating SCN1 A protein.

Example 17: Quantification of SCNA Protein Using ELISA in Primary Human Fibroblasts Carrying a Dravet Syndrome-Associated Mutation Treated with Oligonucleotides Targeting SCNA-Specific Natural Antisense Transcript The purpose of this experiment was to quantify using ELISA the level of SCN1A protein upregulation due to the treatment with oligonucleotides targeting SCN1 A-specific natural antisense transcript (CUR-1740, CUR-1770 and CUR-1916) in primary human fibroblasts carrying a Dravet syndrome-associated mutation.

Materials and Methods

Fibroblasts carrying a Dravet syndrome-associated mutation introduced into culture by Dr. N. Kenyon (University of Miami) were grown in the same conditions as described in Example 8 but only 0 and 80 nM concentrations of oligonucleotides were used for dosing. The cells were then counted and re-plated in 96 well plates. After 24 hours, the cells were fixed exactly in the same conditions as described in Example 8 and 16 except all 300 μї volumes were reduced to IOO μI. Replicate wells were stained with actin and SCN1 A antibodies as described in Example 8, except that all reaction were performed in 100 μї volumes. Anti-actin antibody dilution was 1:500, anti-SCN1A dilution was 1:250 and anti-mouse dilution was 1:250. In addition, instead of diaminobenzidine (DAB) peroxidase substrate solution tetramethylbenzidine (TMB) peroxidase substrate solution was used (Thermo Scientific cat #N301). After the supernatant turned blue, it was transferred to a new 96 well plate (Greiner bio one cat #65121) and 1 M sulfuric acid was added. The absorbance was read at 450 nm using a Multiskan Spectrum spectrophotometer (Thermo Scientific). The background signal (read in the wells stained with an anti-mouse as primary antibody) was subtracted from all SCN1A and actin readings. Then SCN1A signal was normalized to actin signal for each condition.

Figure 19:
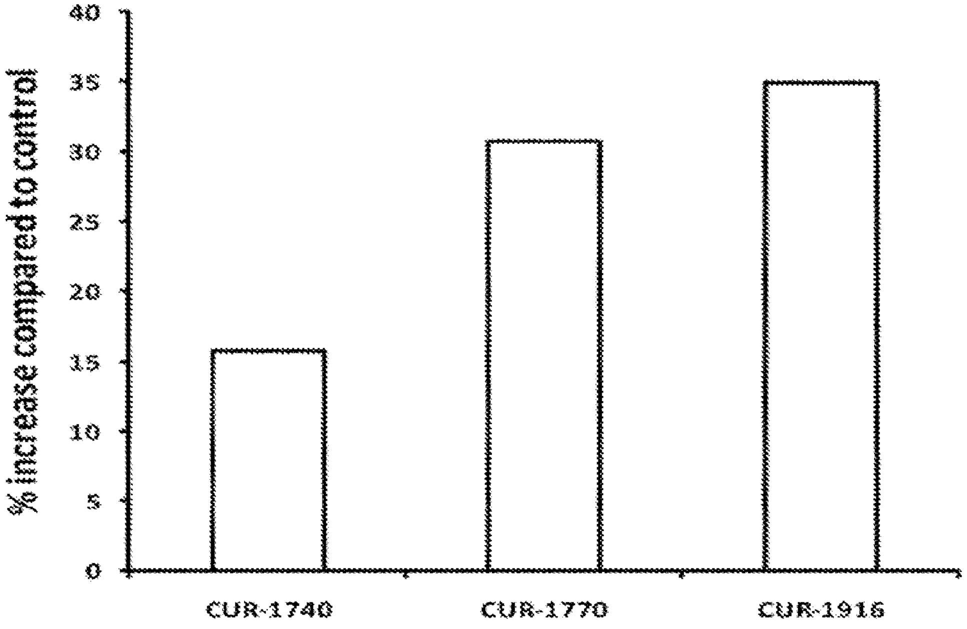
FIG. 19 shows upregulation of SCNIA protein in fibroblasts carrying a Dravet syndrome mutation treated with antisense oligonucleotides complementary to the SCNIA natural antisense quantified using ELISA. Fibroblasts were treated with oligonucleotides complementary to the SCNIA natural antisense at 0 or 80 nM. After 48 h, the cells were transferred to a 96 well plate for 24 h, before being fixed and used for SCN1A and actin ELISAs. The OD readings for SCNIA signal were normalized to actin signal for the same experimental condition. The normalized SCN1A signal in cells dosed with 0 nM of oligonucleotide was used as baseline (100%). Bars denoted as CUR-1740, CUR-1770 and CUR-1916 correspond to samples treated with SEQ ID NOS: 45, 57 and 70 respectively.

Results:

FIG. 19 shows that all antisense oligonucleotides tested (CUR-1740, CUR-1770 and CUR-1916) were efficient at upregulating SCN 1 A protein up to 40%.

Example 18: Quantification of the SCNA Protein Using ELISA in Vero76 Cells Treated with Oligonucleotides Targeting SCNA-Specific Natural Antisense Transcript The purpose of this experiment was to quantify using ELISA the level of SCN1 A protein upregulation due to the treatment with oligonucleotides targeting SCN1A-specific natural antisense transcript (CUR-1740, CUR-1770, CUR-1916, CUR-1924, CUR-1945) in primary human fibroblasts carrying a Dravet syndrome-associated mutation.

Materials and Methods

Vero76 African green monkey embryonic kidney cell were grown in the same conditions that described in Example 10 but only 0 and 80 nM concentrations of oligonucleotides were used for dosing. The cells were then counted and re-plated in 96 well plates. After 24 hours, the cells were fixed exactly in the same conditions as described in Example 8 except all 300 μï volumes were reduced to IOO μI. Replicate wells were stained with actin and SCNIA antibodies as described in Examples 10 and 15, except that all reactions were performed at 100 μï, the anti-actin antibody dilution was 1:500, anti-SCN1A dilution was 1:250 and anti-mouse dilution was 1:250. In addition, instead of using dianu obenzidine (DAB) peroxidase substrate solution tetramethylbenzidine (TMB) peroxidase substrate solution was used (Thermo Scientific car#N301). After the supernatant turned blue, it was transferred to a new 96 well plate (Greiner bio one cat #651201) and 1 M sulfuric acid was added. The absorbance was read at 450 nm using a Multiskan Spectrum spectrophotometer (Thermo Scientific). The background signal (read in the wells stained with an anti-mouse as primary antibody) was subtracted from all SCNIA and actin readings. Then SCN 1 A signal was normalized to actin signal for each condition.

Figure 20:
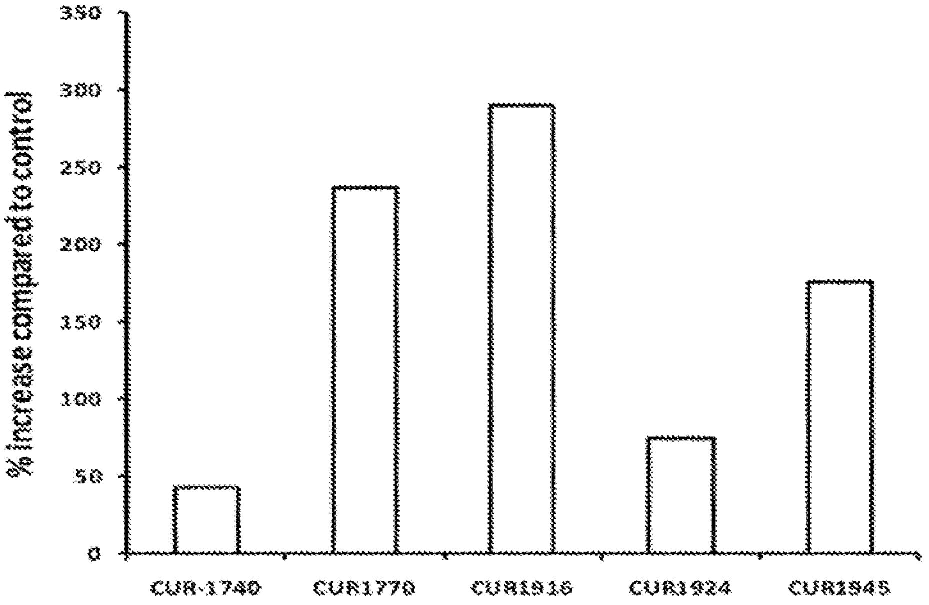
FIG. 20 shows upregulation of SCNIA protein in Vero76 cells treated with antisense oligonucleotides complementary to the SCNIA natural antisense quantified using ELISA. Vero76 cells were treated with antisense oligonucleotides complementary to the SCNIA natural antisense at 0 or 80 nM. After 48 h, the cells were transferred to a 96 well plate for 24 h before being fixed and used for SCNIA and actin ELISAs. The OD readings for SCNIA signal were normalized to actin signal for the same experimental condition. The normalized SCNIA signal in cells dosed with 0 nM of oligonucleotide was used as baseline (100%). Bars denoted as CUR-1740, CUR-1770, CUR-1916, CUR-1924, CUR-1945 correspond to samples treated with SEQ ID NOS: 45, 57, 70, 78 and 93 respectively.

Results:

FIG. 20 shows that all of the antisense oligonucleotides tested (CUR-1740, CUR-1770, CUR-1916, CUR-1924, CUR-1945) were efficient at upregulating SCNIA protein up to 300%.

Example 19: Quantification of the SCNA Protein Using ELISA in SK-N-AS Cells Treated with Oligonucleotides Targeting SCNA-Specific Natural Antisense Transcript The purpose of this experiment was to quantify the level of SCN 1 A protein upregulation due to the treatment with oligonucleotides targeting SCN1A-specific natural antisense transcript (CUR-1740, CUR-1770, CUR-1924 and CUR-1945) in SK-N-AS cells.

Materials and Methods

SK-N-AS human neuroblastoma cells from ATCC (cat # CRL-2137) were grown the same conditions as described in Example 10 but only 0 and 20 nM concentrations of oligonucleotides were used for dosing. The cells were then counted and re-plated in 96 well plates. After 24 hours, the cells were fixed exactly in the same conditions as described in Example 9 except all 300 μï volumes were reduced to IOO μI. Replicate wells were stained with actin and SCNIA antibodies as described in Examples 9 and 13, except that all reactions were performed at 100 μï, the anti-actin antibody dilution was 1:500, anti-SCN1A dilution was 1:250 and anti-mouse dilution was 1:250. In addition, instead of diaminobenzidine (DAB) peroxidase substrate solution tetramethylbenzidine (TMB) peroxidase substrate solution was used spectrophotometer (Thermo Scientific cat #N301). After the supernatant turned blue, it was transferred to a new 96 well plate (Greiner bio one cat #651201) and 1 M sulfuric acid was added. The absorbance was read at 450 nm using a Multiskan Spectrum (Thermo Scientific). The background signal (read in the wells stained with an anti-mouse as primary antibody) was subtracted from all SCNIA and actin readings. Then SCN 1 A signal was normalized to actin signal for each condition.

Figure 21:
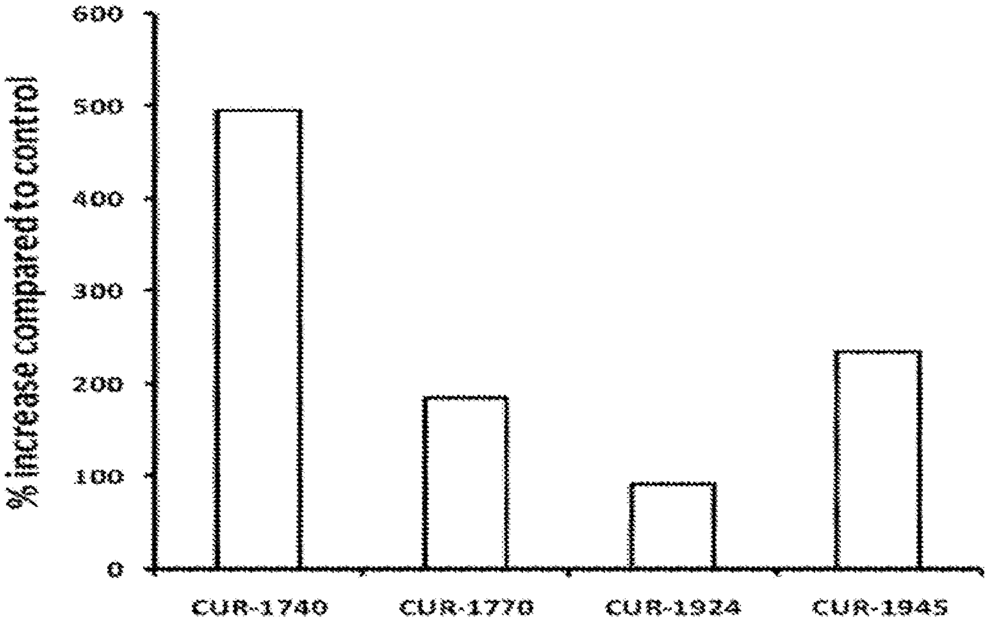
FIG. 21 shows upregulation of SCNIA protein in SK-N-AS cells treated with oligonucleotides complementary to the SCNIA natural antisense quantified using ELISA. SK-N-AS cells were treated with antisense oligonucleotides complementary to the SCNIA natural antisense at 0 or 20 nM. After 48 h, the cells were transferred to a 96 well plate for 24 h, before being fixed and used for SCNIA and actin ELISAs. The OD readings for SCNIA signal were normalized to actin signal for the same experimental condition. The normalized SCNIA signal in cells dosed with 0 nM of oligonucleotide was used as baseline (100%). Bars denoted as CUR-1740, CUR-1770, CUR-1924, CUR-1945 correspond to samples treated with SEQ ID NOS: 45, 57, 78 and 93 respectively.

Results:

FIG. 21 shows that all antisense oligonucleotides tested (CUR-1740, CUR-1770, CUR-1924 and CUR-1945) were efficient at upregulating SCNIA protein in SK-N-AS cells up to 500%.

Example 20: Detection of the Natural Antisense BG724147 in HepG2 Cells and Primary Human Fibroblasts Carrying a Dravet Syndrome-Associated Mutation The purpose of this experiment was to determine whether the natural antisense BG724147 is present in human hepatocellular carcinoma HepG2 cell line and primary human fibroblasts carrying a Dravet syndrome-associated mutation. To achieve this, two different kinds of R A (poly A R A and total R A) isolated from each cell type were used. The PCR products obtained after two successive rounds of PCR using both cell types were analyzed on a gel. Amplification of bands of similar size using BG724147-specific primer confirmed the presence of BG724147 in both cell types.

Materials and Methods

Isolation of total RNA. HepG2 cells or primary human fibroblasts carrying a Dravet syndrome-associated mutation at 80% confluence grown in 75 $cm^2$ culture flasks were washed twice with PBS AccuGENE IX (Lonza Rockeland Inc., Rockeland, Me.). After discarding PBS, 5 ml of RLT buffer with b-mercaptoethanol (QIAGEN Inc-USA, Valencia, Calif.) were added to these cells and the cell lysate was stored in 1 ml aliquots in microcentrifuge tubes at −80° C. until isolation of total RNA. The total RNA isolation from these cells was done using the RNeasy midi kit (QIAGEN Inc.-USA, Valencia, Calif.) following the manufacturer's protocol. Briefly, the cell lysate was centrifuged at 3000×g for 5 min to clear the lysate and discard any pellet. The cleared cell lysate was centrifuged through QIAshredder columns (inside 2 ml microcentrifuge tubes) at 14800×g and the resulting homogenized lysate was mixed with an equal volume of 70% ethanol. The cell lysate mixed with ethanol was applied to RNeasy midi columns (inside a 15 ml conical tube) and centrifuged for 5 min at 3000×g. The column was washed once with 4 ml of RW1 buffer and then subjected to a 15 min on-column DNase digestion with 140 μï of RNase-free DNase in RDD buffer. The DNase digestion was stopped by adding 4 ml of RW1 buffer and centrifuging the column at 3000×g. The column was washed twice with RPE buffer and total RNA binding to the filter was eluted with 150 μï of DNase and RNAse free water. The total RNA was stored at −80° C. until the next step.

Isolation of poly-A RNA from total RNA of HepG2 cells. The isolation of poly A RNA from total RNA of HepG2 cells and primary human fibroblasts carrying a Dravet syndrome-associated mutation was done using a poly-A isolation with magnetic beads kit from Ambion (Applied Biosystems/Ambion, Austin, Tex.) following the manufacturer protocol. Basically, 100μ of total RNA was resuspended to a final concentration of 600 μg/ml in DNase RNAse free water and an equal volume of 2× binding solution was added. During that time, 10 μï of 01igo(dT) magnetic beads were placed in a microcentrifuge tube, captured by placing this tube on the magnetic stand and the storage buffer was discarded. 50 μï of Wash solution 1 was added to the beads and the tube was removed from the magnetic stand and the wash solution was discarded. At this time, the total RNA from HepG2 cells in IX Binding buffer was mixed with the magnetic beads and heated at 70° C. for 5 min, then incubated for 60 min at room temperature with gentle agitation. The poly A RNA bound to the magnetic beads was captured by using the magnetic stand for 5 min. The supernatant was discarded. The 01igo (dT) magnetic beads were washed twice with Wash solution 1 and once with Wash solution 2 to remove the non-specifically bound RNA. The magnetic beads were captured with the magnetic stand and 200 μï of warm RNA storage solution (preheated at 70° C. for 5 min) was added to the beads. The magnetic beads were captured by the magnetic stand, the supernatant was stored (first elution of poly A RNA). Then a second 200 μï of warm RNA storage solution (preheated at 70° C. for 5 min) was added to the beads. The second elution of polyA RNA was added to the first elution. At this time, the eluted RNA was precipitated using 5 M ammonium acetate, glycogen and 100% ethanol at −20° C. overnight. The poly RNA was centrifuged at 14800×g for 30 min at 4° C. The supernatant was discarded and the RNA pellet was washed three times with 1 ml of 70% ethanol, the RNA pellet was recovered each time by centrifuging for 10 min at 4° C. Finally, the poly A RNA pellet was resuspended in RNA storage solution heated to 70° C. to dissolve RNA better. The poly A RNA was stored at −80° C.

Addition of adenosines to the 3' end of an RNA transcript. Total RNA (40 g) from HepG2 cells or primary human fibroblasts carrying a Dravet syndrome-associated mutation was mixed with 2 units of RNA Poly (A) Polymerase using a final reaction volume of 100 μl (Ambion, Applied Biosystems, St. Austin Tex.). The ATP used in the polyadenylation reaction was from Invitrogen. After polyadenylation, the RNA was purified using the phenol chloroform technique followed by glycogen/sodium acetate precipitation. This RNA was resuspended in 40 μï of DNAse RNAse free water and was used in a 3' RACE reaction (FirstChoice RLM-RACE kit from Ambion, Applied Biosystems, St. Austin Tex.).

3' extension of the BG724147 natural antisense transcript of SCN1A. Two different sets of 3' Rapid Amplification of cDNA Ends (RACE) reactions were performed using FirstChoice RLM-RACE kit from Ambion, Applied Biosystems (St. Austin, Tex.). One set used poly A RNA and the other used total RNA with one adenosine added, from HepG2 cells or primary human fibroblasts carrying a Dravet syndrome-associated mutation. Two consecutive rounds of PCR were performed. The first PCR was done using the 3' outer primer supplied in the kit and a 5' primer specific for BG724147 designed by OPKO CURNA (5' GATTCTCCTACAGCAATTGGTA 3'). The second PCR round was conducted using the 3' outer primer supplied in the kit and a different 5' primer specific for BG724147 designed by OPKO CURNA (5' GACATGTAATCACTTTCATCAA 3'). The products of the second PCR reaction were run on a 1% agarose—1×TAE gel.

Figure 22:
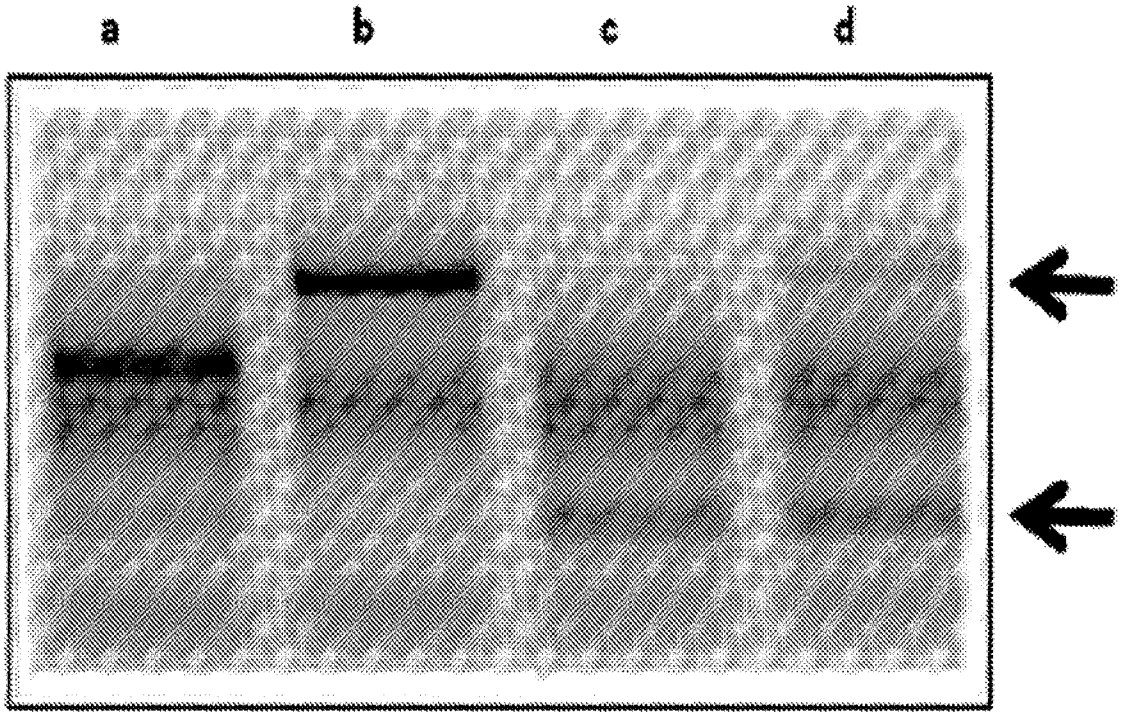
FIG. 22 shows products from a second PCR round of a 3' RACE of the SCNIA natural antisense transcript BG724147. A 3' RACE was performed on: a) total RNA from HepG2 cells with adenosine added; b—poly A RNA isolated from HepG2 cells; c—on total RNA from primary human fibroblasts carrying a Dravet syndrome-associated mutation with adenosine added; d—on poly A RNA isolated from primary human fibroblasts carrying a Dravet syndrome-associated mutation. Figure represents a negative of a 1% agarose gel/1×TAE stained with GelRed (GenScript, cat #M00120). Arrow shows a band common for HepG2 cells and primary human fibroblasts carrying a Dravet syndrome-associated mutation, demonstrating the presence of BG724147 natural antisense transcript in these cells.

Results:

FIG. 22 shows the products from the second round of PCR reactions from a 3' RACE experiments using poly A RNA and total RNA with adenosine added from HepG2 cells and poly A RNA and total RNA with adenosine added from primary human fibroblasts carrying a Dravet syndrome-associated mutation. An identical band is observed in the poly A RNA from HepG2 cells and primary human fibroblasts carrying a Dravet syndrome-associated mutation.

Conclusion:

PCR amplification using primers specific for the BG724147 natural antisense transcript of SCN1A produced a common PCR band in two different cells (HepG2 cells and primary human fibroblasts carrying a Dravet syndrome-associated mutation). In addition, antisense oligonucleotides targeting the SCN1A natural antisense BG724147 have been shown to upregulate SCN1A mRNA and protein in these cells as shown in Examples 2, 7 and 16. This data indicates that the BG724147 is indeed present in these two kinds of cells (HepG2 cells and primary human fibroblasts carrying a Dravet syndrome-associated mutation).

Example 21: Extension of the SCNA Natural Antisense Sequence BG724147

The purpose of this experiment is to extend the known sequence of the SCN1A natural antisense BG724147 by sequencing all its sequence. The original BG724147 RNA transcript was obtained from human testis procured by Miklos Palkovits. The cDNA library was prepared in a pBluescriptR vector by Michael J. Brownstein (at NHGRI), Shiraki Toshiyuki and Piero Carninci (at RIKEN). The cDNA library was arrayed by the I.M.A.G.E. Consortium (or LLNL) and the clones were sequenced by Incyte Genomics, Inc. in May 2001. The BG724147 clone is available at Open Biosystems (Open Biosystems Products, Huntsville, Ala.). In 2001 the cDNA insert in the BG724147 clone was not sequenced completely. OPKO-CURNA obtained the BG724147 clone and sequenced the full insert. To achieve this, a bacterial clone containing a plasmid with the BG724147 insert was acquired from Open Biosystems and plated in a Luria Bertani (LB)-agar plate with ampicillin to isolate individual colonies. Then colonies were amplified in 5 ml of LB broth. The plasmid containing the BG724147 insert was then isolated from these bacteria and sent for sequencing to Davis Sequencing (Davis, Calif.).

Material and Methods

Isolation and sequencing of the plasmid containing the cDNA for the SCNA natural antisense BG724147. Suspension of frozen bacteria containing the BG724147 plasmid was purchased from Open Biosystems (Open Biosystems Products, cat #4829512), diluted 1:10, 1:100, 1:1000, 1:10000, 1:100000 times, then plated on Luria Bertani (LB) (BD, cat #244520)-agar plate (Falcon, cat #351005) with 100μ/ml of ampicillin (Calbiochem, cat #171254). After 15 h, 20 individual colonies of bacteria were isolated from the plate with the 1:100000 dilution and grown separately in 5 ml of LB broth (Fisher Scientific, cat # BP 1426-2) for 15 h-24 h. At this time, the bacteria were pelleted and the plasmid (containing the cDNA from the BG724147 RNA transcript) was isolated using the PureYield™ Plasmid Miniprep System kit from Promega (Promega, cat #A1222) following the manufacturer's protocol. The isolated DNA was diluted to 200 ngml and 12 μï of plasmid from each colony was sent for sequencing to Davis sequencing (Davis, Calif.).

Results:

The sequences obtained from Davis sequencing provide BG724147 extended (SEQ ID NO: 12)

Conclusion:

The successful extension of the known BG724147 sequence by 403 nucleotides served as a basis to design antisense oligonucleotides against the SCN1A natural antisense transcript BG724147.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A modified antisense oligonucleotide of 10-25 nucleotides in length which is at least 95% complementary to a 10-25 nucleotide target region on a natural antisense polynucleotide having SEQ ID NO: 12 wherein said target region is selected from the group consisting of nucleotides 128-147 of SEQ ID NO: 12; nucleotides 208-228 of SEQ ID NO: 12; nucleotides 441-461 of SEQ ID NO: 12; nucleotides 541-561 of SEQ ID NO: 12; nucleotides 456-475 of SEQ ID NO: 12; nucleotides 541-561 of SEQ ID NO: 12; nucleotides 540-563 of SEQ ID NO: 12; nucleotides 544-558 of SEQ ID NO: 12; nucleotides 541-560 of SEQ ID NO: 12; nucleotides 547-561 of SEQ ID NO: 12; nucleotides 541-561 of SEQ ID NO: 12; nucleotides 901-920 of SEQ ID NO: 12; nucleotides 906-924 of SEQ ID NO: 12; nucleotides 1015-1040 of SEQ ID NO: 12; nucleotides 1072-1092 of SEQ ID NO: 12; nucleotides 1018-1032 of SEQ ID NO: 12; nucleotides 1018-1038 of SEQ ID NO: 12; nucleotides 1024-1038 of SEQ ID NO: 12; nucleotides 1026-1038 of SEQ ID NO: 12; and nucleotides 1028-1038 of SEQ ID NO: 12 and wherein said modified oligonucleotide upregulates the expression of an SCN1a polynucleotide.

2. A modified antisense oligonucleotide according to claim 1 selected from the group consisting of oligonucleotides having SEQ ID NOS: 30; 33; 35; 37; 40; 45; 46; 47; 48; 49; 50; 51; 52; 55; 56; 57; 61; 62; 67; 70; 83; 84; 87; 90; 91; 92; 93 and 94 and said modifications are selected from the group consisting of at least one of a modified internucleotide linkage; a modified nucleotide and/or a modified sugar moiety.

3. A modified oligonucleotide according to claim 2 selected from SEQ ID NO: 70.

4. A modified oligonucleotide according to claim 2 wherein the modified sugar moiety comprises at least one nucleotide modified at the 2' position of the sugar with 2-O-alkyl or 2'-O-alky-O-alkyl.

5. The modified oligonucleotide according to claim 4 having a sequence selected from SEQ ID NO: 70.

6. The modified oligonucleotide according to claim 4 or 5 wherein at least one 2' position of the sugar moiety comprises 2'-O—CH2CH2OCH3 or 2'-OMe.

7. A modified oligonucleotide according to claim 3 having SEQ ID NO: 70 mG*mA*mG*C*C*A*G*mU*C*A*mC*A*A*A*mU*T*C*A*G*mA*T*C*A*mC*mC*mC wherein * indicates a phosphorothioate bond and m indicates a methyl group on the 2' oxygen atom on the designated sugar moiety of the oligonucleotide.

8. A pharmaceutical composition comprising a modified oligonucleotide according to claims 1-4 and a pharmaceutical acceptable excipient.

9. A liquid formulation comprising a modified oligonucleotide according to claim 4 and a pharmaceutically acceptable excipient.

10. A modified oligonucleotide selected from the group consisting of SEQ ID NO: 41 or 42.

* * * * *

SEQUENCE LISTING

<160> NUMBER OF SEQ ID NOS: 96

<210> SEQ ID NO 1
<211> LENGTH: 8133
<212> TYPE: DNA
<213> ORGANISM: Homo sapiens

<400> SEQUENCE: 1
aatgtgcagg atgacaagat ggagcaaaca gtgcttgtac caccaggacc tgacagcttc 60
aacttcttca ccagagaatc tcttgcggct attgaaagac gcattgcaga agaaaaggca 120
aagaatccca aaccagacaa aaaagatgac gacgaaaatg gcccaaagcc aaatagtgac 180
ttggaagctg gaaagaacct tccatttatt tatggagaca ttcctccaga gatggtgtca 240
gagcccctgg aggacctgga cccctactat atcaataaga aaacttttat agtattgaat 300
aaagggaagg ccatcttccg gttcagtgcc acctctgccc tgtacatttt aactcccttc 360
aatcctctta ggaaaatagc tattaagatt ttggtacatt cattattcag catgctaatt 420
atgtgcacta ttttgacaaa ctgtgtgttt atgacaatga gtaaccctcc tgattggaca 480
aagaatgtag aatacacctt cacaggaata tatacttttg aatcacttat aaaaattatt 540
gcaaggggat tctgtttaga agattttact ttccttcggg atccatggaa ctggctcgat 600
ttcactgtca ttacatttgc gtacgtcaca gagtttgtgg acctgggcaa tgtctcggca 660
ttgagaacat tcagagttct ccgagcattg aagacgattt cagtcattcc aggcctgaaa 720
accattgtgg gagccctgat ccagtctgtg aagaagctct cagatgtaat gatcctgact 780
gtgttctgtc tgagcgtatt tgctctaatt gggctgcagc tgttcatggg caacctgagg 840
aataaatgta tacaatggcc tcccaccaat gcttccttgg aggaacatag tatagaaaag 900
aatataactg tgaattataa tggtacactt ataaatgaaa ctgtctttga gtttgactgg 960
aagtcatata ttcaagattc aagatatcat tatttcctgg agggtttttt agatgcacta 1020
ctatgtggaa atagctctga tgcaggccaa tgtccagagg gatatatgtg tgtgaaagct 1080
ggtagaaatc ccaattatgg ctacacaagc tttgatacct tcagttgggc tttttgtcc 1140
ttgtttcgac taatgactca ggacttctgg gaaaatcttt atcaactgac attacgtgct 1200
gctgggaaaa cgtacatgat attttttgta ttggtcattt tcttgggctc attctaccta 1260
ataaatttga tcctggctgt ggtggccatg gcctacgagg aacagaatca ggccaccttg 1320
gaagaagcag aacagaaaga ggccgaattt cagcagatga ttgaacagct taaaaagcaa 1380
caggaggcag ctcagcaggc agcaacggca actgcctcag aacattccag agagcccagt 1440
gcagcaggca ggctctcaga cagctcatct gaagcctcta agttgagttc caagagtgct 1500
aaggaaagaa gaaatcggag gaagaaaaga aaacagaaag agcagtctgg tggggaagag 1560
aaagatgagg atgaattcca aaaatctgaa tctgaggaca gcatcaggag gaaaggtttt 1620
cgcttctcca ttgaagggaa ccgattgaca tatgaaaaga ggtactcctc cccacaccag 1680
tctttgttga gcatccgtgg ctccctattt tcaccaaggc gaaatagcag aacaagcctt 1740
ttcagcttta gagggcgagc aaaggatgtg ggatctgaga acgacttcgc agatgatgag 1800
cacagcacct ttgaggataa cgagagccgt agagattcct tgtttgtgcc ccgacgacac 1860
ggagagagac gcaacagcaa cctgagtcag accagtaggt catcccggat gctggcagtg 1920
tttccagcga atgggaagat gcacagcact gtggattgca atggtgtggt ttccttggtt 1980
ggtggacctt cagttcctac atcgcctgtt ggacagcttc tgccagaggt gataatagat 2040
aagccagcta ctgatgacaa tggaacaacc actgaaactg aaatgagaaa gagaaggtca 2100

```
agttctttcc acgtttccat ggactttcta gaagatcctt cccaaaggca acgagcaatg   2160
agtatagcca gcattctaac aaatacagta gaagaacttg aagaatccag gcagaaatgc   2220
ccaccctgtt ggtataaatt ttccaacata ttcttaatct gggactgttc tccatattgg   2280
ttaaaagtga aacatgttgt caacctggtt gtgatggacc catttgttga cctggccatc   2340
accatctgta ttgtcttaaa tactcttttc atggccatgg agcactatcc aatgacggac   2400
catttcaata atgtgcttac agtaggaaac ttggttttca ctgggatctt tacagcagaa   2460
atgtttctga aaattattgc catggatcct tactattatt tccaagaagg ctggaatatc   2520
tttgacggtt ttattgtgac gcttagcctg gtagaacttg gactcgccaa tgtggaagga   2580
ttatctgttc tccgttcatt tcgattgctg cgagttttca agttggcaaa atcttggcca   2640
acgttaaata tgctaataaa gatcatcggc aattccgtgg gggctctggg aaatttaacc   2700
ctcgtcttgg ccatcatcgt cttcattttt gccgtggtcg gcatgcagct ctttggtaaa   2760
agctacaaag attgtgtctg caagatcgcc agtgattgtc aactcccacg ctggcacatg   2820
aatgacttct tccactcctt cctgattgtg ttccgcgtgc tgtgtgggga gtggatagag   2880
accatgtggg actgtatgga ggttgctggt caagccatgt gccttactgt cttcatgatg   2940
gtcatggtga ttggaaacct agtggtcctg aatctctttc tggccttgct tctgagctca   3000
tttagtgcag acaaccttgc agccactgat gatgataatg aaatgaataa tctccaaatt   3060
gctgtggata ggatgcacaa aggagtagct tatgtgaaaa gaaaaatata tgaatttatt   3120
caacagtcct tcattaggaa acaaaagatt ttagatgaaa ttaaaccact tgatgatcta   3180
aacaacaaga aagacagttg tatgtccaat catacagcag aaattgggaa agatcttgac   3240
tatcttaaag atgtaaatgg aactacaagt ggtataggaa ctggcagcag tgttgaaaaa   3300
tacattattg atgaaagtga ttacatgtca ttcataaaca accccagtct tactgtgact   3360
gtaccaattg ctgtaggaga atctgacttt gaaaatttaa acacggaaga ctttagtagt   3420
gaatcggatc tggaagaaag caaagagaaa ctgaatgaaa gcagtagctc atcagaaggt   3480
agcactgtgg acatcggcgc acctgtagaa gaacagcccg tagtggaacc tgaagaaact   3540
cttgaaccag aagcttgttt cactgaaggc tgtgtacaaa gattcaagtg ttgtcaaatc   3600
aatgtggaag aaggcagagg aaaacaatgg tggaacctga gaaggacgtg tttccgaata   3660
gttgaacata actggtttga gaccttcatt gttttcatga ttctccttag tagtggtgct   3720
ctggcatttg aagatatata tattgatcag cgaaagacga ttaagacgat gttggaatat   3780
gctgacaagg ttttcactta cattttcatt ctggaaatgc ttctaaaatg ggtggcatat   3840
ggctatcaaa catatttcac caatgcctgg tgttggctgg acttcttaat tgttgatgtt   3900
tcattggtca gtttaacagc aaatgccttg ggttactcag aacttggagc catcaaatct   3960
ctcaggacac taagagctct gagacctcta agagccttat ctcgatttga agggatgagg   4020
gtggttgtga atgccctttt aggagcaatt ccatccatca tgaatgtgct tctggtttgt   4080
cttatattct ggctaatttt cagcatcatg ggcgtaaatt tgtttgctgg caaattctac   4140
cactgtatta acaccacaac tggtgacagg tttgacatcg aagacgtgaa taatcatact   4200
gattgcctaa aactaataga aagaaatgag actgctcgat ggaaaaatgt gaaagtaaac   4260
tttgataatg taggatttgg gtatctctct ttgcttcaag ttgccacatt caaaggatgg   4320
atggatataa tgtatgcagc agttgattcc agaaatgtgg aactccagcc taagtatgaa   4380
gaaagtctgt acatgtatct ttactttgtt attttcatca tctttgggtc cttcttcacc   4440
```

-continued

```
ttgaacctgt ttattggtgt catcatagat aatttcaacc agcagaaaaa gaagtttgga   4500
ggtcaagaca tctttatgac agaagaacag aagaaatact ataatgcaat gaaaaaatta   4560
ggatcgaaaa aaccgcaaaa gcctatacct cgaccaggaa acaaatttca aggaatggtc   4620
tttgacttcg taaccagaca agtttttgac ataagcatca tgattctcat ctgtcttaac   4680
atggtcacaa tgatggtgga aacagatgac cagagtgaat atgtgactac cattttgtca   4740
cgcatcaatc tggtgttcat tgtgctattt actggagagt gtgtactgaa actcatctct   4800
ctacgccatt attattttac cattggatgg aatatttttg attttgtggt tgtcattctc   4860
tccattgtag gtatgtttct tgccgagctg atagaaaagt atttcgtgtc ccctaccctg   4920
ttccgagtga tccgtcttgc taggattggc cgaatcctac gtctgatcaa aggagcaaag   4980
gggatccgca cgctgctctt tgctttgatg atgtcccttc ctgcgttgtt taacatcggc   5040
ctcctactct tcctagtcat gttcatctac gccatctttg ggatgtccaa ctttgcctat   5100
gttaagaggg aagttgggat cgatgacatg ttcaactttg agacctttgg caacagcatg   5160
atctgcctat tccaaattac aacctctgct ggctgggatg gattgctagc acccattctc   5220
aacagtaagc cacccgactg tgaccctaat aaagttaacc ctggaagctc agttaaggga   5280
gactgtggga acccatctgt tggaattttc ttttttgtca gttacatcat catatccttc   5340
ctggttgtgg tgaacatgta catcgcggtc atcctggaga acttcagtgt tgctactgaa   5400
gaaagtgcag agcctctgag tgaggatgac tttgagatgt tctatgaggt ttgggagaag   5460
tttgatcccg atgcaactca gttcatggaa tttgaaaaat tatctcagtt tgcagctgcg   5520
cttgaaccgc ctctcaatct gccacaacca aacaaactcc agctcattgc catggatttg   5580
cccatggtga gtggtgaccg gatccactgt cttgatatct tatttgcttt tacaaagcgg   5640
gttctaggag agagtggaga gatggatgct ctacgaatac agatggaaga gcgattcatg   5700
gcttccaatc cttccaaggt ctcctatcag ccaatcacta ctactttaaa acgaaaacaa   5760
gaggaagtat ctgctgtcat tattcagcgt gcttacagac gccacctttt aaagcgaact   5820
gtaaaacaag cttcctttac gtacaataaa aacaaaatca aaggtggggc taatcttctt   5880
ataaaagaag acatgataat tgacagaata aatgaaaact ctattacaga aaaaactgat   5940
ctgaccatgt ccactgcagc ttgtccacct tcctatgacc gggtgacaaa gccaattgtg   6000
gaaaaacatg agcaagaagg caaagatgaa aaagccaaag ggaaataaat gaaaataaat   6060
aaaaataatt gggtgacaaa ttgtttacag cctgtgaagg tgatgtattt ttatcaacag   6120
gactccttta ggaggtcaat gccaaactga ctgtttttac acaaatctcc ttaaggtcag   6180
tgcctacaat aagacagtga ccccttgtca gcaaactgtg actctgtgta aaggggagat   6240
gaccttgaca ggaggttact gttctcacta ccagctgaca ctgctgaaga taagatgcac   6300
aatggctagt cagactgtag ggaccagttt caaggggtgc aaacctgtga ttttggggtt   6360
gtttaacatg aaacacttta gtgtagtaat tgtatccact gtttgcattt caactgccac   6420
atttgtcaca tttttatgga atctgttagt ggattcatct ttttgttaat ccatgtgttt   6480
attatatgtg actatttttg taaacgaagt ttctgttgag aaataggcta aggacctcta   6540
taacaggtat gccacctggg gggtatggca accacatggc cctcccagct acacaaagtc   6600
gtggtttgca tgagggcatg ctgcacttag agatcatgca tgagaaaaag tcacaagaaa   6660
aacaaattct taaatttcac catatttctg ggaggggtaa ttgggtgata agtggaggtg   6720
ctttgttgat cttgttttgc gaaatccagc ccctagacca agtagattat ttgtgggtag   6780
gccagtaaat cttagcaggt gcaaacttca ttcaaatgtt tggagtcata aatgttatgt   6840
```

ttctttttgt tgtattaaaa aaaaaacctg aatagtgaat attgcccctc accctccacc 6900
gccagaagac tgaattgacc aaaattactc tttataaatt tctgcttttt cctgcacttt 6960
gtttagccat cttcggctct cagcaaggtt gacactgtat atgttaatga aatgctattt 7020
attatgtaaa tagtcatttt accctgtggt gcacgtttga gcaaacaaat aatgacctaa 7080
gcacagtatt tattgcatca aatatgtacc acaagaaatg tagagtgcaa gctttacaca 7140
ggtaataaaa tgtattctgt accatttata gatagtttgg atgctatcaa tgcatgttta 7200
tattaccatg ctgctgtatc tggtttctct cactgctcag aatctcattt atgagaaacc 7260
atatgtcagt ggtaaagtca aggaaattgt tcaacagatc tcatttattt aagtcattaa 7320
gcaatagttt gcagcacttt aacagctttt tggttatttt tacattttaa gtggataaca 7380
tatggtatat agccagactg tacagacatg tttaaaaaaa cacactgctt aacctattaa 7440
atatgtgttt agaattttat aagcaaatat aaatactgta aaaagtcact ttattttatt 7500
tttcagcatt atgtacataa atatgaagag gaaattatct tcaggttgat atcacaatca 7560
cttttcttac tttctgtcca tagtactttt tcatgaaaga aatttgctaa ataagacatg 7620
aaaacaagac tgggtagttg tagatttctg ctttttaaat tacatttgct aattttagat 7680
tatttcacaa ttttaaggag caaaataggt tcacgattca tatccaaatt atgctttgca 7740
attggaaaag ggtttaaaat tttatttata tttctggtag tacctgcact aactgaattg 7800
aaggtagtgc ttatgttatt tttgttcttt ttttctgact tcggtttatg ttttcatttc 7860
tttggagtaa tgctgctcta gattgttcta aatagaatgt gggcttcata attttttttt 7920
ccacaaaaac agagtagtca acttatatag tcaattacat caggacattt tgtgtttctt 7980
acagaagcaa accataggct cctcttttcc ttaaaactac ttagataaac tgtattcgtg 8040
aactgcatgc tggaaaatgc tactattatg ctaaataatg ctaaccaaca tttaaaatgt 8100
gcaaaactaa taaagattac atttttttatt tta 8133

<210> SEQ ID NO 2
<211> LENGTH: 8876
<212> TYPE: DNA
<213> ORGANISM: Homo sapiens

<400> SEQUENCE: 2
ggctgcttca gacatatgtc tgtgtgtacg ctgtgaaggt gtttctcttc acagttcccc 60
gccctctagt ggtagttaca ataatgccat tttgtagtcc ctgtacagga aatgcctctt 120
cttacttcag ttaccagaat ccttttacag gaagttaggt gtggtctttg aaggagaatt 180
aaaaaaaaaa aaaaaaaaaa aaaaaaaaga tttttttttt tttaaagcat gatggaattt 240
tagctgcagt cttcttggtg ccagcttatc aatcccaaac tctgggtgta aaagattcta 300
cagggcactt tcttatgcaa ggagctaaac agtgattaaa ggagcaggat gaaaagatgg 360
cacagtcagt gctggtaccg ccaggacctg acagcttccg cttctttacc agggaatccc 420
ttgctgctat tgaacaacgc attgcagaag agaaagctaa gagacccaaa caggaacgca 480
aggatgagga tgatgaaaat ggcccaaagc caaacagtga cttggaagca ggaaaatctc 540
ttccatttat ttatggagac attcctccag agatggtgtc agtgcccctg gaggatctgg 600
acccctacta tatcaataag aaaacgttta tagtattgaa taaagggaaa gcaatctctc 660
gattcagtgc cacccctgcc ctttacattt taactccctt caaccctatt agaaaattag 720
ctattaagat tttggtacat tctttattca atatgctcat tatgtgcacg attcttacca 780

```
actgtgtatt tatgaccatg agtaaccctc cagactggac aaagaatgtg gagtatacct    840
ttacaggaat ttatactttt gaatcactta ttaaaatact tgcaaggggc ttttgtttag    900
aagatttcac atttttacgg gatccatgga attggttgga tttcacagtc attacttttg    960
catatgtgac agagtttgtg gacctgggca atgtctcagc gttgagaaca ttcagagttc   1020
tccgagcatt gaaaacaatt tcagtcattc caggcctgaa gaccattgtg gggccctga   1080
tccagtcagt gaagaagctt tctgatgtca tgatcttgac tgtgttctgt ctaagcgtgt   1140
ttgcgctaat aggattgcag ttgttcatgg gcaacctacg aaataaatgt ttgcaatggc   1200
ctccagataa ttcttccttt gaaataaata tcacttcctt ctttaacaat tcattggatg   1260
ggaatggtac tactttcaat aggacagtga gcatatttaa ctgggatgaa tatattgagg   1320
ataaaagtca cttttatttt ttagaggggc aaaatgatgc tctgctttgt ggcaacagct   1380
cagatgcagg ccagtgtcct gaaggataca tctgtgtgaa ggctggtaga aaccccaact   1440
atggctacac gagctttgac acctttagtt gggccttttt gtccttattt cgtctcatga   1500
ctcaagactt ctgggaaaac ctttatcaac tgacactacg tgctgctggg aaaacgtaca   1560
tgatattttt tgtgctggtc attttcttgg gctcattcta tctaataaat ttgatcttgg   1620
ctgtggtggc catggcctat gaggaacaga atcaggccac attggaagag gctgaacaga   1680
aggaagctga atttcagcag atgctcgaac agttgaaaaa gcaacaagaa gaagctcagg   1740
cggcagctgc agccgcatct gctgaatcaa gagacttcag tggtgctggt gggataggag   1800
tttttcaga gagttcttca gtagcatcta agttgagctc caaaagtgaa aaagagctga   1860
aaaacagaag aaagaaaaag aaacagaaag aacagtctgg agaagaagag aaaaatgaca   1920
gagtccgaaa atcggaatct gaagacagca taagaagaaa aggtttccgt ttttccttgg   1980
aaggaagtag gctgacatat gaaaagagat tttcttctcc acaccagtcc ttactgagca   2040
tccgtggctc ccttttctct ccaagacgca acagtagggc gagccttttc agcttcagag   2100
gtcgagcaaa ggacattggc tctgagaatg actttgctga tgatgagcac agcacctttg   2160
aggacaatga cagccgaaga gactctctgt tcgtgccgca cagacatgga gaacggcgcc   2220
acagcaatgt cagccaggcc agccgtgcct ccagggtgct ccccatcctg cccatgaatg   2280
ggaagatgca tagcgctgtg gactgcaatg gtgtggtctc cctggtcggg ggcccttcta   2340
ccctcacatc tgctgggcag ctcctaccag agggcacaac tactgaaaca gaaataagaa   2400
agagacggtc cagttcttat catgtttcca tggatttatt ggaagatcct acatcaaggc   2460
aaagagcaat gagtatagcc agtattttga ccaacaccat ggaagaactt gaagaatcca   2520
gacagaaatg cccaccatgc tggtataaat ttgctaatat gtgtttgatt tgggactgtt   2580
gtaaaccatg gttaaaggtg aaacaccttg tcaacctggt tgtaatggac ccatttgttg   2640
acctggccat caccatctgc attgtcttaa atacactctt catggctatg gagcactatc   2700
ccatgacgga gcagttcagc agtgtactgt ctgttggaaa cctggtcttc acagggatct   2760
tcacagcaga aatgtttctc aagataattg ccatggatcc atattattac tttcaagaag   2820
gctggaatat ttttgatggt tttattgtga gccttagttt aatggaactt ggtttggcaa   2880
atgtggaagg attgtcagtt ctccgatcat tccggctgct ccgagttttc aagttggcaa   2940
aatcttggcc aactctaaat atgctaatta agatcattgg caattctgtg ggggctctag   3000
gaaacctcac cttggtattg gccatcatcg tcttcatttt tgctgtggtc ggcatgcagc   3060
tctttggtaa gagctacaaa gaatgtgtct gcaagatttc caatgattgt gaactcccac   3120
gctggcacat gcatgacttt ttccactcct tcctgatcgt gttccgcgtg ctgtgtggag   3180
```

-continued

```
agtggataga gaccatgtgg gactgtatgg aggtcgctgg ccaaaccatg tgccttactg   3240
tcttcatgat ggtcatggtg attggaaatc tagtggttct gaacctcttc ttggccttgc   3300
ttttgagttc cttcagttct gacaatcttg ctgccactga tgatgataac gaaatgaata   3360
atctccagat tgctgtggga aggatgcaga aaggaatcga ttttgttaaa agaaaaatac   3420
gtgaatttat tcagaaagcc tttgttagga agcagaaagc tttagatgaa attaaaccgc   3480
ttgaagatct aaataataaa aaagacagct gtatttccaa ccataccacc atagaaatag   3540
gcaaagacct caattatctc aaagacggaa atggaactac tagtggcata ggcagcagtg   3600
tagaaaaata tgtcgtggat gaaagtgatt acatgtcatt tataaacaac cctagcctca   3660
ctgtgacagt accaattgct gttggagaat ctgactttga aaatttaaat actgaagaat   3720
tcagcagcga gtcagatatg gaggaaagca aagagaagct aaatgcaact agttcatctg   3780
aaggcagcac ggttgatatt ggagctcccg ccgagggaga acagcctgag gttgaacctg   3840
aggaatccct tgaacctgaa gcctgtttta cagaagactg tgtacggaag ttcaagtgtt   3900
gtcagataag catagaagaa ggcaaaggga aactctggtg gaatttgagg aaaacatgct   3960
ataagatagt ggagcacaat tggttcgaaa ccttcattgt cttcatgatt ctgctgagca   4020
gtggggctct ggcctttgaa gatatataca ttgagcagcg aaaaaccatt aagaccatgt   4080
tagaatatgc tgacaaggtt ttcacttaca tattcattct ggaaatgctg ctaaagtggg   4140
ttgcatatgg ttttcaagtg tattttacca atgcctggtg ctggctagac ttcctgattg   4200
ttgatgtctc actggttagc ttaactgcaa atgccttggg ttactcagaa cttggtgcca   4260
tcaaatccct cagaacacta agagctctga ggccactgag agctttgtcc cggtttgaag   4320
gaatgagggt tgttgtaaat gctcttttag gagccattcc atctatcatg aatgtacttc   4380
tggtttgtct gatcttttgg ctaatattca gtatcatggg agtgaatctc tttgctggca   4440
agttttacca ttgtattaat tacaccactg gagagatgtt tgatgtaagc gtggtcaaca   4500
actacagtga gtgcaaagct ctcattgaga gcaatcaaac tgccaggtgg aaaaatgtga   4560
aagtaaactt tgataacgta ggacttggat atctgtctct acttcaagta gccacgttta   4620
agggatggat ggatattatg tatgcagctg ttgattcacg aaatgtagaa ttacaaccca   4680
agtatgaaga caacctgtac atgtatcttt attttgtcat ctttattatt tttggttcat   4740
tctttacctt gaatcttttc attggtgtca tcatagataa cttcaaccaa cagaaaaaga   4800
agtttggagg tcaagacatt tttatgacag aagaacagaa gaaatactac aatgcaatga   4860
aaaaactggg ttcaaagaaa ccacaaaaac ccatacctcg acctgctaac aaattccaag   4920
gaatggtctt tgattttgta accaaacaag tctttgatat cagcatcatg atcctcatct   4980
gccttaacat ggtcaccatg atggtggaaa ccgatgacca gagtcaagaa atgacaaaca   5040
ttctgtactg gattaatctg gtgtttattg ttctgttcac tggagaatgt gtgctgaaac   5100
tgatctctct tcgttactac tatttcacta ttggatggaa tatttttgat tttgtggtgg   5160
tcattctctc cattgtagga atgtttctgg ctgaactgat agaaaagtat tttgtgtccc   5220
ctaccctgtt ccgagtgatc cgtcttgcca ggattggccg aatcctacgt ctgatcaaag   5280
gagcaaaggg gatccgcacg ctgctctttg ctttgatgat gtcccttcct gcgttgttta   5340
acatcggcct ccttcttttc ctggtcatgt tcatctacgc catctttggg atgtccaatt   5400
ttgcctatgt taagagggaa gttgggatcg atgacatgtt caactttgag acctttggca   5460
acagcatgat ctgcctgttc caaattacaa cctctgctgg ctgggatgga ttgctagcac   5520
```

-continued

```
ctattcttaa tagtggacct ccagactgtg accctgacaa agatcaccct ggaagctcag   5580
ttaaaggaga ctgtgggaac ccatctgttg ggattttctt ttttgtcagt tacatcatca   5640
tatccttcct ggttgtggtg aacatgtaca tcgcggtcat cctggagaac ttcagtgttg   5700
ctactgaaga aagtgcagag cctctgagtg aggatgactt tgagatgttc tatgaggttt   5760
gggagaagtt tgatcccgat gcgacccagt ttatagagtt tgccaaactt tctgattttg   5820
cagatgccct ggatcctcct cttctcatag caaaacccaa caaagtccag ctcattgcca   5880
tggatctgcc catggtgagt ggtgaccgga tccactgtct tgacatctta tttgctttta   5940
caaagcgtgt tttgggtgag agtggagaga tggatgccct tcgaatacag atggaagagc   6000
gattcatggc atcaaacccc tccaaagtct cttatgagcc cattacgacc acgttgaaac   6060
gcaaacaaga ggaggtgtct gctattatta tccagagggc ttacagacgc tacctcttga   6120
agcaaaaagt taaaaaggta tcaagtatat acaagaaaga caaaggcaaa gaatgtgatg   6180
gaacacccat caaagaagat actctcattg ataaactgaa tgagaattca actccagaga   6240
aaaccgatat gacgccttcc accacgtctc caccctcgta tgatagtgtg accaaaccag   6300
aaaaagaaaa atttgaaaaa gacaaatcag aaaaggaaga caaagggaaa gatatcaggg   6360
aaagtaaaaa gtaaaaagaa accaagaatt ttccattttg tgatcaattg tttacagccc   6420
gtgatggtga tgtgtttgtg tcaacaggac tcccacagga ggtctatgcc aaactgactg   6480
tttttacaaa tgtatactta aggtcagtgc ctataacaag acagagacct ctggtcagca   6540
aactggaact cagtaaactg gagaaatagt atcgatggga ggtttctatt ttcacaacca   6600
gctgacactg ctgaagagca gaggcgtaat ggctactcag acgataggaa ccaatttaaa   6660
ggggggaggg aagttaaatt tttatgtaaa ttcaacatgt gacacttgat aatagtaatt   6720
gtcaccagtg tttatgtttt aactgccaca cctgccatat ttttacaaaa cgtgtgctgt   6780
gaatttatca cttttctttt taattcacag gttgtttact attatatgtg actatttttg   6840
taaatgggtt tgtgtttggg gagagggatt aaagggaggg aattctacat ttctctattg   6900
tattgtataa ctggatatat tttaaatgga ggcatgctgc aattctcatt cacacataaa   6960
aaaatcacat cacaaaaggg aagagtttac ttcttgtttc aggatgtttt tagatttttg   7020
aggtgcttaa atagctattc gtatttttaa ggtgtctcat ccagaaaaaa tttaatgtgc   7080
ctgtaaatgt tccatagaat cacaagcatt aaagagttgt tttatttta cataacccat    7140
taaatgtaca tgtatatatg tatatatgta tatgtgcgtg tatatacata tatatgtata   7200
cacacatgca cacacagaga tatacacata ccattacatt gtcattcaca gtcccagcag   7260
catgactatc acatttttga taagtgtcct ttggcataaa ataaaaatat cctatcagtc   7320
ctttctaaga agcctgaatt gaccaaaaaa catccccacc accactttat aaagttgatt   7380
ctgctttatc ctgcagtatt gtttagccat cttctgctct tggtaaggtt gacatagtat   7440
atgtcaattt aaaaaataaa agtctgcttt gtaaatagta attttaccca gtggtgcatg   7500
tttgagcaaa caaaaatgat gatttaagca cactacttat tgcatcaaat atgtaccaca   7560
gtaagtatag tttgcaagct ttcaacaggt aatatgatgt aattggttcc attatagttt   7620
gaagctgtca ctgctgcatg tttatcttgc ctatgctgct gtatcttatt ccttccactg   7680
ttcagaagtc taatatggga agccatatat cagtggtaaa gtgaagcaaa ttgttctacc   7740
aagacctcat tcttcatgtc attaagcaat aggttgcagc aaacaaggaa gagcttcttg   7800
ctttttattc ttccaacctt aattgaacac tcaatgatga aaagcccgac tgtacaaaca   7860
tgttgcaagc tgcttaaatc tgtttaaaat atatggttag agttttctaa gaaaatataa   7920
```

```
atactgtaaa aagttcattt tattttattt ttcagccttt tgtacgtaaa atgagaaatt   7980

aaaagtatct tcaggtggat gtcacagtca ctattgttag tttctgttcc tagcactttt   8040

aaattgaagc acttcacaaa ataagaagca aggactagga tgcagtgtag gtttctgctt   8100

ttttattagt actgtaaact tgcacacatt tcaatgtgaa acaaatctca aactgagttc   8160

aatgtttatt tgctttcaat agtaatgcct tatcattgaa agaggcttaa agaaaaaaaa   8220

aatcagctga tactcttggc attgcttgaa tccaatgttt ccacctagtc tttttattca   8280

gtaatcatca gtcttttcca atgtttgttt acacagatag atcttattga cccatatggc   8340

actagaactg tatcagatat aatatgggat cccagctttt tttcctctcc cacaaaacca   8400

ggtagtgaag ttatattacc agttacagca aaatactttg tgtttcacaa gcaacaataa   8460

atgtagattc tttatactga agctattgac ttgtagtgtg ttggtgaaat gcatgcagga   8520

aaatgctgtt accataaaga acggtaaacc acattacaat caagccaaaa gaataaaggt   8580

ttcgcttttg tttttgtatt taattgttgt ctttgtttct atctttgaaa tgccatttaa   8640

aggtagattt ctatcatgta aaaataatct atctgaaaaa caaatgtaaa gaacacacat   8700

taattactat aattcatctt tcaatttttt catggaatgg aagttaatta agaagagtgt   8760

attggataac tactttaata ttggccaaaa agctagatat ggcatcaggt agactagtgg   8820

aaagttacaa aaattaataa aaaattgact aacattttaa aaaaaaaaaa aaaaaa       8876
```

<210> SEQ ID NO 3
<211> LENGTH: 9141
<212> TYPE: DNA
<213> ORGANISM: Homo sapiens

<400> SEQUENCE: 3

```
accatagagt gaatctcaga acaggaagcg gaggcataag cagagaggat tctggaaagg     60

tctctttgtt ttcttatcca cagagaaaga aagaaaaaaa attgtaacta atttgtaaac    120

ctctgtggtc aaaaaaaaaa aaaaaaaaaa aagctgaaca gctgcagagg aagacacgtt    180

ataccctaac catcttggat gctgggcttt gttatgctgt aattcataag gctctgtttt    240

atcagagatt atggagcaag aaaactgaag ccaagccaca tcaaggtttg acagggatga    300

gatacctgtc aaggattcat agtagagtgg cttactggga aaggagcaaa gaatctcttc    360

tagggatatt gtaagaataa atgagataat tcacagaagg gacctggagc ttttccggaa    420

aaaggtgctg tgactatcta aggtaattcg tatgcaagaa gctacacgta attaaatgtg    480

caggatgaaa agatggcaca ggcactgttg gtacccccag gacctgaaag cttccgcctt    540

tttactagag aatctcttgc tgctatcgaa aaacgtgctg cagaagagaa agccaagaag    600

cccaaaaagg aacaagataa tgatgatgag aacaaaccaa agccaaatag tgacttggaa    660

gctggaaaga accttccatt tatttatgga gacattcctc cagagatggt gtcagagccc    720

ctggaggacc tggatcccta ctatatcaat aagaaaactt ttatagtaat gaataaagga    780

aaggcaattt tccgattcag tgccacctct gccttgtata ttttaactcc actaaaccct    840

gttaggaaaa ttgctatcaa gattttggta cattctttat tcagcatgct tatcatgtgc    900

actattttga ccaactgtgt atttatgacc ttgagcaacc ctcctgactg gacaaagaat    960

gtagagtaca cattcactgg aatctatacc tttgagtcac ttataaaaat cttggcaaga   1020

gggttttgct tagaagattt tacgtttctt cgtgatccat ggaactggct ggatttcagt   1080

gtcattgtga tggcatatgt gacagagttt gtggacctgg gcaatgtctc agcgttgaga   1140
```

-continued

```
acattcagag ttctccgagc actgaaaaca atttcagtca ttccaggttt aaagaccatt   1200
gtgggggccc tgatccagtc ggtaaagaag ctttctgatg tgatgatcct gactgtgttc   1260
tgtctgagcg tgtttgctct cattgggctg cagctgttca tgggcaatct gaggaataaa   1320
tgtttgcagt ggcccccaag cgattctgct tttgaaacca acaccacttc ctactttaat   1380
ggcacaatgg attcaaatgg gacatttgtt aatgtaacaa tgagcacatt taactggaag   1440
gattacattg gagatgacag tcacttttat gttttggatg ggcaaaaaga ccctttactc   1500
tgtggaaatg gctcagatgc aggccagtgt ccagaaggat acatctgtgt gaaggctggt   1560
cgaaacccca actatggcta cacaagcttt gacaccttta gctgggcttt cctgtctcta   1620
tttcgactca tgactcaaga ctactgggaa aatctttacc agttgacatt acgtgctgct   1680
gggaaaacat acatgatatt ttttgtcctg gtcattttct tgggctcatt ttatttggtg   1740
aatttgatcc tggctgtggt ggccatggcc tatgaggagc agaatcaggc caccttggaa   1800
gaagcagaac aaaaagaggc cgaatttcag cagatgctcg aacagcttaa aaagcaacag   1860
gaagaagctc aggcagttgc ggcagcatca gctgcttcaa gagatttcag tggaataggt   1920
gggttaggag agctgttgga aagttcttca gaagcatcaa agttgagttc caaaagtgct   1980
aaagaatgga ggaaccgaag gaagaaaaga agacagagag agcaccttga aggaaacaac   2040
aaaggagaga gagacagctt tcccaaatcc gaatctgaag acagcgtcaa aagaagcagc   2100
ttccttttct ccatggatgg aaacagactg accagtgaca aaaaattctg ctcccctcat   2160
cagtctctct tgagtatccg tggctccctg ttttccccaa gacgcaatag caaaacaagc   2220
attttcagtt tcagaggtcg ggcaaaggat gttggatctg aaaatgactt tgctgatgat   2280
gaacacagca catttgaaga cagcgaaagc aggagagact cactgtttgt gccgcacaga   2340
catggagagc gacgcaacag taacgttagt caggccagta tgtcatccag gatggtgcca   2400
gggcttccag caaatgggaa gatgcacagc actgtggatt gcaatggtgt ggtttccttg   2460
gtgggtggac cttcagctct aacgtcacct actggacaac ttcccccaga gggcaccacc   2520
acagaaacgg aagtcagaaa gagaaggtta agctcttacc agatttcaat ggagatgctg   2580
gaggattcct ctggaaggca aagagccgtg agcatagcca gcattctgac caacacaatg   2640
gaagaacttg aagaatctag acagaaatgt ccgccatgct ggtatagatt tgccaatgtg   2700
ttcttgatct gggactgctg tgatgcatgg ttaaaagtaa aacatcttgt gaatttaatt   2760
gttatggatc catttgttga tcttgccatc actatttgca ttgtcttaaa taccctcttt   2820
atggccatgg agcactaccc catgactgag caattcagta gtgtgttgac tgtaggaaac   2880
ctggtcttta ctgggatttt cacagcagaa atggttctca agatcattgc catggatcct   2940
tattactatt tccaagaagg ctggaatatc tttgatggaa ttattgtcag cctcagttta   3000
atggagcttg gtctgtcaaa tgtggaggga ttgtctgtac tgcgatcatt cagactgctt   3060
agagttttca agttggcaaa atcctggccc acactaaata tgctaattaa gatcattggc   3120
aattctgtgg gggctctagg aaacctcacc ttggtgttgg ccatcatcgt cttcattttt   3180
gctgtggtcg gcatgcagct ctttggtaag agctacaaag aatgtgtctg caagatcaat   3240
gatgactgta cgctcccacg gtggcacatg aacgacttct tccactcctt cctgattgtg   3300
ttccgcgtgc tgtgtggaga gtggatagag accatgtggg actgtatgga ggtcgctggc   3360
caaaccatgt gccttattgt tttcatgttg gtcatggtca ttggaaacct tgtggttctg   3420
aacctctttc tggccttatt gttgagttca tttagctcag acaaccttgc tgctactgat   3480
gatgacaatg aaatgaataa tctgcagatt gcagtaggaa gaatgcaaaa gggaattgat   3540
```

-continued

```
tatgtgaaaa ataagatgcg ggagtgtttc caaaaagcct tttttagaaa gccaaaagtt   3600
atagaaatcc atgaaggcaa taagatagac agctgcatgt ccaataatac tggaattgaa   3660
ataagcaaag agcttaatta tcttagagat gggaatggaa ccaccagtgg tgtaggtact   3720
ggaagcagtg ttgaaaaata cgtaatcgat gaaaatgatt atatgtcatt cataaacaac   3780
cccagcctca ccgtcacagt gccaattgct gttggagagt ctgactttga aaacttaaat   3840
actgaagagt tcagcagtga gtcagaacta gaagaaagca aagagaaatt aaatgcaacc   3900
agctcatctg aaggaagcac agttgatgtt gttctacccc gagaaggtga acaagctgaa   3960
actgaacccg aagaagacct taaaccggaa gcttgtttta ctgaaggatg tattaaaaag   4020
tttccattct gtcaagtaag tacagaagaa ggcaaaggga agatctggtg gaatcttcga   4080
aaaacctgct acagtattgt tgagcacaac tggtttgaga ctttcattgt gttcatgatc   4140
cttctcagta gtggtgcatt ggcctttgaa gatatataca ttgaacagcg aaagactatc   4200
aaaaccatgc tagaatatgc tgacaaagtc tttacctata tattcattct ggaaatgctt   4260
ctcaaatggg ttgcttatgg atttcaaaca tatttcacta atgcctggtg ctggctagat   4320
ttcttgatcg ttgatgtttc tttggttagc ctggtagcca atgctcttgg ctactcagaa   4380
ctcggtgcca tcaaatcatt acggacatta agagctttaa gacctctaag agccttatcc   4440
cggtttgaag gcatgagggt ggttgtgaat gctcttgttg gagcaattcc ctctatcatg   4500
aatgtgctgt tggtctgtct catcttctgg ttgatcttta gcatcatggg tgtgaatttg   4560
tttgctggca agttctacca ctgtgttaac atgacaacgg gtaacatgtt tgacattagt   4620
gatgttaaca atttgagtga ctgtcaggct cttggcaagc aagctcggtg gaaaaacgtg   4680
aaagtaaact ttgataatgt tggcgctggc tatcttgcac tgcttcaagt ggccacattt   4740
aaaggctgga tggatattat gtatgcagct gttgattcac gagatgttaa acttcagcct   4800
gtatatgaag aaaatctgta catgtattta tactttgtca tctttatcat ctttgggtca   4860
ttcttcactc tgaatctatt cattggtgtc atcatagata acttcaacca gcagaaaaag   4920
aagtttggag gtcaagacat ctttatgaca gaggaacaga aaaaatatta caatgcaatg   4980
aagaaacttg gatccaagaa acctcagaaa cccatacctc gcccagcaaa caaattccaa   5040
ggaatggtct ttgattttgt aaccagacaa gtctttgata tcagcatcat gatcctcatc   5100
tgcctcaaca tggtcaccat gatggtggaa acggatgacc agggcaaata catgacccta   5160
gttttgtccc ggatcaacct agtgttcatt gttctgttca ctggagaatt tgtgctgaag   5220
ctcgtctccc tcagacacta ctacttcact ataggctgga acatctttga ctttgtggtg   5280
gtgattctct ccattgtagg tatgtttctg gctgagatga tagaaaagta ttttgtgtcc   5340
cctaccttgt tccgagtgat ccgtcttgcc aggattggcc gaatcctacg tctgatcaaa   5400
ggagcaaagg ggatccgcac gctgctcttt gctttgatga tgtcccttcc tgcgttgttt   5460
aacatcggcc tcctgctctt cctggtcatg tttatctatg ccatctttgg gatgtccaac   5520
tttgcctatg ttaaaaagga agctggaatt gatgacatgt tcaactttga gacctttggc   5580
aacagcatga tctgcttgtt ccaaattaca acctctgctg gctgggatgg attgctagca   5640
cctattctta atagtgcacc acccgactgt gaccctgaca caattcaccc tggcagctca   5700
gttaagggag actgtgggaa cccatctgtt gggattttct tttttgtcag ttacatcatc   5760
atatccttcc tggttgtggt gaacatgtac atcgcggtca tcctggagaa cttcagtgtt   5820
gctactgaag aaagtgcaga gcccctgagt gaggatgact ttgagatgtt ctatgaggtt   5880
```

-continued

```
tgggaaaagt ttgatcccga tgcgacccag tttatagagt tctctaaact ctctgatttt   5940
gcagctgccc tggatcctcc tcttctcata gcaaaaccca acaaagtcca gcttattgcc   6000
atggatctgc ccatggtcag tggtgaccgg atccactgtc ttgatatttt atttgccttt   6060
acaaagcgtg ttttgggtga gagtggagag atggatgccc ttcgaataca gatggaagac   6120
aggtttatgg catcaaaccc ctccaaagtc tcttatgagc ctattacaac cactttgaaa   6180
cgtaaacaag aggaggtgtc tgccgctatc attcagcgta atttcagatg ttatctttta   6240
aagcaaaggt taaaaaatat atcaagtaac tataacaaag aggcaattaa agggaggatt   6300
gacttaccta taaaacaaga catgattatt gacaaactaa atgggaactc cactccagaa   6360
aaaacagatg ggagttcctc taccacctct cctccttcct atgatagtgt aacaaaacca   6420
gacaaggaaa agtttgagaa agacaaacca gaaaaagaaa gcaaaggaaa agaggtcaga   6480
gaaaatcaaa agtaaaaaga aacaaagaat tatctttgtg atcaattgtt tacagcctat   6540
gaaggtaaag tatatgtgtc aactggactt caagaggagg tccatgccaa actgactgtt   6600
ttaacaaata ctcatagtca gtgcctatac aagacagtga agtgacctct ctgtcactgc   6660
aactctgtga agcagggtat caacattgac aagaggttgc tgtttttatt accagctgac   6720
actgctgagg agaaacccaa tggctaccta gactataggg atagttgtgc aaagtgaaca   6780
ttgtaactac accaaacacc tttagtacag tccttgcatc cattctattt ttaacttcca   6840
tatctgccat atttttacaa aatttgttct agtgcatttc catggtcccc aattcatagt   6900
ttattcataa tgctatgtca ctatttttgt aaatgaggtt tacgttgaag aaacagtata   6960
caagaaccct gtctctcaaa tgatcagaca aaggtgtttt gccagagaga taaaattttt   7020
gctcaaaacc agaaaaagaa ttgtaatggc tacagtttca gttacttcca ttttctagat   7080
ggctttaatt ttgaaagtat tttagtctgt tatgtttgtt tctatctgaa cagttatgtg   7140
cctgtaaagt ctcctctaat atttaaagga ttatttttat gcaaagtatt ctgtttcagc   7200
aagtgcaaat tttattctaa gtttcagagc tctatattta atttaggtca aatgctttcc   7260
aaaaagtaat ctaataaatc cattctagaa aaatatatct aaagtattgc tttagaatag   7320
ttgttccact ttctgctgca gtattgcttt gccatcttct gctctcagca aagctgatag   7380
tctatgtcaa ttaaataccc tatgttatgt aaatagttat tttatcctgt ggtgcatgtt   7440
tgggcaaata tatatatagc ctgataaaca acttctatta aatcaaatat gtaccacagt   7500
gtatgtgtct tttgcaagct tccaacaggg atgtatcctg tatcattcat taaacatagt   7560
ttaaaggcta tcactaatgc atgttaatat tgcctatgct gctctatttt actcaatcca   7620
ttcttcacaa gtcttggtta aagaatgtca catattggtg atagaatgaa ttcaacctgc   7680
tctgtccatt atgtcaagca gaataatttg aagctattta caaacacctt tacttttgca   7740
cttttaattc aacatgagta tcatatggta tctctctaga tttcaaggaa acacactgga   7800
tactgcctac tgacaaaacc tattcttcat attttgctaa aaatatgtct aaaacttgtt   7860
taaatataaa taatgtaaaa atataatcaa ctttatttgt cagcattttg tacataagaa   7920
aattattttc aggttgatga catcacaatt tattttactt tatgcttttg cttttgattt   7980
ttaatcacaa ttccaaactt ttgaatccat aagatttttc aatggataat ttcctaaaat   8040
aaaagttaga taatgggttt tatggatttc tttgttataa tatattttct accattccaa   8100
taggagatac attggtcaaa cactcaaacc tagatcattt tctaccaact atggttgcct   8160
caatataacc ttttattcat agatgttttt ttttattcaa cttttgtagt atttacgtat   8220
gcagactagt cttatttttt taattcctgc tgcactaaag ctattacaaa tataacatgg   8280
```

```
actttgttct ttttagccat gaacaaagtg gcaaagttgt gcaattacct aacatgatat   8340
aaatttttgt tttttgcaca aaccaaaagt ttaatgttaa ttctttttac aaaactattt   8400
actgtagtgt attgaagaac tgcatgcagg gaattgctat tgctaaaaag aatggtgagc   8460
tacgtcatta ttgagccaaa agaataaatt tcatttttta ttgcatttca cttattggcc   8520
tctggggttt tttgtttttg ttttttgctg ttggcagttt aaaatatata taattaataa   8580
aacctgtgct tgatctgaca tttgtataca taaaagttta catgaatttt acaacaaact   8640
agtgcatgat tcaccaagca gtactacaga acaaaggcaa attaaaagca gctttgtgaa   8700
cttttatgtg tgcaaaggat caagttcaca tgttccaact ttcaggtttg ataataatag   8760
tagtaaccac ctacaatagc tttcaatttc aattaactcc cttggctata agcatctaaa   8820
ctcatcttct ttcaatataa ttgatgctat ctcctaatta cttggtggct aataaatgtt   8880
acattctttg ttacttaaat gcattatata aactcctatg tatacataag gtattaatga   8940
tatagttatt gagaatttat attaactttt ttttcaagaa cccttggatt tatgtgaggt   9000
caaaaccaaa ctcttattct cagtggaaaa ctccagttgt aatgcatatt tttaaagaca   9060
atttggatct aaatatgtat ttcataattc tcccataata aattatataa ggtggctaat   9120
tggaaaaaaa aaaaaaaaaa a                                             9141
```

<210> SEQ ID NO 4
<211> LENGTH: 7805
<212> TYPE: DNA
<213> ORGANISM: Homo sapiens

<400> SEQUENCE: 4

```
ccagcacccc ggggctgcgc actgcagctc cccaggccac ccaccaccct tctggtctct     60
gagcccagga tgcgaggatg gccagaccat ctctgtgcac cctggtgcct ctgggccctg    120
agtgcttgcg ccccttcacc cgggagtcac tggcagccat agaacagcgg gcggtggagg    180
aggaggcccg gctgcagcgg aataagcaga tggagattga ggagcccgaa cggaagccac    240
gaagtgactt ggaggctggc aagaacctac ccatgatcta cggagacccc ccgccggagg    300
tcatcggcat ccccctggag gacctggatc cctactacag caataagaag accttcatcg    360
tactcaacaa gggcaaggcc atcttccgct tctccgccac acctgctctc tacctgctga    420
gccccttcag cgtagtcagg cgcggggcca tcaaggtgct catccatgcg ctgttcagca    480
tgttcatcat gatcaccatc ttgaccaact gcgtattcat gaccatgagt gacccgcctc    540
cctggtccaa gaatgtggag tacaccttca cagggatcta cacctttgag tccctcatca    600
agatactggc ccgaggcttc tgtgtcgacg acttcacatt cctccgggac ccctggaact    660
ggctggactt cagtgtcatc atgatggcgt acctgacaga gtttgtggac ttgggcaaca    720
tctcagccct gaggaccttc cgggtgctgc gggccctcaa aaccatcacg gtcatcccag    780
ggctgaagac gatcgtgggg gccctgatcc agtcggtgaa aaagctgtcg gatgtgatga    840
tcctcactgt cttctgcctg agcgtctttg cgctggtagg actgcagctc ttcatgggaa    900
acctgaggca gaagtgtgtg cgctggcccc cgccgttcaa cgacaccaac accacgtggt    960
acagcaatga cacgtggtac ggcaatgaca catggtatgg caatgagatg tggtacggca   1020
atgactcatg gtatgccaac gacacgtgga acagccatgc aagctgggcc accaacgata   1080
cctttgattg ggacgcctac atcagtgatg aagggaactt ctacttcctg gagggctcca   1140
acgatgccct gctctgtggg aacagcagtg atgctgggca ctgccctgag ggttatgagt   1200
```

```
gcatcaagac cgggcggaac cccaactatg gctacaccag ctatgacacc ttcagctggg   1260
ccttcttggc tctcttccgc ctcatgacac aggactattg ggagaacctc ttccagctga   1320
cccttcgagc agctggcaag acctacatga tcttcttcgt ggtcatcatc ttcctgggct   1380
ctttctacct catcaatctg atcctggccg tggtggccat ggcatatgcc gagcagaatg   1440
aggccaccct ggccgaggat aaggagaaag aggaggagtt tcagcagatg cttgagaagt   1500
tcaaaaagca ccaggaggag ctggagaagg ccaaggccgc ccaagctctg gaaggtgggg   1560
aggcagatgg ggacccagcc catggcaaag actgcaatgg cagcctggac acatcgcaag   1620
gggagaaggg agccccgagg cagagcagca gcggagacag cggcatctcc gacgccatgg   1680
aagaactgga agaggcccac caaaagtgcc caccatggtg gtacaagtgc gcccacaaag   1740
tgctcatatg gaactgctgc gccccgtggc tgaagttcaa gaacatcatc cacctgatcg   1800
tcatggaccc gttcgtggac ctgggcatca ccatctgcat cgtgctcaac accctcttca   1860
tggccatgga acattacccc atgacggagc actttgacaa cgtgctcact gtgggcaacc   1920
tggtcttcac aggcatcttc acagcagaga tggttctgaa gctgattgcc atggacccct   1980
acgagtattt ccagcagggt tggaatatct tcgacagcat catcgtcacc ctcagcctgg   2040
tagagctagg cctggccaac gtacagggac tgtctgtgct acgctccttc cgtctgctgc   2100
gggtcttcaa gctggccaag tcgtggccaa cgctgaacat gctcatcaag atcattggca   2160
attcagtggg ggcgctgggt aacctgacgc tggtgctggc tatcatcgtg ttcatcttcg   2220
ccgtggtggg catgcagctg tttggcaaga gctacaagga gtgcgtgtgc aagattgcct   2280
tggactgcaa cctgccgcgc tggcacatgc atgatttctt ccactccttc ctcatcgtct   2340
tccgcatcct gtgcggggag tggatcgaga ccatgtggga ctgcatggag gtggccggcc   2400
aagccatgtg cctcaccgtc ttcctcatgg tcatggtcat cggcaatctt gtggtcctga   2460
acctgttcct ggctctgctg ctgagctcct tcagcgccga cagtctggca gcctcggatg   2520
aggatggcga gatgaacaac ctgcagattg ccatcgggcg catcaagttg ggcatcggct   2580
ttgccaaggc cttcctcctg gggctgctgc atggcaagat cctgagcccc aaggacatca   2640
tgctcagcct cggggaggct gacggggccg gggaggctgg agaggcgggg gagactgccc   2700
ccgaggatga gaagaaggag ccgccccgag aggacctgaa gaaggacaat cacatcctga   2760
accacatggg cctggctgac ggcccccccat ccagcctcga gctggaccac cttaacttca   2820
tcaacaaccc ctacctgacc atacaggtgc ccatcgcctc cgaggagtcc gacctggaga   2880
tgcccaccga ggaggaaacc gacactttct cagagcctga ggatagcaag aagccgccgc   2940
agcctctcta tgatgggaac tcgtccgtct gcagcacagc tgactacaag cccccccgagg   3000
aggaccctga ggagcaggca gaggagaacc ccgaggggga gcagcctgag gagtgcttca   3060
ctgaggcctg cgtgcagcgc tggccctgcc tctacgtgga catctcccag ggccgtggga   3120
agaagtggtg gactctgcgc agggcctgct tcaagattgt cgagcacaac tggttcgaga   3180
ccttcattgt cttcatgatc ctgctcagca gtggggctct ggccttcgag gacatctaca   3240
ttgagcagcg gcgagtcatt cgcaccatcc tagaatatgc cgacaaggtc ttcacctaca   3300
tcttcatcat ggagatgctg ctcaaatggg tggcctacgg ctttaaggtg tacttcacca   3360
acgcctggtg ctggctcgac ttcctcatcg tggatgtctc catcatcagc ttggtggcca   3420
actggctggg ctactcggag ctgggaccca tcaaatccct gcggacactg cgggccctgc   3480
gtcccctgag ggcactgtcc cgattcgagg gcatgagggt ggtggtgaac gccctcctag   3540
gcgccatccc ctccatcatg aatgtgctgc ttgtctgcct catcttctgg ctgatcttca   3600
```

-continued

```
gcatcatggg tgtcaacctg tttgccggca agttctacta ctgcatcaac accaccacct   3660
ctgagaggtt cgacatctcc gaggtcaaca acaagtctga gtgcgagagc ctcatgcaca   3720
caggccaggt ccgctggctc aatgtcaagg tcaactacga caacgtgggt ctgggctacc   3780
tctccctcct gcaggtggcc accttcaagg gttggatgga catcatgtat gcagccgtgg   3840
actcccggga gaaggaggag cagccgcagt acgaggtgaa cctctacatg tacctctact   3900
ttgtcatctt catcatcttt ggctccttct tcaccctcaa cctcttcatt ggcgtcatca   3960
ttgacaactt caaccagcag aagaagaagt taggggggaa agacatcttt atgacggagg   4020
aacagaagaa atactataac gccatgaaga agcttggctc caagaagcct cagaagccaa   4080
ttccccggcc ccagaacaag atccagggca tggtgtatga cctcgtgacg aagcaggcct   4140
tcgacatcac catcatgatc ctcatctgcc tcaacatggt caccatgatg gtggagacag   4200
acaaccagag ccagctcaag gtggacatcc tgtacaacat caacatgatc ttcatcatca   4260
tcttcacagg ggagtgcgtg ctcaagatgc tcgccctgcg ccagtactac ttcaccgttg   4320
gctggaacat ctttgacttc gtggtcgtca tcctgtccat tgtgggcctt gccctctctg   4380
acctgatcca gaagtacttc gtgtcaccca cgctgttccg tgtgatccgc ctggcgcgga   4440
ttgggcgtgt cctgcggctg atccgcgggg ccaagggcat ccggacgctg ctgttcgccc   4500
tcatgatgtc gctgcctgcc ctcttcaaca tcggcctcct cctcttcctg gtcatgttca   4560
tctactccat cttcggcatg tccaactttg cctacgtcaa gaaggagtcg ggcatcgatg   4620
atatgttcaa cttcgagacc ttcggcaaca gcatcatctg cctgttcgag atcaccacgt   4680
cggccggctg ggacgggctc ctcaacccca tcctcaacag cgggccccca gactgtgacc   4740
ccaacctgga gaacccgggc accagtgtca agggtgactg cggcaacccc tccatcggca   4800
tctgcttctt ctgcagctat atcatcatct ccttcctcat cgtggtcaac atgtacatcg   4860
ccatcatcct ggagaacttc aatgtggcca cagaggagag cagcgagccc cttggtgaag   4920
atgactttga gatgttctac gagacatggg agaagttcga ccccgacgcc acccagttca   4980
tcgcctacag ccgcctctca gacttcgtgg acaccctgca ggaaccgctg aggattgcca   5040
agcccaacaa gatcaagctc atcacactgg acttgcccat ggtgccaggg gacaagatcc   5100
actgcctgga catcctcttt gccctgacca aagaggtcct gggtgactct ggggaaatgg   5160
acgccctcaa gcagaccatg gaggagaagt tcatggcagc caacccctcc aaggtgtcct   5220
acgagcccat caccaccacc ctcaagagga agcacgagga ggtgtgcgcc atcaagatcc   5280
agagggccta ccgccggcac ctgctacagc gctccatgaa gcaggcatcc tacatgtacc   5340
gccacagcca cgacggcagc ggggatgacg cccctgagaa ggaggggctg cttgccaaca   5400
ccatgagcaa gatgtatggc cacgagaatg ggaacagcag ctcgccaagc ccggaggaga   5460
agggcgaggc aggggacgcc ggacccacta tggggctgat gcccatcagc ccctcagaca   5520
ctgcctggcc tcccgcccct cccccagggc agactgtgcg cccaggtgtc aaggagtctc   5580
ttgtctagca ggcagcatcg ggtggcccca ctgagtctcg gcatagtccc cagagctccc   5640
ccgtggtgcc tgcacacaga gtgagggagg agggctttga atctgggact gtgcctggct   5700
ccctgatggg ggacaggatt tggccacact ggggctgaca cccaggcccg agcgcctgcg   5760
ttcccagacc atgggaaatg ggaattgcgc tcaggggctc catgctgggt ctgaggcccc   5820
tgcctccaag atttaacctg caagttgctc tgacctcctc tgggccctgt cgcccctcct   5880
tttggcctgg gggaggtcag aacattcgaa tctctgcccc tcacttgagg aggagctggc   5940
```

-continued

```
ctgcggtgga gggatcagtt gccccccatc accagagtct taagggtcac tggcctctcc   6000

ccaggaagtg gctcagaccc ctcagcccca gcccagacaa agatgtctta acctcaggga   6060

gtgcagacac ctaaccccag ggcactgcca gcccaccccc tttgactctg ggtgcagct    6120

tcacccacca ggccagctca ggaattccct ggaaaaggga aatgtgactg gttcagaaat   6180

agctcctcaa agcctcaaaa cctgattggc cactggatcc tgctgctttg ggctgggatg   6240

gtgactcctg aaacctcttc ctaggccacg tccaggtccg tagctcccct ggctggctcc   6300

taggggaaga gcagaaggaa ggatgccact tgggaatgaa ttgtcctttt ctaggaagca   6360

cgggggagtg agacaggctg ggtcctgcca gctggatcgc tgcacatggc ctgagcatcc   6420

agacctgagc gggagtcagg gacctgctgc tcagtaagaa gattctcgcc ccttccctct   6480

ctccctgcct cactcctccg tgagcaccac cagggctcca ggagcctcat ccagcctcag   6540

agatctccct tctcatctcc ccacgcccgt ctctttctca cctttcccac ctctctcccc   6600

aaagtgatcc taagaatgta cagttgagct caggttagat atttcgaccc tggggcgtgc   6660

agcagggaag gcccaactgg ttcaggctca accttccaac ttcctgtggc ctgaagaagc   6720

acttctgctg catcgctgtt ctgggcatgg cagggccagg cctctgctgg ctcaggagga   6780

ggggtgagag acctgctcag gcgtcgctgg atttattcac ttgtgtgtgt acctgtggct   6840

gtgtgtctgc ttgtatgctt ttataggcct gtgtgtatag ctgtgtgtgt gttcaagtgc   6900

gtgactgtat gtgtgtgtgt gaaccactgt gtactggagc ctgcattatg cacgtgtctg   6960

ggtatctttg tatatatgtg tatatatgtg tgccctggac tgtttcaagg tccatggagt   7020

acggctggtg tgtcatactg tgcaggcctg tccctgggag tgttcccgtg cctgggagag   7080

tggacctgtg ctgtgagtgt gtggatgcgt gtgaacgcat gtggtaaggt gtgtactcag   7140

ggcattctgt tggcctaagt gcctcttctt tttcttcttg tttctcatga aaagtttgat   7200

taaaattcag gaagcagcaa aaccttcaaa acaagacatg tatgtgtgct tgagtgtgtg   7260

aacacgtgtg tgtgtgtgca catctacatg ccatgcctat gggccagagt tgtctttatt   7320

gtccaccatg ctctctcacc tgctcccagt cctgcctgaa cagccctctc tctcactccc   7380

ctctcctccc cttcctgttt ctcgttgtca cacccatggc ctcagccctg ctccctgcct   7440

cctgcctatg tctcctctat ggaaggaggc ctccactcct tccatctctt ccttcagaag   7500

tttcgtctaa tgggggcagt ctccccttcc tggcacattg cccctctgcc ttgccctcct   7560

gggccctggg ctggcacagc ccctggagcc tcagaaatct gtttgattgg atattctcct   7620

cggactgtgt gcaggttgca gaggaagagt agatgagccg ggtccggcct ctccctgcct   7680

gtggcccctc ccctgcagac ggatgcccat tcctgcctgg tccagtgggg aacaggtccc   7740

acgccaggcc agcaggcggg ctcctttgta cagttcttac aataaaccct ccttggtgcc   7800

tctgg                                                               7805
```

<210> SEQ ID NO 5
<211> LENGTH: 8504
<212> TYPE: DNA
<213> ORGANISM: Homo sapiens

<400> SEQUENCE: 5

```
agacggcggc ggcgcccgta ggatgcaggg atcgctcccc cggggccgct gagcctgcgc     60

ccagtgcccc gagccccgcg ccgagccgag tccgcgccaa gcagcagccg cccaccccgg    120

ggcccggccg ggggaccagc agcttcccca caggcaacgt gaggagagcc tgtgcccaga    180

agcaggatga gaagatggca aacttcctat tacctcgggg caccagcagc ttccgcaggt    240
```

-continued

```
tcacacggga gtccctggca gccatcgaga agcgcatggc agagaagcaa gcccgcggct    300
caaccacctt gcaggagagc cgagaggggc tgcccgagga ggaggctccc cggccccagc    360
tggacctgca ggcctccaaa aagctgccag atctctatgg caatccaccc caagagctca    420
tcggagagcc cctggaggac ctggacccct tctatagcac ccaaaagact ttcatcgtac    480
tgaataaagg caagaccatc ttccggttca gtgccaccaa cgccttgtat gtcctcagtc    540
ccttccaccc catccggaga gcggctgtga agattctggt tcactcgctc ttcaacatgc    600
tcatcatgtg caccatcctc accaactgcg tgttcatggc ccagcacgac cctccaccct    660
ggaccaagta tgtcgagtac accttcaccg ccatttacac ctttgagtct ctggtcaaga    720
ttctggctcg aggcttctgc ctgcacgcgt tcactttcct tcgggaccca tggaactggc    780
tggactttag tgtgattatc atggcataca caactgaatt tgtggacctg ggcaatgtct    840
cagccttacg caccttccga gtcctccggg ccctgaaaac tatatcagtc atttcagggc    900
tgaagaccat cgtgggggcc ctgatccagt ctgtgaagaa gctggctgat gtgatggtcc    960
tcacagtctt ctgcctcagc gtctttgccc tcatcggcct gcagctcttc atgggcaacc   1020
taaggcacaa gtgcgtgcgc aacttcacag cgctcaacgg caccaacggc tccgtggagg   1080
ccgacggctt ggtctgggaa tccctggacc tttacctcag tgatccagaa aattacctgc   1140
tcaagaacgg cacctctgat gtgttactgt gtgggaacag ctctgacgct gggacatgtc   1200
cggagggcta ccggtgccta aaggcaggcg agaaccccga ccacggctac accagcttcg   1260
attcctttgc ctgggccttt cttgcactct tccgcctgat gacgcaggac tgctgggagc   1320
gcctctatca gcagaccctc aggtccgcag ggaagatcta catgatcttc ttcatgcttg   1380
tcatcttcct ggggtccttc tacctggtga acctgatcct ggccgtggtc gcaatggcct   1440
atgaggagca aaaccaagcc accatcgctg agaccgagga gaaggaaaag cgcttccagg   1500
aggccatgga aatgctcaag aaagaacacg aggccctcac catcaggggt gtggataccg   1560
tgtcccgtag ctccttggag atgtcccctt tggccccagt aaacagccat gagagaagaa   1620
gcaagaggag aaaacggatg tcttcaggaa ctgaggagtg tggggaggac aggctcccca   1680
agtctgactc agaagatggt cccagagcaa tgaatcatct cagcctcacc cgtggcctca   1740
gcaggacttc tatgaagcca cgttccagcc gcgggagcat tttcaccttt cgcaggcgag   1800
acctgggttc tgaagcagat tttgcagatg atgaaaacag cacagcgggg gagagcgaga   1860
gccaccacac atcactgctg gtgccctggc ccctgcgccg gaccagtgcc cagggacagc   1920
ccagtcccgg aacctcggct cctggccacg ccctccatgg caaaaagaac agcactgtgg   1980
actgcaatgg ggtggtctca ttactggggg caggcgaccc agaggccaca tccccaggaa   2040
gccacctcct ccgccctgtg atgctagagc acccgccaga cacgaccacg ccatcggagg   2100
agccaggcgg gccccagatg ctgacctccc aggctccgtg tgtagatggc ttcgaggagc   2160
caggagcacg gcagcgggcc ctcagcgcag tcagcgtcct caccagcgca ctggaagagt   2220
tagaggagtc tcgccacaag tgtccaccat gctggaaccg tctcgcccag cgctacctga   2280
tctgggagtg ctgcccgctg tggatgtcca tcaagcaggg agtgaagttg gtggtcatgg   2340
acccgtttac tgacctcacc atcactatgt gcatcgtact caacacactc ttcatggcgc   2400
tggagcacta caacatgaca agtgaattcg aggagatgct gcaggtcgga aacctggtct   2460
tcacagggat tttcacagca gagatgacct tcaagatcat tgccctcgac ccctactact   2520
acttccaaca gggctggaac atcttcgaca gcatcatcgt catccttagc ctcatggagc   2580
```

-continued

```
tgggcctgtc ccgcatgagc aacttgtcgg tgctgcgctc cttccgcctg ctgcgggtct   2640
tcaagctggc caaatcatgg cccaccctga acacactcat caagatcatc gggaactcag   2700
tgggggcact ggggaacctg acactggtgc tagccatcat cgtgttcatc tttgctgtgg   2760
tgggcatgca gctctttggc aagaactact cggagctgag ggacagcgac tcaggcctgc   2820
tgcctcgctg gcacatgatg gacttctttc atgccttcct catcatcttc cgcatcctct   2880
gtggagagtg gatcgagacc atgtgggact gcatggaggt gtcggggcag tcattatgcc   2940
tgctggtctt cttgcttgtt atggtcattg gcaaccttgt ggtcctgaat ctcttcctgg   3000
ccttgctgct cagctccttc agtgcagaca acctcacagc ccctgatgag gacagagaga   3060
tgaacaacct ccagctggcc ctggcccgca tccagagggg cctgcgcttt gtcaagcgga   3120
ccacctggga tttctgctgt ggtctcctgc ggcagcggcc tcagaagccc gcagcccttg   3180
ccgcccaggg ccagctgccc agctgcattg ccaccccta ctccccgcca cccccagaga   3240
cggagaaggt gcctcccacc cgcaaggaaa cacggtttga ggaaggcgag caaccaggcc   3300
agggcacccc cggggatcca gagcccgtgt gtgtgcccat cgctgtggcc gagtcagaca   3360
cagatgacca agaagaagat gaggagaaca gcctgggcac ggaggaggag tccagcaagc   3420
agcaggaatc ccagcctgtg tccggtggcc cagaggcccc tccggattcc aggacctgga   3480
gccaggtgtc agcgactgcc tcctctgagg ccgaggccag tgcatctcag gccgactggc   3540
ggcagcagtg gaaagcggaa ccccaggccc cagggtgcgg tgagacccca gaggacagtt   3600
gctccgaggg cagcacagca gacatgacca acaccgctga gctcctggag cagatccctg   3660
acctcggcca ggatgtcaag gacccagagg actgcttcac tgaaggctgt gtccggcgct   3720
gtccctgctg tgcggtggac accacacagg ccccagggaa ggtctggtgg cggttgcgca   3780
agacctgcta ccacatcgtg gagcacagct ggttcgagac attcatcatc ttcatgatcc   3840
tactcagcag tggagcgctg gccttcgagg acatctacct agaggagcgg aagaccatca   3900
aggttctgct tgagtatgcc gacaagatgt tcacatatgt cttcgtgctg gagatgctgc   3960
tcaagtgggt ggcctacggc ttcaagaagt acttcaccaa tgcctggtgc tggctcgact   4020
tcctcatcgt agacgtctct ctggtcagcc tggtggccaa caccctgggc tttgccgaga   4080
tgggccccat caagtcactg cggacgctgc gtgcactccg tcctctgaga gctctgtcac   4140
gatttgaggg catgagggtg gtggtcaatg ccctggtggg cgccatcccg tccatcatga   4200
acgtcctcct cgtctgcctc atcttctggc tcatcttcag catcatgggc gtgaacctct   4260
ttgcggggaa gtttgggagg tgcatcaacc agacagaggg agacttgcct ttgaactaca   4320
ccatcgtgaa caacaagagc cagtgtgagt ccttgaactt gaccggagaa ttgtactgga   4380
ccaaggtgaa agtcaacttt gacaacgtgg gggccgggta cctggccctt ctgcaggtgg   4440
caacatttaa aggctggatg gacattatgt atgcagctgt ggactccagg gggtatgaag   4500
agcagcctca gtgggaatac aacctctaca tgtacatcta ttttgtcatt ttcatcatct   4560
ttgggtcttt cttcaccctg aacctcttta ttggtgtcat cattgacaac ttcaaccaac   4620
agaagaaaaa gttagggggc caggacatct tcatgacaga ggagcagaag aagtactaca   4680
atgccatgaa gaagctgggc tccaagaagc cccagaagcc catcccacgg cccctgaaca   4740
agtaccaggg cttcatattc gacattgtga ccaagcaggc ctttgacgtc accatcatgt   4800
ttctgatctg cttgaatatg gtgaccatga tggtggagac agatgaccaa agtcctgaga   4860
aaatcaacat cttggccaag atcaacctgc tctttgtggc catcttcaca ggcgagtgta   4920
ttgtcaagct ggctgccctg cgccactact acttcaccaa cagctggaat atcttcgact   4980
```

```
tcgtggttgt catcctctcc atcgtgggca ctgtgctctc ggacatcatc cagaagtact   5040
tcttctcccc gacgctcttc cgagtcatcc gcctggcccg aataggccgc atcctcagac   5100
tgatccgagg ggccaagggg atccgcacgc tgctctttgc cctcatgatg tccctgcctg   5160
ccctcttcaa catcgggctg ctgctcttcc tcgtcatgtt catctactcc atctttggca   5220
tggccaactt cgcttatgtc aagtgggagg ctggcatcga cgacatgttc aacttccaga   5280
ccttcgccaa cagcatgctg tgcctcttcc agatcaccac gtcggccggc tgggatggcc   5340
tcctcagccc catcctcaac actgggccgc cctactgcga ccccactctg cccaacagca   5400
atggctctcg gggggactgc gggagcccag ccgtgggcat cctcttcttc accacctaca   5460
tcatcatctc cttcctcatc gtggtcaaca tgtacattgc catcatcctg gagaacttca   5520
gcgtggccac ggaggagagc accgagcccc tgagtgagga cgacttcgat atgttctatg   5580
agatctggga gaaatttgac ccagaggcca ctcagtttat tgagtattcg gtcctgtctg   5640
actttgccga tgccctgtct gagccactcc gtatcgccaa gcccaaccag ataagcctca   5700
tcaacatgga cctgcccatg gtgagtgggg accgcatcca ttgcatggac attctctttg   5760
ccttcaccaa aagggtcctg ggggagtctg gggagatgga cgccctgaag atccagatgg   5820
aggagaagtt catggcagcc aacccatcca agatctccta cgagcccatc accaccacac   5880
tccggcgcaa gcacgaagag gtgtcggcca tggttatcca gagagccttc cgcaggcacc   5940
tgctgcaacg ctctttgaag catgcctcct tcctcttccg tcagcaggcg ggcagcggcc   6000
tctccgaaga ggatgcccct gagcgagagg gcctcatcgc ctacgtgatg agtgagaact   6060
tctcccgacc ccttggccca ccctccagct cctccatctc ctccacttcc ttcccaccct   6120
cctatgacag tgtcactaga gccaccagcg ataacctcca ggtgcggggg tctgactaca   6180
gccacagtga agatctcgcc gacttccccc cttctccgga cagggaccgt gagtccatcg   6240
tgtgagcctc ggcctggctg gccaggacac actgaaaagc agcctttttc accatggcaa   6300
acctaaatgc agtcagtcac aaaccagcct ggggccttcc tggctttggg agtaagaaat   6360
gggcctcagc cccgcggatc aaccaggcag agttctgtgg cgccgcgtgg acagccggag   6420
cagttggcct gtgcttggag gcctcagata gacctgtgac ctggtctggt caggcaatgc   6480
cctgcggctc tggaaagcaa cttcatccca gctgctgagg cgaaatataa aactgagact   6540
gtatatgttg tgaatgggct ttcataaatt tattatattt gatatttttt tacttgagca   6600
aagaactaag gatttttcca tggacatggg cagcaattca cgctgtctct tcttaaccct   6660
gaacaagagt gtctatggag cagccggaag tctgttctca aagcagaagt ggaatccagt   6720
gtggctccca caggtcttca ctgcccaggg gtcgaatggg gtccccctcc cacttgacct   6780
gagatgctgg gagggctgaa cccccactca cacaagcaca cacacacagt cctcacacac   6840
ggaggccaga cacaggccgt gggacccagg ctcccagcct aagggagaca ggcctttccc   6900
tgccggcccc ccaaggatgg ggttcttgtc cacggggctc actctggccc cctattgtct   6960
ccaaggtccc attttccccc tgtgttttca cgcaggtcat attgtcagtc ctacaaaaat   7020
aaaaggcttc cagaggagag tggcctgggt cccagggctg gccctaggca ctgatagttg   7080
ccttttcttc ccctcctgta agagtattaa caaaaccaaa ggacacaagg gtgcaagccc   7140
cattcacggc ctggcatgca gcttgtcctt gctcctggaa cctggcaggc cctgcccagc   7200
cagccatcgg aagagagggc tgagccatgg gggtttgggg ctaagaagtt caccagccct   7260
gagccatggc ggcccctcag cctgcctgaa gagaggaaac tggcgatctc ccagggctct   7320
```

ctggaccata cgcggaggag ttttctgtgt ggtctccagc tcctctccag acacagagac 7380
atgggagtgg ggagcggagc ttggccctgc gccctgtgca gggaaaggga tggtcaggcc 7440
cagttctcgt gcccttagag gggaatgaac catggcacct ttgagagagg gggcactgtg 7500
gtcaggccca gcctctctgg ctcagcccgg gatcctgatg gcacccacac agaggacctc 7560
tttggggcaa gatccaggtg gtcccatagg tcttgtgaaa aggctttttc agggaaaaat 7620
attttactag tccaatcacc cccaggacct cttcagctgc tgacaatcct atttagcata 7680
tgcaaatctt ttaacataga gaactgtcac cctgaggtaa cagggtcaac tggcgaagcc 7740
tgagcaggca ggggcttggc tgccccattc cagctctccc atggagcccc tccaccgggc 7800
gcatgcctcc caggccacct cagtctcacc tgccggctct gggctggctg ctcctaacct 7860
acctcgccga gctgtcggag ggctggacat ttgtggcagt gctgaagggg gcattgccgg 7920
cgagtaaagt attatgtttc ttcttgtcac cccagttccc ttggtggcaa ccccagaccc 7980
aacccatgcc cctgacagat ctagttctct tctcctgtgt tccctttgag tccagtgtgg 8040
gacacggttt aactgtccca gcgacatttc tccaagtgga aatcctattt ttgtagatct 8100
ccatgctttg ctctcaaggc ttggagaggt atgtgcccct cctgggtgct caccgcctgc 8160
tacacaggca ggaatgcggt tgggaggcag gtcgggctgc cagcccagct ggccggaagg 8220
agactgtggt ttttgtgtgt gtggacagcc cgggagcttt gagacaggtg cctggggctg 8280
gctgcagacg gtgtggttgg gggtgggagg tgagctagac ccaaccctta gcttttagcc 8340
tggctgtcac ctttttaatt tccagaactg cacaatgacc agcaggaggg aaggacagac 8400
atcaagtgcc agatgttgtc tgaactaatc gagcacttct caccaaactt catgtataaa 8460
taaaatacat atttttaaaa caaaccaata aatggcttac atga 8504

<210> SEQ ID NO 6
<211> LENGTH: 7186
<212> TYPE: DNA
<213> ORGANISM: Homo sapiens

<400> SEQUENCE: 6
caggtcctcc accatgtgaa tgccaacatg gccaggtcat tagagctgag ggaaaactag 60
tgcccaaaga tatgaaaaga gtgtggatct tctggagaag tgctgttgtt caacaggtac 120
aaaattggaa atgttggctt caccagaacc taagggcctt gttcccttca ctaaagagtc 180
ttttgaactt ataaaacagc atattgctaa aacacataat gaagaccatg aagaagaaga 240
cttaaagcca actcctgatt tggaagttgg caaaaagctt ccatttattt atggaaacct 300
ttctcaagga atggtgtcag agcccttgga agatgtggac ccatattact acaagaaaaa 360
aaatactttc atagtattaa ataaaaatag aacaatcttc agattcaatg cggcttccat 420
cttgtgtaca ttgtctcctt tcaattgtat tagaagaaca actatcaagg ttttggtaca 480
tccctttttc caactgttta ttctaattag tgtcctgatt gattgcgtat tcatgtccct 540
gactaatttg ccaaaatgga gaccagtatt agagaatact ttgcttggaa tttacacatt 600
tgaaatactt gtaaaactct ttgcaagagg tgtctgggca ggatcatttt ccttcctcgg 660
tgatccatgg aactggctcg atttcagcgt aactgtgttt gaggttatta taagatactc 720
acctctggac ttcattccaa cgcttcaaac tgcaagaact ttgagaattt taaaaattat 780
tcctttaaat caaggtctga aatcccttgt aggggtcctg atccactgct tgaagcagct 840
tattggtgtc attatcctaa ctctgttttt tctgagcata ttttctctaa ttgggatggg 900
gctcttcatg ggcaacttga aacataaatg ttttcgatgg ccccaagaga atgaaaatga 960

```
aaccctgcac aacagaactg gaaacccata ttatattcga gaaacagaaa acttttatta   1020
tttggaagga gaaagatatg ctctcctttg tggcaacagg acagatgctg gtcagtgtcc   1080
tgaaggatat gtgtgtgtaa aagctggcat aaatcctgat caaggcttca caaatttga    1140
cagttttggc tgggccttat ttgccctatt tcggttaatg gctcaggatt accctgaagt   1200
actttatcac cagatacttt atgcttctgg gaaggtctac atgatatttt ttgtggtggt   1260
aagtttttg ttttcctttt atatggcaag tttgttctta ggcatacttg ccatggccta    1320
tgaagaagaa aagcagagag ttggtgaaat atctaagaag attgaaccaa aatttcaaca   1380
gactggaaaa gaacttcaag aaggaaatga aacagatgag gccaagacca tacaaataga   1440
aatgaagaaa aggtcaccaa tttccacaga cacatcattg gatgtgttgg aagatgctac   1500
tctcagacat aaggaagaac ttgaaaaatc caagaagata tgcccattat actggtataa   1560
gtttgctaaa actttcttga tctggaattg ttctccctgt tggttaaaat tgaaagagtt   1620
tgtccatagg attataatgg caccatttac tgatcttttc cttatcatat gcataatttt   1680
aaacgtatgt tttctgacct tggagcatta tccaatgagt aaacaaacta acactcttct   1740
caacattgga aacctggttt tcattggaat tttcacagca gaaatgattt ttaaaataat   1800
tgcaatgcat ccatatgggt atttccaagt aggttggaac atttttgata gcatgatagt   1860
gttccatggt ttaatagaac tttgtctagc aaatgttgca ggaatggctc ttcttcgatt   1920
attcaggatg ttaagaattt tcaagttggg aaagtattgg ccaacattcc agattttgat   1980
gtggtctctt agtaactcat gggtggccct gaaagacttg gtcctgttgt tgttcacatt   2040
catcttcttt tctgctgcat tcggcatgaa gctgtttggt aagaattatg aagaatttgt   2100
ctgccacata gacaaagact gtcaactccc acgctggcac atgcatgact tttttccactc  2160
cttcctgaat gtgttccgaa ttctctgtgg agagtgggta gagaccttgt gggactgtat   2220
ggaggttgca ggccaatcct ggtgtattcc tttttacctg atggtcattt taattggaaa   2280
tttactggta ctttacctgt ttctggcatt ggtgagctca tttagttcat gcaaggatgt   2340
aacagctgaa gagaataatg aagcaaaaaa tctccagctt gcagtggcaa gaattaaaaa   2400
aggaataaac tatgtgcttc ttaaaatact atgcaaaaca caaaatgtcc caaaggacac   2460
aatggaccat gtaaatgagg tatatgttaa agaagatatt tctgaccata ccctttctga   2520
attgagcaac acccaagatt ttctcaaaga taaggaaaaa agcagtggca cagagaaaaa   2580
cgctactgaa aatgagagcc aatcacttat ccccagtcct agtgtctcag aaactgtacc   2640
aattgcttca ggagaatctg atatagaaaa tctggataat aaggagattc agagtaagtc   2700
tggtgatgga ggcagcaaag agaaaataaa gcaatctagc tcatctgaat gcagtactgt   2760
tgatattgct atctctgaag aagaagaaat gttctatgga ggtgaaagat caaagcatct   2820
gaaaaatggt tgcagacgcg gatcttcact tggtcaaatc agtggagcat ccaagaaagg   2880
aaaaatctgg cagaacatca ggaaaacctg ctgcaagatt gtagagaaca attggtttaa   2940
gtgttttatt gggcttgtta ctctgctcag cactggcact ctggcttttg aagatatata   3000
tatggatcag agaaagacaa ttaaaatttt attagaatat gctgacatga tctttactta   3060
tatcttcatt ctggaaatgc ttctaaaatg gatggcatat ggttttaagg cctatttctc   3120
taatggctgg tacaggctgg acttcgtggt tgttattgtg ttttgtctta gcttaatagg   3180
caaaactcgg gaagaactaa aacctcttat ttccatgaaa ttccttcggc ccctcagagt   3240
tctatctcaa tttgaaagaa tgaaggtggt tgtgagagct ttgatcaaaa caaccttacc   3300
```

-continued

```
cactttgaat gtgtttcttg tctgcctgat gatctggctg atttttagta tcatgggagt   3360
agacttattt gctggcagat tctatgaatg cattgaccca acaagtggag aaaggtttcc   3420
ttcatctgaa gtcatgaata agagtcggtg tgaaagcctt ctgtttaacg aatccatgct   3480
atgggaaaat gcaaaaatga actttgataa tgttggaaat ggtttccttt ctctgcttca   3540
agtagcaaca tttaatggat ggatcactat tatgaattca gcaattgatt ctgttgctgt   3600
taatatacag cctcattttg aagtcaacat ctacatgtat tgttacttta tcaactttat   3660
tatatttgga gtatttctcc ctctgagtat gctgattact gttattattg ataatttcaa   3720
caagcataaa ataaagctgg gaggctcaaa tatctttata acggttaaac agagaaaaca   3780
gtaccgcagg ctgaagaagc taatgtatga ggattctcaa agaccagtac ctcgcccatt   3840
aaacaagctc caaggattca tctttgatgt ggtaacaagc caagctttta atgtcattgt   3900
tatggttctt atatgtttcc aagcaatagc catgatgata gacactgatg ttcagagtct   3960
acaaatgtcc attgctctct actggattaa ctcaattttt gttatgctat atactatgga   4020
atgtatactg aagctcatcg ctttccgttg tttttatttc accattgcgt ggaacatttt   4080
tgattttatg gtggttattt tctccatcac aggactatgt ctgcctatga cagtaggatc   4140
ctaccttgtg cctccttcac ttgtgcaact gatacttctc tcacggatca ttcacatgct   4200
gcgtcttgga aaaggaccaa aggtgtttca taatctgatg cttcctttga tgctgtccct   4260
cccagcatta ttgaacatca ttcttctcat cttcctggtc atgttcatct atgccgtatt   4320
tggaatgtat aattttgcct atgttaaaaa agaagctgga attaatgatg tgtctaattt   4380
tgaaaccttt ggcaacagta tgctctgtct tttcaagtt gcaatatttg ctggttggga   4440
tgggatgctt gatgcaattt tcaacagtaa atggtctgac tgtgatcctg ataaaattaa   4500
ccctgggact caagttagag gagattgtgg gaacccctct gttgggattt tttattttgt   4560
cagttatatc ctcatatcat ggctgatcat tgtaaatatg tacattgttg ttgtcatgga   4620
gtttttaaat attgcttcta agaagaaaaa caagaccttg agtgaagatg attttaggaa   4680
attctttcag gtatggaaaa ggtttgatcc tgataggacc cagtacatag actctagcaa   4740
gctttcagat tttgcagctg ctcttgatcc tcctcttttc atggcaaaac caaacaaggg   4800
ccagctcatt gctttggacc tccccatggc tgttggggac agaattcatt gcctcgatat   4860
cttacttgct tttacaaaga gagttatggg tcaagatgtg aggatggaga aagttgtttc   4920
agaaatagaa tcagggtttt tgttagccaa cccttttaag atcacatgtg agccaattac   4980
gactactttg aaacgaaaac aagaggcagt ttcagcaacc atcattcaac gtgcttataa   5040
aaattaccgc ttgaggcgaa atgacaaaaa tacatcagat attcatatga tagatggtga   5100
cagagatgtt catgctacta aagaaggtgc ctattttgac aaagctaagg aaaagtcacc   5160
tattcaaagc cagatctaat accacttacc acctcttttc atatttcttc acatatctga   5220
aaaatgttga aagcctaagc caggaataaa agaaaagtag agataataat cagttcttta   5280
caaccgatgg taattaagct tgtattcaca agacttcatg ccaaattcac tttttagcat   5340
tatatctaac aaatcaagag aatccttaat attgctgcag tgagtttaaa gtgggttaaa   5400
gtggccattt gacaatctca tatttgtttt ctctacatgg cttatatgat gtgtgccttc   5460
tagggaatga agggaagtgg tgatagagat cagcagcagc aggggctttc ttttatattt   5520
tatgtataat ttaatgggct ttaagtcacc actattaaga cttacaaata agcaaatact   5580
ttcctgatgt gggatggtga aatgctaatg gccattaaat cataaacttg cctagacaaa   5640
agccaattgg aagaagggag agagcagttc tttagaaagt gcctttgaga tcaacctcag   5700
```

agattcttgg gctgattaaa actgcatttg aaaaagattg gttgaagctc tgtgtttatt 5760
tttgtatgtt cttgttttca tttggaactg ggaatgaata ggatttcatt gtgctcaagc 5820
tcctggtttc tcatctctgg atagtttcac ctaagctctg gctcttaagc aggacagatt 5880
cgtaaaacaa gaagcataaa ggagaggtat agcctttttt tttttttttt ttttcatttt 5940
cttctcattt acacctattt ttttaaaaag tatacattta ctaaaatgat gtaataaata 6000
acatgttaat agactcaagc tttaccttat gaaattgatg tatttttacc agttatttct 6060
aatgtaacat tgaatatata agatctgaca aatgtatgtt taaacatgaa ttagaagagt 6120
tgagaactac cattatgtat agggattctc atagtgtctt ggcccttaat tggaaagttg 6180
tggcaacttt aaagtacttt ttactgtatg ttataattct ttataactta gagagagaca 6240
atggtcactc aaactatgag aactatgaat taggagataa aagtttaaat ttgttgttgt 6300
tttataacag tatgtacaag ttagttttcc cttatatatt tacgttttca agttttttaa 6360
tctcatcata tacatccata ctctataaaa tgttttatat tcaaagaact gtaaaatcct 6420
aaacattagt tttcactatt gaaattgttt tttaaagata ggcataaata gttgtcctta 6480
gacttattca tacaaatata gtcatttact tctatgtagt ttgagattct gagagttatt 6540
ccaactttat gaagattgat ttcaatgtgc ctgctaagtc ctaaaagatt cagaaagaaa 6600
atttatatat tattgattta aatatcatcc tttaaatatg ttgtataaca ttcaatatag 6660
tttatgtatc agtgattgta ttttattctg aatgcatgat ctcaagcctt aactactata 6720
atctttttct gcccctcaga aattgaataa cctaaccaag atgcctttag ggatgccct 6780
aagtaaatgt aatttcagat ttcagggttt tttttttttc ctctctaagt gttccttccc 6840
tttcttctcc tgctctccat catgttatgg agaccagtga ggaaccagtg ttaacttggt 6900
gacaatgtga cagctggtgc tttatctaag ctccgttttc tatttcttgg gaatgcttta 6960
ttgtggaaac tgcttcagat acttaaattg aatcataact tgcttctgta aattgcgtaa 7020
agacaacaaa ctgattttag tttgaaaagt ttatctttta cttgtaaacc ttgtttgcca 7080
gttaccttcc gaaagctgtg taaagagtta tttttaacaa agtcttaaca atatatgtta 7140
ctttttagat actatagaaa ataataaata taacctgtaa accaca 7186

<210> SEQ ID NO 7
<211> LENGTH: 7215
<212> TYPE: DNA
<213> ORGANISM: Homo sapiens

<400> SEQUENCE: 7
gagcgctcca agatggcgcc caccgcagtc ccgcccgccg catcctcggc gcctttgcag 60
tccggccgcg cctcccgggc cccgcgttag ggccgccgct gcctccctcg ccgccgccgc 120
tgccagctga cctgtcctgg acgcagcata actaacgaag ctgctgcagg atgagaagat 180
ggcagcgcgg ctgcttgcac caccaggccc tgatagtttc aagcctttca cccctgagtc 240
actggcaaac attgagaggc gcattgctga gagcaagctc aagaaaccac caaaggccga 300
tggcagtcat cgggaggacg atgaggacag caagcccaag ccaaacagcg acctggaagc 360
agggaagagt ttgcctttca tctacgggga catcccccaa ggcctggttg cagttcccct 420
ggaggacttt gacccatact atttgacgca gaaaaccttt gtagtattaa acagagggaa 480
aactctcttc agatttagtg ccacgcctgc cttgtacatt ttaagtcctt ttaacctgat 540
aagaagaata gctattaaaa ttttgataca ttcagtattt agcatgatca ttatgtgcac 600

```
tattttgacc aactgtgtat tcatgacttt tagtaaccct cctgactggt cgaagaatgt    660
ggagtacacg ttcacaggga tttatacatt tgaatcacta gtgaaaatca ttgcaagagg    720
tttctgcata gatggcttta cctttttacg ggacccatgg aactggttag atttcagtgt    780
catcatgatg gcgtatataa cagagtttgt aaacctaggc aatgtttcag ctctacgcac    840
tttcagggta ctgagggctt tgaaaactat ttcggtaatc ccaggcctga agacaattgt    900
gggtgccctg attcagtctg tgaagaaact gtcagatgtg atgatcctga cagtgttctg    960
cctgagtgtt tttgccttga tcggactgca gctgttcatg ggaaccttcc gaaacaagtg   1020
tgttgtgtgg cccataaact tcaacgagag ctatcttgaa aatggcacca aaggctttga   1080
ttgggaagag tatatcaaca ataaaacaaa tttctacaca gttcctggca tgctggaacc   1140
tttactctgt gggaacagtt ctgatgctgg gcaatgccca gagggatacc agtgtatgaa   1200
agcaggaagg aaccccaact atggttacac aagttttgac acttttagct gggccttctt   1260
ggcattattt cgccttatga cccaggacta ttgggaaaac ttgtatcaat tgactttacg   1320
agcagccggg aaaacataca tgatcttctt cgtcttggtc atctttgtgg gttctttcta   1380
tctggtgaac ttgatcttgg ctgtggtggc catggcttat gaagaacaga atcaggcaac   1440
actggaggag gcagaacaaa aagaggctga atttaaagca atgttggagc aacttaagaa   1500
gcaacaggaa gaggcacagg ctgctgcgat ggccacttca gcaggaactg tctcagaaga   1560
tgccatagag gaagaaggtg aagaaggagg gggctcccct cggagctctt ctgaaatctc   1620
taaactcagc tcaaagagtg caaaggaaag acgtaacagg agaaagaaga ggaagcaaaa   1680
ggaactctct gaaggagagg agaaaggggga tcccgagaag gtgtttaagt cagagtcaga   1740
agatggcatg agaaggaagg cctttcggct gccagacaac agaataggga ggaaattttc   1800
catcatgaat cagtcactgc tcagcatccc aggctcgccc ttcctctccc gccacaacag   1860
caagagcagc atcttcagtt tcaggggacc tgggcggttc cgagacccgg gctccgagaa   1920
tgagttcgcg gatgacgagc acagcacggt ggaggagagc gagggccgcc gggactccct   1980
cttcatcccc atccgggccc gcgagcgccg gagcagctac agcggctaca gcggctacag   2040
ccagggcagc cgctcctcgc gcatcttccc cagcctgcgg cgcagcgtga agcgcaacag   2100
cacggtggac tgcaacggcg tggtgtccct catcggcggc cccggctccc acatcggcgg   2160
gcgtctcctg ccagaggcta caactgaggt ggaaattaag aagaaaggcc ctggatctct   2220
tttagtttcc atggaccaat tagcctccta cgggcggaag gacagaatca acagtataat   2280
gagtgttgtt acaaatacac tagtagaaga actggaagag tctcagagaa agtgcccgcc   2340
atgctggtat aaatttgcca acactttcct catctgggag tgccacccct actggataaa   2400
actgaaagag attgtgaact tgatagttat ggaccctttt gtggatttag ccatcaccat   2460
ctgcatcgtc ctgaatacac tgtttatggc aatggagcac catcctatga caccacaatt   2520
tgaacatgtc ttggctgtag gaaatctggt tttcactgga attttcacag cggaaatgtt   2580
cctgaagctc atagccatgg atccctacta ttatttccaa gaaggttgga acatttttga   2640
cggatttatt gtctccctca gtttaatgga actgagtcta gcagacgtgg aggggctttc   2700
agtgctgcga tctttccgat tgctccgagt cttcaaattg gccaaatcct ggcccaccct   2760
gaacatgcta atcaagatta ttggaaattc agtgggtgcc ctgggcaacc tgacactggt   2820
gctggccatt attgtcttca tctttgccgt ggtggggatg caactctttg gaaaaagcta   2880
caaagagtgt gtctgcaaga tcaaccagga ctgtgaactc cctcgctggc atatgcatga   2940
ctttttccat tccttcctca ttgtctttcg agtgttgtgc ggggagtgga ttgagaccat   3000
```

```
gtgggactgc atggaagtgg caggccaggc catgtgcctc attgtcttta tgatggtcat   3060
ggtgattggc aacttggtgg tgctgaacct gtttctggcc ttgctcctga gctccttcag   3120
tgcagacaac ctggctgcca cagatgacga tggggaaatg aacaacctcc agatctcagt   3180
gatccgtatc aagaagggtg tggcctggac caaactaaag gtgcacgcct tcatgcaggc   3240
ccactttaag cagcgtgagg ctgatgaggt gaagcctctg gatgagttgt atgaaaagaa   3300
ggccaactgt atcgccaatc acaccggtgc agacatccac cggaatggtg acttccagaa   3360
gaatggcaat ggcacaacca gcggcattgg cagcagcgtg gagaagtaca tcattgatga   3420
ggaccacatg tccttcatca acaaccccaa cttgactgta cgggtaccca ttgctgtggg   3480
cgagtctgac tttgagaacc tcaacacaga ggatgttagc agcgagtcgg atcctgaagg   3540
cagcaaagat aaactagatg acaccagctc ctctgaagga agcaccattg atatcaaacc   3600
agaagtagaa gaggtccctg tggaacagcc tgaggaatac ttggatccag atgcctgctt   3660
cacagaaggt tgtgtccagc ggttcaagtg ctgccaggtc aacatcgagg aagggctagg   3720
caagtcttgg tggatcctgc ggaaaacctg cttcctcatc gtggagcaca actggtttga   3780
gaccttcatc atcttcatga ttctgctgag cagtggcgcc ctggccttcg aggacatcta   3840
cattgagcag agaaagacca tccgcaccat cctggaatat gctgacaaag tcttcaccta   3900
tatcttcatc ctggagatgt tgctcaagtg gacagcctat ggcttcgtca agttcttcac   3960
caatgcctgg tgttggctgg acttcctcat tgtggctgtc tctttagtca gccttatagc   4020
taatgccctg ggctactcgg aactaggtgc cataaagtcc cttaggaccc taagagcttt   4080
gagaccctta agagccttat cacgatttga agggatgagg gtggtggtga atgccttggt   4140
gggcgccatc cctccatca tgaatgtgct gctggtgtgt ctcatcttct ggctgatttt    4200
cagcatcatg ggagttaact tgtttgcggg aaagtaccac tactgcttta atgagacttc   4260
tgaaatccga tttgaaattg aagatgtcaa caataaaact gaatgtgaaa agcttatgga   4320
ggggaacaat acagagatca gatggaagaa cgtgaagatc aactttgaca atgttggggc   4380
aggatacctg gcccttcttc aagtagcaac cttcaaaggc tggatggaca tcatgtatgc   4440
agctgtagat tcccggaagc ctgatgagca gcctaagtat gaggacaata tctacatgta   4500
catctatttt gtcatcttca tcatcttcgg ctccttcttc accctgaacc tgttcattgg   4560
tgtcatcatt gataacttca atcaacaaaa gaaaaagttc ggaggtcagg acatcttcat   4620
gaccgaagaa cagaagaagt actacaatgc catgaaaaag ctgggctcaa agaagccaca   4680
gaaacctatt ccccgcccct tgaacaaaat ccaaggaatc gtctttgatt ttgtcactca   4740
gcaagccttt gacattgtta tcatgatgct catctgcctt aacatggtga caatgatggt   4800
ggagacagac actcaaagca agcagatgga gaacatcctc tactggatta acctggtgtt   4860
tgttatcttc ttcacctgtg agtgtgtgct caaaatgttt gcgttgaggc actactactt   4920
caccattggc tggaacatct tcgacttcgt ggtagtcatc ctctccattg tgggaatgtt   4980
cctggcagat ataattgaga aatactttgt ttccccaacc ctattccgag tcatccgatt   5040
ggcccgtatt gggcgcatct tgcgtctgat caaaggcgcc aaagggattc gtaccctgct   5100
ctttgcctta atgatgtcct tgcctgccct gttcaacatc ggccttctgc tcttcctggt   5160
catgttcatc ttctccattt ttgggatgtc caattttgca tatgtgaagc acgaggctgg   5220
tatcgatgac atgttcaact ttgagacatt tggcaacagc atgatctgcc tgtttcaaat   5280
cacaacctca gctggttggg atggcctgct gctgcccatc ctaaaccgcc cccctgactg   5340
```

-continued cagcctagat aaggaacacc cagggagtgg ctttaaggga gattgtggga acccctcagt 5400
gggcatcttc ttctttgtaa gctacatcat catctctttc ctaattgtcg tgaacatgta 5460
cattgccatc atcctggaga acttcagtgt agccacagag gaaagtgcag accctctgag 5520
tgaggatgac tttgagacct tctatgagat ctgggagaag ttcgaccccg atgccaccca 5580
gttcattgag tactgtaagc tggcagactt tgcagatgcc ttggagcatc ctctccgagt 5640
gcccaagccc aataccattg agctcatcgc tatggatctg ccaatggtga gcggggatcg 5700
catccactgc ttggacatcc tttttgcctt caccaagcgg gtcctgggag atagcgggga 5760
gttggacatc ctgcggcagc agatggaaga gcggttcgtg gcatccaatc cttccaaagt 5820
gtcttacgag ccaatcacaa ccacactgcg tcgcaagcag gaggaggtat ctgcagtggt 5880
cctgcagcgt gcctaccggg gacatttggc aaggcggggc ttcatctgca aaaagacaac 5940
ttctaataag ctggagaatg gaggcacaca ccgggagaaa aaagagagca ccccatctac 6000
agcctccctc ccgtcctatg acagtgtaac taaacctgaa aaggagaaac agcagcgggc 6060
agaggaagga agaagggaaa gagccaaaag acaaaaagag gtcagagaat ccaagtgtta 6120
gaggagaaca aaaattcagt attatacaga tctaaaactc gcaagtgaaa gattgtttac 6180
aaacttcctg aatattatca atgcagaaca gctgtggaga ctctaacctg aagatctata 6240
ccaaacgtcg tctgcttacc acgtaacaca gctgcatctt gagcagtgac ctgccaaggg 6300
caaaggaccc cgctccctag acttacagat tttctaatgc ttgggcaggt ggttactgca 6360
tgttccacat cagtcaatgc aacttaggac aaaactaacc agatacagaa acagaagaga 6420
ggctgccggg accagcatat ttccgttgca gccaaatgga ttttattttt tcattttatt 6480
gattctcaga agcagaaagc atcactttaa aagttcgttt gttcatgcaa actatatttg 6540
cattcttaca ttagttaagc taagcagcaa aaagaaaaca cacacacaca ctcacattta 6600
gcccatgtca tttaattgtc agtttctttg acataaagcg catcttctcc acatgggctt 6660
cacgtggttt ggagatgggt gggggaaaac aatcaggttt cttcaggctg aggaggactt 6720
gctcaggccg attccaaaca ttgtgctcgt tcaatgcgta gaaatgattt gcatgatggc 6780
atgccgtgat cagaagtcat gcatgagatc catacaccac aggacactac taatctagtc 6840
ccttgcactg ggtcagcctt tggacaggac ccagccctgc accgttcact gtatttggag 6900
aaaatggtaa gagttccata ccggctacaa ttctttgagt tcttaaaagt ccttcataca 6960
ccttctgggt agggaaacaa ccaactaatt gactaacacc accaacaaca aaaaacaaac 7020
ccaatccaac aagcagatgg atccgttgcg tgtatatgtt taacagacat ctctaacata 7080
cagccattgt tgcacatttt gcaagatgaa ctatttaatg ctgctctgtg tccagtacat 7140
gggggagact ttgatcccaa atggcttgta ctatttatgt cactgtaaaa ccaaatccta 7200
gggctaaaaa aaaaa 7215

<210> SEQ ID NO 8
<211> LENGTH: 9771
<212> TYPE: DNA
<213> ORGANISM: Homo sapiens

<400> SEQUENCE: 8
cggggctgct acctccacgg gcgcgccctg gcaggagggg cgcagtctgc ttgcaggcgg 60
tcgccagcgc tccagcggcg gctgtcggct ttccaattcc gccagctcgg ctgaggctgg 120
gctagcctgg gtgccagtgg ctgctagcgg caggcgtccc ctgagcaaca ggagcccaga 180
gaaaaagaag cagccctgag agagcgccgg ggaaggagag gcccgcgccc tctcctggag 240

```
ccagattctg caggtgcact gggtggggat gatcggcggg ctaggttgca agcctcttat    300
gtgaggagct gaagaggaat taaaatatac aggatgaaaa gatggcaatg ttgcctcccc    360
caggacctca gagctttgtc catttcacaa aacagtctct tgccctcatt gaacaacgca    420
ttgctgaaag aaaatcaaag gaacccaaag aagaaaagaa agatgatgat gaagaagccc    480
caaagccaag cagtgacttg gaagctggca aacagctgcc cttcatctat ggggacattc    540
ctcccggcat ggtgtcagag cccctggagg acttggaccc ctactatgca gacaaaaaga    600
ctttcatagt attgaacaaa gggaaaacaa tcttccgttt caatgccaca cctgctttat    660
atatgctttc tcctttcagt cctctaagaa gaatatctat taagatttta gtacactcct    720
tattcagcat gctcatcatg tgcactattc tgacaaactg catatttatg accatgaata    780
acccaccgga ctggaccaaa aatgtcgagt acacttttac tggaatatat acttttgaat    840
cacttgtaaa aatccttgca agaggcttct gtgtaggaga attcactttt cttcgtgacc    900
cgtggaactg gctggatttt gtcgtcattg tttttgcgta tttaacagaa tttgtaaacc    960
taggcaatgt ttcagctctt cgaactttca gagtattgag agctttgaaa actatttctg   1020
taatcccagg cctgaagaca attgtagggg ctttgatcca gtcagtgaag aagctttctg   1080
atgtcatgat cctgactgtg ttctgtctga gtgtgtttgc actaattgga ctacagctgt   1140
tcatgggaaa cctgaagcat aaatgttttc gaaattcact tgaaaataat gaaacattag   1200
aaagcataat gaataccccta gagagtgaag aagactttag aaaatatttt tattacttgg   1260
aaggatccaa agatgctctc ctttgtggtt tcagcacaga ttcaggtcag tgtccagagg   1320
ggtacacctg tgtgaaaatt ggcagaaacc ctgattatgg ctacacgagc tttgacactt   1380
tcagctgggc cttcttagcc ttgtttaggc taatgaccca agattactgg gaaaaccttt   1440
accaacagac gctgcgtgct gctggcaaaa cctacatgat cttctttgtc gtagtgattt   1500
tcctgggctc cttttatcta ataaacttga tcctggctgt ggttgccatg gcatatgaag   1560
aacagaacca ggcaaacatt gaagaagcta aacagaaaga attagaattt caacagatgt   1620
tagaccgtct taaaaaagag caagaagaag ctgaggcaat tgcagcggca gcggctgaat   1680
atacaagtat taggagaagc agaattatgg gcctctcaga gagttcttct gaaacatcca   1740
aactgagctc taaaagtgct aaagaaagaa gaaacagaag aaagaaaaag aatcaaaaga   1800
agctctccag tggagaggaa aagggagatg ctgagaaatt gtcgaaatca gaatcagagg   1860
acagcatcag aagaaaaagt ttccaccttg gtgtcgaagg gcataggcga gcacatgaaa   1920
agaggttgtc taccccccaat cagtcaccac tcagcattcg tggctccttg ttttctgcaa   1980
ggcgaagcag cagaacaagt ctttttagtt tcaaaggcag aggaagagat ataggatctg   2040
agactgaatt tgccgatgat gagcacagca tttttggaga caatgagagc agaaggggct   2100
cactgtttgt gccccacaga ccccaggagc gacgcagcag taacatcagc caagccagta   2160
ggtccccacc aatgctgccg gtgaacggga aaatgcacag tgctgtggac tgcaacggtg   2220
tggtctccct ggttgatgga cgctcagccc tcatgctccc caatggacag cttctgccag   2280
agggcacgac caatcaaata cacaagaaaa ggcgttgtag ttcctatctc ctttcagagg   2340
atatgctgaa tgatcccaac ctcagacaga gagcaatgag tagagcaagc atattaacaa   2400
acactgtgga agaacttgaa gagtccagac aaaaatgtcc accttggtgg tacagatttg   2460
cacacaaatt cttgatctgg aattgctctc catattggat aaaattcaaa aagtgtatct   2520
attttattgt aatggatcct tttgtagatc ttgcaattac catttgcata gttttaaaca   2580
```

-continued

```
cattatttat ggctatggaa caccacccaa tgactgagga attcaaaaat gtacttgcta   2640
taggaaattt ggtctttact ggaatctttg cagctgaaat ggtattaaaa ctgattgcca   2700
tggatccata tgagtatttc caagtaggct ggaatatttt tgacagcctt attgtgactt   2760
taagtttagt ggagctcttt ctagcagatg tggaaggatt gtcagttctg cgatcattca   2820
gactgctccg agtcttcaag ttggcaaaat cctggccaac attgaacatg ctgattaaga   2880
tcattggtaa ctcagtaggg gctctaggta acctcacctt agtgttggcc atcatcgtct   2940
tcatttttgc tgtggtcggc atgcagctct ttggtaagag ctacaaagaa tgtgtctgca   3000
agatcaatga tgactgtacg ctcccacggt ggcacatgaa cgacttcttc cactccttcc   3060
tgattgtgtt ccgcgtgctg tgtggagagt ggatagagac catgtgggac tgtatggagg   3120
tcgctggtca agctatgtgc cttattgttt acatgatggt catggtcatt ggaaacctgg   3180
tggtcctaaa cctatttctg gccttattat tgagctcatt tagttcagac aatcttacag   3240
caattgaaga agaccctgat gcaaacaacc tccagattgc agtgactaga attaaaaagg   3300
gaataaatta tgtgaaacaa accttacgtg aatttattct aaaagcattt tccaaaaagc   3360
caaagatttc cagggagata agacaagcag aagatctgaa tactaagaag gaaaactata   3420
tttctaacca tacacttgct gaaatgagca aaggtcacaa tttcctcaag gaaaaagata   3480
aaatcagtgg ttttggaagc agcgtggaca aacacttgat ggaagacagt gatggtcaat   3540
catttattca caatcccagc ctcacagtga cagtgccaat tgcacctggg gaatccgatt   3600
tggaaaatat gaatgctgag gaacttagca gtgattcgga tagtgaatac agcaaagtga   3660
gattaaaccg gtcaagctcc tcagagtgca gcacagttga taaccctttg cctggagaag   3720
gagaagaagc agaggctgaa cctatgaatt ccgatgagcc agaggcctgt ttcacagatg   3780
gttgtgtacg gaggttctca tgctgccaag ttaacataga gtcagggaaa ggaaaaatct   3840
ggtggaacat caggaaaacc tgctacaaga ttgttgaaca cagttggttt gaaagcttca   3900
ttgtcctcat gatcctgctc agcagtggtg ccctggcttt tgaagatatt tatattgaaa   3960
ggaaaaagac cattaagatt atcctggagt atgcagacaa gatcttcact tacatcttca   4020
ttctggaaat gcttctaaaa tggatagcat atggttataa aacatatttc accaatgcct   4080
ggtgttggct ggatttccta attgttgatg tttctttggt tactttagtg gcaaacactc   4140
ttggctactc agatcttggc cccattaaat cccttcggac actgagagct ttaagacctc   4200
taagagcctt atctagattt gaaggaatga gggtcgttgt gaatgcactc ataggagcaa   4260
ttccttccat catgaatgtg ctacttgtgt gtcttatatt ctggctgata ttcagcatca   4320
tgggagtaaa tttgtttgct ggcaagttct atgagtgtat taacaccaca gatgggtcac   4380
ggtttcctgc aagtcaagtt ccaaatcgtt ccgaatgttt tgcccttatg aatgttagtc   4440
aaaatgtgcg atggaaaaac ctgaaagtga actttgataa tgtcggactt ggttacctat   4500
ctctgcttca agttgcaact tttaagggat ggacgattat tatgtatgca gcagtggatt   4560
ctgttaatgt agacaagcag cccaaatatg aatatagcct ctacatgtat atttattttg   4620
tcgtctttat catctttggg tcattcttca ctttgaactt gttcattggt gtcatcatag   4680
ataatttcaa ccaacagaaa aagaagcttg gaggtcaaga catctttatg acagaagaac   4740
agaagaaata ctataatgca atgaaaaagc tggggtccaa gaagccacaa aagccaattc   4800
ctcgaccagg gaacaaaatc caaggatgta tatttgacct agtgacaaat caagcctttg   4860
atattagtat catggttctt atctgtctca acatggtaac catgatggta gaaaaggagg   4920
gtcaaagtca acatatgact gaagttttat attggataaa tgtggttttt ataatccttt   4980
```

tcactggaga atgtgtgcta aaactgatct ccctcagaca ctactacttc actgtaggat 5040
ggaatatttt tgattttgtg gttgtgatta tctccattgt aggtatgttt ctagctgatt 5100
tgattgaaac gtattttgtg tcccctaccc tgttccgagt gatccgtctt gccaggattg 5160
gccgaatcct acgtctagtc aaaggagcaa aggggatccg cacgctgctc tttgctttga 5220
tgatgtccct tcctgcgttg tttaacatcg gcctcctgct cttcctggtc atgttcatct 5280
acgccatctt tggaatgtcc aactttgcct atgttaaaaa ggaagatgga attaatgaca 5340
tgttcaattt tgagaccttt ggcaacagta tgatttgcct gttccaaatt acaacctctg 5400
ctggctggga tggattgcta gcacctattc ttaacagtaa gccacccgac tgtgacccaa 5460
aaaaagttca tcctggaagt tcagttgaag gagactgtgg taacccatct gttggaatat 5520
tctactttgt tagttatatc atcatatcct tcctggttgt ggtgaacatg tacattgcag 5580
tcatactgga gaattttagt gttgccactg aagaaagtac tgaacctctg agtgaggatg 5640
actttgagat gttctatgag gtttgggaga agtttgatcc cgatgcgacc cagtttatag 5700
agttctctaa actctctgat tttgcagctg ccctggatcc tcctcttctc atagcaaaac 5760
ccaacaaagt ccagctcatt gccatggatc tgcccatggt tagtggtgac cggatccatt 5820
gtcttgacat cttatttgct tttacaaagc gtgttttggg tgagagtggg gagatggatt 5880
ctcttcgttc acagatggaa gaaaggttca tgtctgcaaa tccttccaaa gtgtcctatg 5940
aacccatcac aaccacacta aaacggaaac aagaggatgt gtctgctact gtcattcagc 6000
gtgcttatag acgttaccgc ttaaggcaaa atgtcaaaaa tatatcaagt atatacataa 6060
aagatggaga cagagatgat gatttactca ataaaaaaga tatggctttt gataatgtta 6120
atgagaactc aagtccagaa aaaacagatg ccacttcatc caccacctct ccaccttcat 6180
atgatagtgt aacaaagcca gacaaagaga aatatgaaca agacagaaca gaaaaggaag 6240
acaaagggaa agacagcaag gaaagcaaaa aatagagctt catttttgat atattgttta 6300
cagcctgtga aagtgattta tttgtgttaa taaaactctt ttgaggaagt ctatgccaaa 6360
atccttttta tcaaaatatt ctcgaaggca gtgcagtcac taactctgat ttcctaagaa 6420
aggtgggcag cattagcaga tggttatttt tgcactgatg attctttaag aatcgtaaga 6480
gaactctgta ggaattattg attatagcat acaaaagtga ttcagttttt tggtttttaa 6540
taaatcagaa gaccatgtag aaaactttta catctgcctt gtcatctttt cacaggattg 6600
taattagtct tgtttcccat gtaaataaac aacacacgca tacagaaaaa tctattattt 6660
atctattatt tggaaatcaa caaaagtatt tgccttggct ttgcaatgaa atgcttgata 6720
gaagtaatgg acattagtta tgaatgttta gttaaaatgc attattaggg agcttgactt 6780
tttatcaatg tacagaggtt attctatatt ttgaggtgct taaatttatt ctacattgca 6840
tcagaaccaa tttatatgtg cctataaaat gccatgggat taaaaatata tgtaggctat 6900
tcatttctac aaatgttttt cattcatctt gactcacatg ccaacaagga taagacttac 6960
ctttagagta ttgtgtttca tagcctttct tctttcatat cccttttgt tcatagaata 7020 accacagaac ttgaaaaatt attctaagta catattacac tcctcaaaaa aaacaaagat 7080
aactgagaaa aaagttattg acagaagttc tatttgctat tatttacata gcctaacatt 7140
tgactgtgct gcccaaaata ctgataatag tctcttaaac tcttttgtca aattttcctg 7200
ctttcttatg cagtattgtt tagtcatcct ttcgctgtaa gcaaagttga tgaaatcctt 7260
cctgatatgc agttagttgt ttgaccacgg tacatacttg agcagataat aacttgggca 7320

-continued

```
cagtatttat tgcatcactt gtatacaatc ccgtgtttgg caagctttca aatcatgtaa   7380
tatgacagac tttacacaga tatgtgttta gtatgaataa aaaagcattg aaatagggat   7440
tcttgccaac ttgctctctt gccaccaact tactttccta aattatggaa gtaatctttt   7500
ttggatatac ttcaatgtat acaatgagga agatgtcacc ttctccttaa aattctatga   7560
tgtgaaatat attttgcctc aatcaacaca gtaccatggg cttctaattt atcaagcaca   7620
tattcatttt gcattagctg tagacatcta gttttttgaa aacacctatt aatagtaatt   7680
tgaaaagaaa taaccataat gcttttttc gtgagtttat ttcaggaata tgagatcttt   7740
cttctataaa gttattcatg cacaggcaaa aattgagcta cacaggtaga atgtagtttt   7800
acttagaaga tttttgtggg aggttttgaa gcaaatatat aaaacaactt tcactaattt   7860
gctttccata tttaaaaaat aataaattac atttatataa taaatgttta aagcacatat   7920
tttttgttgt tctggcaatt taaaaagaaa gaggatttaa acgtacctat agaaacaaag   7980
atttatggtt aaagaatgag atcagaagtc tagaatgttt ttaaattgtg atatatttta   8040
caacatccgt tattactttg agacatttgt cctaatctac gtataaaact caatctaggg   8100
ctaaagattc tttataccat cttaggttca ttcatcttag gctatttgaa ccacttttta   8160
atttaatatg aaagacacca tgcagtgttt tccgagacta catagatcat tttatcacat   8220
acctaccaag cctgttggaa ataggttttg ataatttaag tagggaccta tacaaaatat   8280
attacattta tcagattttt aaatacattc aattaagaat ttaacatcac cttaaatttg   8340
aattcaatct accgttattt caaactcaca aatataactg cattatgaat acttacataa   8400
tgtagtaaga caagatgttt gacaggttcg tgtgtaattt tctattaatg tttttacatt   8460
gccttgtttt tatgtaaaat aaaaaatatg ggcaactggt ttgttaacaa cacaatttct   8520
tcttagcatt tcaaaaatat atataaagtt gttctttttc ctatttcatg aactatgttt   8580
tttttaaaa taacatggtt aagttttata tatatttacg tttgtttcag gaatgtctac   8640
ttgtgacttt ttatcaatta aaaataatat ttggaagaaa gagcttatta agtataagct   8700
tgaagtaaaa ttagacctct ctttccatgt agattactgt ttgtactgat ggtttcaccc   8760
ttcagaaggc actgtcatat taatatttaa attttataat cgctgaactt attacaccca   8820
acaatacaga aaggcagtta cactgaagaa cttaacttag aataaaatgg aagcaaacag   8880
gttttctaaa aactttttta agtgaccagg tctcgctctg tcacccaggc tagagtgcaa   8940
tggcatgatc atagctctct gcagcctcaa ctctgggctc aagcaaccct cctgcctcag   9000
cctcccaagt agctaagact acaggtacat gccaccatgc ctggctaata tttaaatttt   9060
tgtagataag gggtcttgct atgttgccca ggctagtctc aaactcctgg cttcaagtgt   9120
tcctactgtc atgacctgcc aacatgctgg ggttacaggc atgagccacc atgccccaaa   9180
caggtttgaa cacaaatctt tcggatgaaa attagagaac ctaattttag ctttttgata   9240
gttacctagt ttgcaaaaga tttgggtgac ttgtgagctg tttttaaatg ctgattgttg   9300
aacatcacaa cccaaaatac ttagcatgat tttatagagt tttgatagct ttattaaaaa   9360
gagtgaaaat aaaatgcata tgtaaataaa gcagttctaa atagctattt cagagaaatg   9420
ttaatagaag tgctgaaaga agggccaact aaattaggat ggccagggaa ttggcctggg   9480
tttaggacct atgtatgaag gccaccaatt ttttaaaaat atctgtggtt tattatgtta   9540
ttatcttctt gaggaaaaca atcaagaatt gcttcatgaa aataaataaa tagccatgaa   9600
tatcataaag ctgtttacat aggattcttt acaaatttca tagatctatg aatgctcaaa   9660
atgtttgagt ttgccataaa ttatattgta gttatattgt agttatactt gagactgaca   9720
```

cattgtaata taatctaaga ataaaagtta tacaaaataa aaaaaaaaaa a 9771

<210> SEQ ID NO 9
<211> LENGTH: 5874
<212> TYPE: DNA
<213> ORGANISM: Homo sapiens

<400> SEQUENCE: 9
atggaattcc ccattggatc cctcgaaact aacaacttcc gtcgctttac tccggagtca 60
ctggtggaga tagagaagca aattgctgcc aagcagggaa caaagaaagc cagagagaag 120
catagggagc agaaggacca agaagagaag cctcggcccc agctggactt gaaagcctgc 180
aaccagctgc ccaagttcta tggtgagctc ccagcagaac tgatcgggga gcccctggag 240
gatctagatc cgttctacag cacacaccgg acatttatgg tgctgaacaa agggaggacc 300
atttcccggt ttagtgccac tcgggccctg tggctattca gtcctttcaa cctgatcaga 360
agaacggcca tcaaagtgtc tgtccactcg tggttcagtt tatttattac ggtcactatt 420
ttggttaatt gtgtgtgcat gacccgaact gaccttccag agaaaattga atatgtcttc 480
actgtcattt acacctttga agccttgata aagatactgg caagaggatt ttgtctaaat 540
gagttcacgt acctgagaga tccttggaac tggctggatt ttagcgtcat taccctggca 600
tatgttggca cagcaataga tctccgtggg atctcaggcc tgcggacatt cagagttctt 660
agagcattaa aaacagtttc tgtgatccca ggcctgaagg tcattgtggg ggccctgatt 720
cactcagtga agaaactggc tgatgtgacc atcctcacca tcttctgcct aagtgttttt 780
gccttggtgg ggctgcaact cttcaagggc aacctcaaaa ataaatgtgt caagaatgac 840
atggctgtca atgagacaac caactactca tctcacagaa aaccagatat ctacataaat 900
aagcgaggca cttctgaccc cttactgtgt ggcaatggat ctgactcagg ccactgccct 960
gatggttata tctgccttaa aacttctgac aacccggatt ttaactacac cagctttgat 1020
tcctttgctt gggctttcct ctcactgttc cgcctcatga cacaggattc ctgggaacgc 1080
ctctaccagc agaccctgag gacttctggg aaaatctata tgatcttttt tgtgctcgta 1140
atcttcctgg gatctttcta cctggtcaac ttgatcttgg ctgtagtcac catggcgtat 1200
gaggagcaga accaggcaac cactgatgaa attgaagcaa aggagaagaa gttccaggag 1260
gccctcgaga tgctccggaa ggagcaggag gtgctagcag cactagggat tgacacaacc 1320
tctctccact cccacaatgg atcaccttta acctccaaaa atgccagtga gagaaggcat 1380
agaataaagc caagagtgtc agagggctcc acagaagaca acaaatcacc ccgctctgat 1440
ccttacaacc agcgcaggat gtcttttcta ggcctcgcct ctggaaaacg ccgggctagt 1500
catggcagtg tgttccattt ccggtcccct ggccgagata tctcactccc tgagggagtc 1560
acagatgatg gagtctttcc tggagaccac gaaagccatc ggggctctct gctgctgggt 1620
gggggtgctg gccagcaagg cccccctccct agaagccctc ttcctcaacc cagcaaccct 1680
gactccaggc atggagaaga tgaacaccaa ccgccgccca ctagtgagct tgcccctgga 1740
gctgtcgatg tctcggcatt cgatgcagga caaaagaaga ctttcttgtc agcagaatac 1800
ttagatgaac ctttccgggc ccaaagggca atgagtgttg tcagtatcat aacctccgtc 1860
cttgaggaac tcgaggagtc tgaacagaag tgcccaccct gcttgaccag cttgtctcag 1920
aagtatctga tctgggattg ctgccccatg tgggtgaagc tcaagacaat tctctttggg 1980
cttgtgacgg atccctttgc agagctcacc atcaccttgt gcatcgtggt gaacaccatc 2040

-continued

```
ttcatggcca tggagcacca tggcatgagc cctaccttcg aagccatgct ccagataggc   2100
aacatcgtct ttaccatatt ttttactgct gaaatggtct tcaaaatcat tgccttcgac   2160
ccatactatt atttccagaa gaagtggaat atctttgact gcatcatcgt cactgtgagt   2220
ctgctagagc tgggcgtggc caagaaggga agcctgtctg tgctgcggag cttccgcttg   2280
ctgcgcgtat tcaagctggc caaatcctgg cccaccttaa acacactcat caagatcatc   2340
ggaaactcag tgggggcact ggggaacctc accatcatcc tggccatcat tgtctttgtc   2400
tttgctctgg ttggcaagca gctcctaggg gaaaactacc gtaacaaccg aaaaaatatc   2460
tccgcgcccc atgaagactg gccccgctgg cacatgcacg acttcttcca ctctttcctc   2520
attgtcttcc gtatcctctg tggagagtgg attgagaaca tgtgggcctg catggaagtt   2580
ggccaaaaat ccatatgcct catccttttc ttgacggtga tggtgctagg gaacctggtg   2640
gtgcttaacc tgttcatcgc cctgctattg aactctttca gtgctgacaa cctcacagcc   2700
ccggaggacg atggggaggt gaacaacctg caggtggccc tggcacggat ccaggtcttt   2760
ggccatcgta ccaaacaggc tctttgcagc ttcttcagca ggtcctgccc attcccccag   2820
cccaaggcag agcctgagct ggtggtgaaa ctcccactct ccagctccaa ggctgagaac   2880
cacattgctg ccaacactgc caggggggagc tctggagggc tccaagctcc cagaggcccc   2940
agggatgagc acagtgactt catcgctaat ccgactgtgt gggtctctgt gcccattgct   3000
gagggtgaat ctgatcttga tgacttggag gatgatggtg gggaagatgc tcagagcttc   3060
cagcaggaag tgatccccaa aggacagcag gagcagctgc agcaagtcga gaggtgtggg   3120
gaccacctga cacccaggag cccaggcact ggaacatctt ctgaggacct ggctccatcc   3180
ctgggtgaga cgtggaaaga tgagtctgtt cctcaggtcc ctgctgaggg agtggacgac   3240
acaagctcct ctgagggcag cacggtggac tgcctagatc ctgaggaaat cctgaggaag   3300
atccctgagc tggcagatga cctggaagaa ccagatgact gcttcacaga aggatgcatt   3360
cgccactgtc cctgctgcaa actggatacc accaagagtc catgggatgt gggctggcag   3420
gtgcgcaaga cttgctaccg tatcgtggag cacagctggt ttgagagctt catcatcttc   3480
atgatcctgc tcagcagtgg atctctggcc tttgaagact attacctgga ccagaagccc   3540
acggtgaaag ctttgctgga gtacactgac agggtcttca cctttatctt tgtgttcgag   3600
atgctgctta agtgggtggc ctatggcttc aaaaagtact tcaccaatgc ctggtgctgg   3660
ctggacttcc tcattgtgaa tatctcactg ataagtctca cagcgaagat tctggaatat   3720
tctgaagtgg ctcccatcaa agcccttcga acccttcgcg ctctgcggcc actgcgggct   3780
ctttctcgat ttgaaggcat gcgggtggtg gtggatgccc tggtgggcgc catcccatcc   3840
atcatgaatg tcctcctcgt ctgcctcatc ttctggctca tcttcagcat catgggtgtg   3900
aacctcttcg cagggaagtt ttggaggtgc atcaactata ccgatggaga gttttccctt   3960
gtacctttgt cgattgtgaa taacaagtct gactgcaaga ttcaaaactc cactggcagc   4020
ttcttctggg tcaatgtgaa agtcaacttt gataatgttg caatgggtta ccttgcactt   4080
ctgcaggtgg caacctttaa aggctggatg gacattatgt atgcagctgt tgattcccgg   4140
gaggtcaaca tgcaacccaa gtgggaggac aacgtgtaca tgtatttgta ctttgtcatc   4200
ttcatcattt ttggaggctt cttcacactg aatctctttg ttggggtcat aattgacaac   4260
ttcaatcaac agaaaaaaaa gttagggggc caggacatct tcatgacaga ggagcagaag   4320
aaatactaca atgccatgaa gaagttgggc tccaagaagc cccagaagcc catcccacgg   4380
cccctgaaca agttccaggg ttttgtcttt gacatcgtga ccagacaagc ttttgacatc   4440
```

accatcatgg tcctcatctg cctcaacatg atcaccatga tggtggagac tgatgaccaa 4500
agtgaagaaa agacgaaaat tctgggcaaa atcaaccagt tctttgtggc cgtcttcaca 4560
ggcgaatgtg tcatgaagat gttcgctttg aggcagtact acttcacaaa tggctggaat 4620
gtgtttgact tcattgtggt ggttctctcc attgcgagcc tgattttttc tgcaattctt 4680
aagtcacttc aaagttactt ctccccaacg ctcttcagag tcatccgcct ggcccgaatt 4740
ggccgcatcc tcagactgat ccgagcggcc aaggggatcc gcacactgct ctttgccctc 4800
atgatgtccc tgcctgccct cttcaacatc gggctgttgc tattccttgt catgttcatc 4860
tactctatct tcggtatgtc cagctttccc catgtgaggt gggaggctgg catcgacgac 4920
atgttcaact tccagacctt cgccaacagc atgctgtgcc tcttccagat taccacgtcg 4980
gccggctggg atggcctcct cagccccatc ctcaacacag ggccccccta ctgtgacccc 5040
aatctgccca acagcaatgg caccagaggg gactgtggga gcccagccgt aggcatcatc 5100
ttcttcacca cctacatcat catctccttc ctcatcatgg tcaacatgta cattgcagtg 5160
attctggaga acttcaatgt ggccacggag gagagcactg agcccctgag tgaggacgac 5220
tttgacatgt tctatgagac ctgggagaag tttgacccag aggccactca gtttattacc 5280
ttttctgctc tctcggactt tgcagacact ctctctggtc ccctgagaat cccaaaaccc 5340
aatcgaaata tactgatcca gatggacctg cctttggtcc ctggagataa gatccactgc 5400
ttggacatcc tttttgcttt caccaagaat gtcctaggag aatccgggga gttggattct 5460
ctgaaggcaa atatggagga gaagtttatg gcaactaatc tttcaaaatc atcctatgaa 5520
ccaatagcaa ccactctccg atggaagcaa gaagacattt cagccactgt cattcaaaag 5580
gcctatcgga gctatgtgct gcaccgctcc atggcactct ctaacacccc atgtgtgccc 5640
agagctgagg aggaggctgc atcactccca gatgaaggtt ttgttgcatt cacagcaaat 5700
gaaaattgtg tactcccaga caaatctgaa actgcttctg ccacatcatt cccaccgtcc 5760
tatgagagtg tcactagagg ccttagtgat agagtcaaca tgaggacatc tagctcaata 5820
caaaatgaag atgaagccac cagtatggag ctgattgccc ctgggcccta gtga 5874

<210> SEQ ID NO 10
<211> LENGTH: 6500
<212> TYPE: DNA
<213> ORGANISM: Homo sapiens

<400> SEQUENCE: 10
tcctgctata cccacagtgg tggtcatctc ttctgatctt cacagccaat cagctcccaa 60
ggcccctgac ctcagctcag cttttgtaga tccttatgac accatccttt aagactggaa 120
tcctagggca ggctgtttta ttcccgcctc ctgaggcctt tctgaggatc tgtggcttgt 180
ctctgtcctg agggtgaaga tggatgacag atgctaccca gtaatctttc cagatgagcg 240
gaatttccgc cccttcactt ccgactctct ggctgcaatt gagaagcgga ttgccatcca 300
aaaggagaaa aagaagtcta aagaccagac aggagaagta ccccagcctc ggcctcagct 360
tgacctaaag gcctccagga agttgcccaa gctctatggc gacattcctc gtgagctcat 420
aggaaagcct ctggaagact tggacccatt ctaccgaaat cataagacat ttatggtgtt 480
aaacagaaag aggacaatct accgcttcag tgccaagcat gccttgttca tttttgggcc 540
tttcaattca atcagaagtt tagccattag agtctcagtc cattcattgt tcagcatgtt 600
cattatcggc accgttatca tcaactgcgt gttcatggct acagggcctg ctaaaaacag 660

-continued

```
caacagtaac aatactgaca ttgcagagtg tgtcttcact gggatttata tttttgaagc    720
tttgattaaa atattggcaa gaggtttcat tctggatgag ttttctttcc ttcgagatcc    780
atggaactgg ctggactcca ttgtcattgg aatagcgatt gtgtcatata ttccaggaat    840
caccatcaaa ctattgcccc tgcgtacctt ccgtgtgttc agagctttga aagcaatttc    900
agtagtttca cgtctgaagg tcatcgtggg ggccttgcta cgctctgtga agaagctggt    960
caacgtgatt atcctcacct tcttttgcct cagcatcttt gccctggtag gtcagcagct   1020
cttcatggga agtctgaacc tgaaatgcat ctcgagggac tgtaaaaata tcagtaaccc   1080
ggaagcttat gaccattgct ttgaaaagaa agaaaattca cctgaattca aaatgtgtgg   1140
catctggatg ggtaacagtg cctgttccat acaatatgaa tgtaagcaca ccaaaattaa   1200
tcctgactat aattatacga attttgacaa ctttggctgg tcttttcttg ccatgttccg   1260
gctgatgacc caagattcct gggagaagct ttatcaacag accctgcgta ctactgggct   1320
ctactcagtc ttcttcttca ttgtggtcat tttcctgggc tccttctacc tgattaactt   1380
aaccctggct gttgttacca tggcatatga ggagcagaac aagaatgtag ctgcagagat   1440
agaggccaag gaaaagatgt ttcaggaagc ccagcagctg ttaaaggagg aaaaggaggc   1500
tctggttgcc atgggaattg acagaagttc acttacttcc cttgaaacat catattttac   1560
cccaaaaaag agaaagctct ttggtaataa gaaaaggaag tccttctttt tgagagagtc   1620
tgggaaagac cagcctcctg ggtcagattc tgatgaagat tgccaaaaaa agccacagct   1680
cctagagcaa accaaacgac tgtcccagaa tctatcactg gaccactttg atgagcatgg   1740
agatcctctc caaaggcaga gagcactgag tgctgtcagc atcctcacca tcaccatgaa   1800
ggaacaagaa aaatcacaag agccttgtct cccttgtgga gaaaacctgg catccaagta   1860
cctcgtgtgg aactgttgcc cccagtggct gtgcgttaag aaggtcctga gaactgtgat   1920
gactgacccg tttactgagc tggccatcac catctgcatc atcatcaaca ctgtcttctt   1980
ggccatggag catcacaaga tggaggccag ttttgagaag atgttgaata tagggaattt   2040
ggttttcact agcattttta tagcagaaat gtgcctaaaa atcattgcgc tcgatcccta   2100
ccactacttt cgccgaggct ggaacatttt tgacagcatt gttgctcttc tgagttttgc   2160
agatgtaatg aactgtgtac ttcaaaagag aagctggcca ttcttgcgtt ccttcagagt   2220
gctcagggtc ttcaagttag ccaaatcctg gccaactttg aacacactaa ttaagataat   2280
cggcaactct gtcggagccc ttggaagcct gactgtggtc ctggtcattg tgatctttat   2340
tttctcagta gttggcatgc agctttttgg ccgtagcttc aattcccaaa agagtccaaa   2400
actctgtaac ccgacaggcc cgacagtctc atgtttacgg cactggcaca tgggggattt   2460
ctggcactcc ttcctagtgg tattccgcat cctctgcggg gaatggatcg aaaatatgtg   2520
ggaatgtatg caagaagcga atgcatcatc atcattgtgt gttattgtct tcatattgat   2580
cacggtgata ggaaaacttg tggtgctcaa cctcttcatt gccttactgc tcaattcctt   2640
tagcaatgag gaaagaaatg gaaacttaga aggagaggcc aggaaaacta aagtccagtt   2700
agcactggat cgattccgcc gggctttttg ttttgtgaga cacactcttg agcatttctg   2760
tcacaagtgg tgcaggaagc aaaacttacc acagcaaaaa gaggtggcag gaggctgtgc   2820
tgcacaaagc aaagacatca ttcccctggt catggagatg aaaaggggct cagagaccca   2880
ggaggagctt ggtatactaa cctctgtacc aaagaccctg ggcgtcaggc atgattggac   2940
ttggttggca ccacttgcgg aggaggaaga tgacgttgaa ttttctggtg aagataatgc   3000
acagcgcatc acacaacctg agcctgaaca acaggcctat gagctccatc aggagaacaa   3060
```

```
gaagcccacg agccagagag ttcaaagtgt ggaaattgac atgttctctg aagatgagcc   3120
tcatctgacc atacaggatc cccgaaagaa gtctgatgtt accagtatac tatcagaatg   3180
tagcaccatt gatcttcagg atggctttgg atggttacct gagatggttc ccaaaaagca   3240
accagagaga tgtttgccca aaggctttgg ttgctgcttt ccatgctgta gcgtggacaa   3300
gagaaagcct ccctgggtca tttggtggaa cctgcggaaa acctgctacc aaatagtgaa   3360
acacagctgg tttgagagct ttattatctt tgtgattctg ctgagcagtg gggcactgat   3420
atttgaagat gttcaccttg agaaccaacc caaaatccaa gaattactaa attgtactga   3480
cattattttt acacatattt ttatcctgga gatggtacta aaatgggtag ccttcggatt   3540
tggaaagtat ttcaccagtg cctggtgctg ccttgatttc atcattgtga ttgtctctgt   3600
gaccaccctc attaacttaa tggaattgaa gtccttccgg actctacgag cactgaggcc   3660
tcttcgtgcg ctgtcccagt ttgaaggaat gaaggtggtg gtcaatgctc tcataggtgc   3720
catacctgcc attctgaatg ttttgcttgt ctgcctcatt ttctggctcg tattttgtat   3780
tctgggagta tacttctttt ctggaaaatt tgggaaatgc attaatggaa cagactcagt   3840
tataaattat accatcatta caaataaaag tcaatgtgaa agtggcaatt tctcttggat   3900
caaccagaaa gtcaactttg acaatgtggg aaatgcttac ctcgctctgc tgcaagtggc   3960
aacatttaag ggctggatgg atattatata tgcagctgtt gattccacag agaaagaaca   4020
acagccagag tttgagagca attcactcgg ttacatttac ttcgtagtct ttatcatctt   4080
tggctcattc ttcactctga atctcttcat tggcgttatc attgacaact tcaaccaaca   4140
gcagaaaaag ttaggtggcc aagacatttt tatgacagaa gaacagaaga aatactataa   4200
tgcaatgaaa aaattaggat ccaaaaaacc tcaaaaaccc attccacggc ctctgaacaa   4260
atgtcaaggt ctcgtgttcg acatagtcac aagccagatc tttgacatca tcatcataag   4320
tctcattatc ctaaacatga ttagcatgat ggctgaatca tacaaccaac ccaaagccat   4380
gaaatccatc cttgaccatc tcaactgggt ctttgtggtc atctttacgt tagaatgtct   4440
catcaaaatc tttgctttga ggcaatacta cttcaccaat ggctggaatt tatttgactg   4500
tgtggtcgtg cttctttcca ttgttagtac aatgatttct accttggaaa atcaggagca   4560
cattcctttc cctccgacgc tcttcagaat tgtccgcttg gctcggattg gccgaatcct   4620
gaggcttgtc cgggctgcac gaggaatcag gactctcctc tttgctctga tgatgtcgct   4680
tccttctctg ttcaacattg gtcttctact ctttctgatt atgtttatct atgccattct   4740
gggtatgaac tggttttcca aagtgaatcc agagtctgga atcgatgaca tattcaactt   4800
caagactttt gccagcagca tgctctgtct cttccagata agcacatcag caggttggga   4860
ttccctgctc agccccatgc tgcgatcaaa agaatcatgt aactcttcct cagaaaactg   4920
ccacctccct ggcatagcca catcctactt tgtcagttac attatcatct cctttctcat   4980
tgttgtcaac atgtacattg ctgtgatttt agagaacttc aatacagcca ctgaagaaag   5040
tgaggaccct ttgggtgaag atgactttga catattttat gaagtgtggg aaaagtttga   5100
cccagaagca acacaattta tcaaatattc tgccctttct gactttgctg atgccttgcc   5160
tgagcctttg cgtgtcgcaa agccaaataa atatcaattt ctagtaatgg acttgcccat   5220
ggtgagtgaa gatcgcctcc actgcatgga tattcttttc gccttcaccg ctagggtact   5280
cggtggctct gatggcctag atagtatgaa agcaatgatg gaagagaagt tcatggaagc   5340
caatcctctc aagaagttgt atgaacccat agtcaccacc accaagagaa aggaagagga   5400
```

aagaggtgct gctattattc aaaaggcctt tcgaaagtac atgatgaagg tgaccaaggg 5460
tgaccaaggt gaccaaaatg acttggaaaa cgggcctcat tcaccactcc agactctttg 5520
caatggagac ttgtctagct ttggggtggc caagggcaag gtccactgtg actgagccct 5580
cacctccacg cctacctcat agcttcacag ccttgccttc agcctctgag ctccaggggt 5640
cagcagctta gtgtatcaac agggagtgga ttcaccaaat tagccattcc atttctcttt 5700
ctggctaaaa taaatgatat ttcaatttca ttttaaataa tacttacaga gatataagat 5760
aaggctactt gacaaccagt ggtactatta taataaggaa gaagacacca ggaaggactg 5820
taaaaggaca taccaatttt aggattgaaa tagttcaggc cgggcgcagt ggctcatgcc 5880
tgtaatccca gcactttgag aggccaaggc aggtggatca cgaggtcaag agatcgagac 5940
catcctggcc aacatgatga aactccgtct ctactaaaaa tacaaaaatt agctgggcat 6000
ggtggcgtgc gcctgtagtc ccagctactt gggaggctga ggcaggagaa tcgcttaaac 6060
ctgggagacg gaggttgcag tgagccaaga tcgtgccact gcactccagc ctggtgacag 6120
agtgagactc tgtttcaaaa aagaaaagaa aagaaacatg gttcaaatta tatctaaaca 6180
aaaaagaata agaaacaaaa aacacattaa aattttaagt tgtattttct atgtttctag 6240
atacatcatt tttgtttgat attttcctga tgcaagtatg tggtttatca catgtagctc 6300
ttttgcatgc taaatgaaaa ttcaaaactt gccaataaat gaatagctta ttgcagacat 6360
tttttaccaa cattaattat tttgggtttg tttaaaacct agaggcacaa tcttgacttg 6420
tcaattacta ccctttcaca agctaccatc tcagatatat atatatatat aaattcaata 6480
aagctttctg tttgtgttcc 6500

<210> SEQ ID NO 11
<211> LENGTH: 6528
<212> TYPE: DNA
<213> ORGANISM: Homo sapiens

<400> SEQUENCE: 11
tcctgctata cccacagtgg tggtcatctc ttctgatctt cacagccaat cagctcccaa 60
ggcccctgac ctcagctcag cttttgtaga tccttatgac accatccttt aagactggaa 120
tcctagggca ggctgtttta ttcccgcctc ctgaggcctt tctgaggatc tgtggcttgt 180
ctctgtcctg agggtgaaga tggatgacag atgctaccca gtaatctttc cagatgagcg 240
gaatttccgc cccttcactt ccgactctct ggctgcaatt gagaagcgga ttgccatcca 300
aaaggagaaa aagaagtcta aagaccagac aggagaagta ccccagcctc ggcctcagct 360
tgacctaaag gcctccagga agttgcccaa gctctatggc gacattcctc gtgagctcat 420
aggaaagcct ctggaagact tggacccatt ctaccgaaat cataagacat ttatggtgtt 480
aaacagaaag aggacaatct accgcttcag tgccaagcat gccttgttca tttttgggcc 540
tttcaattca atcagaagtt tagccattag agtctcagtc cattcattgt tcagcatgtt 600
cattatcggc accgttatca tcaactgcgt gttcatggct acagggcctg ctaaaaacag 660
caacagtaac aatactgaca ttgcagagtg tgtcttcact gggatttata tttttgaagc 720
tttgattaaa atattggcaa gaggtttcat tctggatgag ttttctttcc ttcgagatcc 780
atggaactgg ctggactcca ttgtcattgg aatagcgatt gtgtcatata ttccaggaat 840
caccatcaaa ctattgcccc tgcgtacctt ccgtgtgttc agagctttga aagcaatttc 900
agtagtttca cgtctgaagg tcatcgtggg ggccttgcta cgctctgtga agaagctggt 960
caacgtgatt atcctcacct tcttttgcct cagcatcttt gccctggtag gtcagcagct 1020

-continued

```
cttcatggga agtctgaacc tgaaatgcat ctcgagggac tgtaaaaata tcagtaaccc   1080
ggaagcttat gaccattgct ttgaaaagaa agaaaattca cctgaattca aaatgtgtgg   1140
catctggatg ggtaacagtg cctgttccat acaatatgaa tgtaagcaca ccaaaattaa   1200
tcctgactat aattatacga attttgacaa ctttggctgg tcttttcttg ccatgttccg   1260
gctgatgacc caagattcct gggagaagct ttatcaacag accctgcgta ctactgggct   1320
ctactcagtc ttcttcttca ttgtggtcat tttcctgggc tccttctacc tgattaactt   1380
aaccctggct gttgttacca tggcatatga ggagcagaac aagaatgtag ctgcagagat   1440
agaggccaag gaaaagatgt ttcaggaagc ccagcagctg ttaaaggagg aaaaggaggc   1500
tctggttgcc atgggaattg acagaagttc acttacttcc cttgaaacat catattttac   1560
cccaaaaaag agaaagctct ttggtaataa gaaaaggaag tccttctttt tgagagagtc   1620
tgggaaagac cagcctcctg ggtcagattc tgatgaagat tgccaaaaaa agccacagct   1680
cctagagcaa accaaacgac tgtcccagaa tctatcactg gaccactttg atgagcatgg   1740
agatcctctc caaaggcaga gagcactgag tgccgtcagc atcctcacca tcaccatgaa   1800
ggaacaagaa aaatcacaag agccttgtct cccttgcgga gaaaacctgg catccaagta   1860
cctcgtgtgg aactgttgcc cccagtggct gtgcgttaag aaggtcctga gaactgtgat   1920
gactgacccg tttactgagc tggccatcac catctgcatc atcatcaaca ctgtcttctt   1980
ggccatggag catcacaaga tggaggccag ttttgagaag atgttgaata tagggaattt   2040
ggttttcact agcattttta tagcagaaat gtgcctaaaa atcattgcgc tcgatcccta   2100
ccactacttt cgccgaggct ggaacatttt tgacagcatt gttgctcttc tgagttttgc   2160
agatgtaatg aactgtgtac ttcaaaagag aagctggcca ttcttgcgtt ccttcagggt   2220
gctcagggtc ttcaagttag ccaaatcctg gccaactttg aacacactaa ttaagataat   2280
cggcaactct gtcggagccc ttggaaacct gactgtggtc ctggtcattg tgatctttat   2340
tttctcagta gttggcatgc agctttttgg ccgtagcttc aattcccaaa agagtccaaa   2400
actctgtaac ccgacaggcc cgacagtctc atgtttacgg cactggcaca tgggggattt   2460
ctggcactcc ttcctagtgg tattccgcat cctctgcggg gaatggatcg aaaatatgtg   2520
ggaatgtatg caagaagcga atgcatcatc atcattgtgt gttattgtct tcatattgat   2580
cacggtgata ggaaaacttg tggtgctcaa cctcttcatt gccttactgc tcaattcctt   2640
tagcaatgag gaaagaaatg gaaacttaga aggagaggcc aggaaaacta aagtccagtt   2700
agcactggat cgattccgcc gggctttttg ttttgtgaga cacactcttg agcatttctg   2760
tcacaagtgg tgcaggaagc aaaacttacc acagcaaaaa gaggtggcag gaggctgtgc   2820
tgcacaaagc aaagacatca ttccccctggt catggagatg aaaaggggct cagagaccca   2880
ggaggagctt ggtatactaa cctctgtacc aaagaccctg ggcgtcaggc atgattggac   2940
ttggttggca ccacttgcgg aggaggaaga tgacgttgaa ttttctggtg aagataatgc   3000
acagcgcatc acacaacctg agcctgaaca acaggcctat gagctccatc aggagaacaa   3060
gaagcccacg agccagagag ttcaaagtgt ggaaattgac atgttctctg aagatgagcc   3120
tcatctgacc atacaggatc cccgaaagaa gtctgatgtt accagtatac tatcagaatg   3180
tagcaccatt gatcttcagg atggctttgg atggttacct gagatggttc ccaaaaagca   3240
accagagaga tgtttgccca aaggctttgg ttgctgcttt ccatgctgta gcgtggacaa   3300
gagaaagcct ccctgggtca tttggtggaa cctgcggaaa acctgctacc aaatagtgaa   3360
```

acacagctgg tttgagagct ttattatctt tgtgattctg ctgagcagtg gggcactgat 3420
atttgaagat gttcaccttg agaaccaacc caaaatccaa gaattactaa attgtactga 3480
cattattttt acacatattt ttatcctgga gatggtacta aaatgggtag ccttcggatt 3540
tggaaagtat ttcaccagtg cctggtgctg ccttgatttc atcattgtga ttgtctctgt 3600
gaccaccctc attaacttaa tggaattgaa gtccttccgg actctacgag cactgaggcc 3660
tcttcgtgcg ctgtcccagt ttgaaggaat gaaggtggtg gtcaatgctc tcataggtgc 3720
catacctgcc attctgaatg ttttgcttgt ctgcctcatt ttctggctcg tattttgtat 3780
tctgggagta tacttctttt ctggaaaatt tgggaaatgc attaatggaa cagactcagt 3840
tataaattat accatcatta caaataaaag tcaatgtgaa agtggcaatt tctcttggat 3900
caaccagaaa gtcaactttg acaatgtggg aaatgcttac ctcgctctgc tgcaagtggc 3960
aacatttaag ggctggatgg atattatata tgcagctgtt gattccacag agaaagaaca 4020
acagccagag tttgagagca attcactcgg ttacatttac ttcgtagtct ttatcatctt 4080
tggctcattc ttcactctga atctcttcat tggcgttatc attgacaact tcaaccaaca 4140
gcagaaaaag ttaggtggcc aagacatttt tatgacagaa gaacagaaga aatactataa 4200
tgcaatgaaa aaattaggat ccaaaaaacc tcaaaaaccc attccacggc ctctgaacaa 4260
atgtcaaggt ctcgtgttcg acatagtcac aagccagatc tttgacatca tcatcataag 4320
tctcattatc ctaaacatga ttagcatgat ggctgaatca tacaaccaac ccaaagccat 4380
gaaatccatc cttgaccatc tcaactgggt ctttgtggtc atctttacgt tagaatgtct 4440
catcaaaatc tttgctttga ggcaatacta cttcaccaat ggctggaatt tatttgactg 4500
tgtggtcgtg cttctttcca ttgttagtac aatgatttct accttggaaa atcaggagca 4560
cattcctttc cctccgacgc tcttcagaat tgtccgcttg gctcggattg gccgaatcct 4620
gaggcttgtc cgggctgcac gaggaatcag gactctcctc tttgctctga tgatgtcgct 4680
tccttctctg ttcaacattg gtcttctact ctttctgatt atgtttatct atgccattct 4740
gggtatgaac tggttttcca aagtgaatcc agagtctgga atcgatgaca tattcaactt 4800
caagactttt gccagcagca tgctctgtct cttccagata agcacatcag caggttggga 4860
ttccctgctc agccccatgc tgcgatcaaa agaatcatgt aactcttcct cagaaaactg 4920
ccacctccct ggcatagcca catcctactt tgtcagttac attatcatct cctttctcat 4980
tgttgtcaac atgtacattg ctgtgatttt agagaacttc aatacagcca ctgaagaaag 5040
tgaggaccct ttgggtgaag atgactttga catattttat gaagtgtggg aaaagtttga 5100
cccagaagca acacaattta tcaaatattc tgccctttct gactttgctg atgccttgcc 5160
tgagcctttg cgtgtcgcaa agccaaataa atatcaattt ctagtaatgg acttgcccat 5220
ggtgagtgaa gatcgcctcc actgcatgga tattcttttc gccttcaccg ctagggtact 5280
cggtggctct gatggcctag atagtatgaa agcaatgatg gaagagaagt tcatggaagc 5340
caatcctctc aagaagttgt atgaacccat agtcaccacc accaagagaa aggaagagga 5400
aagaggtgct gctattattc aaaaggcctt tcgaaagtac atgatgaagg tgaccaaggg 5460
tgaccaaggt gaccaaaatg acttggaaaa cgggcctcat tcaccactcc agactctttg 5520
caatggagac ttgtctagct ttggggtggc caagggcaag gtccactgtg actgagccct 5580
cacctccacg cctacctcat agcttcacag ccttgccctc agcctctgag ctccaggggt 5640
cagcagctta gtgtatcaac agggagtgga ttcaccaaat tagccattcc attttctttt 5700
ctggctaaat aaatgatatt tcaatttcat tttaaatgat acttacagag atataagata 5760

```
aggctacttg acaaccagcg gtactatttt aataaggaag aagacaccag gaaggactgt   5820

aaaaggacat tccaatttta ggattggaat agttcaagcc gggcgcagtg gctcatgcct   5880

ggaatcccag cactttgaga ggccaaggca ggtggatcac gaggtcaaga gatcgagacc   5940

atcctggcca accatgatga aactccgtct ctactaaaat acaaaaatta gctgggcatg   6000

gttgcgtgcg cctgtagtcc cagctacttg ggaggctgag gcaggagaat cgcttaaacc   6060

tgggagacgg aggttgcagt gagccaagat cgtgtcactg cactccagcc tggtgacaga   6120

gtgagactct gtttcaaaaa agaaaagaaa agaaacatgg ttcaaattat atctaaacaa   6180

aaaagaataa gaaacaaaaa acacattaaa attttaagtt gtattttcta tgtttctaga   6240

tacatcattt ttgtttgata ttttcctgat gcaagtatgt ggtttatcac atgtagctct   6300

tttgcatgct aaatgaaaat tcaagacttg ccaataaatg aatagcttat tgcagacatt   6360

ttttaccaac attaattatt ttgggtttgt ttaaaaccta gaggcacaat cttgacttgt   6420

caattactac cctttcacaa gctaccatct cagatatata tatatatata aattcaataa   6480

agctttctgt ttgtgttcca taaaaaaaaa aaaaaaaaaa aaaaaaaa                 6528
```

<210> SEQ ID NO 12
<211> LENGTH: 1123
<212> TYPE: DNA
<213> ORGANISM: Homo sapiens

<400> SEQUENCE: 12

```
agcggggggt tcccgcccgc gcctctccct ccacacctcc ccgcaagcag agggagccgg     60

ctccggcctt ggccagccca gagacaggct cccacagtgc agcggcgggc tgaagggctc    120

ctcaagcact gccagagtgg acaccgaggc cgaggagacg ccaagagcga tgaaacaagc    180

ttctggttca agagtttctt caggttccac tacgggctgt tcttctacag gtgcgccgat    240

gtccacagtg ctaccttctg atgagctact gctttcattc agtttctgct gacttaatat    300

gtgagctgac agaatgcaga gaccacgttg tatatgaagc atccactttg ccttgtacac    360

cagggcattc aataaccact taataactac aaccctgatg atccgattca ctactaaagt    420

cttccgtgtt taaattttca aagtcagatt ctcctacagc aattggtaca gtcacagtaa    480

gactggggtt gtttatgaat gacatgtaat cactttcatc aataatgtat ttttcaacac    540

tgctgccagt tcctatacca cttgtagttc catttacatc tttaagatag tcaagatctt    600

tcccaatttc tgctgtatga ttggacatac aactgtcttt cttgttgttt agatcatcaa    660

gtggtttaat ttcatctaaa atcttttgtt tcctaatgaa ggactgttga ataaattcat    720

atatttttct tttcacataa gctactcctt tgtgcatcct atccacagca atttggagat    780

tattcatttc attatcatca tcagtggctg caaggttgtc tgcactaaat gagctcagaa    840

gcaaggccag aaagagattc aggaccttaa aaacaacaaa aacatgatta taattttaca    900

ccaatgtagg gaagagcaga ttacaatcac ttattctttc ttttaagtgt ggaaaaaact    960

ctaagttcta aaacttgatg agaaggaaac accacagcat agtgattaga agatgggtga   1020

tctgaatttg tgactggctc aatagcacat ccttggacaa agacatgatt tctgttgctc   1080

tcaagttctc ccattcgtaa agtgaaattg aatgagctaa tct                     1123
```

<210> SEQ ID NO 13
<211> LENGTH: 2352
<212> TYPE: DNA
<213> ORGANISM: Homo sapiens

<400> SEQUENCE: 13

```
gtcttagtcc tctgaatatt ttttctttgt tcagaacctg agaaagatga atgaaattta     60
gtgtttccca tccccgagag acacccagca tccacaactt cacactctga tgccattgtg    120
tatttatgca agaaatacca taactaagat gaggtctcgc tatgttgcct aggctagtct    180
tgaactcctg gcctcaagtg atccttctgc ctcagcatcg ggagtcactg ggattaaagg    240
catgagccac catgctcagg aacttgacat catcagacag taaatcaaga ggtactgaca    300
actgagactg agtgatggtc cctgcctagg atttggaatc tttgcatgaa atagggactc    360
tagccaccag cgacaaagaa gtcagggaga ctgcggtctc taggaagcac ttccaggaaa    420
caggaattca ggcaaagttg gacattccaa agatggcgta gatgaacatg accaggaaga    480
gcaggaggcc gatgttaaac aacgcaggaa gggacatcat caaagcaaag agcagcgtgc    540
ggatcccctt tgctcctttg actagacgta ggattcggcc aatcctggca agacggatca    600
ctcggaacag ggtaacagag atctctggag gtgaaacatt gctctgaact ggcattgatt    660
ctagcccagc tcttgtagac caattaccaa cttgtccatc tccctccagt gcctggaact    720
ggacctggca cacaggcctc tggctcatcg gaattcatag gttcagcctc tgcttcttct    780
ccttctccag gcaaagggtt atcaactgtg ctgcactctg aggagcttga ccggtttaat    840
ctctagaaag gaattcacca ccccaccagc acgcggaaca caatcaggaa ggagtggaag    900
aagtcgttca tgtgccaccg tgggagcgta cagtcatcat tgatcttgca gacacattct    960
ttgtagctct taccaaagag ctgcatgccg accacagcaa aaatgaagac gatgatggcc   1020
aacactaagc ctttagacta aaaagaaaac aaatattaca taccctgaat ctgtgctgaa   1080
accacaaagg agagcatctt tggatccttc caagtaataa aaatattctg ttgaagaaga   1140
atttgaacag ttataacatc acagacttta atctgtgatt gtgataaagg aggtcaaatt   1200
aaaaaatctg attattggga gacttttgga gtaatcatgg aagaaagact atgaaatcag   1260
atattcttgg atttgaatgt tgcttctatc ccttcttaac ttaaatccat gggcattcat   1320
tatcatcagt gcctaacctg gcagaaccac agtctacaca taatctggca tctgtctttt   1380
ccatgctggc taccaaatgg ctgaatgttg gtggagaaac tctcacaacc aagtgaatgg   1440
ttatatttta atttcgctct tgttgcccag tctggagtgc aatggcacga tctcggctca   1500
ccgcaacctc tgcctcccga gttcaagcga ttctcctgcc tcagcctcct gagtagctgg   1560
aattacaggc acccaccacc atgcccggct aattttttgt atttttagta gagacggggt   1620
ttcttttttt ttcttctttt tttgtattat tttttagcaa aaaaaaaaaa aaaatacatg   1680
aagcaattcc agaaagcgat gaattaaatt aaatttgatt aaaggctgtc tgtgtacata   1740
gagaattgca atctaacttc atatgtaaac aaattgcatt ctaatctatt agtatattct   1800
tgtaacaagt agctgtctca gccaatcaca gcagctgagc ttcagccaac cacagcctgc   1860
tgatttatca gacaatgtcc acataaggca aatgtcaagc tataagcaat caagctgttt   1920
ttgtgcgtca ctcccttttt ctgtctataa atactcctgc tcatgttgct gagttgagct   1980
ctccgaactt ctcttggttc tgagtgctgc ctaaatcatt attattatta tcttatttca   2040
gcaataaata ctatttcatt gctgaaataa gctgctaaat ttaatttgtt gaaaattttt   2100
cttttaacaa aggttaagaa aaccattcac agtataaact cagaaatagg agcaagactc   2160
agaataaaag gacagatccc agtgagaaaa cttaagttta aataagtgtg gtaaaataat   2220
ctacaatatt aaatgtaagt tactcatcag atatattaat tttacagcat ataaattaag   2280
aaataaaatt ctccatcaat tggaaaaaaa aaaaaaaaaa aaaaaaaaaa aaaaaaaaaa   2340
```

aaaaaaaaaa aa 2352

<210> SEQ ID NO 14
<211> LENGTH: 267
<212> TYPE: DNA
<213> ORGANISM: Homo sapiens
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (166)..(166)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (230)..(230)
<223> OTHER INFORMATION: n is a, c, g, or t

<400> SEQUENCE: 14
gtgcggntcc cctttgctcc tttgactaga cgtaggattc ggccaatcct ggcaagacgg 60
atcactcgga acagggtaac agagatctct ggaggtgaaa cattgctctg aactggcatt 120
gattctagcc cagctcttgt agaccaatta ccaacttgtc catctncctc cagtgcctgg 180
gaactggacc tggnacacag gcaaagggtt atcaactgtg ctgcactctn aggagcttga 240
ccggtttaat ctctagaaag gaattca 267

<210> SEQ ID NO 15
<211> LENGTH: 1080
<212> TYPE: DNA
<213> ORGANISM: Homo sapiens

<400> SEQUENCE: 15
gagtttaaga agaggttggt gttacatgga gcagcagcac agtcaagcag ggaacagatc 60
acgtaaagcc ctttagagag tgaagtcggc tttttatgct aggtgcaact gggagttctg 120
aacacggcaa agttggacat tccaaagatg gcgtagatga acatgaccag gaagagcagg 180
aggccgatgt taaacaacgc aggaagggac atcatcaaag caaagagcag cgtgcggatc 240
ccctttgctc ctttgactag acgtaggatt cggccaatcc tggcaagacg gatcactcgg 300
aacagggtaa cagagatctc tggaggtgaa acattgctct gaactggcat tgattctagc 360
ccagctcttg tagaccaatt accaacttgt ccatctccct ccagtgcctg gaactggacc 420
tggcacacag gcctctggct catcggaatt cataggttca gcctctgctt cttctccttc 480
tccaggcaaa gggttatcaa ctgtgctgca ctctgaggag cttgaccggt ttaatctcta 540
gaaaggaatt caccacccca ccaggtaaca gagatctctg gaggtgaaac attgctctga 600
actggcattg attctagccc agctcttgta gaccaattac caacttgtcc atctccctcc 660
agtgcctgga actggacctg gcacacaggc aaagggttat caactgtgct gcactctgag 720
gagcttgacc ggtttaatct ctagaaagga attcaccacc ccaccagaca caatgaagat 780
gaggtcattg tgtgggtcca aatccaatat aactggggtc cttataagaa gaaaagaccg 840
agacacacag ggagaaaact acgtgagtac cgggccagag attgggatga tgcagctgca 900
agctgcaagg attgccaaca acctccaaag ttagaaagca gcaaggcagg atacttacta 960
gagcctttag agaaatcatg gccttgctca gaccttgatt tcagacttct agcctccaga 1020

-continued attggcaaaa gaataaattt ctgttgttgt aaaaaaaaaa aaaaaaaaaa aaaaaaaaaa 1080

<210> SEQ ID NO 16
<211> LENGTH: 173
<212> TYPE: DNA
<213> ORGANISM: Homo sapiens

<400> SEQUENCE: 16
tttttttttt tttttttttt tccaattgat ggagaatttt atttcttaat ttatatgctg 60
taaaattaat atatctgatg agtaacttac atttaatatt gtagattatt ttaccacact 120
tatttaaact taagttttct cactgggatc tgtcctttta ttctgagtct tgc 173

<210> SEQ ID NO 17
<211> LENGTH: 618
<212> TYPE: DNA
<213> ORGANISM: Homo sapiens

<400> SEQUENCE: 17
tgtacatgga gcagcagcac agtcaagcag ggaacagatc acgtaaagcc ctttagaaga 60
gtgaagtcgg ctttttatgc taggtgcaac tgggagttct gaacacggca aagttggaca 120
ttccaaagat ggcgtagatg aacatgacca ggaagagcag gaggccgatg ttaaacaacg 180
caggaaggga catcatcaaa gcaaagagca gcgtgcggat cccctttgct cctttgacta 240
gacgtaggat tcggccaatc ctggcaagac ggatcactcg gaacagggta acagagatct 300
ctggaggtga aacattgctc tgaactggca ttgattctag cccagctctt gtaagaccaa 360
ttaccaactt gtccatctcc ctccagtgcc tggaactgga cctggcacac aggcctctgg 420
tcaatcggaa ttcataggtt cagcctctgt tcttctcctt ctccaggcaa gggttatcaa 480
ctgtgctgca ctctgaggag cttgaccggt taaatctcta gaaaggaatt caccacccca 540
caggtaacca gagatctctg aggtgaacat tgtctgaacg gattgttcta gccagtctgt 600
aaccattaca tgtcattc 618

<210> SEQ ID NO 18
<211> LENGTH: 871
<212> TYPE: DNA
<213> ORGANISM: Homo sapiens

<400> SEQUENCE: 18
gaaactggcc ttttataagt aaatcattat gtagtttctt cctttggagg gcagctctgt 60
gtgactgctt gggcctctgt ggttagatct gtttggttaa cgggctttgg gctttcacac 120
aaagctatac tctccacaaa cttctgtgag ataaaaaggt gatatctgtc ttagtcctct 180
gaatattttt tctttgttca gaacctgaga aagatgaatg aaatttagtg tttcccatcc 240
ccgagagaca cccagcatcc acaacttcac actctgatgc cattgtgtat ttatgcaaga 300
aataccataa ctaaggtaat gtcttgagat ttttggttca ataatgtcct taaattctat 360
gtgtttttaa agcctaaaag aaattccccc tcttcactcc cccgtctctc cctacaacct 420
ggtgagacaa ttctctcatt ttctcctccc agtttccaat gctattgtta tgatctatta 480
gaataattgc tattattttt ttggccttat ctgaccctag aagtgattac agggaaaaaa 540
attactaacc aattgattag gggaactgga atataaagtg cagctcttat ggtttattca 600
cagaccaaga atatacatag tacttaatgt gataggtatt tgctcgttga ctgtggaacc 660
aggttagtct ataatacagg tttcaggcag aacagactta tttacctgaa ctctggactt 720
cggaaaaggt gagtaaggta tttaagagaa ctgaccacgt ttgtattcca cccatatagg 780

```
ggatttaaca gaaattcttc ctctttataa acaacgttcc caaagggctt tgtaaatgtg    840

cccttaaaaa tttgcgcccg tgggggacac t                                   871


<210> SEQ ID NO 19
<211> LENGTH: 304
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t

<400> SEQUENCE: 19

nctttcggag caagattgcg ccatttccaa antaggcgta gnagnaacag naccaggnaa     60

gacaggaggc cgatgttaaa caacgcagga agggacatca tcaaagcaaa gagcagcgtg    120

cggatcccct ttgctccttt gactagacgt aggattcggc caatcctggc aagacggatc    180

actcggaaca gggtagggga aacaaaatac gtttcaatca aatcagctag aaacatacct    240

gtatgtggag gaaaataata gaaataaaat atttaaagat gtatgctacc taaaaaaaaa    300

aaaa                                                                 304


<210> SEQ ID NO 20
<211> LENGTH: 293
<212> TYPE: DNA
<213> ORGANISM: Homo sapiens

<400> SEQUENCE: 20

ctggcaaagc tggcattcca agatggcgta gatgaacatg accaggaaga gcaggaggcc     60

gatgttaaac aacgcaggaa gggacgtcat caaagcaaag agcagcgtgc ggatcccctt    120

tgctcctttg actagacgta ggattcggcc aatcctggca agacggatca ctcggaacag    180

ggtaggggaa acaaaatacg tttcaatcaa atcagctaga aacatacctg tatgtggagg    240

aatataattg aaataaaata tttaaagatg tatgctacct aaaaaaaaaa aaa           293


<210> SEQ ID NO 21
<211> LENGTH: 892
<212> TYPE: DNA
<213> ORGANISM: Homo sapiens
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (685)..(685)
```

<223> OTHER INFORMATION: n is a, c, g, or t
<220> FEATURE:
<221> NAME/KEY: misc_feature
<222> LOCATION: (784)..(784)
<223> OTHER INFORMATION: n is a, c, g, or t
<220> FEATURE:
<221> NAME/KEY: misc_feature
<222> LOCATION: (845)..(845)
<223> OTHER INFORMATION: n is a, c, g, or t

<400> SEQUENCE: 21
tttctaggcg aagattggca cattccaaag atggcgtagc aggaacatga ccagggaaga 60
gcaggaggcc gatgttaaac aacgcaggaa gggacatcat caaagcaaag agcagcgtgc 120
ggatcccctt tgctcctttg actagacgta ggattcggcc aatcctggca agacggatca 180
ctcggaacag ggtaaccgag atctctggag gtgaaacatt gctctgaact ggcattgatt 240
ctagcccagc tcttgtagac caattaccaa cttgtccatc tccctccagt gcctggaact 300
ggacctggca cacaggcaaa gggttatcaa ctgtgctgca ctctgaggag cttgaccggt 360
ttaatctcta gaaaggagtt caccacccca ccagcacgcg gaacacaatc aggaaggagt 420
ggaagaagtc gttcatgtgc caccgtggga gcgtacagtc atcattgatc ttgcagacac 480
attctttgta gctcttacca aagagctgca tgccgaccac agcaaaaatg aagacgatga 540
tggccaacac taagaagctg tccattgggg agcatgaggg ctgagcgtcc atcaaccagg 600
gagaccacac cgttgcagtc cacagcactg tgcattttcc cgttcaccgg cagcattggt 660
ggngacctac tggcttggct gatgntactg ctgcgtcgct cctggggtct gtggagcaca 720
aacagtgagc cccttctgct ctcattgtct acaagatgct gtgctcatca tcggcaaatt 780
cagnctcaga tcctatatct cttcctcttg cctttgaact aaaaagactt gttctgctgc 840
ttcgncctgc agaaacaagg agcacgatgc tcgagtggga ctgcaaaaaa at 892

<210> SEQ ID NO 22
<211> LENGTH: 260
<212> TYPE: DNA
<213> ORGANISM: Homo sapiens

<400> SEQUENCE: 22
taacattgcc tggaagagca ggaggccgat gtttaacaac gcaggaaggg acatcatcaa 60
agcaaagagc agcgtgcgga tcccctttgc tcctttgact agacgtagga ttcggccaat 120
cctggcaaga cggatcactc ggaacagggt aggggaaaca aaatacgttt caatcaaatc 180
agctagaaac atacctgtat gtggaggaaa ataatagaaa taaaatattt aaagatgtat 240
gctacccaaa aaaaaaaaaa 260

<210> SEQ ID NO 23
<211> LENGTH: 982
<212> TYPE: DNA
<213> ORGANISM: Homo sapiens

<400> SEQUENCE: 23
cacgcgtccg gtcttagtcc tctgaatatt ttttctttgt tcagaacctg agaaagatga 60
atgaaattta gtgtttccca tccccgagag acacccagca tccacaactt cacactctga 120
tgccattgtg tatttatgca agaaatacca taactaagat gaggtctcgc tatgttgcct 180
aggctagtct tgaactcctg gcctcaagtg atccttctgc ctcagcatcg ggagtcactg 240
ggattaaagg catgagccac catgctcagg aacttgacat catcagacag taaatcaaga 300
ggtactgaca actgagactg agtgatggtc cctgcctagg atttggaatc tttgcatgaa 360
atagggactc tagccaccag cgacaaagaa gtcagggaga ctgcggtctc taggaagcac 420
ttccaggaaa caggaattca ggcaaagttg gacattccaa agatggcgta gatgaacatg 480
accaggaaga gcaggaggcc gatgttaaac aacgcaggaa gggacatcat caaagcaaag 540
agcagcgtgc ggatcccctt tgctcctttg actagacgta ggattcggcc aatcctggca 600
agacggatca ctcggaacag ggtaacagag atctctggag gtgaaacatt gctctgaact 660
ggcattgatt ctagcccagc tcttgtagac caattaccaa cttgtccatc tccctccagt 720
gcctggaact ggacctggca cacaggcctc tggctcatcg gaattcatag gttcagcctc 780
tgcttcttct ccttctccag gcaaaggggt tatcaactgt gctgcactct gaggagcttg 840
accggtttaa tctctagaaa ggaattcacc acccccccag cacgcggaac acaatcaggg 900
aaggagtggg aggaagtcct tcctgggccc acggggggag acggacaggc attcattgat 960
cttgcagaaa cctttctttg ta 982

<210> SEQ ID NO 24
<211> LENGTH: 906
<212> TYPE: DNA
<213> ORGANISM: Homo sapiens

<400> SEQUENCE: 24
taaggcttgt tcctaagact gggggcagat ctatccttgt atagtaaatg tttaaatgac 60
taaaaaacct tttgtcatct ctcttaaata tctattctac tataagaacc tgacttccta 120
ttttactcag gtcaaattaa aaaatctgat tattgggaga cttttggagt aatcatggaa 180
gaaagactat gaaatcagat attcttggat ttgaatgttg cttctatccc ttcttaagta 240
agtgaattat ctttaagcca ttaagcctta gctgctgcat ctgtaaaata cgtataagaa 300
tacctacttt ataaagttgt taaatagtat aaataggata ttgcatgtaa accacttgat 360
actgtgatcc acacattctg tactagctgc tcaaaaacag gagttattat aattagttaa 420
actattatac aatttgagat aaaactattg attgaattac acatcatcat tttatcttac 480
ttagaagaca cagataaaac aataaagcct tgcagtttga ggtgcaaatg taggtgaaaa 540
tgtgcatgaa aagctttcct gaaaacactc ctgaacctcg ggaaggatgg gcctggtaga 600
gtgagtatgg gagaggataa gatgcaattt tgcatacata aacatccaaa atattttaat 660
aaggatggat tactttagaa ttatccttta aactaatgct ggttcacatt tatcaaccac 720
tgaggagctg aattatatga atgggctctg gagctgtcta ttagcacact gctatactac 780
tgtatttaac acagtataag aatgatgaaa ggtaaagcaa tgcaggtagc tcactctagg 840
gttgtagaaa actttacaat aatttctaaa caactagaca taaaatatta agatgggttg 900
gcttca 906

<210> SEQ ID NO 25
<211> LENGTH: 476
<212> TYPE: DNA
<213> ORGANISM: Mus musculus

<400> SEQUENCE: 25
gatctgattc actgctaaag tcttctgtgt ttaagttctc aaagtcagac tctcccacag 60
caatgggcac agtcacagtg aggctggggt tgtttatgaa tgacatataa tcactctcat 120
caatgatgta cttctccaca ctgctgcccg tccctatgcc acttgtggtt ccattcacat 180
ctttcagaca gtccagatct ttcccaattt ctgttgtgtg gttagagata caattgtctt 240
ttctgttgtt tagatcatca agtggcttaa tttcatctag aatcttctgt ttcttaacaa 300
aggattgttg aatgaattca tatatttttc tttttacata agctattcct ttgtgcatcc 360
tgtccacagc aatctgcagg ttgttcatct cattgtcatc atcagtggct gcaaggttgt 420
ctgcactaaa tgagctcaga agcaaggcca gaaagaggtt caagaccttg aaaaca 476

<210> SEQ ID NO 26
<211> LENGTH: 185
<212> TYPE: DNA
<213> ORGANISM: Mus musculus

<400> SEQUENCE: 26
aggcaaagtt ggacatccca aagatggcgt agatgaacat gacgagaaaa agcaggaggc 60
cgatgttaaa cagcgcagga agggacatca tcagagcaaa gagcagcgtg cggatcccct 120
tggcaccttt gatcaggcgt aggattcgtc caatcctggc caggcggatg actcggaaca 180
gggta 185

<210> SEQ ID NO 27
<211> LENGTH: 162
<212> TYPE: DNA
<213> ORGANISM: Mus musculus

<400> SEQUENCE: 27
ccccacacag cacacggaac acgatcagga aggagtggaa gaagtcgttc atgtgccagc 60
gtgggagctt gcagttctcg ttgatcttgc aaacacactc cttgtagctc tttccaaaca 120
gctgcatgcc gaccacggca aaaatgaaga cgatgatggc ca 162

<210> SEQ ID NO 28
<211> LENGTH: 94
<212> TYPE: DNA
<213> ORGANISM: Mus musculus

<400> SEQUENCE: 28
ttacataccc tgaatctgtg ctgaaaccgc aaagaagagc atctttggat ccctccaagt 60
aataaaaata tcctgtttag gaagaatttg aaca 94

<210> SEQ ID NO 29
<211> LENGTH: 24
<212> TYPE: DNA
<213> ORGANISM: Artificial Sequence
<220> FEATURE:
<223> OTHER INFORMATION: Antisense oligonucleotide

<400> SEQUENCE: 29
ccuaucuuuc cccccccuac cuuu 24

<210> SEQ ID NO 30
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 30
tcggtgtcca ctctggcagt 20

<210> SEQ ID NO 31
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 31
tgcactgtgg gagcctgtct 20

<210> SEQ ID NO 32
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 32
gtagcactgt ggacatcggc 20

<210> SEQ ID NO 33
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 33
gtagaagaac agcccgtagt g 21

<210> SEQ ID NO 34
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 34
gtggtctctg cattctgtca 20

<210> SEQ ID NO 35
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 35
gtggtatagg aactggcagc a 21

<210> SEQ ID NO 36
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 36
gtccaatcat acagcagaa 19

<210> SEQ ID NO 37
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 37
gtgactgtac caattgctgt 20

<210> SEQ ID NO 38
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 38
acttcttcca ctccttcct 19

<210> SEQ ID NO 39
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 39
gatgtccctt cctgcgttgt 20

<210> SEQ ID NO 40
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 40
tgtggatgct gggtgtctct c 21

<210> SEQ ID NO 41
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 41
tcccagtgac tcccgatgct 20

<210> SEQ ID NO 42
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 42
agtctcagtt gtcagtacct c 21

<210> SEQ ID NO 43
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 43
gttattgaat gccctggtgt 20

<210> SEQ ID NO 44
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 44
tcggatcatc agggttgtag t 21

<210> SEQ ID NO 45
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 45
gtggtatagg aactggcagc a 21

<210> SEQ ID NO 46
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 46
tctgctcttc cctacattgg 20

<210> SEQ ID NO 47
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 47
gtaatctgct cttccctac 19

<210> SEQ ID NO 48
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 48
gggagaactt gagagcaaca g 21

<210> SEQ ID NO 49
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 49
gccagtcaca aattcagatc a 21

<210> SEQ ID NO 50
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 50
gtataggaac tggca 15

<210> SEQ ID NO 51

<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 51
gtggtatagg aactg 15

<210> SEQ ID NO 52
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 52
gugguauagg aactggcagc a 21

<210> SEQ ID NO 53
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 53
agaacttgag agcaa 15

<210> SEQ ID NO 54
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 54
gggagaactu gagagcaaca g 21

<210> SEQ ID NO 55
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 55
gccagtcaca aattc 15

<210> SEQ ID NO 56
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 56
cacaaattca gatca 15

<210> SEQ ID NO 57
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 57
gccagtcaca aautcagauc a 21

<210> SEQ ID NO 58
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 58
auuuaaacac ggaagacuuu aguagug 27

<210> SEQ ID NO 59
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 59
ucacaaauuc agaucaccca ucuucua 27

<210> SEQ ID NO 60
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 60
gtggtatagg aactg 15

<210> SEQ ID NO 61
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 61
gugguauagg aactggcagc a 21

<210> SEQ ID NO 62
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 62
gccagtcaca aattc 15

<210> SEQ ID NO 63
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 63
cacaaattca gatca 15

<210> SEQ ID NO 64
<211> LENGTH: 25
<212> TYPE: DNA

<213> ORGANISM: Artificial Sequence
<220> FEATURE:
<223> OTHER INFORMATION: Antisense oligonucleotide

<400> SEQUENCE: 64
gguauaggaa cuggcagcag uguug 25

<210> SEQ ID NO 65
<211> LENGTH: 22
<212> TYPE: DNA
<213> ORGANISM: Artificial Sequence
<220> FEATURE:
<223> OTHER INFORMATION: Antisense oligonucleotide

<400> SEQUENCE: 65
uggtauagga actggcagca gu 22

<210> SEQ ID NO 66
<211> LENGTH: 25
<212> TYPE: DNA
<213> ORGANISM: Artificial Sequence
<220> FEATURE:
<223> OTHER INFORMATION: Antisense oligonucleotide

<400> SEQUENCE: 66
ggtauaggaa ctggcagcag tgttg 25

<210> SEQ ID NO 67
<211> LENGTH: 24
<212> TYPE: DNA
<213> ORGANISM: Artificial Sequence
<220> FEATURE:
<223> OTHER INFORMATION: Antisense oligonucleotide

<400> SEQUENCE: 67
aagcgguata ggaactggca gcag 24

<210> SEQ ID NO 68
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 68
gtggcatagg gacgggcagc a 21

<210> SEQ ID NO 69
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 69
guggcauagg gacgggcagc a 21

<210> SEQ ID NO 70
<211> LENGTH: 26
<212> TYPE: DNA
<213> ORGANISM: Artificial Sequence
<220> FEATURE:
<223> OTHER INFORMATION: Antisense oligonucleotide

<400> SEQUENCE: 70
gagccaguca caaautcaga tcaccc 26

-continued

<210> SEQ ID NO 71
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 71
aaugggagaa cuugagagca a 21

<210> SEQ ID NO 72
<211> LENGTH: 25
<212> TYPE: DNA
<213> ORGANISM: Artificial Sequence
<220> FEATURE:
<223> OTHER INFORMATION: Antisense oligonucleotide

<400> SEQUENCE: 72
acaaguggca tagggacggg cagca 25

<210> SEQ ID NO 73
<211> LENGTH: 25
<212> TYPE: DNA
<213> ORGANISM: Artificial Sequence
<220> FEATURE:
<223> OTHER INFORMATION: Antisense oligonucleotide

<400> SEQUENCE: 73
acaaguggca tagggacggg cagca 25

<210> SEQ ID NO 74
<211> LENGTH: 25
<212> TYPE: DNA
<213> ORGANISM: Artificial Sequence
<220> FEATURE:
<223> OTHER INFORMATION: Antisense oligonucleotide

<400> SEQUENCE: 74
aaguggcaua gggacgggca gcagu 25

<210> SEQ ID NO 75
<211> LENGTH: 25
<212> TYPE: DNA
<213> ORGANISM: Artificial Sequence
<220> FEATURE:
<223> OTHER INFORMATION: Antisense oligonucleotide

<400> SEQUENCE: 75
aaguggcata gggacgggca gcagu 25

<210> SEQ ID NO 76
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 76
gtgactgtgc ccattgctg 19

<210> SEQ ID NO 77
<211> LENGTH: 19
<212> TYPE: DNA
<213> ORGANISM: Artificial Sequence
<220> FEATURE:

<223> OTHER INFORMATION: Antisense oligonucleotide

<400> SEQUENCE: 77
gccacttgat gatctaaac 19

<210> SEQ ID NO 78
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 78
gtggacagga tgcacaaagg a 21

<210> SEQ ID NO 79
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 79
gtgacugtgc ccattgctg 19

<210> SEQ ID NO 80
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 80
gtgactgtgc ccattgctg 19

<210> SEQ ID NO 81
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 81
cctcuttcug gccttgcttc 20

<210> SEQ ID NO 82
<211> LENGTH: 26
<212> TYPE: DNA
<213> ORGANISM: Artificial Sequence
<220> FEATURE:
<223> OTHER INFORMATION: Antisense oligonucleotide

<400> SEQUENCE: 82
gacaaccttg cagccactga ugatga 26

<210> SEQ ID NO 83
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 83
tggtatagga actggcagca 20

-continued

<210> SEQ ID NO 84
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 84
ugguauagga actggcagca 20

<210> SEQ ID NO 85
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 85
ccagtcacaa autcagauca 20

<210> SEQ ID NO 86
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 86
ugguauagga actggcagca 20

<210> SEQ ID NO 87
<211> LENGTH: 25
<212> TYPE: DNA
<213> ORGANISM: Artificial Sequence
<220> FEATURE:
<223> OTHER INFORMATION: Antisense oligonucleotide

<400> SEQUENCE: 87
agccagucac aaautcagat caccc 25

<210> SEQ ID NO 88
<211> LENGTH: 17
<212> TYPE: DNA
<213> ORGANISM: Artificial Sequence
<220> FEATURE:
<223> OTHER INFORMATION: Antisense oligonucleotide

<400> SEQUENCE: 88
gccagucaca aautcag 17

<210> SEQ ID NO 89
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 89
gccagucaca aauuc 15

<210> SEQ ID NO 90
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 90
gccagucaca aautc 15

<210> SEQ ID NO 91
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 91
gccagtcaca aattc 15

<210> SEQ ID NO 92
<211> LENGTH: 13
<212> TYPE: DNA
<213> ORGANISM: Artificial Sequence
<220> FEATURE:
<223> OTHER INFORMATION: Antisense oligonucleotide

<400> SEQUENCE: 92
gccagucaca aat 13

<210> SEQ ID NO 93
<211> LENGTH: 13
<212> TYPE: DNA
<213> ORGANISM: Artificial Sequence
<220> FEATURE:
<223> OTHER INFORMATION: Antisense oligonucleotide

<400> SEQUENCE: 93
gccagtcaca aat 13

<210> SEQ ID NO 94
<211> LENGTH: 11
<212> TYPE: DNA
<213> ORGANISM: Artificial Sequence
<220> FEATURE:
<223> OTHER INFORMATION: Antisense oligonucleotide

<400> SEQUENCE: 94
gccagtcaca a 11

<210> SEQ ID NO 95
<211> LENGTH: 25
<212> TYPE: DNA
<213> ORGANISM: Artificial Sequence
<220> FEATURE:
<223> OTHER INFORMATION: Reverse complement of the antisense
oligonucleotide SEQ ID NO: 48

<400> SEQUENCE: 95
cuacuaaagu cuuccguguu uaaat 25

<210> SEQ ID NO 96
<211> LENGTH: 25
<212> TYPE: DNA
<213> ORGANISM: Artificial Sequence
<220> FEATURE:
<223> OTHER INFORMATION: Reverse complement of the antisense
oligonucleotide SEQ ID NO: 49

<400> SEQUENCE: 96
gaagaugggu gaucugaauu uguga 25